(12) United States Patent
An et al.

(10) Patent No.: US 12,202,895 B2
(45) Date of Patent: Jan. 21, 2025

(54) LILRB4 ANTIBODIES AND USES THEREOF

(71) Applicants: THE BOARD OF REGENTS OF THE UNIVERSITY OF TEXAS SYSTEM, Austin, TX (US); IMMUNE-ONC THERAPEUTICS, INC., Palo Alto, CA (US)

(72) Inventors: Zhiqiang An, Houston, TX (US); Chengcheng Zhang, Dallas, TX (US); Ningyan Zhang, Houston, TX (US); Xun Gui, Houston, TX (US); Mi Deng, Dallas, TX (US); Tao Huang, Palo Alto, CA (US); Qiang Liu, Palo Alto, CA (US); X. Charlene Liao, Palo Alto, CA (US)

(73) Assignees: THE BOARD OF REGENTS OF THE UNIVERSITY OF TEXAS SYSTEM, Austin, TX (US); IMMUNE-ONC THERAPEUTICS, INC., Palo Alto, CA (US)

(*) Notice: Subject to any disclaimer, the term of this patent is extended or adjusted under 35 U.S.C. 154(b) by 955 days.

(21) Appl. No.: 17/275,838

(22) PCT Filed: Sep. 12, 2019

(86) PCT No.: PCT/US2019/050727
§ 371 (c)(1),
(2) Date: Mar. 12, 2021

(87) PCT Pub. No.: WO2020/056077
PCT Pub. Date: Mar. 19, 2020

(65) Prior Publication Data
US 2021/0371518 A1  Dec. 2, 2021

Related U.S. Application Data

(60) Provisional application No. 62/730,715, filed on Sep. 13, 2018.

(51) Int. Cl.
*C07K 16/28* (2006.01)
*A61K 39/395* (2006.01)
(Continued)

(52) U.S. Cl.
CPC ...... *C07K 16/2803* (2013.01); *A61K 39/3955* (2013.01); *A61K 45/06* (2013.01);
(Continued)

(58) Field of Classification Search
CPC ............ C07K 16/2803; C07K 2317/24; C07K 2317/33; C07K 2317/565; C07K 2317/76;
(Continued)

(56) References Cited

U.S. PATENT DOCUMENTS 9,090,684 B2 * 7/2015 Borras ................ A61P 37/00
10,906,971 B2 * 2/2021 Fischer ............... C07K 16/245
(Continued)

FOREIGN PATENT DOCUMENTS

WO  WO 2008/094176  8/2008
WO  WO 2016/144728  9/2016
(Continued)

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
(Continued)

*Primary Examiner* — Jeffrey Stucker
*Assistant Examiner* — Laura Ann Essex
(74) *Attorney, Agent, or Firm* — Parker Highlander PLLC

(57) ABSTRACT

The present disclosure provides an isolated monoclonal antibody or an antigen-binding fragment thereof that binds specifically to leukocyte immunoglobulin-like receptor 4 (LILRB4). In certain embodiments, the antibody or antigen-binding fragment, when bound to LILRB4, modulates the activation of LILRB4. In certain embodiments, the antibody
(Continued)

or antigen-binding fragment, when bound to LILRB4, activates LILRB4. In certain embodiments, the antibody or antigen binding fragment, when bound to LILRB4, suppresses activation of LILRB4. In certain embodiments, the antibody or antigen-binding fragment, when bound to LILRB4, specifically blocks binding of ApoE to LILRB4. In another aspect, there is provided a method of treating or ameliorating the effects of a cancer in a subject, comprising administering to the subject a therapeutically effective amount of the antibody or an antigen-binding fragment thereof or an engineered cell as provided herein.

42 Claims, 100 Drawing Sheets

Specification includes a Sequence Listing.

(51) Int. Cl.
*A61K 45/06* (2006.01)
*A61K 47/68* (2017.01)
*A61K 47/69* (2017.01)
*A61K 51/10* (2006.01)
*A61P 35/02* (2006.01)
*G01N 33/574* (2006.01)

(52) U.S. Cl.
CPC ...... *A61K 47/6849* (2017.08); *A61K 47/6867* (2017.08); *A61K 47/6913* (2017.08); *A61K 51/1027* (2013.01); *A61K 51/1069* (2013.01); *A61P 35/02* (2018.01); *G01N 33/57426* (2013.01); *G01N 33/57492* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
CPC ............ C07K 2317/92; A61K 39/3955; A61K 45/06; A61K 47/6849; A61K 47/6867; A61K 47/6913; A61K 51/1027; A61K 51/1069; A61P 35/02; G01N 33/57426; G01N 33/57492
See application file for complete search history.

(56) References Cited

U.S. PATENT DOCUMENTS

| 11,326,182 | B2* | 5/2022 | Paul .................. C07K 16/18 |
| 2015/0110714 | A1 | 4/2015 | Suciu-Foca et al. |
| 2018/0086829 | A1 | 3/2018 | Zhang et al. |
| 2018/0177847 | A1 | 6/2018 | Chen et al. |

FOREIGN PATENT DOCUMENTS

| WO | WO 2018/022881 | 2/2018 |
| WO | WO 2018/089300 | 5/2018 |
| WO | WO 2018/148494 | 8/2018 |
| WO | WO 2019/094360 | 5/2019 |

OTHER PUBLICATIONS

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
International Search Report and Written Opinion issued in corresponding PCT Application No. PCT/US2019/050727, mailed on Dec. 4, 2019.
International Preliminary Report on Patentability issued in corresponding PCT Application No. PCT/US2019/050727, mailed on Mar. 25, 2021.
Vlad et al., "Membrane and soluble ILT3 are critical to the generation of T suppressor cells and induction of immunological tolerance." *Int Rev Immunol*, 29:119-132, 2010.
Deng. Mi, et al. "LILRB4 signalling in leukaemia cells mediates T cell suppression and tumour infiltration." *Nature* 562.7728 (2018): 605-609.
Extended European Search Report issued in corresponding European Application No. 19860440.7, mailed on May 12, 2022.
Gui, Xun, et al. "Disrupting LILRB4/APOE Interaction by an Efficacious Humanized Antibody Reverses T-cell Suppression and Blocks AML DevelopmentLILRB4 Blocking Antibody for AML Treatment." *Cancer immunology research* 7.8 (2019): 1244-1257.

* cited by examiner

|  | LILRA1 | LILRA3 | LILRB1 | LILRA2 | LILRB2 | LILRA4 | LILRB5 | LILRA6 | LILRB3 | LILRA5 | LILRB4 |
|---|---|---|---|---|---|---|---|---|---|---|---|
| LILRA1 | | 87 | 89 | 74 | 78 | 57 | 58 | 63 | 62 | 62 | 63 |
| LILRA3 | | | 90 | 76 | 75 | 53 | 53 | 58 | 58 | 57 | 54 |
| LILRB1 | | | | 74 | 76 | 55 | 56 | 59 | 60 | 60 | 58 |
| LILRA2 | | | | | 78 | 56 | 55 | 60 | 58 | 58 | 58 |
| LILRB2 | | | | | | 56 | 53 | 60 | 59 | 57 | 54 |
| LILRA4 | | | | | | | 60 | 66 | 64 | 67 | 65 |
| LILRB5 | | | | | | | | 58 | 66 | 66 | 70 |
| LILRA6 | | | | | | | | | 94 | 81 | 82 |
| LILRB3 | | | | | | | | | | 81 | 80 |
| LILRA5 | | | | | | | | | | | 82 |
| LILRB4 | | | | | | | | | | | |

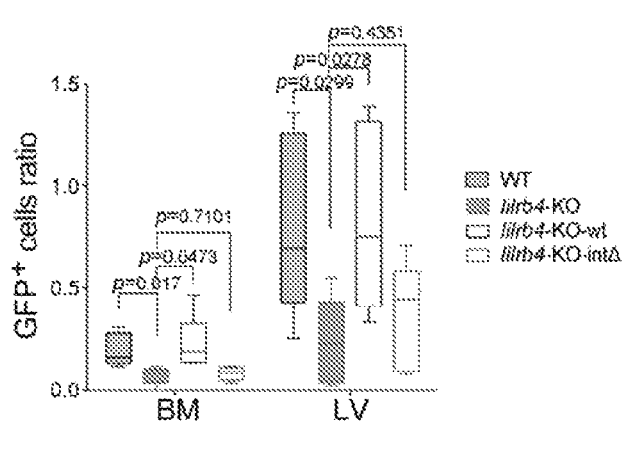
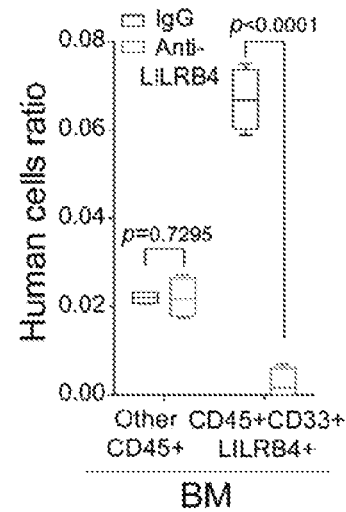
FIG. 3A
FIG. 3B
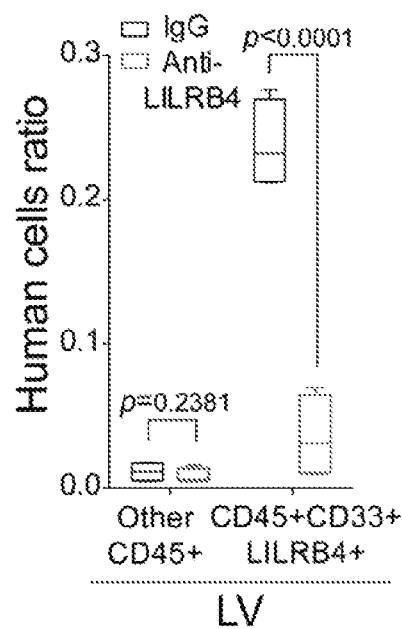
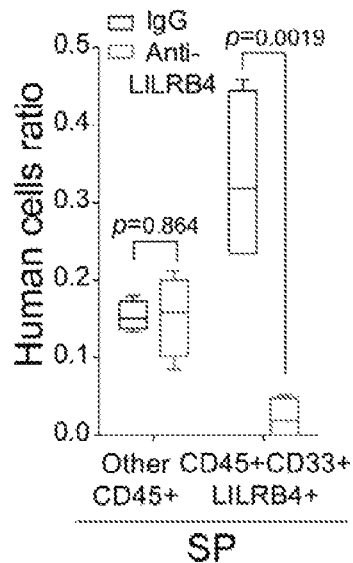
FIG. 3C
FIG. 3D

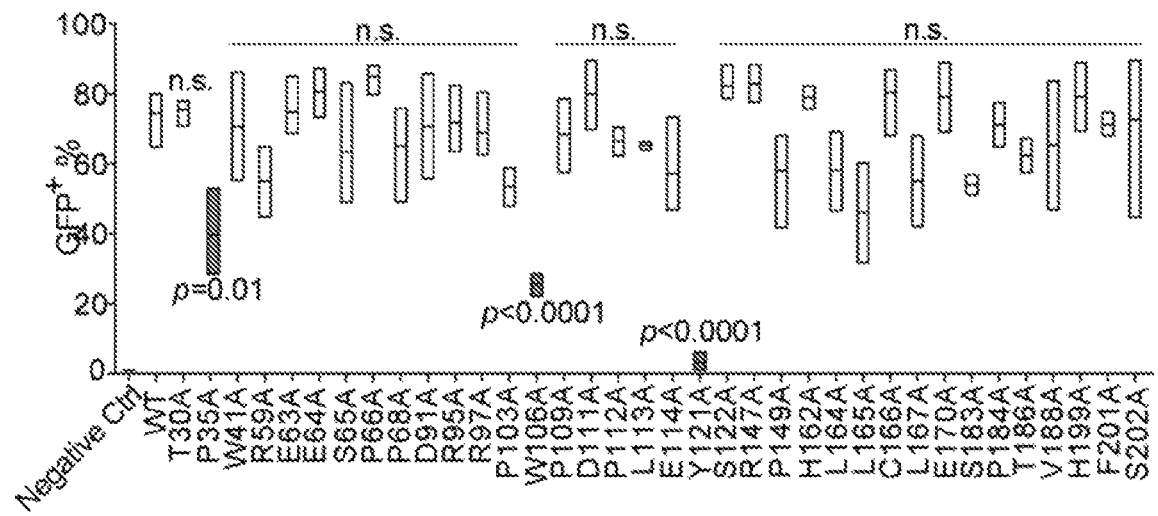
FIG. 4H
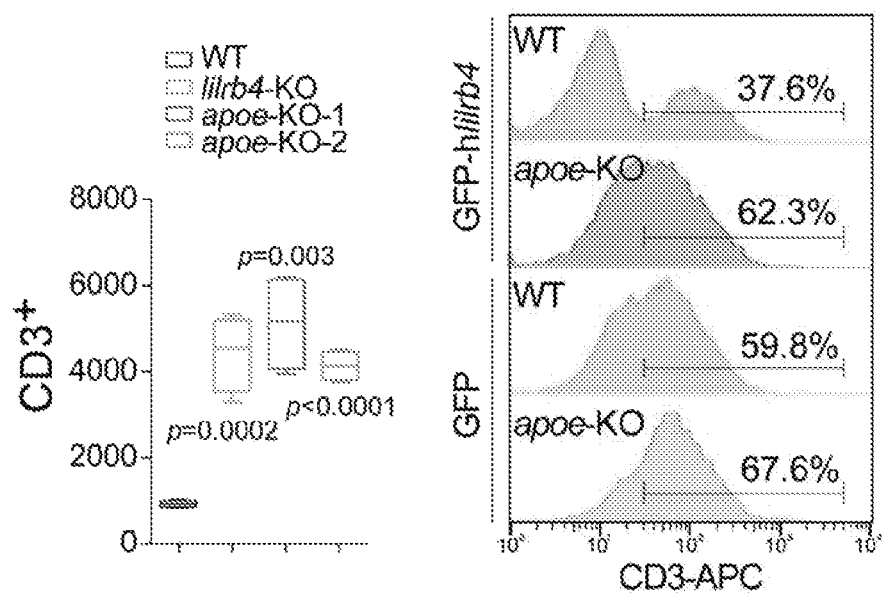
FIG. 4I
FIG. 4J

| | Hazard Ratio (95% CI) | p-value |
|---|---|---|
| LILRB4 (medium vs. low) | 1.518 (0.593, 3.887) | 0.3843 |
| LILRB4 (high vs. low) | 2.339 (1.095, 4.999) | 0.0283 * |
| Age (>=60 yrs vs. <60 yrs) | 3.720 (1.895, 7.302) | 0.0001 * |
| Cytogenetic (abnormal vs. normal) | 0.761 (0.375, 1.545) | 0.4497 |
| PML-RAR (mutated vs. normal) | 0.835 (0.451, 1.548) | 0.5675 |

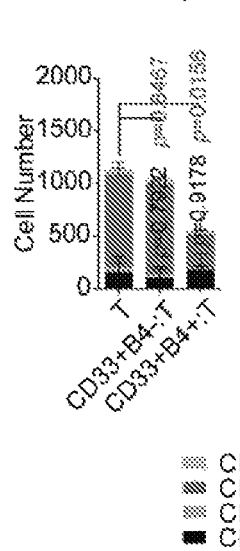
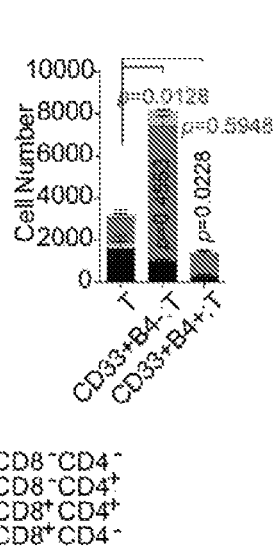
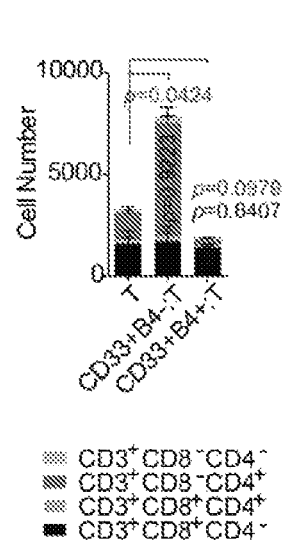
FIG. 7C
FIG. 7D
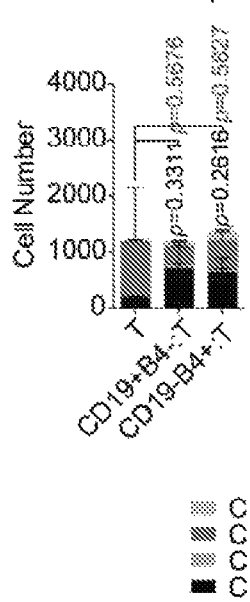
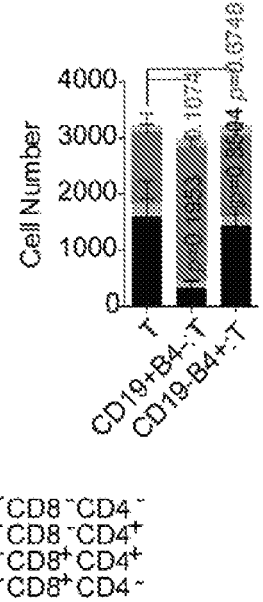
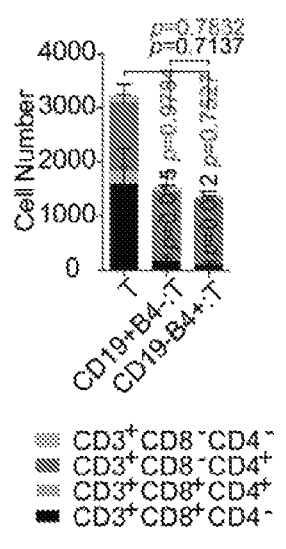
FIG. 7E
FIG. 7F

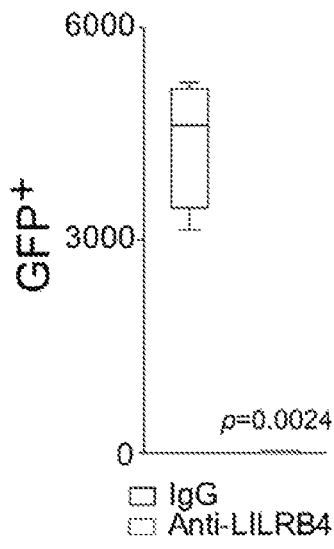
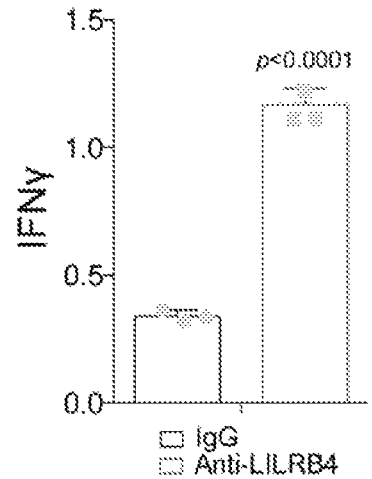
FIG. 8N
FIG. 8O
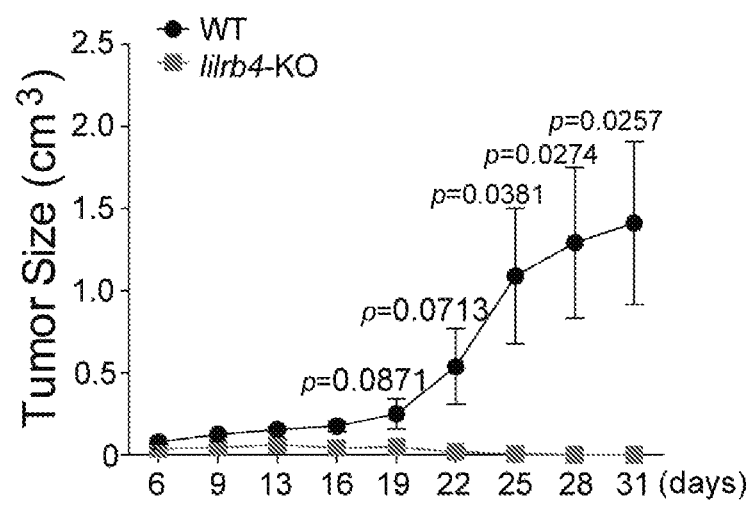
FIG. 9A

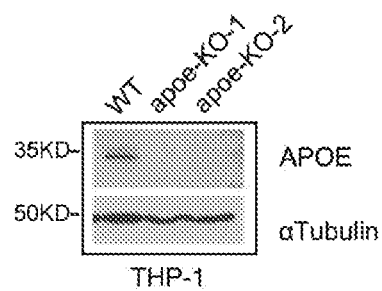
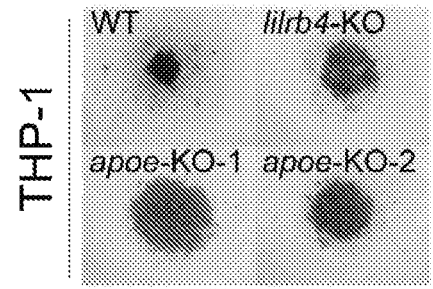
FIG. 14A　　　　　　　FIG. 14B
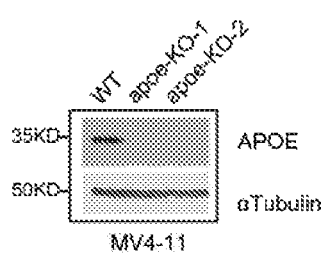
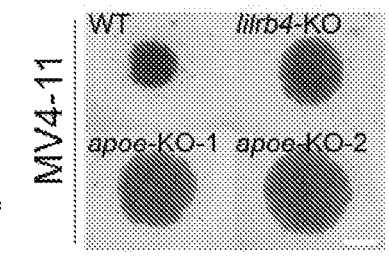
FIG. 14C　　　　　　　FIG. 14D
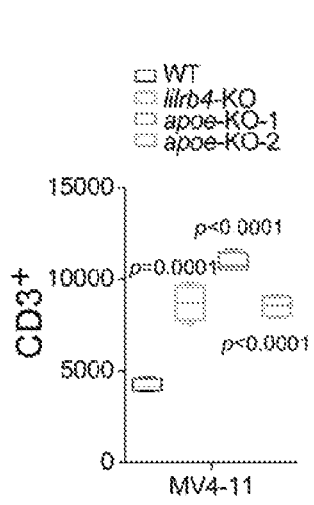
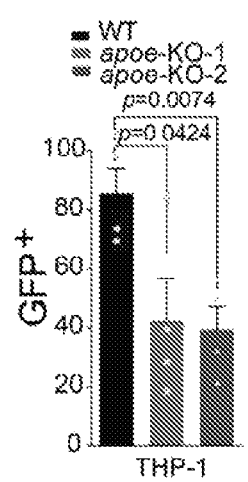
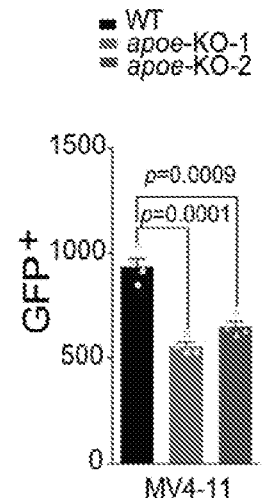
FIG. 14E　　　　FIG. 14F　　　　FIG. 14G

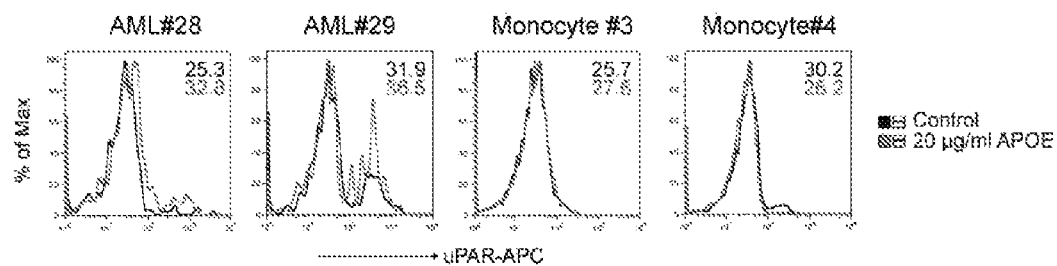
FIG. 19D
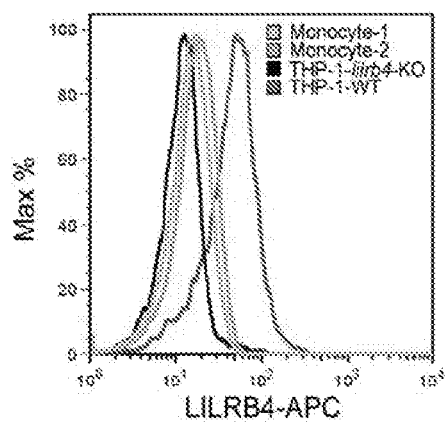 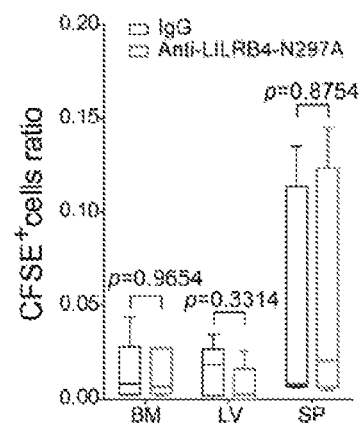
FIG. 20A                FIG. 20B

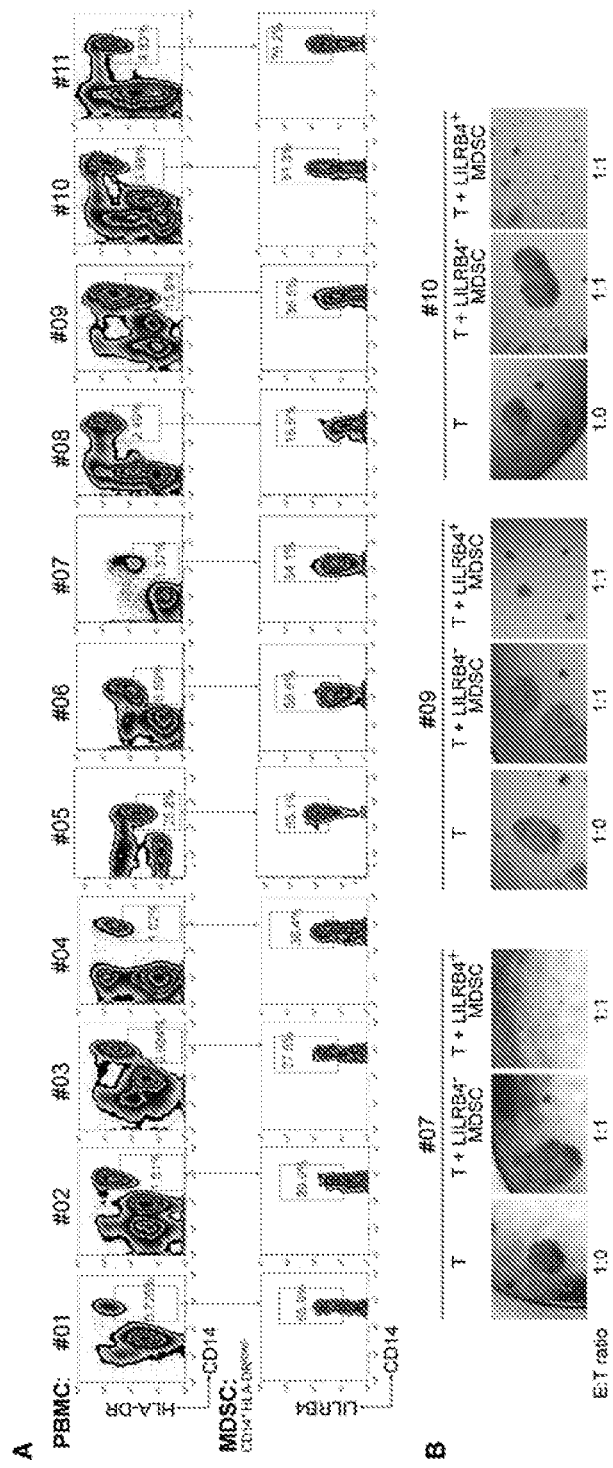
FIGS. 21A-B

>B4-15-1-VH (SEQ ID NO: 1)

EQSLEESGGLEESGGRLVTPGTPLTLTCTASGFTINSAHMSWVRQAPGKGLEWIGFSTTGGPSYYANWAKGRFTIS
RTSTTVDLEITSPTIEDTATYFCARDGPGNNIDMDLWGQGTLVTITS

>B4-15-2-VH (SEQ ID NO: 8)

QSVEESGGRLVTPGTPLTLTCTVSGIDLTNYAINWVRQAPGEGLEYIGTITGSSNTFYASWAKGRFTISKTSTTVDLKI
TSPTTEDTGTYFCASNPDSHNANGVWGQGTLVTVSS

>B4-116-1-VH (SEQ ID NO: 15)

EQSVEESGGDLVKPGASLTLTCAASGFSFSSTYCMCWVRQAPGKGLEWIACIHGVSTNNRWYASWPKGRFTISKT
SSTTVTLQMTSLTAADTATYFCARSDTDYEWGLSLWGPGTLVTISS

>B4-116-2-VH (SEQ ID NO: 22)

EQSVEESGGDLVKPGASLTLTCAASGFSFSSTYCMCWVRQAPGKGLEWIACIHGVSTNNRWYASWPKGRFTISKT
SSTTVTLQMTSLTAADTATYFCARSDTDYEWGLSLWGPGTLVTISS

>B4-116-3-VH (SEQ ID NO: 29)

QSVKESGGRLVTPGTPLTLTCTVSGFSLSNNGMSWVRQAPGKGLEWIGIIYVGSGTTDYATWAKGRFTISRTSTTV
DLKMTSLTTEDTATYLCARGFGVGDWQEWFFDLWGPGTLVTISS

>B4-116-4-VH (SEQ ID NO: 36)

QSLEESGGRLVTPGTPLTLTCTVSGFSLSNNGMSWVRQAPGKGLEWIGIIYVGSGTTDYASWPKGRFTISRTSTTVD
LKMTSLTTEDTATYLCARGFGVGDWQEWFFDLWGPGTLVTVSS

>B4-55-1-VH (SEQ ID NO: 43)

SSVEESGGRLVTPGTPLTLTCTVSGFSLSSYAMAWVRQAPGKGLEWIGIIGTGTTTYYATWVNGRFTISKTSTTVDL
KMTSLTTEDTATYFCVRNDVYWAFNLWGQGTLVTVSS

>B4-55-2-VH (SEQ ID NO: 50)

SSVEESGGRLVTPGTPLTLTCTVSGFSLSSYAMAWVRQAPGKGLEWIGIIGTGTTTYYATWVNGRFTISKTSTTVDL
KMTSLTTEDTATYFCVRNDVYWAFNLWGQGTLVTVSS

>B4-19-VH (SEQ ID NO: 57)

EQSVEESGGGLVTPGGTLTLTCTASGFSISTYAMIWVRQAPGEGLEYIGCIGTGGSAFYAIWAKGRFTISRTSTTVDL
KMTSLTTEDTATYFCARNDIYWAFGLWGQGTLVTVSS

FIG. 28A

\>B4-49-VH (SEQ ID NO: 64)

QSLEESGGDLVKPGASLTLTCTASGFDFSSSGWICWVRQAPGKGLELIACIYSGRSGSTYYASWAKGRVTISKTSSTT
VTLQMTSLTAADTATYFCARALYVDYVDYDYIDLWGPGTLVTVSS

\>B4-72-1-VH (SEQ ID NO: 71)

EQSVEESGGRLVTPGTPLTLTCTASGFSLSSYYMSWVRQAPGRGLEYIGVINTGGSAVYATWTKGRFTISRTSTTVD
LKMTGLTTEDTATYFCARGWSRGDLWGQGTLVTISS

\>B4-72-2-VH (SEQ ID NO: 78)

EQSVEESGGRLVTPGTPLTLTCTASGFSLSSYYMSWVRQAPGRGLEYIGVINTGGSAVYATWTKGRFTISRTSTTVD
LKMTGLTTEDTATYFCARGWSRGDLWGQGTLVTISS

\>B4-86-VH (SEQ ID NO: 85)

EQSVESGGDLVKPEGSLTLTCTVSGFSFSSSYWICWVRQAPGKGLEWIGCIGTGSGSTYYGSWAKGRFTISKTSSTT
VTLQMTSLTAADTATYFCVRGAGYSSYRLWGPGTLVTISS

\>B4-87-VH (SEQ ID NO: 92)

QSVKESGGDLVKPGASLTLTCTASGFSFISTYWICWVRQAPGKGLELIACIYTGGSGSTYYASWAKGRFTISKTSSTT
VTLQLNSLTAADTATYFCARALYVDYVDYDYIDLWGPGTLVTVSS

\>B4-193-VH (SEQ ID NO: 99)

EQSVEESGGDLVKPGTSLTLTCKMSGFSLSSSYWICWVRQAPGKGLEWIGCIDSGSVGITYYATWAKGRFTISRSTS
LNTVTLQMTSLTGADTAMYFSVRHGDNWALDLWGPGTLVTISS

\>h193-VH1 (SEQ ID NO: 223)

EVQLVESGGGLVQPGGSLRLSCAASGFSLSSSYWICWVRQAPGKGLEWIGSIDSGSVGITYYATWAKGRFTISRDN
SKNTLYLQMNSLRAEDTAVYYCVRHGDNWALDLWGQGTLVTVSS

\>h193-VH2 (SEQ ID NO: 225)

EVQLVESGGGLVQPGGSLRLSCAASGFSLSSSYWICWVRQAPGKGLEWVSSIDSGSVGITYYATWAKGRFTISRDN
SKNTLYLQMNSLRAEDTAVYYCVRHGDNWALDLWGQGTLVTVSS

\>h193-VH3 (SEQ ID NO: 226)

EVQLVESGGGLVQPGGSLRLSCAASGFSLSSSYWISWVRQAPGKGLEWIGSIDSGSVGITYYATWAKGRFTISRDN
SKNTLYLQMNSLRAEDTAVYYCARHGDNWALDLWGQGTLVTVSS

FIG. 28B

>h193-VH4 (SEQ ID NO: 228)

EVQLVESGGGLVQPGGSLRLSCAASGFSLSSSYWISWVRQAPGKGLEWVSSIDSGSVGITYYATWAKGRFTISRDN
SKNTLYLQMNSLRAEDTAVYYCARHGDNWALDLWGQGTLVTVSS

>h193-VH5 (SEQ ID NO: 229)

EVQLVESGGGLVQPGGSLRLSCAASGFSLSSSYWISWVRQAPGKGLEWIGVIDSGSVGITYYATWAKGRFTISRDN
SKNTLYLQMNSLRAEDTAVYYCARHGDNWALDLWGQGTLVTVSS

>h193-VH6 (SEQ ID NO: 230)

EVQLVESGGGLVQPGGSLRLSCAASGFSLSSSYWISWVRQAPGKGLEWIGSIDSGSVGITYYATSAKGRFTISRDNS
KNTLYLQMNSLRAEDTAVYYCARHGDNWALDLWGQGTLVTVSS

>h193-VH7 (SEQ ID NO: 231)

EVQLVESGGGLVQPGGSLRLSCAASGFSLSSSYWISWVRQAPGKGLEWIGSIDSGSVGITYYATWVKGRFTISRDN
SKNTLYLQMNSLRAEDTAVYYCARHGDNWALDLWGQGTLVTVSS

FIG. 28C

>B4-15-1-VH (SEQ ID NO: 106)

GAGCAGTCGTTGGAGGAGTCCGGGGGTCTGGAGGAGTCCGGGGGTCGCCTGGTCACGCCTGGGACACCCCT
GACACTCACCTGCACAGCCTCTGGATTCACCATCAATAGCGCCCACATGTCTTGGGTCCGCCAGGCTCCAGGG
AAGGGGCTGGAATGGATCGGATTCAGTACTACTGGTGGTCCCTCATATTACGCGAACTGGGCAAAAGGCCGA
TTCACCATCTCCAGAACCTCGACCACGGTGGATCTGGAGATCACCAGTCCGACAATCGAGGACACGGCCACCT
ATTTCTGTGCCAGAGATGGTCCTGGTAATAATATTGATATGGACTTGTGGGGCCAAGGCACCCTGGTCACCAT
CACCTCA

>B4-15-2-VH (SEQ ID NO: 113)

CAGTCGGTGGAGGAGTCCGGGGGTCGCCTGGTCACGCCTGGGACACCCCTGACACTCACCTGCACAGTCTCT
GGAATCGACCTCACTAACTATGCAATAAACTGGGTCCGCCAGGCTCCAGGGGAGGGGCTGGAATACATCGGA
ACCATTACTGGTAGTAGTAACACATTCTACGCGAGCTGGGCGAAAGGCCGATTCACCATCTCCAAAACCTCGA
CCACGGTGGATCTGAAAATCACCAGTCCGACAACTGAGGACACGGGCACCTATTTCTGTGCCAGTAATCCTGA
TAGTCACAACGCTAATGGCGTGTGGGGCCAAGGCACCCTGGTCACCGTCTCCTCA

>B4-116-1-VH (SEQ ID NO: 120)

GAGCAGTCGGTGGAGGAGTCCGGGGGAGACCTGGTCAAGCCTGGGGCATCCCTGACACTCACCTGCGCAGC
CTCTGGATTCTCCTTCAGTAGCACCTACTGCATGTGCTGGGTCCGCCAGGCTCCAGGGAAGGGCCTGGAGTGG
ATCGCATGCATTCATGGTGTAAGTACTAATAATAGATGGTACGCGAGCTGGCCGAAAGGCCGATTCACCATCT
CCAAAACCTCGTCGACCACGGTGACTCTGCAAATGACCAGTCTGACAGCCGCGGACACGGCCACCTACTTCTG
TGCGAGAAGTGACACTGACTATGAGTGGGGTCTTTCCTTGTGGGGCCCAGGCACCCTGGTCACCATCTCTTCA

>B4-116-2-VH (SEQ ID NO: 127)

GAGCAGTCGGTGGAGGAGTCCGGGGGAGACCTGGTCAAGCCTGGGGCATCCCTGACACTCACCTGCGCAGC
CTCTGGATTCTCCTTCAGTAGCACCTACTGCATGTGCTGGGTCCGCCAGGCTCCAGGGAAGGGCCTGGAGTGG
ATCGCATGCATTCATGGTGTAAGTACTAATAATAGATGGTACGCGAGCTGGCCGAAAGGCCGATTCACCATCT
CCAAAACCTCGTCGACCACGGTGACTCTGCAAATGACCAGTCTGACAGCCGCGGACACGGCCACCTACTTCTG
TGCGAGAAGTGACACTGACTATGAGTGGGGTCTTTCCTTGTGGGGCCCAGGCACCCTGGTCACCATCTCTTCA

>B4-116-3-VH (SEQ ID NO: 134)

CAGTCGGTGAAGGAGTCCGGGGGTCGCCTGGTCACGCCTGGGACACCCCTGACACTCACCTGCACCGTCTCT
GGATTCTCCCTCAGTAACAATGGAATGAGCTGGGTCCGCCAGGCTCCAGGGAAGGGGCTGGAGTGGATCGG
AATCATTTATGTTGGGAGTGGTACCACAGACTACGCGACCTGGGCGAAAGGCCGATTCACCATCTCCAGAACC
TCGACCACGGTGGATCTGAAAATGACCAGTCTGACAACCGAGGACACGGCCACCTATTTATGTGCCAGAGGTT
TTGGTGTTGGGGATTGGCAAGAATGGTTTTTTGATCTCTGGGGCCCAGGCACCCTGGTCACCATCTCTTCA

FIG. 29A

>B4-116-4-VH (SEQ ID NO: 141)

CAGTCGTTGGAGGAGTCCGGGGGTCGCCTGGTCACGCCTGGGACACCCCTGACACTCACCTGCACCGTCTCTG
GATTCTCCCTCAGTAACAATGGAATGAGCTGGGTCCGCCAGGCTCCAGGGAAGGGGCTGGAGTGGATCGGA
ATCATTTATGTTGGGAGTGGTACCACAGACTACGCGAGCTGGCCGAAAGGCCGATTCACCATCTCCAGAACCT
CGACCACGGTGGATCTGAAAATGACCAGTCTGACAACCGAGGACACGGCCACCTATTTATGTGCCAGAGGTTT
TGGTGTTGGGGATTGGCAAGAATGGTTTTTTGATCTCTGGGGCCCAGGCACCCTGGTCACCGTCTCTTCT

>B4-55-1-VH (SEQ ID NO: 148)

AGCAGTTCGGTGGAGGAGTCCGGGGGTCGCCTGGTCACGCCTGGGACACCCCTGACACTCACCTGCACAGTC
TCTGGATTCTCCCTCAGTAGCTATGCAATGGCCTGGGTCCGCCAGGCTCCAGGGAAGGGGCTGGAATGGATC
GGAATCATTGGTACTGGTACCACCACATACTACGCGACCTGGGTGAATGGTCGATTCACCATCTCCAAAACCT
CGACCACGGTGGACCTGAAAATGACCAGTCTGACAACCGAGGACACGGCCACTTATTTCTGTGTCAGAAATG
ATGTTTATTGGGCGTTTAATTTGTGGGGCCAAGGCACCCTGGTCACCGTCTCTTCA

>B4-55-2-VH (SEQ ID NO: 155)

AGCAGTTCGGTGGAGGAGTCCGGGGGTCGCCTGGTCACGCCTGGGACACCCCTGACACTCACCTGCACAGTC
TCTGGATTCTCCCTCAGTAGCTATGCAATGGCCTGGGTCCGCCAGGCTCCAGGGAAGGGGCTGGAATGGATC
GGAATCATTGGTACTGGTACCACCACATACTACGCGACCTGGGTGAATGGTCGATTCACCATCTCCAAAACCT
CGACCACGGTGGACCTGAAAATGACCAGTCTGACAACCGAGGACACGGCCACTTATTTCTGTGTCAGAAATG
ATGTTTATTGGGCGTTTAATTTGTGGGGCCAAGGCACCCTGGTCACCGTCTCTTCA

>B4-19-VH (SEQ ID NO: 162)

GAGCAGTCGGTGGAGGAGTCCGGAGGAGGCCTGGTAACGCCTGGAGGAACCCTGACACTCACCTGCACAGC
CTCTGGATTCTCCATCAGTACCTATGCAATGATCTGGGTCCGCCAGGCTCCAGGGGAGGGGCTGGAATACATC
GGATGCATTGGTACTGGTGGTAGCGCATTCTACGCGATCTGGGCAAAAGGCCGATTCACCATCTCCAGAACCT
CGACCACGGTGGATCTGAAGATGACCAGTCTGACAACCGAGGACACGGCCACATATTTCTGTGCCAGAAATG
ATATTTATTGGGCCTTTGGCTTATGGGGCCAAGGCACGCTGGTCACCGTCTCCTCA

>B4-49-VH (SEQ ID NO: 169)

GAGCAGTCGTTGGAGGAGTCCGGGGGAGACCTGGTCAAGCCTGGGGCATCCCTGACACTCACCTGCACAGCC
TCTGGATTCGACTTTAGTAGTAGTGGTTGGATATGTTGGGTCCGCCAGGCTCCAGGGAAGGGACTGGAGTTG
ATCGCATGCATTTATAGTGGTCGCAGTGGTAGCACTTACTACGCGAGCTGGGCGAAAGGCCGAGTCACCATCT
CCAAAACCTCGTCGACCACGGTGACTCTGCAGATGACCAGTCTGACAGCCGCGGACACGGCCACCTATTTCTG
TGCGAGAGCCCTCTATGTTGATTATGTTGATTATGATTATATAGATTTGTGGGGCCCAGGCACCCTGGTCACCG
TCTCCTCA

FIG. 29B

>B4-72-1-VH (SEQ ID NO: 176)

GAGCAGTCGGTGGAGGAGTCCGGGGGTCGCCTGGTCACGCCTGGGACACCCCTGACACTCACCTGCACAGCC
TCTGGATTCTCCCTCAGTAGCTACTACATGAGCTGGGTCCGCCAGGCTCCAGGGAGGGGACTGGAATACATCG
GAGTCATTAATACTGGTGGTAGCGCAGTCTACGCGACCTGGACAAAAGGCCGATTCACCATCTCCAGAACCTC
GACCACGGTGGATCTGAAAATGACCGGTCTGACAACCGAGGACACGGCCACCTATTTCTGTGCCAGAGGATG
GAGTAGGGGTGACTTGTGGGGCCAAGGCACCCTGGTCACCATCTCCTCA

>B4-72-2-VH (SEQ ID NO: 183)

GAGCAGTCGGTGGAGGAGTCCGGGGGTCGCCTGGTCACGCCTGGGACACCCCTGACACTCACCTGCACAGCC
TCTGGATTCTCCCTCAGTAGCTACTACATGAGCTGGGTCCGCCAGGCTCCAGGGAGGGGACTGGAATACATCG
GAGTCATTAATACTGGTGGTAGCGCAGTCTACGCGACCTGGACAAAAGGCCGATTCACCATCTCCAGAACCTC
GACCACGGTGGATCTGAAAATGACCGGTCTGACAACCGAGGACACGGCCACCTATTTCTGTGCCAGAGGATG
GAGTAGGGGTGACTTGTGGGGCCAAGGCACCCTGGTCACCATCTCCTCA

>B4-86-VH (SEQ ID NO: 190)

GAGCAGTCGGTGGAGTCCGGGGGAGACCTGGTCAAGCCTGAGGGATCCCTGACACTCACCTGCACAGTCTCT
GGATTCTCCTTCAGTAGCAGCTACTGGATATGCTGGGTCCGCCAGGCTCCAGGGAAGGGGCTGGAATGGATC
GGATGCATTGGTACTGGTAGTGGTAGCACTTACTACGGGAGCTGGGCGAAAGGCCGATTCACCATCTCCAAA
ACCTCGTCGACCACGGTGACTCTGCAAATGACCAGTCTGACAGCCGCGGACACGGCCACCTATTTCTGTGTGA
GAGGGGCTGGTTATAGTTCTTATAGGTTGTGGGGCCCAGGCACCCTGGTCACCATCTCCTCA

>B4-87-VH (SEQ ID NO: 197)

CAGTCGGTGAAGGAGTCCGGGGGAGACCTGGTCAAGCCTGGGGCATCCCTGACACTCACCTGCACAGCCTCT
GGATTCTCCTTCATTAGCACCTACTGGATATGCTGGGTCCGCCAGGCTCCAGGGAAGGGGCTGGAGTTGATC
GCATGCATTTATACTGGTGGTAGTGGTAGCACTTACTACGCGAGCTGGGCGAAAGGCCGATTCACCATCTCCA
AAACCTCGTCGACCACGGTGACTCTGCAACTGAACAGTCTGACAGCCGCGGACACGGCCACCTATTTCTGTGC
GAGAGCCCTCTATGTTGATTATGTTGATTATGATTATATAGATTTGTGGGGCCCAGGCACCCTGGTCACCGTCT
CCTCA

>B4-193-VH (SEQ ID NO: 204)

GAGCAGTCGGTGGAGGAGTCCGGGGGAGACCTGGTCAAGCCTGGGACATCCCTGACACTCACTTGTAAAATG
TCTGGATTCTCCCTCAGTAGCAGCTATTGGATATGCTGGGTCCGCCAGGCTCCAGGGAAGGGACTGGAGTGG
ATCGGATGCATCGATAGTGGTAGTGTTGGTATCACTTACTACGCGACCTGGGCGAAAGGCCGATTCACCATCT
CCAGAAGCACCAGCCTAAACACGGTGACTCTGCAAATGACCAGTCTGACAGGCGCGGACACGGCCATGTATT
TCTCTGTGAGGCATGGTGATAATTGGGCTTTGGATTTGTGGGGCCCAGGCACCCTGGTCACCATCTCCTCA

FIG. 29C

>B4-15-1-VK (SEQ ID NO: 5)

ELDLTQTPASVSEPVGGTVTIKCQASQNRGGSIAWYQQKPGQPPKLLIYSASTLASGVPSRFSGSGYGTEFTLTISGV
QCADAGTYYCQSTIYSISDIGAFGGGTEVVVK

>B4-15-2-VK (SEQ ID NO: 12)

ELVMTQTPASVSEPVEGTVTIKCQASQSVYDNNLAWYQQKPGQPPKLLIYSASTLASGVPSRFSGSGYGTEFTLTIS
GVECADAATYYCQSYGITNKNNYNSFGGGTEVVVK

>B4-116-1-VK (SEQ ID NO: 19)

ELDLTQTPASVSEPVGGTVTIKCQASESIGSRLAWYQQKPGQRPKLLIYKASTLASGVPSRFSGSGSGTEFTLTVSDLE
CADVAAYYCQCAGQSSTWAFGGGTEVEIK

>B4-116-2-VK (SEQ ID NO: 26)

ELVMTQTPASVEAVVGGTVTIKCQASESIGSRLAWYQQKPGQRPKLLIYKASTLASGVPSRFSGSGSGTEFTLTVSDL
ECADVAAYYCQCAGQSSTWAFGGGTEVVVK

>B4-116-3-VK (SEQ ID NO: 33)

ELVMTQTPASVSEPVGGTVTIKCQASESISNYLSWYQQKPGQPPKLLIYKASTLASGVSSRFKGSGSGTEFTLTISDLE
CADAATYYCQAYWGTSTMAFGGGTEVEIN

>B4-116-4-VK (SEQ ID NO: 40)

ELVMTQTPASVSEPVGGTVTIKCQASESISNYLSWYQQKPGQPPKLLIYKASTLASGVSSRFKGSGSGTEFTLTISDLE
CADAATYYCQAYWGTSTMAFGGGTEVEIN

>B4-55-1-VK (SEQ ID NO: 47)

ELVMTQTPAPVSAAVGGTVTINCQASQSVVNNNALSWYQQKPGQPPKLLIYKASTLASGVPSRFKGSGSGAQFTL
TISGVQCDDAATYYCQGGYYIGISDYPFGGGTEVVVK

>B4-55-2-VK (SEQ ID NO: 54)

ELDLTQTPSSVSAAVGGTVSISCQSSQSVVNNNALSWYQQKPGQPPKLLIYKASTLASGVPSRFKGSGSGAQFTLTI
SGVQCDDAATYYCQGGYYIGISDYPFGGGTEVEIK

>B4-19-VK (SEQ ID NO: 61)

ELDLTQTPASVSEPVGGTVTINCQASEGIRNWLAWYQQKPGQPPKLLIYGASTLESGVPSRFKGSGSGTEFTLTIRG
VQCDDAATYYCQGGVYSSSIYGYPFGGGTELEIK

FIG. 30A

>B4-49-VK (SEQ ID NO: 68)

ELDLTQTPASVEAAVGGTVTIKCQASQSTGIRLAWYQQKPGQPPKLLMYATSNLASGVSSRFKGSGSGTEFTLTISD
LECADAATYYCQYSYYGSSYVFDFGGGTEVEIK

>B4-72-1-VK (SEQ ID NO: 75)

ELDLTQTPASVSEPVGGTVTIKCQASESVDNWLAWYQQKPGQPPKLLIYDASKLASGVPDRFSGSGSGTQFTLTISG
VQCDDAATYYCLGVFHDGINNAFGGGTEVEIK

>B4-72-2-VK (SEQ ID NO: 82)

ELDMTQTPSPVSAAVGGTVTIKCQSSQNVYDDDTLSWYQQKPGQPPKLLIYDASKLASGVPDRFSGSGSGTQFTLT
ISGVQCDDAATYYCLGVFHDGINNAFGGGTEVEIK

>B4-86-VK (SEQ ID NO: 89)

ELDMTQTPASVSEPVGGTVTIKCQASESVSNWLAWYQQKPGQRPKLLIYGASTLESGVPSRFSGSGSGTEFTLTISN
LECADAATYYCQQGYDWDNIDNAFGGGTEVVVK

>B4-87-VK (SEQ ID NO: 96)

ELDLTQTPASVEAAVGGTVTIKCQASENIGSRLAWYQQKPGQPPKLLIYAASNLASGVSSRFKGSRSGTQFTLTISDL
ECADAAIYYCQCSYYGSTYVFGFGGGTEVEIK

>B4-193-VK (SEQ ID NO: 103)

ELVLTQTPASVSEPVGGTVTIKCQASQSINSWLAWYQQKPGQPPKLLIYKASTLASGVPSRFSASGSGTEFTLTITGV
QCDDAATYYCQHGYIRGDLDNVFGGGTEVVVK

>h193-VK1 (SEQ ID NO: 232)

DIQMTQSPSTLSASVGDRVTITCQASQSINSWLAWYQQKPGKAPKLLIYKASTLASGVPSRFSGSGSGTEFTLTISSL
QPDDFATYYCQHGYIRGDLDNVFGGGTKVEIK

>h193-VK2 (SEQ ID NO: 235)

DLVMTQSPSTLSASVGDRVTITCQASQSINSWLAWYQQKPGKPPKLLIYKASTLASGVSSRFSGSGSGTEFTLTISSL
QPDDVATYYCQHGYIRGDLDNVFGGGTKVEIK

>h193-VK3 (SEQ ID NO: 236)

DIQMTQSPSTLSASVGDRVTITCRASQSINSWLAWYQQKPGKAPKLLIYKASTLASGVPSRFSGSGSGTEFTLTISSL
QPDDFATYYCQHGYIRGDLDNVFGGGTKVEIK

FIG. 30B

>h193-VK4 (SEQ ID NO: 237)

DIQMTQSPSTLSASVGDRVTITCRASQSINSWLAWYQQKPGKAPKLLIYKASTLASGVPSRFSGSGSGTEFTLTISSL
QPDDAATYYCQHGYIRGDLDNVFGGGTKVEIK

FIG. 30C

>B4-15-1-VK (SEQ ID NO: 110)

GAGCTCGATCTGACCCAGACACCAGCCTCCGTGTCTGAACCTGTGGGAGGCACAGTCACCATCAAGTGCCAG
GCCAGTCAGAATAGGGGCGGTAGCATAGCCTGGTATCAGCAGAAACCAGGGCAGCCTCCCAAGCTCCTGATC
TATTCTGCATCCACTCTGGCATCTGGGGTCCCATCGCGGTTCAGCGGCAGTGGATATGGGACAGAGTTCACTC
TCACCATCAGCGGCGTGCAGTGTGCCGATGCTGGCACTTACTACTGCCAATCTACTATTTATAGTATAAGTGAT
ATTGGGGCTTTCGGCGGAGGGACCGAGGTGGTGGTCAAA

>B4-15-2-VK (SEQ ID NO: 117)

GAGCTCGTGATGACCCAGACACCAGCCTCCGTGTCTGAACCTGTGGAAGGCACAGTCACCATCAAGTGTCAG
GCCAGTCAGAGTGTTTATGATAACAACTTAGCCTGGTATCAGCAGAAACCAGGGCAGCCTCCCAAGCTCCTGA
TCTATTCTGCATCCACTCTGGCATCTGGGGTCCCATCGCGGTTCAGCGGCAGTGGATATGGGACAGAGTTCAC
TCTCACCATCAGCGGCGTGGAGTGTGCCGATGCTGCCACTTACTATTGTCAAAGCTATGGTATTACTAATAAGA
ATAATTATAATAGTTTCGGCGGAGGGACCGAGGTGGTGGTCAAA

>B4-116-1-VK (SEQ ID NO: 124)

GAGCTCGATCTGACCCAGACACCAGCCTCCGTGTCTGAGCCTGTGGGAGGCACAGTCACCATCAAGTGCCAG
GCCAGTGAGAGCATTGGTAGTAGATTAGCCTGGTATCAACAGAAACCAGGGCAGCGTCCCAAGCTCCTGATC
TACAAGGCATCCACTCTGGCATCTGGGGTCCCATCGCGGTTCAGTGGCAGTGGATCTGGGACAGAGTTCACTC
TCACCGTCAGCGACCTGGAGTGTGCCGATGTTGCCGCTTACTATTGTCAATGCGCTGGTCAGAGTAGTACTTG
GGCTTTCGGCGGAGGGACCGAGGTGGAAATCAAA

>B4-116-2-VK (SEQ ID NO: 131)

GAGCTCGTGATGACCCAGACACCAGCCTCCGTGGAGGCAGTTGTGGGAGGCACAGTCACCATCAAGTGCCAG
GCCAGTGAGAGCATTGGTAGTAGATTAGCCTGGTATCAACAGAAACCAGGGCAGCGTCCCAAGCTCCTGATC
TACAAGGCATCCACTCTGGCATCTGGGGTCCCATCGCGGTTCAGTGGCAGTGGATCTGGGACAGAGTTCACTC
TCACCGTCAGCGACCTGGAGTGTGCCGATGTTGCCGCTTACTATTGTCAATGCGCTGGTCAGAGTAGTACTTG
GGCTTTCGGCGGAGGGACCGAGGTGGTGGTCAAA

>B4-116-3-VK (SEQ ID NO: 138)

GAGCTCGTGATGACCCAGACACCAGCCTCCGTGTCTGAGCCTGTGGGAGGCACAGTCACCATCAAGTGCCAG
GCCAGTGAAAGCATTAGCAACTACTTATCCTGGTATCAGCAGAAACCAGGGCAGCCTCCCAAGCTCCTGATCT
ATAAGGCATCCACTCTGGCATCTGGGGTCTCATCGCGGTTCAAAGGCAGTGGATCTGGGACAGAATTCACTCT
CACCATCAGCGACCTGGAGTGTGCCGATGCTGCCACTTACTACTGTCAAGCCTATTGGGGTACTTCTACTATGG
CTTTCGGCGGAGGGACCGAGGTGGAAATCAAC

FIG. 31A

>B4-116-4-VK (SEQ ID NO: 145)

GAGCTCGTGATGACCCAGACACCAGCCTCCGTGTCTGAGCCTGTGGGAGGCACAGTCACCATCAAGTGCCAG
GCCAGTGAAAGCATTAGCAACTACTTATCCTGGTATCAGCAGAAACCAGGGCAGCCTCCCAAGCTCCTGATCT
ATAAGGCATCCACTCTGGCATCTGGGGTCTCATCGCGGTTCAAAGGCAGTGGATCTGGGACAGAATTCACTCT
CACCATCAGCGACCTGGAGTGTGCCGATGCTGCCACTTACTACTGTCAAGCCTATTGGGGTACTTCTACTATGG
CTTTCGGCGGAGGGACCGAGGTGGAAATCAAC

>B4-55-1-VK (SEQ ID NO: 152)

GAGCTCGTGATGACCCAGACACCAGCCCCGTGTCTGCAGCTGTGGGAGGCACAGTCACCATCAACTGCCAG
GCCAGTCAGAGTGTTGTTAATAATAATGCCTTATCTTGGTATCAGCAGAAACCAGGGCAGCCTCCCAAGCTCC
TGATCTACAAGGCTTCCACTCTGGCATCTGGGGTCCCATCGCGGTTCAAAGGCAGTGGATCTGGGGCACAGTT
CACTCTCACCATCAGCGGCGTGCAGTGTGACGATGCTGCCACTTATTATTGTCAAGGCGGTTATTATATTGGTA
TTAGTGACTATCCTTTCGGCGGCGGGACCGAGGTGGTGGTCAAA

>B4-55-2-VK (SEQ ID NO: 159)

GAGCTCGATCTGACCCAGACACCATCCTCCGTGTCTGCAGCTGTGGGAGGCACAGTCAGCATCAGTTGCCAGT
CCAGTCAGAGTGTTGTTAATAATAATGCCTTATCTTGGTATCAGCAGAAACCAGGGCAGCCTCCCAAGCTCCT
GATCTACAAGGCTTCCACTCTGGCATCTGGGGTCCCATCGCGGTTCAAAGGCAGTGGATCTGGGGCACAGTTC
ACTCTCACCATCAGCGGCGTGCAGTGTGACGATGCTGCCACTTATTATTGTCAAGGCGGTTATTATATTGGTAT
TAGTGACTATCCTTTCGGCGGCGGGACCGAGGTGGAAATCAAA

>B4-19-VK (SEQ ID NO: 166)

GAGCTCGATCTGACCCAGACACCAGCCTCCGTGTCTGAACCTGTGGGAGGCACAGTCACCATCAACTGCCAGG
CCAGTGAGGGCATTAGGAACTGGTTAGCCTGGTATCAGCAGAAACCAGGGCAGCCTCCCAAGCTCCTGATCT
ATGGTGCATCCACTCTGGAATCTGGGGTCCCATCGCGGTTCAAAGGCAGTGGATCTGGGACAGAGTTCACTCT
CACCATCAGAGGTGTGCAGTGTGACGATGCTGCCACTTACTACTGTCAAGGCGGTGTTTATAGTAGTAGTATT
TATGGTTATCCTTTCGGCGGAGGGACCGAGCTGGAAATCAAA

>B4-49-VK (SEQ ID NO: 173)

GAGCTCGATCTGACCCAGACTCCAGCCTCCGTGGAGGCAGCTGTGGGAGGCACAGTCACCATCAAGTGCCAG
GCCAGTCAGAGCACTGGTATTAGATTAGCCTGGTATCAGCAGAAACCAGGGCAGCCTCCCAAACTCCTGATGT
ATGCTACATCCAATCTGGCATCTGGGGTCTCATCGCGGTTCAAAGGCAGTGGATCTGGGACAGAGTTCACTCT
CACCATCAGCGACCTGGAGTGTGCCGATGCTGCCACTTACTACTGTCAATATAGTTATTATGGTAGTAGTTATG
TTTTTGATTTCGGCGGAGGGACCGAGGTGGAAATCAAA

FIG. 31B

>B4-72-1-VK (SEQ ID NO: 180)

GAGCTCGATCTGACCCAGACACCAGCCTCCGTGTCTGAACCTGTGGGAGGCACAGTCACCATCAAGTGCCAG
GCCAGTGAAAGCGTTGACAACTGGTTAGCCTGGTATCAGCAGAAACCAGGGCAGCCTCCCAAACTCCTGATCT
ACGATGCATCCAAATTGGCATCTGGGGTCCCAGATAGGTTCAGCGGCAGTGGATCTGGGACACAGTTCACTCT
CACCATCAGCGGCGTGCAGTGTGACGATGCTGCCACTTACTACTGTCTAGGCGTTTTTCATGATGGTATTAATA
ATGCTTTCGGCGGAGGGACCGAGGTGGAAATCAAA

>B4-72-2-VK (SEQ ID NO: 187)

GAGCTCGATATGACCCAGACACCATCGCCCGTGTCTGCAGCTGTGGGAGGCACAGTCACCATCAAGTGCCAG
TCCAGTCAGAATGTTTATGATGACGATACTTTATCCTGGTATCAGCAGAAACCAGGGCAGCCTCCCAAACTCCT
GATCTACGATGCATCCAAATTGGCATCTGGGGTCCCAGATAGGTTCAGCGGCAGTGGATCTGGGACACAGTT
CACTCTCACCATCAGCGGCGTGCAGTGTGACGATGCTGCCACTTACTACTGTCTAGGCGTTTTTCATGATGGTA
TTAATAATGCTTTCGGCGGAGGGACCGAGGTGGAAATCAAA

>B4-86-VK (SEQ ID NO: 194)

GAGCTCGATATGACCCAGACACCAGCCTCCGTGTCTGAACCTGTGGGAGGCACAGTCACCATCAAGTGCCAG
GCCAGTGAAAGCGTTAGCAACTGGTTAGCCTGGTATCAGCAGAAACCAGGGCAGCGTCCCAAGCTCCTGATC
TATGGTGCATCCACTCTGGAATCTGGGGTCCCATCGCGGTTCAGCGGCAGTGGATCTGGGACAGAGTTCACTC
TCACCATCAGCAACCTGGAGTGTGCCGATGCTGCCACTTACTACTGTCAACAGGGTTATGATTGGGATAATAT
CGATAATGCTTTCGGCGGAGGGACCGAGGTGGTGGTCAAA

>B4-87-VK (SEQ ID NO: 201)

GAGCTCGATCTGACCCAGACACCAGCCTCCGTGGAGGCAGCTGTGGGAGGCACAGTCACCATCAAGTGCCAG
GCCAGTGAGAACATTGGTAGTAGATTAGCCTGGTATCAGCAGAAACCAGGGCAGCCTCCCAAGCTCCTGATCT
ATGCTGCATCCAATCTGGCATCTGGGGTCTCATCGCGGTTCAAAGGCAGTAGATCTGGGACACAGTTCACTCT
CACCATCAGCGACCTAGAGTGTGCCGATGCTGCCATTTACTACTGTCAATGTAGTTATTATGGTAGTACTTATG
TTTTTGGTTTCGGCGGAGGGACCGAGGTGGAAATCAAA

>B4-193-VK (SEQ ID NO: 208)

GAGCTCGTGCTGACCCAGACACCAGCCTCCGTGTCTGAGCCTGTGGGAGGCACAGTCACCATCAAGTGCCAG
GCCAGTCAGAGTATCAACAGTTGGTTAGCCTGGTATCAGCAGAAACCAGGACAGCCTCCCAAGCTCCTGATCT
ACAAGGCGTCCACTCTGGCATCTGGGGTCCCATCGCGGTTCAGTGCCAGTGGATCTGGGACAGAGTTCACTCT
CACCATCACCGGCGTGCAGTGCGACGATGCTGCCACTTACTACTGTCAACATGGCTATATTCGTGGTGATCTTG
ATAATGTTTTCGGCGGAGGGACCGAGGTGGTGGTCAAA

FIG. 31C

SEQUENCE LISTING

<160> NUMBER OF SEQ ID NOS: 238

<210> SEQ ID NO 1
<211> LENGTH: 123
<212> TYPE: PRT
<213> ORGANISM: Artificial sequence
<220> FEATURE:
<223> OTHER INFORMATION: Synthetic amino acid

<400> SEQUENCE: 1

```
Glu Gln Ser Leu Glu Glu Ser Gly Gly Leu Glu Glu Ser Gly Gly Arg
1               5                   10                  15

Leu Val Thr Pro Gly Thr Pro Leu Thr Leu Thr Cys Thr Ala Ser Gly
            20                  25                  30

Phe Thr Ile Asn Ser Ala His Met Ser Trp Val Arg Gln Ala Pro Gly
        35                  40                  45

Lys Gly Leu Glu Trp Ile Gly Phe Ser Thr Thr Gly Gly Pro Ser Tyr
    50                  55                  60
```

```
Tyr Ala Asn Trp Ala Lys Gly Arg Phe Thr Ile Ser Arg Thr Ser Thr
 65                  70                  75                  80

Thr Val Asp Leu Glu Ile Thr Ser Pro Thr Ile Glu Asp Ala Thr
             85                  90                  95

Tyr Phe Cys Ala Arg Asp Gly Pro Gly Asn Asn Ile Asp Met Asp Leu
            100                 105                 110

Trp Gly Gln Gly Thr Leu Val Thr Ile Thr Ser
        115                 120

<210> SEQ ID NO 2
<211> LENGTH: 8
<212> TYPE: PRT
<213> ORGANISM: Artificial sequence
<220> FEATURE:
<223> OTHER INFORMATION: Synthetic amino acid

<400> SEQUENCE: 2

Gly Phe Thr Ile Asn Ser Ala His
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic amino acid

<400> SEQUENCE: 3

Ser Thr Thr Gly Gly Pro Ser
1               5

<210> SEQ ID NO 4
<211> LENGTH: 13
<212> TYPE: PRT
<213> ORGANISM: Artificial sequence
<220> FEATURE:
<223> OTHER INFORMATION: Synthetic amino acid

<400> SEQUENCE: 4

Ala Arg Asp Gly Pro Gly Asn Asn Ile Asp Met Asp Leu
1               5                   10

<210> SEQ ID NO 5
<211> LENGTH: 110
<212> TYPE: PRT
<213> ORGANISM: Artificial sequence
<220> FEATURE:
<223> OTHER INFORMATION: Synthetic amino acid

<400> SEQUENCE: 5

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Asn Arg Gly Gly Ser
            20                  25                  30

Ile Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Tyr Gly Thr Glu Phe Thr Leu Thr Ile Ser Gly Val Gln Cys
65                  70                  75                  80

Ala Asp Ala Gly Thr Tyr Tyr Cys Gln Ser Thr Ile Tyr Ser Ile Ser
                85                  90                  95
```

Asp Ile Gly Ala Phe Gly Gly Gly Thr Glu Val Val Val Lys
            100                 105                 110

<210> SEQ ID NO 6
<211> LENGTH: 6
<212> TYPE: PRT
<213> ORGANISM: Artificial sequence
<220> FEATURE:
<223> OTHER INFORMATION: Synthetic amino acid

<400> SEQUENCE: 6

Gln Asn Arg Gly Gly Ser
1               5

<210> SEQ ID NO 7
<211> LENGTH: 12
<212> TYPE: PRT
<213> ORGANISM: Artificial sequence
<220> FEATURE:
<223> OTHER INFORMATION: Synthetic amino acid

<400> SEQUENCE: 7

Gln Ser Thr Ile Tyr Ser Ile Ser Asp Ile Gly Ala
1               5                   10

<210> SEQ ID NO 8
<211> LENGTH: 115
<212> TYPE: PRT
<213> ORGANISM: Artificial sequence
<220> FEATURE:
<223> OTHER INFORMATION: Synthetic amino acid

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Thr Asn Tyr Ala
            20                  25                  30

Ile Asn Trp Val Arg Gln Ala Pro Gly Glu Gly Leu Glu Tyr Ile Gly
        35                  40                  45

Thr Ile Thr Gly Ser Ser Asn Thr Phe Tyr Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Gly Thr Tyr Phe Cys Ala Ser Asn Pro
                85                  90                  95

Asp Ser His Asn Ala Asn Gly Val Trp Gly Gln Gly Thr Leu Val Thr
            100                 105                 110

Val Ser Ser
        115

<210> SEQ ID NO 9
<211> LENGTH: 8
<212> TYPE: PRT
<213> ORGANISM: Artificial sequence
<220> FEATURE:
<223> OTHER INFORMATION: Synthetic amino acid

<400> SEQUENCE: 9

Gly Ile Asp Leu Thr Asn Tyr Ala
1               5

<210> SEQ ID NO 10

```
<211> LENGTH: 7
<212> TYPE: PRT
<213> ORGANISM: Artificial sequence
<220> FEATURE:
<223> OTHER INFORMATION: Synthetic amino acid

<400> SEQUENCE: 10

Ile Thr Gly Ser Ser Asn Thr
1               5

<210> SEQ ID NO 11
<211> LENGTH: 12
<212> TYPE: PRT
<213> ORGANISM: Artificial sequence
<220> FEATURE:
<223> OTHER INFORMATION: Synthetic amino acid

<400> SEQUENCE: 11

Ala Ser Asn Pro Asp Ser His Asn Ala Asn Gly Val
1               5                   10

<210> SEQ ID NO 12
<211> LENGTH: 112
<212> TYPE: PRT
<213> ORGANISM: Artificial sequence
<220> FEATURE:
<223> OTHER INFORMATION: Synthetic amino acid

<400> SEQUENCE: 12

Glu Leu Val Met Thr Gln Thr Pro Ala Ser Val Ser Glu Pro Val Glu
1               5                   10                  15

Gly Thr Val Thr Ile Lys Cys Gln Ala Ser Gln Ser Val Tyr Asp Asn
            20                  25                  30

Asn Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Tyr Gly Thr Glu Phe Thr Leu Thr Ile Ser Gly Val Glu
65                  70                  75                  80

Cys Ala Asp Ala Ala Thr Tyr Tyr Cys Gln Ser Tyr Gly Ile Thr Asn
                85                  90                  95

Lys Asn Asn Tyr Asn Ser Phe Gly Gly Gly Thr Glu Val Val Val Lys
            100                 105                 110

<210> SEQ ID NO 13
<211> LENGTH: 7
<212> TYPE: PRT
<213> ORGANISM: Artificial sequence
<220> FEATURE:
<223> OTHER INFORMATION: Synthetic amino acid

<400> SEQUENCE: 13

Gln Ser Val Tyr Asp Asn Asn
1               5

<210> SEQ ID NO 14
<211> LENGTH: 13
<212> TYPE: PRT
<213> ORGANISM: Artificial sequence
<220> FEATURE:
<223> OTHER INFORMATION: Synthetic amino acid

<400> SEQUENCE: 14

Gln Ser Tyr Gly Ile Thr Asn Lys Asn Asn Tyr Asn Ser
```

<210> SEQ ID NO 15
<211> LENGTH: 121
<212> TYPE: PRT
<213> ORGANISM: Artificial sequence
<220> FEATURE:
<223> OTHER INFORMATION: Synthetic amino acid

<400> SEQUENCE: 15

Glu Gln Ser Val Glu Glu Ser Gly Gly Asp Leu Val Lys Pro Gly Ala
1               5                   10                  15
Ser Leu Thr Leu Thr Cys Ala Ala Ser Gly Phe Ser Phe Ser Ser Thr
            20                  25                  30
Tyr Cys Met Cys Trp Val Arg Gln Ala Pro Gly Lys Gly Leu Glu Trp
        35                  40                  45
Ile Ala Cys Ile His Gly Val Ser Thr Asn Asn Arg Trp Tyr Ala Ser
    50                  55                  60
Trp Pro Lys Gly Arg Phe Thr Ile Ser Lys Thr Ser Thr Thr Val
65                  70                  75                  80
Thr Leu Gln Met Thr Ser Leu Thr Ala Ala Asp Thr Ala Thr Tyr Phe
                85                  90                  95
Cys Ala Arg Ser Asp Thr Asp Tyr Glu Trp Gly Leu Ser Leu Trp Gly
            100                 105                 110
Pro Gly Thr Leu Val Thr Ile Ser Ser
        115                 120

<210> SEQ ID NO 16
<211> LENGTH: 9
<212> TYPE: PRT
<213> ORGANISM: Artificial sequence
<220> FEATURE:
<223> OTHER INFORMATION: Synthetic amino acid

<400> SEQUENCE: 16

Gly Phe Ser Phe Ser Ser Thr Tyr Cys
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic amino acid

<400> SEQUENCE: 17

Ile His Gly Val Ser Thr Asn Asn Arg
1               5

<210> SEQ ID NO 18
<211> LENGTH: 13
<212> TYPE: PRT
<213> ORGANISM: Artificial sequence
<220> FEATURE:
<223> OTHER INFORMATION: Synthetic amino acid

<400> SEQUENCE: 18

Ala Arg Ser Asp Thr Asp Tyr Glu Trp Gly Leu Ser Leu
1               5                   10

<210> SEQ ID NO 19
<211> LENGTH: 108
<212> TYPE: PRT

<213> ORGANISM: Artificial sequence
<220> FEATURE:
<223> OTHER INFORMATION: Synthetic amino acid

<400> SEQUENCE: 19

```
Glu Leu Asp Leu Thr Gln Thr Pro Ala Ser Val Ser Glu Pro Val Gly
1               5                   10                  15

Gly Thr Val Thr Ile Lys Cys Gln Ala Ser Glu Ser Ile Gly Ser Arg
            20                  25                  30

Leu Ala Trp Tyr Gln Gln Lys Pro Gly Gln Arg Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Val Ser Asp Leu Glu Cys
65                  70                  75                  80

Ala Asp Val Ala Ala Tyr Tyr Cys Gln Cys Ala Gly Gln Ser Ser Thr
                85                  90                  95

Trp Ala Phe Gly Gly Gly Thr Glu Val Glu Ile Lys
            100                 105
```

<210> SEQ ID NO 20
<211> LENGTH: 6
<212> TYPE: PRT
<213> ORGANISM: Artificial sequence
<220> FEATURE:
<223> OTHER INFORMATION: Synthetic amino acid

<400> SEQUENCE: 20

```
Glu Ser Ile Gly Ser Arg
1               5
```

<210> SEQ ID NO 21
<211> LENGTH: 10
<212> TYPE: PRT
<213> ORGANISM: Artificial sequence
<220> FEATURE:
<223> OTHER INFORMATION: Synthetic amino acid

<400> SEQUENCE: 21

```
Gln Cys Ala Gly Gln Ser Ser Thr Trp Ala
1               5                   10
```

<210> SEQ ID NO 22
<211> LENGTH: 121
<212> TYPE: PRT
<213> ORGANISM: Artificial sequence
<220> FEATURE:
<223> OTHER INFORMATION: Synthetic amino acid

<400> SEQUENCE: 22

```
Glu Gln Ser Val Glu Glu Ser Gly Gly Asp Leu Val Lys Pro Gly Ala
1               5                   10                  15

Ser Leu Thr Leu Thr Cys Ala Ala Ser Gly Phe Ser Phe Ser Ser Thr
            20                  25                  30

Tyr Cys Met Cys Trp Val Arg Gln Ala Pro Gly Lys Gly Leu Glu Trp
        35                  40                  45

Ile Ala Cys Ile His Gly Val Ser Thr Asn Asn Arg Trp Tyr Ala Ser
    50                  55                  60

Trp Pro Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
```

```
                    85                  90                  95
Cys Ala Arg Ser Asp Thr Asp Tyr Glu Trp Gly Leu Ser Leu Trp Gly
                100                 105                 110

Pro Gly Thr Leu Val Thr Ile Ser Ser
            115                 120
```

<210> SEQ ID NO 23
<211> LENGTH: 9
<212> TYPE: PRT
<213> ORGANISM: Artificial sequence
<220> FEATURE:
<223> OTHER INFORMATION: Synthetic amino acid

<400> SEQUENCE: 23

```
Gly Phe Ser Phe Ser Ser Thr Tyr Cys
1               5
```

<210> SEQ ID NO 24
<211> LENGTH: 9
<212> TYPE: PRT
<213> ORGANISM: Artificial sequence
<220> FEATURE:
<223> OTHER INFORMATION: Synthetic amino acid

<400> SEQUENCE: 24

```
Ile His Gly Val Ser Thr Asn Asn Arg
1               5
```

<210> SEQ ID NO 25
<211> LENGTH: 13
<212> TYPE: PRT
<213> ORGANISM: Artificial sequence
<220> FEATURE:
<223> OTHER INFORMATION: Synthetic amino acid

<400> SEQUENCE: 25

```
Ala Arg Ser Asp Thr Asp Tyr Glu Trp Gly Leu Ser Leu
1               5                   10
```

<210> SEQ ID NO 26
<211> LENGTH: 108
<212> TYPE: PRT
<213> ORGANISM: Artificial sequence
<220> FEATURE:
<223> OTHER INFORMATION: Synthetic amino acid

<400> SEQUENCE: 26

```
Glu Leu Val Met Thr Gln Thr Pro Ala Ser Val Glu Ala Val Val Gly
1               5                   10                  15

Gly Thr Val Thr Ile Lys Cys Gln Ala Ser Glu Ser Ile Gly Ser Arg
            20                  25                  30

Leu Ala Trp Tyr Gln Gln Lys Pro Gly Gln Arg Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Val Ser Asp Leu Glu Cys
65                  70                  75                  80

Ala Asp Val Ala Ala Tyr Tyr Cys Gln Cys Ala Gly Gln Ser Ser Thr
                85                  90                  95

Trp Ala Phe Gly Gly Gly Thr Glu Val Val Val Lys
                100                 105
```

```
<210> SEQ ID NO 27
<211> LENGTH: 6
<212> TYPE: PRT
<213> ORGANISM: Artificial sequence
<220> FEATURE:
<223> OTHER INFORMATION: Synthetic amino acid

<400> SEQUENCE: 27

Glu Ser Ile Gly Ser Arg
1               5

<210> SEQ ID NO 28
<211> LENGTH: 10
<212> TYPE: PRT
<213> ORGANISM: Artificial sequence
<220> FEATURE:
<223> OTHER INFORMATION: Synthetic amino acid

<400> SEQUENCE: 28

Gln Cys Ala Gly Gln Ser Ser Thr Trp Ala
1               5                   10

<210> SEQ ID NO 29
<211> LENGTH: 120
<212> TYPE: PRT
<213> ORGANISM: Artificial sequence
<220> FEATURE:
<223> OTHER INFORMATION: Synthetic amino acid

<400> SEQUENCE: 29

Gln Ser Val Lys Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Gly
            20                  25                  30

Met Ser Trp Val Arg Gln Ala Pro Gly Lys Gly Leu Glu Trp Ile Gly
        35                  40                  45

Ile Ile Tyr Val Gly Ser Gly Thr Thr Asp Tyr Ala Thr Trp Ala Lys
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Leu Cys Ala Arg Gly
                85                  90                  95

Phe Gly Val Gly Asp Trp Gln Glu Trp Phe Pro Asp Leu Trp Gly Pro
            100                 105                 110

Gly Thr Leu Val Thr Ile Ser Ser
        115                 120

<210> SEQ ID NO 30
<211> LENGTH: 8
<212> TYPE: PRT
<213> ORGANISM: Artificial sequence
<220> FEATURE:
<223> OTHER INFORMATION: Synthetic amino acid

<400> SEQUENCE: 30

Gly Phe Ser Leu Ser Asn Asn Gly
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic amino acid
```

-continued

<400> SEQUENCE: 31

Ile Tyr Val Gly Ser Gly Thr Thr
1               5

<210> SEQ ID NO 32
<211> LENGTH: 16
<212> TYPE: PRT
<213> ORGANISM: Artificial sequence
<220> FEATURE:
<223> OTHER INFORMATION: Synthetic amino acid

<400> SEQUENCE: 32

Ala Arg Gly Phe Gly Val Gly Asp Trp Gln Glu Trp Phe Phe Asp Leu
1               5                   10                  15

<210> SEQ ID NO 33
<211> LENGTH: 108
<212> TYPE: PRT
<213> ORGANISM: Artificial sequence
<220> FEATURE:
<223> OTHER INFORMATION: Synthetic amino acid

<400> SEQUENCE: 33

Glu Leu Val Met Thr Gln Thr Pro Ala Ser Val Ser Glu Pro Val Gly
1               5                   10                  15

Gly Thr Val Thr Ile Lys Cys Gln Ala Ser Glu Ser Ile Ser Asn Tyr
            20                  25                  30

Leu Ser Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Tyr Trp Gly Thr Ser Thr
                85                  90                  95

Met Ala Phe Gly Gly Gly Thr Glu Val Glu Ile Asn
            100                 105

<210> SEQ ID NO 34
<211> LENGTH: 6
<212> TYPE: PRT
<213> ORGANISM: Artificial sequence
<220> FEATURE:
<223> OTHER INFORMATION: Synthetic amino acid

<400> SEQUENCE: 34

Glu Ser Ile Ser Asn Tyr
1               5

<210> SEQ ID NO 35
<211> LENGTH: 10
<212> TYPE: PRT
<213> ORGANISM: Artificial sequence
<220> FEATURE:
<223> OTHER INFORMATION: Synthetic amino acid

<400> SEQUENCE: 35

Gln Ala Tyr Trp Gly Thr Ser Thr Met Ala
1               5                   10

<210> SEQ ID NO 36
<211> LENGTH: 120

```
<212> TYPE: PRT
<213> ORGANISM: Artificial sequence
<220> FEATURE:
<223> OTHER INFORMATION: Synthetic amino acid

<400> SEQUENCE: 36

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Gly
            20                  25                  30

Met Ser Trp Val Arg Gln Ala Pro Gly Lys Gly Leu Glu Trp Ile Gly
        35                  40                  45

Ile Ile Tyr Val Gly Ser Gly Thr Thr Asp Tyr Ala Ser Trp Pro Lys
50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Leu Cys Ala Arg Gly
                85                  90                  95

Phe Gly Val Gly Asp Trp Gln Glu Trp Phe Phe Asp Leu Trp Gly Pro
            100                 105                 110

Gly Thr Leu Val Thr Val Ser Ser
        115                 120

<210> SEQ ID NO 37
<211> LENGTH: 8
<212> TYPE: PRT
<213> ORGANISM: Artificial sequence
<220> FEATURE:
<223> OTHER INFORMATION: Synthetic amino acid

<400> SEQUENCE: 37

Gly Phe Ser Leu Ser Asn Asn Gly
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic amino acid

<400> SEQUENCE: 38

Ile Tyr Val Gly Ser Gly Thr Thr
1               5

<210> SEQ ID NO 39
<211> LENGTH: 16
<212> TYPE: PRT
<213> ORGANISM: Artificial sequence
<220> FEATURE:
<223> OTHER INFORMATION: Synthetic amino acid

<400> SEQUENCE: 39

Ala Arg Gly Phe Gly Val Gly Asp Trp Gln Glu Trp Phe Phe Asp Leu
1               5                   10                  15

<210> SEQ ID NO 40
<211> LENGTH: 108
<212> TYPE: PRT
<213> ORGANISM: Artificial sequence
<220> FEATURE:
<223> OTHER INFORMATION: Synthetic amino acid

<400> SEQUENCE: 40
```

```
Glu Leu Val Met Thr Gln Thr Pro Ala Ser Val Ser Glu Pro Val Gly
1               5                   10                  15

Gly Thr Val Thr Ile Lys Cys Gln Ala Ser Glu Ser Ile Ser Asn Tyr
                20                  25                  30

Leu Ser Trp Tyr Gln Gln Lys Pro Gly Gln Pro Pro Lys Leu Leu Ile
            35                  40                  45

Tyr Lys Ala Ser Thr Leu Ala Ser Gly Val Ser Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Tyr Trp Gly Thr Ser Thr
                85                  90                  95

Met Ala Phe Gly Gly Gly Thr Glu Val Glu Ile Asn
            100                 105
```

<210> SEQ ID NO 41
<211> LENGTH: 6
<212> TYPE: PRT
<213> ORGANISM: Artificial sequence
<220> FEATURE:
<223> OTHER INFORMATION: Synthetic amino acid

<400> SEQUENCE: 41

```
Glu Ser Ile Ser Asn Tyr
1               5
```

<210> SEQ ID NO 42
<211> LENGTH: 10
<212> TYPE: PRT
<213> ORGANISM: Artificial sequence
<220> FEATURE:
<223> OTHER INFORMATION: Synthetic amino acid

<400> SEQUENCE: 42

```
Gln Ala Tyr Trp Gly Thr Ser Thr Met Ala
1               5                   10
```

<210> SEQ ID NO 43
<211> LENGTH: 114
<212> TYPE: PRT
<213> ORGANISM: Artificial sequence
<220> FEATURE:
<223> OTHER INFORMATION: Synthetic amino acid

<400> SEQUENCE: 43

```
Ser Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
                20                  25                  30

Met Ala Trp Val Arg Gln Ala Pro Gly Lys Gly Leu Glu Trp Ile Gly
            35                  40                  45

Ile Ile Gly Thr Gly Thr Thr Thr Tyr Tyr Ala Thr Trp Val Asn Gly
50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Val Arg Asn Asp
                85                  90                  95

Val Tyr Trp Ala Phe Asn Leu Trp Gly Gln Gly Thr Leu Val Thr Val
            100                 105                 110
```

Ser Ser

<210> SEQ ID NO 44
<211> LENGTH: 8
<212> TYPE: PRT
<213> ORGANISM: Artificial sequence
<220> FEATURE:
<223> OTHER INFORMATION: Synthetic amino acid

<400> SEQUENCE: 44

Gly Phe Ser Leu Ser Ser Tyr Ala
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic amino acid

<400> SEQUENCE: 45

Ile Gly Thr Gly Thr Thr Thr
1               5

<210> SEQ ID NO 46
<211> LENGTH: 11
<212> TYPE: PRT
<213> ORGANISM: Artificial sequence
<220> FEATURE:
<223> OTHER INFORMATION: Synthetic amino acid

<400> SEQUENCE: 46

Val Arg Asn Asp Val Tyr Trp Ala Phe Asn Leu
1               5                   10

<210> SEQ ID NO 47
<211> LENGTH: 112
<212> TYPE: PRT
<213> ORGANISM: Artificial sequence
<220> FEATURE:
<223> OTHER INFORMATION: Synthetic amino acid

<400> SEQUENCE: 47

Glu Leu Val Met Thr Gln Thr Pro Ala Pro Val Ser Ala Ala Val Gly
1               5                   10                  15

Gly Thr Val Thr Ile Asn Cys Gln Ala Ser Gln Ser Val Val Asn Asn
            20                  25                  30

Asn Ala Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Ala Gln Phe Thr Leu Thr Ile Ser Gly Val
65                  70                  75                  80

Gln Cys Asp Asp Ala Ala Thr Tyr Tyr Cys Gln Gly Gly Tyr Tyr Ile
                85                  90                  95

Gly Ile Ser Asp Tyr Pro Phe Gly Gly Gly Thr Glu Val Val Val Lys
            100                 105                 110

<210> SEQ ID NO 48
<211> LENGTH: 8
<212> TYPE: PRT
<213> ORGANISM: Artificial sequence
<220> FEATURE:
<223> OTHER INFORMATION: Synthetic amino acid

<400> SEQUENCE: 48

Gln Ser Val Val Asn Asn Asn Ala
1               5

<210> SEQ ID NO 49
<211> LENGTH: 12
<212> TYPE: PRT
<213> ORGANISM: Artificial sequence
<220> FEATURE:
<223> OTHER INFORMATION: Synthetic amino acid

<400> SEQUENCE: 49

Gln Gly Gly Tyr Tyr Ile Gly Ile Ser Asp Tyr Pro
1               5                   10

<210> SEQ ID NO 50
<211> LENGTH: 114
<212> TYPE: PRT
<213> ORGANISM: Artificial sequence
<220> FEATURE:
<223> OTHER INFORMATION: Synthetic amino acid

<400> SEQUENCE: 50

Ser Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ala Trp Val Arg Gln Ala Pro Gly Lys Gly Leu Glu Trp Ile Gly
        35                  40                  45

Ile Ile Gly Thr Gly Thr Thr Thr Tyr Tyr Ala Thr Trp Val Asn Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Val Arg Asn Asp
                85                  90                  95

Val Tyr Trp Ala Phe Asn Leu Trp Gly Gln Gly Thr Leu Val Thr Val
            100                 105                 110

Ser Ser

<210> SEQ ID NO 51
<211> LENGTH: 8
<212> TYPE: PRT
<213> ORGANISM: Artificial sequence
<220> FEATURE:
<223> OTHER INFORMATION: Synthetic amino acid

<400> SEQUENCE: 51

Gly Phe Ser Leu Ser Ser Tyr Ala
1               5

<210> SEQ ID NO 52
<211> LENGTH: 7
<212> TYPE: PRT
<213> ORGANISM: Artificial sequence
<220> FEATURE:
<223> OTHER INFORMATION: Synthetic amino acid

<400> SEQUENCE: 52

Ile Gly Thr Gly Thr Thr Thr
1               5

```
<210> SEQ ID NO 53
<211> LENGTH: 11
<212> TYPE: PRT
<213> ORGANISM: Artificial sequence
<220> FEATURE:
<223> OTHER INFORMATION: Synthetic amino acid

<400> SEQUENCE: 53

Val Arg Asn Asp Val Tyr Trp Ala Phe Asn Leu
1               5                   10

<210> SEQ ID NO 54
<211> LENGTH: 112
<212> TYPE: PRT
<213> ORGANISM: Artificial sequence
<220> FEATURE:
<223> OTHER INFORMATION: Synthetic amino acid

<400> SEQUENCE: 54

Glu Leu Asp Leu Thr Gln Thr Pro Ser Ser Val Ser Ala Ala Val Gly
1               5                   10                  15

Gly Thr Val Ser Ile Ser Cys Gln Ser Ser Gln Ser Val Val Asn Asn
            20                  25                  30

Asn Ala Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Ala Gln Phe Thr Leu Thr Ile Ser Gly Val
65              70                  75                  80

Gln Cys Asp Asp Ala Ala Thr Tyr Tyr Cys Gly Gly Tyr Tyr Ile
                85                  90                  95

Gly Ile Ser Asp Tyr Pro Phe Gly Gly Gly Thr Glu Val Glu Ile Lys
            100                 105                 110

<210> SEQ ID NO 55
<211> LENGTH: 8
<212> TYPE: PRT
<213> ORGANISM: Artificial sequence
<220> FEATURE:
<223> OTHER INFORMATION: Synthetic amino acid

<400> SEQUENCE: 55

Gln Ser Val Val Asn Asn Asn Ala
1               5

<210> SEQ ID NO 56
<211> LENGTH: 12
<212> TYPE: PRT
<213> ORGANISM: Artificial sequence
<220> FEATURE:
<223> OTHER INFORMATION: Synthetic amino acid

<400> SEQUENCE: 56

Gln Gly Gly Tyr Tyr Ile Gly Ile Ser Asp Tyr Pro
1               5                   10

<210> SEQ ID NO 57
<211> LENGTH: 115
<212> TYPE: PRT
<213> ORGANISM: Artificial sequence
<220> FEATURE:
<223> OTHER INFORMATION: Synthetic amino acid

<400> SEQUENCE: 57
```

```
Glu Gln Ser Val Glu Ser Gly Gly Gly Leu Val Thr Pro Gly Gly
1               5                   10                  15

Thr Leu Thr Leu Thr Cys Thr Ala Ser Gly Phe Ser Ile Ser Thr Tyr
            20                  25                  30

Ala Met Ile Trp Val Arg Gln Ala Pro Gly Glu Gly Leu Glu Tyr Ile
        35                  40                  45

Gly Cys Ile Gly Thr Gly Gly Ser Ala Phe Tyr Ala Ile Trp Ala Lys
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Ala Arg Asn
                85                  90                  95

Asp Ile Tyr Trp Ala Phe Gly Leu Trp Gly Gln Gly Thr Leu Val Thr
            100                 105                 110

Val Ser Ser
        115
```

<210> SEQ ID NO 58
<211> LENGTH: 8
<212> TYPE: PRT
<213> ORGANISM: Artificial sequence
<220> FEATURE:
<223> OTHER INFORMATION: Synthetic amino acid

<400> SEQUENCE: 58

```
Gly Phe Ser Ile Ser Thr Tyr Ala
1               5
```

<210> SEQ ID NO 59
<211> LENGTH: 7
<212> TYPE: PRT
<213> ORGANISM: Artificial sequence
<220> FEATURE:
<223> OTHER INFORMATION: Synthetic amino acid

<400> SEQUENCE: 59

```
Ile Gly Thr Gly Gly Ser Ala
1               5
```

<210> SEQ ID NO 60
<211> LENGTH: 11
<212> TYPE: PRT
<213> ORGANISM: Artificial sequence
<220> FEATURE:
<223> OTHER INFORMATION: Synthetic amino acid

<400> SEQUENCE: 60

```
Ala Arg Asn Asp Ile Tyr Trp Ala Phe Gly Leu
1               5                   10
```

<210> SEQ ID NO 61
<211> LENGTH: 111
<212> TYPE: PRT
<213> ORGANISM: Artificial sequence
<220> FEATURE:
<223> OTHER INFORMATION: Synthetic amino acid

<400> SEQUENCE: 61

```
Glu Leu Asp Leu Thr Gln Thr Pro Ala Ser Val Ser Glu Pro Val Gly
1               5                   10                  15

Gly Thr Val Thr Ile Asn Cys Gln Ala Ser Glu Gly Ile Arg Asn Trp
            20                  25                  30
```

```
Leu Ala Trp Tyr Gln Gln Lys Pro Gly Gln Pro Pro Lys Leu Leu Ile
            35                  40                  45

Tyr Gly Ala Ser Thr Leu Glu Ser Gly Val Pro Ser Arg Phe Lys Gly
 50                  55                  60

Ser Gly Ser Gly Thr Glu Phe Thr Leu Thr Ile Arg Gly Val Gln Cys
 65                  70                  75                  80

Asp Asp Ala Ala Thr Tyr Tyr Cys Gln Gly Gly Val Tyr Ser Ser Ser
                 85                  90                  95

Ile Tyr Gly Tyr Pro Phe Gly Gly Thr Glu Leu Glu Ile Lys
                100                 105                 110

<210> SEQ ID NO 62
<211> LENGTH: 6
<212> TYPE: PRT
<213> ORGANISM: Artificial sequence
<220> FEATURE:
<223> OTHER INFORMATION: Synthetic amino acid

<400> SEQUENCE: 62

Glu Gly Ile Arg Asn Trp
1               5

<210> SEQ ID NO 63
<211> LENGTH: 13
<212> TYPE: PRT
<213> ORGANISM: Artificial sequence
<220> FEATURE:
<223> OTHER INFORMATION: Synthetic amino acid

<400> SEQUENCE: 63

Gln Gly Gly Val Tyr Ser Ser Ser Ile Tyr Gly Tyr Pro
1               5                   10

<210> SEQ ID NO 64
<211> LENGTH: 123
<212> TYPE: PRT
<213> ORGANISM: Artificial sequence
<220> FEATURE:
<223> OTHER INFORMATION: Synthetic amino acid

<400> SEQUENCE: 64

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Asp Phe Ser Ser Ser Gly
                20                  25                  30

Trp Ile Cys Trp Val Arg Gln Ala Pro Gly Lys Gly Leu Glu Leu Ile
                35                  40                  45

Ala Cys Ile Tyr Ser Gly Arg Ser Gly Ser Thr Tyr Tyr Ala Ser Trp
 50                  55                  60

Ala Lys Gly Arg Val Thr Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Arg Ala Leu Tyr Val Asp Tyr Val Asp Tyr Asp Tyr Ile Asp Leu
                100                 105                 110

Trp Gly Pro Gly Thr Leu Val Thr Val Ser Ser
                115                 120

<210> SEQ ID NO 65
<211> LENGTH: 9
<212> TYPE: PRT
```

```
<213> ORGANISM: Artificial sequence
<220> FEATURE:
<223> OTHER INFORMATION: Synthetic amino acid

<400> SEQUENCE: 65

Gly Phe Asp Phe Ser Ser Ser Gly Trp
1               5

<210> SEQ ID NO 66
<211> LENGTH: 9
<212> TYPE: PRT
<213> ORGANISM: Artificial sequence
<220> FEATURE:
<223> OTHER INFORMATION: Synthetic amino acid

<400> SEQUENCE: 66

Ile Tyr Ser Gly Arg Ser Gly Ser Thr
1               5

<210> SEQ ID NO 67
<211> LENGTH: 16
<212> TYPE: PRT
<213> ORGANISM: Artificial sequence
<220> FEATURE:
<223> OTHER INFORMATION: Synthetic amino acid

<400> SEQUENCE: 67

Ala Arg Ala Leu Tyr Val Asp Tyr Val Asp Tyr Asp Tyr Ile Asp Leu
1               5                   10                  15

<210> SEQ ID NO 68
<211> LENGTH: 110
<212> TYPE: PRT
<213> ORGANISM: Artificial sequence
<220> FEATURE:
<223> OTHER INFORMATION: Synthetic amino acid

<400> SEQUENCE: 68

Glu Leu Asp Leu Thr Gln Thr Pro Ala Ser Val Glu Ala Ala Val Gly
1               5                   10                  15

Gly Thr Val Thr Ile Lys Cys Gln Ala Ser Gln Ser Thr Gly Ile Arg
            20                  25                  30

Leu Ala Trp Tyr Gln Gln Lys Pro Gly Gln Pro Pro Lys Leu Leu Met
        35                  40                  45

Tyr Ala Thr Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Tyr Ser Tyr Tyr Gly Ser Ser
                85                  90                  95

Tyr Val Phe Asp Phe Gly Gly Gly Thr Glu Val Glu Ile Lys
            100                 105                 110

<210> SEQ ID NO 69
<211> LENGTH: 6
<212> TYPE: PRT
<213> ORGANISM: Artificial sequence
<220> FEATURE:
<223> OTHER INFORMATION: Synthetic amino acid

<400> SEQUENCE: 69

Gln Ser Thr Gly Ile Arg
1               5
```

```
<210> SEQ ID NO 70
<211> LENGTH: 12
<212> TYPE: PRT
<213> ORGANISM: Artificial sequence
<220> FEATURE:
<223> OTHER INFORMATION: Synthetic amino acid

<400> SEQUENCE: 70

Gln Tyr Ser Tyr Tyr Gly Ser Ser Tyr Val Phe Asp
1               5                   10

<210> SEQ ID NO 71
<211> LENGTH: 113
<212> TYPE: PRT
<213> ORGANISM: Artificial sequence
<220> FEATURE:
<223> OTHER INFORMATION: Synthetic amino acid

<400> SEQUENCE: 71

Glu Gln Ser Val Glu Glu Ser Gly Gly Arg Leu Val Thr Pro Gly Thr
1               5                   10                  15

Pro Leu Thr Leu Thr Cys Thr Ala Ser Gly Phe Ser Leu Ser Ser Tyr
            20                  25                  30

Tyr Met Ser Trp Val Arg Gln Ala Pro Gly Arg Gly Leu Glu Tyr Ile
        35                  40                  45

Gly Val Ile Asn Thr Gly Gly Ser Ala Val Tyr Ala Thr Trp Thr Lys
    50                  55                  60

Gly Arg Phe Thr Ile Ser Arg Thr Ser Thr Thr Val Asp Leu Lys Met
65                  70                  75                  80

Thr Gly Leu Thr Thr Glu Asp Thr Ala Thr Tyr Phe Cys Ala Arg Gly
                85                  90                  95

Trp Ser Arg Gly Asp Leu Trp Gly Gln Gly Thr Leu Val Thr Ile Ser
            100                 105                 110

Ser

<210> SEQ ID NO 72
<211> LENGTH: 8
<212> TYPE: PRT
<213> ORGANISM: Artificial sequence
<220> FEATURE:
<223> OTHER INFORMATION: Synthetic amino acid

<400> SEQUENCE: 72

Gly Phe Ser Leu Ser Ser Tyr Tyr
1               5

<210> SEQ ID NO 73
<211> LENGTH: 7
<212> TYPE: PRT
<213> ORGANISM: Artificial sequence
<220> FEATURE:
<223> OTHER INFORMATION: Synthetic amino acid

<400> SEQUENCE: 73

Ile Asn Thr Gly Gly Ser Ala
1               5

<210> SEQ ID NO 74
<211> LENGTH: 9
<212> TYPE: PRT
<213> ORGANISM: Artificial sequence
<220> FEATURE:
<223> OTHER INFORMATION: Synthetic amino acid
```

<400> SEQUENCE: 74

Ala Arg Gly Trp Ser Arg Gly Asp Leu
1               5

<210> SEQ ID NO 75
<211> LENGTH: 109
<212> TYPE: PRT
<213> ORGANISM: Artificial sequence
<220> FEATURE:
<223> OTHER INFORMATION: Synthetic amino acid

<400> SEQUENCE: 75

Glu Leu Asp Leu Thr Gln Thr Pro Ala Ser Val Ser Glu Pro Val Gly
1               5                   10                  15

Gly Thr Val Thr Ile Lys Cys Gln Ala Ser Glu Ser Val Asp Asn Trp
            20                  25                  30

Leu Ala Trp Tyr Gln Gln Lys Pro Gly Gln Pro Pro Lys Leu Leu Ile
        35                  40                  45

Tyr Asp Ala Ser Lys Leu Ala Ser Gly Val Pro Asp Arg Phe Ser Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Leu Gly Val Phe His Asp Gly Ile
                85                  90                  95

Asn Asn Ala Phe Gly Gly Gly Thr Glu Val Glu Ile Lys
            100                 105

<210> SEQ ID NO 76
<211> LENGTH: 6
<212> TYPE: PRT
<213> ORGANISM: Artificial sequence
<220> FEATURE:
<223> OTHER INFORMATION: Synthetic amino acid

<400> SEQUENCE: 76

Glu Ser Val Asp Asn Trp
1               5

<210> SEQ ID NO 77
<211> LENGTH: 11
<212> TYPE: PRT
<213> ORGANISM: Artificial sequence
<220> FEATURE:
<223> OTHER INFORMATION: Synthetic amino acid

<400> SEQUENCE: 77

Leu Gly Val Phe His Asp Gly Ile Asn Asn Ala
1               5                   10

<210> SEQ ID NO 78
<211> LENGTH: 113
<212> TYPE: PRT
<213> ORGANISM: Artificial sequence
<220> FEATURE:
<223> OTHER INFORMATION: Synthetic amino acid

<400> SEQUENCE: 78

Glu Gln Ser Val Glu Glu Ser Gly Gly Arg Leu Val Thr Pro Gly Thr
1               5                   10                  15

Pro Leu Thr Leu Thr Cys Thr Ala Ser Gly Phe Ser Leu Ser Ser Tyr
            20                  25                  30

```
Tyr Met Ser Trp Val Arg Gln Ala Pro Gly Arg Gly Leu Glu Tyr Ile
            35                  40                  45

Gly Val Ile Asn Thr Gly Gly Ser Ala Val Tyr Ala Thr Trp Thr Lys
 50                  55                  60

Gly Arg Phe Thr Ile Ser Arg Thr Ser Thr Thr Val Asp Leu Lys Met
 65                  70                  75                  80

Thr Gly Leu Thr Thr Glu Asp Thr Ala Thr Tyr Phe Cys Ala Arg Gly
                 85                  90                  95

Trp Ser Arg Gly Asp Leu Trp Gly Gln Gly Thr Leu Val Thr Ile Ser
            100                 105                 110

Ser

<210> SEQ ID NO 79
<211> LENGTH: 8
<212> TYPE: PRT
<213> ORGANISM: Artificial sequence
<220> FEATURE:
<223> OTHER INFORMATION: Synthetic amino acid

<400> SEQUENCE: 79

Gly Phe Ser Leu Ser Ser Tyr Tyr
1               5

<210> SEQ ID NO 80
<211> LENGTH: 7
<212> TYPE: PRT
<213> ORGANISM: Artificial sequence
<220> FEATURE:
<223> OTHER INFORMATION: Synthetic amino acid

<400> SEQUENCE: 80

Ile Asn Thr Gly Gly Ser Ala
1               5

<210> SEQ ID NO 81
<211> LENGTH: 9
<212> TYPE: PRT
<213> ORGANISM: Artificial sequence
<220> FEATURE:
<223> OTHER INFORMATION: Synthetic amino acid

<400> SEQUENCE: 81

Ala Arg Gly Trp Ser Arg Gly Asp Leu
1               5

<210> SEQ ID NO 82
<211> LENGTH: 111
<212> TYPE: PRT
<213> ORGANISM: Artificial sequence
<220> FEATURE:
<223> OTHER INFORMATION: Synthetic amino acid

<400> SEQUENCE: 82

Glu Leu Asp Met Thr Gln Thr Pro Ser Pro Val Ser Ala Ala Val Gly
1               5                  10                  15

Gly Thr Val Thr Ile Lys Cys Gln Ser Ser Gln Asn Val Tyr Asp Asp
            20                  25                  30

Asp Thr Leu Ser Trp Tyr Gln Gln Lys Pro Gly Gln Pro Pro Lys Leu
            35                  40                  45

Leu Ile Tyr Asp Ala Ser Lys Leu Ala Ser Gly Val Pro Asp Arg Phe
 50                  55                  60

Ser Gly Ser Gly Ser Gly Thr Gln Phe Thr Leu Thr Ile Ser Gly Val
```

```
                65                  70                  75                  80
Gln Cys Asp Asp Ala Ala Thr Tyr Tyr Cys Leu Gly Val Phe His Asp
                        85                  90                  95
Gly Ile Asn Asn Ala Phe Gly Gly Thr Glu Val Glu Ile Lys
                100                 105                 110
```

<210> SEQ ID NO 83
<211> LENGTH: 8
<212> TYPE: PRT
<213> ORGANISM: Artificial sequence
<220> FEATURE:
<223> OTHER INFORMATION: Synthetic amino acid

<400> SEQUENCE: 83

```
Gln Asn Val Tyr Asp Asp Asp Thr
1               5
```

<210> SEQ ID NO 84
<211> LENGTH: 11
<212> TYPE: PRT
<213> ORGANISM: Artificial sequence
<220> FEATURE:
<223> OTHER INFORMATION: Synthetic amino acid

<400> SEQUENCE: 84

```
Leu Gly Val Phe His Asp Gly Ile Asn Asn Ala
1               5                   10
```

<210> SEQ ID NO 85
<211> LENGTH: 117
<212> TYPE: PRT
<213> ORGANISM: Artificial sequence
<220> FEATURE:
<223> OTHER INFORMATION: Synthetic amino acid

<400> SEQUENCE: 85

```
Glu Gln Ser Val Glu Ser Gly Gly Asp Leu Val Lys Pro Gly Gly Ser
1               5                   10                  15
Leu Thr Leu Thr Cys Thr Val Ser Gly Phe Ser Phe Ser Ser Ser Tyr
                20                  25                  30
Trp Ile Cys Trp Val Arg Gln Ala Pro Gly Lys Gly Leu Glu Trp Ile
                35                  40                  45
Gly Cys Ile Gly Thr Gly Ser Gly Ser Thr Tyr Tyr Gly Ser Trp Ala
            50                  55                  60
Lys Gly Arg Phe Thr Ile Ser Lys Thr Ser Thr Thr Val Thr Leu
65                  70                  75                  80
Gln Met Thr Ser Leu Thr Ala Ala Asp Thr Ala Thr Tyr Phe Cys Val
                85                  90                  95
Arg Gly Ala Gly Tyr Ser Ser Tyr Arg Leu Trp Gly Pro Gly Thr Leu
                100                 105                 110
Val Thr Ile Ser Ser
            115
```

<210> SEQ ID NO 86
<211> LENGTH: 9
<212> TYPE: PRT
<213> ORGANISM: Artificial sequence
<220> FEATURE:
<223> OTHER INFORMATION: Synthetic amino acid

<400> SEQUENCE: 86

```
Gly Phe Ser Phe Ser Ser Ser Tyr Trp
```

```
<210> SEQ ID NO 87
<211> LENGTH: 7
<212> TYPE: PRT
<213> ORGANISM: Artificial sequence
<220> FEATURE:
<223> OTHER INFORMATION: Synthetic amino acid

<400> SEQUENCE: 87

Ile Gly Thr Gly Ser Gly Ser
1               5

<210> SEQ ID NO 88
<211> LENGTH: 11
<212> TYPE: PRT
<213> ORGANISM: Artificial sequence
<220> FEATURE:
<223> OTHER INFORMATION: Synthetic amino acid

<400> SEQUENCE: 88

Val Arg Gly Ala Gly Tyr Ser Ser Tyr Arg Leu
1               5                   10

<210> SEQ ID NO 89
<211> LENGTH: 110
<212> TYPE: PRT
<213> ORGANISM: Artificial sequence
<220> FEATURE:
<223> OTHER INFORMATION: Synthetic amino acid

<400> SEQUENCE: 89

Glu Leu Asp Met Thr Gln Thr Pro Ala Ser Val Ser Glu Pro Val Gly
1               5                   10                  15

Gly Thr Val Thr Ile Lys Cys Gln Ala Ser Glu Ser Val Ser Asn Trp
                20                  25                  30

Leu Ala Trp Tyr Gln Gln Lys Pro Gly Gln Arg Pro Lys Leu Leu Ile
            35                  40                  45

Tyr Gly Ala Ser Thr Leu Glu Ser Gly Val Pro Ser Arg Phe Ser Gly
        50                  55                  60

Ser Gly Ser Gly Thr Glu Phe Thr Leu Thr Ile Ser Asn Leu Glu Cys
65                  70                  75                  80

Ala Asp Ala Ala Thr Tyr Tyr Cys Gln Gln Gly Tyr Asp Trp Asp Asn
                85                  90                  95

Ile Asp Asn Ala Phe Gly Gly Gly Thr Glu Val Val Val Lys
            100                 105                 110

<210> SEQ ID NO 90
<211> LENGTH: 6
<212> TYPE: PRT
<213> ORGANISM: Artificial sequence
<220> FEATURE:
<223> OTHER INFORMATION: Synthetic amino acid

<400> SEQUENCE: 90

Glu Ser Val Ser Asn Trp
1               5

<210> SEQ ID NO 91
<211> LENGTH: 12
<212> TYPE: PRT
<213> ORGANISM: Artificial sequence
<220> FEATURE:
<223> OTHER INFORMATION: Synthetic amino acid
```

<400> SEQUENCE: 91

Gln Gln Gly Tyr Asp Trp Asp Asn Ile Asp Asn Ala
1               5                   10

<210> SEQ ID NO 92
<211> LENGTH: 123
<212> TYPE: PRT
<213> ORGANISM: Artificial sequence
<220> FEATURE:
<223> OTHER INFORMATION: Synthetic amino acid

<400> SEQUENCE: 92

Gln Ser Val Lys Glu Ser Gly Gly Asp Leu Val Lys Pro Gly Ala Ser
1               5                   10                  15

Leu Thr Leu Thr Cys Thr Ala Ser Gly Phe Ser Phe Ile Ser Thr Tyr
                20                  25                  30

Trp Ile Cys Trp Val Arg Gln Ala Pro Gly Lys Gly Leu Glu Leu Ile
            35                  40                  45

Ala Cys Ile Tyr Thr Gly Gly Ser Gly Ser Thr Tyr Tyr Ala Ser Trp
        50                  55                  60

Ala Lys Gly Arg Phe Thr Ile Ser Lys Thr Ser Ser Thr Thr Val Thr
65                  70                  75                  80

Leu Gln Leu Asn Ser Leu Thr Ala Ala Asp Thr Ala Thr Tyr Phe Cys
                85                  90                  95

Ala Arg Ala Leu Tyr Val Asp Tyr Val Asp Tyr Asp Tyr Ile Asp Leu
            100                 105                 110

Trp Gly Pro Gly Thr Leu Val Thr Val Ser Ser
        115                 120

<210> SEQ ID NO 93
<211> LENGTH: 9
<212> TYPE: PRT
<213> ORGANISM: Artificial sequence
<220> FEATURE:
<223> OTHER INFORMATION: Synthetic amino acid

<400> SEQUENCE: 93

Gly Phe Ser Phe Ile Ser Thr Tyr Trp
1               5

<210> SEQ ID NO 94
<211> LENGTH: 9
<212> TYPE: PRT
<213> ORGANISM: Artificial sequence
<220> FEATURE:
<223> OTHER INFORMATION: Synthetic amino acid

<400> SEQUENCE: 94

Ile Tyr Thr Gly Gly Ser Gly Ser Thr
1               5

<210> SEQ ID NO 95
<211> LENGTH: 16
<212> TYPE: PRT
<213> ORGANISM: Artificial sequence
<220> FEATURE:
<223> OTHER INFORMATION: Synthetic amino acid

<400> SEQUENCE: 95

Ala Arg Ala Leu Tyr Val Asp Tyr Val Asp Tyr Asp Tyr Ile Asp Leu
1               5                   10                  15

```
<210> SEQ ID NO 96
<211> LENGTH: 110
<212> TYPE: PRT
<213> ORGANISM: Artificial sequence
<220> FEATURE:
<223> OTHER INFORMATION: Synthetic amino acid

<400> SEQUENCE: 96

Glu Leu Asp Leu Thr Gln Thr Pro Ala Ser Val Glu Ala Ala Val Gly
1               5                   10                  15

Gly Thr Val Thr Ile Lys Cys Gln Ala Ser Glu Asn Ile Gly Ser Arg
                20                  25                  30

Leu Ala Trp Tyr Gln Gln Lys Pro Gly Gln Pro Pro Lys Leu Leu Ile
            35                  40                  45

Tyr Ala Ala Ser Asn Leu Ala Ser Gly Val Ser Ser Arg Phe Lys Gly
50                  55                  60

Ser Arg Ser Gly Thr Gln Phe Thr Leu Thr Ile Ser Asp Leu Glu Cys
65                  70                  75                  80

Ala Asp Ala Ala Ile Tyr Tyr Cys Gln Cys Ser Tyr Tyr Gly Ser Thr
                85                  90                  95

Tyr Val Phe Gly Phe Gly Gly Thr Glu Val Glu Ile Lys
            100                 105                 110

<210> SEQ ID NO 97
<211> LENGTH: 6
<212> TYPE: PRT
<213> ORGANISM: Artificial sequence
<220> FEATURE:
<223> OTHER INFORMATION: Synthetic amino acid

<400> SEQUENCE: 97

Glu Asn Ile Gly Ser Arg
1               5

<210> SEQ ID NO 98
<211> LENGTH: 12
<212> TYPE: PRT
<213> ORGANISM: Artificial sequence
<220> FEATURE:
<223> OTHER INFORMATION: Synthetic amino acid

<400> SEQUENCE: 98

Gln Cys Ser Tyr Tyr Gly Ser Thr Tyr Val Phe Gly
1               5                   10

<210> SEQ ID NO 99
<211> LENGTH: 120
<212> TYPE: PRT
<213> ORGANISM: Artificial sequence
<220> FEATURE:
<223> OTHER INFORMATION: Synthetic amino acid

<400> SEQUENCE: 99

Glu Gln Ser Val Glu Glu Ser Gly Gly Asp Leu Val Lys Pro Gly Thr
1               5                   10                  15

Ser Leu Thr Leu Thr Cys Lys Met Ser Gly Phe Ser Leu Ser Ser Ser
                20                  25                  30

Tyr Trp Ile Cys Trp Val Arg Gln Ala Pro Gly Lys Gly Leu Glu Trp
            35                  40                  45

Ile Gly Cys Ile Asp Ser Gly Ser Val Gly Ile Thr Tyr Tyr Ala Thr
50                  55                  60
```

```
Trp Ala Lys Gly Arg Phe Thr Ile Ser Arg Ser Thr Ser Leu Asn Thr
 65                  70                  75                  80

Val Thr Leu Gln Met Thr Ser Leu Thr Gly Ala Asp Thr Ala Met Tyr
                 85                  90                  95

Phe Ser Val Arg His Gly Asp Asn Trp Ala Leu Asp Leu Trp Gly Pro
            100                 105                 110

Gly Thr Leu Val Thr Ile Ser Ser
            115                 120

<210> SEQ ID NO 100
<211> LENGTH: 9
<212> TYPE: PRT
<213> ORGANISM: Artificial sequence
<220> FEATURE:
<223> OTHER INFORMATION: Synthetic amino acid

<400> SEQUENCE: 100

Gly Phe Ser Leu Ser Ser Ser Tyr Trp
1               5

<210> SEQ ID NO 101
<211> LENGTH: 9
<212> TYPE: PRT
<213> ORGANISM: Artificial sequence
<220> FEATURE:
<223> OTHER INFORMATION: Synthetic amino acid

<400> SEQUENCE: 101

Ile Asp Ser Gly Ser Val Gly Ile Thr
1               5

<210> SEQ ID NO 102
<211> LENGTH: 12
<212> TYPE: PRT
<213> ORGANISM: Artificial sequence
<220> FEATURE:
<223> OTHER INFORMATION: Synthetic amino acid

<400> SEQUENCE: 102

Ser Val Arg His Gly Asp Asn Trp Ala Leu Asp Leu
1               5                   10

<210> SEQ ID NO 103
<211> LENGTH: 110
<212> TYPE: PRT
<213> ORGANISM: Artificial sequence
<220> FEATURE:
<223> OTHER INFORMATION: Synthetic amino acid

<400> SEQUENCE: 103

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Asn Ser Trp
            20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Pro Ser Arg Phe Ser Ala
 50                  55                  60

Ser Gly Ser Gly Thr Glu Phe Thr Leu Thr Ile Thr Gly Val Gln Cys
 65                  70                  75                  80

Asp Asp Ala Ala Thr Tyr Tyr Cys Gln His Gly Tyr Ile Arg Gly Asp
                 85                  90                  95
```

Leu Asp Asn Val Phe Gly Gly Gly Thr Glu Val Val Val Lys
            100                 105                 110

<210> SEQ ID NO 104
<211> LENGTH: 6
<212> TYPE: PRT
<213> ORGANISM: Artificial sequence
<220> FEATURE:
<223> OTHER INFORMATION: Synthetic amino acid

<400> SEQUENCE: 104

Gln Ser Ile Asn Ser Trp
1               5

<210> SEQ ID NO 105
<211> LENGTH: 12
<212> TYPE: PRT
<213> ORGANISM: Artificial sequence
<220> FEATURE:
<223> OTHER INFORMATION: Synthetic amino acid

<400> SEQUENCE: 105

Gln His Gly Tyr Ile Arg Gly Asp Leu Asp Asn Val
1               5                   10

<210> SEQ ID NO 106
<211> LENGTH: 369
<212> TYPE: DNA
<213> ORGANISM: Artificial sequence
<220> FEATURE:
<223> OTHER INFORMATION: Synthetic nucleic acid

<400> SEQUENCE: 106
gagcagtcgt tggaggagtc cgggggtctg gaggagtccg ggggtcgcct ggtcacgcct      60
gggacacccc tgacactcac ctgcacagcc tctggattca ccatcaatag cgcccacatg     120
tcttgggtcc gccaggctcc agggaagggg ctggaatgga tcggattcag tactactggt     180
ggtccctcat attacgcgaa ctgggcaaaa ggccgattca ccatctccag aacctcgacc     240
acggtggatc tggagatcac cagtccgaca atcgaggaca cggccaccta tttctgtgcc     300
agagatggtc tggtaataa tattgatatg gacttgtggg gccaaggcac cctggtcacc      360
atcacctca                                                             369

<210> SEQ ID NO 107
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 107
ggattcacca tcaatagcgc ccac                                             24

<210> SEQ ID NO 108
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 108
agtactactg gtggtccctc a                                                21

<210> SEQ ID NO 109

```
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 109
gccagagatg gtcctggtaa taatattgat atggacttg                      39

<210> SEQ ID NO 110
<211> LENGTH: 330
<212> TYPE: DNA
<213> ORGANISM: Artificial sequence
<220> FEATURE:
<223> OTHER INFORMATION: Synthetic nucleic acid

<400> SEQUENCE: 110
gagctcgatc tgacccagac accagcctcc gtgtctgaac ctgtgggagg cacagtcacc     60
atcaagtgcc aggccagtca aataggggc ggtagcatag cctggtatca gcagaaacca    120
gggcagcctc ccaagctcct gatctattct gcatccactc tggcatctgg ggtcccatcg    180
cggttcagcg gcagtggata tgggacagag ttcactctca ccatcagcgg cgtgcagtgt    240
gccgatgctg gcacttacta ctgccaatct actatttata gtataagtga tattggggct    300
ttcggcggag ggaccgaggt ggtggtcaaa                                     330

<210> SEQ ID NO 111
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 111
cagaataggg gcggtagc                                                  18

<210> SEQ ID NO 112
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 112
caatctacta tttatagtat aagtgatatt ggggct                              36

<210> SEQ ID NO 113
<211> LENGTH: 345
<212> TYPE: DNA
<213> ORGANISM: Artificial sequence
<220> FEATURE:
<223> OTHER INFORMATION: Synthetic nucleic acid

<400> SEQUENCE: 113
cagtcggtgg aggagtccgg gggtcgcctg gtcacgcctg gacacccct gacactcacc      60 tgcacagtct ctggaatcga cctcactaac tatgcaataa actgggtccg ccaggctcca    120 ggggagggc tggaatacat cggaaccatt actggtagta gtaacacatt ctacgcgagc     180
tgggcgaaag gccgattcac catctccaaa acctcgacca cggtggatct gaaaatcacc    240
agtccgacaa ctgaggacac gggcacctat ttctgtgcca gtaatcctga tagtcacaac    300
gctaatggcg tgtggggcca aggcaccctg gtcaccgtct cctca                    345
```

```
<210> SEQ ID NO 114
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 114
ggaatcgacc tcactaacta tgca                                          24

<210> SEQ ID NO 115
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 115
attactggta gtagtaacac a                                             21

<210> SEQ ID NO 116
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 116
gccagtaatc ctgatagtca caacgctaat ggcgtg                             36

<210> SEQ ID NO 117
<211> LENGTH: 336
<212> TYPE: DNA
<213> ORGANISM: Artificial sequence
<220> FEATURE:
<223> OTHER INFORMATION: Synthetic nucleic acid

<400> SEQUENCE: 117
gagctcgtga tgacccagac accagcctcc gtgtctgaac ctgtggaagg cacagtcacc    60
atcaagtgtc aggccagtca gagtgtttat gataacaact tagcctggta tcagcagaaa   120
ccagggcagc ctcccaagct cctgatctat tctgcatcca ctctggcatc tggggtccca   180
tcgcggttca gcggcagtgg atatgggaca gagttcactc tcaccatcag cggcgtggag   240
tgtgccgatg ctgccactta ctattgtcaa agctatggta ttactaataa gaataattat   300
aatagtttcg gcggagggac cgaggtggtg gtcaaa                             336

<210> SEQ ID NO 118
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 118
cagagtgttt atgataacaa c                                             21

<210> SEQ ID NO 119
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 119
```

```
caaagctatg gtattactaa taagaataat tataatagt                              39
```

<210> SEQ ID NO 120
<211> LENGTH: 363
<212> TYPE: DNA
<213> ORGANISM: Artificial sequence
<220> FEATURE:
<223> OTHER INFORMATION: Synthetic nucleic acid

<400> SEQUENCE: 120

```
gagcagtcgg tggaggagtc cgggggagac ctggtcaagc ctggggcatc cctgacactc    60
acctgcgcag cctctggatt ctccttcagt agcacctact gcatgtgctg ggtccgccag   120
gctccaggga agggcctgga gtggatcgca tgcattcatg gtgtaagtac taataataga   180
tggtacgcga gctggccgaa aggccgattc accatctcca aaacctcgtc gaccacggtg   240
actctgcaaa tgaccagtct gacagccgcg gacacggcca cctacttctg tgcgagaagt   300
gacactgact atgagtgggg tctttccttg tggggcccag gcaccctggt caccatctct   360
tca                                                                  363
```

<210> SEQ ID NO 121
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 121

```
ggattctcct tcagtagcac ctactgc                                         27
```

<210> SEQ ID NO 122
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 122

```
attcatggtg taagtactaa taataga                                         27
```

<210> SEQ ID NO 123
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 123

```
gcgagaagtg acactgacta tgagtggggt ctttccttg                            39
```

<210> SEQ ID NO 124
<211> LENGTH: 324
<212> TYPE: DNA
<213> ORGANISM: Artificial sequence
<220> FEATURE:
<223> OTHER INFORMATION: Synthetic nucleic acid

<400> SEQUENCE: 124

```
gagctcgatc tgacccagac accagcctcc gtgtctgagc ctgtgggagg cacagtcacc    60
atcaagtgcc aggccagtga gagcattggt agtagattag cctggtatca acagaaacca   120
gggcagcgtc ccaagctcct gatctacaag gcatccactc tggcatctgg ggtcccatcg   180
cggttcagtg gcagtggatc tgggacagag ttcactctca ccgtcagcga cctggagtgt   240
```

```
gccgatgttg ccgcttacta ttgtcaatgc gctggtcaga gtagtacttg ggctttcggc    300
ggagggaccg aggtggaaat caaa                                            324

<210> SEQ ID NO 125
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 125
gagagcattg gtagtaga                                                    18

<210> SEQ ID NO 126
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 126
caatgcgctg gtcagagtag tacttgggct                                       30

<210> SEQ ID NO 127
<211> LENGTH: 363
<212> TYPE: DNA
<213> ORGANISM: Artificial sequence
<220> FEATURE:
<223> OTHER INFORMATION: Synthetic nucleic acid

<400> SEQUENCE: 127
gagcagtcgg tggaggagtc cggggggagac ctggtcaagc ctggggcatc cctgacactc     60
acctgcgcag cctctggatt ctccttcagt agcacctact gcatgtgctg ggtccgccag    120
gctccaggga agggcctgga gtggatcgca tgcattcatg gtgtaagtac taataataga    180
tggtacgcga gctggccgaa aggccgattc accatctcca aaacctcgtc gaccacggtg    240
actctgcaaa tgaccagtct gacagccgcg gacacggcca cctacttctg tgcgagaagt    300
gacactgact atgagtgggg tctttccttg tggggcccag gcaccctggt caccatctct    360
tca                                                                   363

<210> SEQ ID NO 128
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 128
ggattctcct tcagtagcac ctactgc                                          27

<210> SEQ ID NO 129
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 129
attcatggtg taagtactaa taataga                                          27

<210> SEQ ID NO 130
```

```
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 130
gcgagaagtg acactgacta tgagtggggt ctttccttg                                  39

<210> SEQ ID NO 131
<211> LENGTH: 324
<212> TYPE: DNA
<213> ORGANISM: Artificial sequence
<220> FEATURE:
<223> OTHER INFORMATION: Synthetic nucleic acid

<400> SEQUENCE: 131
gagctcgtga tgacccagac accagcctcc gtggaggcag ttgtgggagg cacagtcacc           60
atcaagtgcc aggccagtga gagcattggt agtagattag cctggtatca acagaaacca         120
gggcagcgtc ccaagctcct gatctacaag gcatccactc tggcatctgg ggtcccatcg         180
cggttcagtg gcagtggatc tgggacagag ttcactctca ccgtcagcga cctggagtgt         240
gccgatgttg ccgcttacta ttgtcaatgc gctggtcaga gtagtacttg ggctttcggc         300
ggagggaccg aggtggtggt caaa                                                324

<210> SEQ ID NO 132
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 132
gagagcattg gtagtaga                                                        18

<210> SEQ ID NO 133
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 133
caatgcgctg gtcagagtag tacttgggct                                           30

<210> SEQ ID NO 134
<211> LENGTH: 360
<212> TYPE: DNA
<213> ORGANISM: Artificial sequence
<220> FEATURE:
<223> OTHER INFORMATION: Synthetic nucleic acid

<400> SEQUENCE: 134
cagtcggtga aggagtccgg gggtcgcctg gtcacgcctg gacacccct gacactcacc           60 tgcaccgtct ctggattctc cctcagtaac aatggaatga gctgggtccg ccaggctcca         120
gggaaggggc tggagtggat cggaatcatt tatgttggga gtggtaccac agactacgcg         180
acctgggcga aaggccgatt caccatctcc agaacctcga ccacggtgga tctgaaaatg         240
accagtctga caaccgagga cacggccacc tatttatgtg ccagaggttt tggtgttggg         300
gattggcaag aatggttttt tgatctctgg ggcccaggca cctggtcac catctcttca          360
```

```
<210> SEQ ID NO 135
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 135
ggattctccc tcagtaacaa tgga                                              24

<210> SEQ ID NO 136
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 136
atttatgttg ggagtggtac caca                                              24

<210> SEQ ID NO 137
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 137
gccagaggtt ttggtgttgg ggattggcaa gaatggtttt ttgatctc                    48

<210> SEQ ID NO 138
<211> LENGTH: 324
<212> TYPE: DNA
<213> ORGANISM: Artificial sequence
<220> FEATURE:
<223> OTHER INFORMATION: Synthetic nucleic acid

<400> SEQUENCE: 138
gagctcgtga tgacccagac accagcctcc gtgtctgagc ctgtgggagg cacagtcacc       60
atcaagtgcc aggccagtga aagcattagc aactacttat cctggtatca gcagaaacca      120
gggcagcctc ccaagctcct gatctataag gcatccactc tggcatctgg ggtctcatcg      180
cggttcaaag gcagtggatc tgggacagaa ttcactctca ccatcagcga cctggagtgt      240
gccgatgctg ccacttacta ctgtcaagcc tattgggta cttctactat ggctttcggc       300
ggagggaccg aggtggaaat caac                                             324

<210> SEQ ID NO 139
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 139
gaaagcatta gcaactac                                                     18

<210> SEQ ID NO 140
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 140
```

```
caagcctatt ggggtacttc tactatggct                                      30
```

<210> SEQ ID NO 141
<211> LENGTH: 360
<212> TYPE: DNA
<213> ORGANISM: Artificial sequence
<220> FEATURE:
<223> OTHER INFORMATION: Synthetic nucleic acid

<400> SEQUENCE: 141

```
cagtcgttgg aggagtccgg gggtcgcctg gtcacgcctg gacacccct gacactcacc       60
tgcaccgtct ctggattctc cctcagtaac aatggaatga ctgggtccg ccaggctcca     120
gggaaggggc tggagtggat cggaatcatt tatgttggga gtggtaccac agactacgcg    180
agctggccga aggccgatt caccatctcc agaacctcga ccacggtgga tctgaaaatg     240
accagtctga caaccgagga cacggccacc tatttatgtg ccagaggttt tggtgttggg    300
gattggcaag aatggttttt tgatctctgg ggcccaggca ccctggtcac cgtctcttct    360
```

<210> SEQ ID NO 142
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 142

```
ggattctccc tcagtaacaa tgga                                            24
```

<210> SEQ ID NO 143
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 143

```
atttatgttg ggagtggtac caca                                            24
```

<210> SEQ ID NO 144
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 144

```
gccagaggtt ttggtgttgg ggattggcaa gaatggtttt ttgatctc                  48
```

<210> SEQ ID NO 145
<211> LENGTH: 324
<212> TYPE: DNA
<213> ORGANISM: Artificial sequence
<220> FEATURE:
<223> OTHER INFORMATION: Synthetic nucleic acid

<400> SEQUENCE: 145

```
gagctcgtga tgacccagac accagcctcc gtgtctgagc tgtgggagg cacagtcacc       60
atcaagtgcc aggccagtga aagcattagc aactacttat cctggtatca gcagaaacca    120
gggcagcctc ccaagctcct gatctataag gcatccactc tggcatctgg ggtctcatcg    180
cggttcaaag gcagtggatc tgggacagaa ttcactctca ccatcagcga cctggagtgt    240
gccgatgctg ccacttacta ctgtcaagcc tattggggta cttctactat ggctttcggc    300
```
ggagggaccg aggtggaaat caac                                          324

<210> SEQ ID NO 146
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 146
gaaagcatta gcaactac                                                 18

<210> SEQ ID NO 147
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 147
caagcctatt ggggtacttc tactatggct                                    30

<210> SEQ ID NO 148
<211> LENGTH: 345
<212> TYPE: DNA
<213> ORGANISM: Artificial sequence
<220> FEATURE:
<223> OTHER INFORMATION: Synthetic nucleic acid

<400> SEQUENCE: 148
agcagttcgg tggaggagtc cggggggtcgc ctggtcacgc ctgggacacc cctgacactc    60
acctgcacag tctctggatt ctccctcagt agctatgcaa tggcctgggt ccgccaggct   120
ccagggaagg ggctggaatg gatcggaatc attggtactg gtaccaccac atactacgcg   180
acctgggtga atggtcgatt caccatctcc aaaacctcga ccacggtgga cctgaaaatg   240
accagtctga caaccgagga cacggccact tatttctgtg tcagaaatga tgtttattgg   300
gcgtttaatt tgtgggggcca aggcacccctg gtcaccgtct cttca                 345

<210> SEQ ID NO 149
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 149
ggattctccc tcagtagcta tgca                                          24

<210> SEQ ID NO 150
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 150
attggtactg gtaccaccac a                                             21

<210> SEQ ID NO 151
<211> LENGTH: 33
<212> TYPE: DNA
<213> ORGANISM: Artificial sequence
<220> FEATURE:

<223> OTHER INFORMATION: Synthetic nucleic acid

<400> SEQUENCE: 151

```
gtcagaaatg atgtttattg ggcgtttaat ttg                          33
```

<210> SEQ ID NO 152
<211> LENGTH: 336
<212> TYPE: DNA
<213> ORGANISM: Artificial sequence
<220> FEATURE:
<223> OTHER INFORMATION: Synthetic nucleic acid

<400> SEQUENCE: 152

```
gagctcgtga tgacccagac accagccccc gtgtctgcag ctgtgggagg cacagtcacc   60
atcaactgcc aggccagtca gagtgttgtt aataataatg ccttatcttg gtatcagcag  120
aaaccagggc agcctcccaa gctcctgatc tacaaggctt ccactctggc atctggggtc  180
ccatcgcggt tcaaaggcag tggatctggg gcacagttca ctctcaccat cagcggcgtg  240
cagtgtgacg atgctgccac ttattattgt caaggcggtt attatattgg tattagtgac  300
tatccttcg cggcgggac cgaggtggtg gtcaaa                              336
```

<210> SEQ ID NO 153
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 153

```
cagagtgttg ttaataataa tgcc                                   24
```

<210> SEQ ID NO 154
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 154

```
caaggcggtt attatattgg tattagtgac tatcct                      36
```

<210> SEQ ID NO 155
<211> LENGTH: 345
<212> TYPE: DNA
<213> ORGANISM: Artificial sequence
<220> FEATURE:
<223> OTHER INFORMATION: Synthetic nucleic acid

<400> SEQUENCE: 155

```
agcagttcgg tggaggagtc cggggggtcgc ctggtcacgc ctgggacacc cctgacactc   60
acctgcacag tctctggatt ctccctcagt agctatgcaa tggcctgggt ccgccaggct  120
ccagggaagg ggctggaatg gatcggaatc attggtactg gtaccaccac atactacgcg  180
acctgggtga atggtcgatt caccatctcc aaaacctcga ccacggtgga cctgaaaatg  240
accagtctga caaccgagga cacggccact tatttctgtg tcagaaatga tgtttattgg  300
gcgtttaatt tgtggggcca aggcaccctg gtcaccgtct cttca                 345
```

<210> SEQ ID NO 156
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 156
ggattctccc tcagtagcta tgca                                    24

<210> SEQ ID NO 157
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 157
attggtactg gtaccaccac a                                       21

<210> SEQ ID NO 158
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 158
gtcagaaatg atgtttattg ggcgtttaat ttg                          33

<210> SEQ ID NO 159
<211> LENGTH: 336
<212> TYPE: DNA
<213> ORGANISM: Artificial sequence
<220> FEATURE:
<223> OTHER INFORMATION: Synthetic nucleic acid

<400> SEQUENCE: 159
gagctcgatc tgacccagac accatcctcc gtgtctgcag ctgtgggagg cacagtcagc    60
atcagttgcc agtccagtca gagtgttgtt aataataatg ccttatcttg gtatcagcag   120
aaaccagggc agcctcccaa gctcctgatc tacaaggctt ccactctggc atctggggtc   180
ccatcgcggt tcaaaggcag tggatctggg gcacagttca ctctcaccat cagcggcgtg   240
cagtgtgacg atgctgccac ttattattgt caaggcggtt attatattgg tattagtgac   300
tatcctttcg gcggcgggac cgaggtggaa atcaaa                            336

<210> SEQ ID NO 160
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 160
cagagtgttg ttaataataa tgcc                                    24

<210> SEQ ID NO 161
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 161
caaggcggtt attatattgg tattagtgac tatcct                       36

<210> SEQ ID NO 162

```
<211> LENGTH: 345
<212> TYPE: DNA
<213> ORGANISM: Artificial sequence
<220> FEATURE:
<223> OTHER INFORMATION: Synthetic nucleic acid

<400> SEQUENCE: 162
gagcagtcgg tggaggagtc cggaggaggc tggtaacgc ctggaggaac cctgacactc      60
acctgcacag cctctggatt ctccatcagt acctatgcaa tgatctgggt ccgccaggct    120
ccaggggagg ggctggaata catcggatgc attggtactg gtggtagcgc attctacgcg    180
atctgggcaa aaggccgatt caccatctcc agaacctcga ccacggtgga tctgaagatg    240
accagtctga caaccgagga cacggccaca tatttctgtg ccagaaatga tatttattgg    300
gcctttggct tatggggcca aggcacgctg gtcaccgtct cctca                    345

<210> SEQ ID NO 163
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 163
ggattctcca tcagtaccta tgca                                            24

<210> SEQ ID NO 164
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 164
attggtactg gtggtagcgc a                                               21

<210> SEQ ID NO 165
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 165
gccagaaatg atatttattg ggcctttggc tta                                  33

<210> SEQ ID NO 166
<211> LENGTH: 333
<212> TYPE: DNA
<213> ORGANISM: Artificial sequence
<220> FEATURE:
<223> OTHER INFORMATION: Synthetic nucleic acid

<400> SEQUENCE: 166
gagctcgatc tgacccagac accagcctcc gtgtctgaac tgtgggagg cacagtcacc       60 atcaactgcc aggccagtga gggcattagg aactggttag cctggtatca gcagaaacca    120
gggcagcctc ccaagctcct gatctatggt gcatccactc tggaatctgg ggtcccatcg    180
cggttcaaag gcagtggatc tgggacagag ttcactctca ccatcagagg tgtgcagtgt    240
gacgatgctg ccacttacta ctgtcaaggc ggtgtttata gtagtagtat ttatggttat    300
cctttcggcg gagggaccga gctggaaatc aaa                                 333
```

<210> SEQ ID NO 167
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 167
gagggcatta ggaactgg                                            18

<210> SEQ ID NO 168
<211> LENGTH: 39
<212> TYPE: DNA
<213> ORGANISM: Artificial sequence
<220> FEATURE:
<223> OTHER INFORMATION: Synthetic nucleic acid

<400> SEQUENCE: 168
caaggcggtg tttatagtag tagtatttat ggttatcct                     39

<210> SEQ ID NO 169
<211> LENGTH: 372
<212> TYPE: DNA
<213> ORGANISM: Artificial sequence
<220> FEATURE:
<223> OTHER INFORMATION: Synthetic nucleic acid

<400> SEQUENCE: 169
gagcagtcgt tggaggagtc cggggggagac ctggtcaagc ctggggcatc cctgacactc     60
acctgcacag cctctggatt cgactttagt agtagtggtt ggatatgttg ggtccgccag     120
gctccaggga agggactgga gttgatcgca tgcatttata gtggtcgcag tggtagcact     180
tactacgcga gctgggcgaa aggccgagtc accatctcca aaacctcgtc gaccacggtg    240
actctgcaga tgaccagtct gacagccgcg gacacggcca cctatttctg tgcgagagcc    300
ctctatgttg attatgttga ttatgattat atagatttgt ggggcccagg caccctggtc    360
accgtctcct ca                                                  372

<210> SEQ ID NO 170
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 170
ggattcgact ttagtagtag tggttgg                                  27

<210> SEQ ID NO 171
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 171
atttatagtg gtcgcagtgg tagcact                                  27

<210> SEQ ID NO 172
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 172
gcgagagccc tctatgttga ttatgttgat tatgattata tagatttg          48

<210> SEQ ID NO 173
<211> LENGTH: 330
<212> TYPE: DNA
<213> ORGANISM: Artificial sequence
<220> FEATURE:
<223> OTHER INFORMATION: Synthetic nucleic acid

<400> SEQUENCE: 173
gagctcgatc tgacccagac tccagcctcc gtggaggcag ctgtgggagg cacagtcacc      60
atcaagtgcc aggccagtca gagcactggt attagattag cctggtatca gcagaaacca     120
gggcagcctc ccaaactcct gatgtatgct acatccaatc tggcatctgg ggtctcatcg     180
cggttcaaag gcagtggatc tgggacagag ttcactctca ccatcagcga cctggagtgt     240
gccgatgctg ccacttacta ctgtcaatat agttattatg gtagtagtta tgttttttgat    300 ttcggcggag ggaccgaggt ggaaatcaaa                                      330

<210> SEQ ID NO 174
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 174
cagagcactg gtattaga          18

<210> SEQ ID NO 175
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 175
caatatagtt attatggtag tagttatgtt tttgat          36

<210> SEQ ID NO 176
<211> LENGTH: 339
<212> TYPE: DNA
<213> ORGANISM: Artificial sequence
<220> FEATURE:
<223> OTHER INFORMATION: Synthetic nucleic acid

<400> SEQUENCE: 176
gagcagtcgg tggaggagtc cggggtcgc ctggtcacgc ctgggacacc cctgacactc       60
acctgcacag cctctggatt ctccctcagt agctactaca tgagctgggt ccgccaggct     120
ccagggaggg gactggaata catcggagtc attaatactg gtggtagcgc agtctacgcg     180
acctggacaa aaggccgatt caccatctcc agaacctcga ccacggtgga tctgaaaatg     240
accggtctga caaccgagga cacggccacc tatttctgtg ccagaggatg gagtaggggt     300
gacttgtggg gccaaggcac cctggtcacc atctcctca                            339

<210> SEQ ID NO 177
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 177
ggattctccc tcagtagcta ctac                                          24

<210> SEQ ID NO 178
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 178
attaatactg gtggtagcgc a                                             21

<210> SEQ ID NO 179
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 179
gccagaggat ggagtagggg tgacttg                                       27

<210> SEQ ID NO 180
<211> LENGTH: 327
<212> TYPE: DNA
<213> ORGANISM: Artificial sequence
<220> FEATURE:
<223> OTHER INFORMATION: Synthetic nucleic acid

<400> SEQUENCE: 180
gagctcgatc tgacccagac accagcctcc gtgtctgaac ctgtgggagg cacagtcacc    60
atcaagtgcc aggccagtga aagcgttgac aactggttag cctggtatca gcagaaacca   120
gggcagcctc ccaaactcct gatctacgat gcatccaaat tggcatctgg ggtcccagat   180
aggttcagcg gcagtggatc tgggacacag ttcactctca ccatcagcgg cgtgcagtgt   240
gacgatgctg ccacttacta ctgtctaggc gttttcatg atggtattaa taatgctttc   300
ggcggaggga ccgaggtgga aatcaaa                                      327

<210> SEQ ID NO 181
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 181
gaaagcgttg acaactgg                                                 18

<210> SEQ ID NO 182
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 182
ctaggcgttt ttcatgatgg tattaataat gct                                33

<210> SEQ ID NO 183
<211> LENGTH: 339
<212> TYPE: DNA

<213> ORGANISM: Artificial sequence
<220> FEATURE:
<223> OTHER INFORMATION: Synthetic nucleic acid

<400> SEQUENCE: 183

```
gagcagtcgg tggaggagtc cgggggtcgc ctggtcacgc ctgggacacc cctgacactc    60
acctgcacag cctctggatt ctccctcagt agctactaca tgagctgggt ccgccaggct   120
ccagggaggg gactggaata catcggagtc attaatactg gtggtagcgc agtctacgcg   180
acctggacaa aaggccgatt caccatctcc agaacctcga ccacggtgga tctgaaaatg   240
accggtctga caaccgagga cacggccacc tatttctgtg ccagaggatg gagtaggggt   300
gacttgtggg gccaaggcac cctggtcacc atctcctca                          339
```

<210> SEQ ID NO 184
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 184

```
ggattctccc tcagtagcta ctac                                           24
```

<210> SEQ ID NO 185
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 185

```
attaatactg gtggtagcgc a                                              21
```

<210> SEQ ID NO 186
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 186

```
gccagaggat ggagtagggg tgacttg                                        27
```

<210> SEQ ID NO 187
<211> LENGTH: 333
<212> TYPE: DNA
<213> ORGANISM: Artificial sequence
<220> FEATURE:
<223> OTHER INFORMATION: Synthetic nucleic acid

<400> SEQUENCE: 187

```
gagctcgata tgacccagac accatcgccc gtgtctgcag ctgtgggagg cacagtcacc    60
atcaagtgcc agtccagtca gaatgtttat gatgacgata ctttatcctg gtatcagcag   120
aaaccagggc agcctcccaa actcctgatc tacgatgcat ccaaattggc atctggggtc   180
ccagataggt tcagcggcag tggatctggg acacagttca ctctcaccat cagcggcgtg   240
cagtgtgacg atgctgccac ttactactgt ctaggcgttt tcatgatgg tattaataat    300 gctttcggcg gagggaccga ggtggaaatc aaa                                 333
```

<210> SEQ ID NO 188
<211> LENGTH: 24

```
<212> TYPE: DNA
<213> ORGANISM: Artificial sequence
<220> FEATURE:
<223> OTHER INFORMATION: Synthetic nucleic acid

<400> SEQUENCE: 188
cagaatgttt atgatgacga tact                                        24

<210> SEQ ID NO 189
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 189
ctaggcgttt ttcatgatgg tattaataat gct                              33

<210> SEQ ID NO 190
<211> LENGTH: 351
<212> TYPE: DNA
<213> ORGANISM: Artificial sequence
<220> FEATURE:
<223> OTHER INFORMATION: Synthetic nucleic acid

<400> SEQUENCE: 190
gagcagtcgg tggagtccgg gggagacctg gtcaagcctg agggatccct gacactcacc   60
tgcacagtct ctggattctc cttcagtagc agctactgga tatgctgggt ccgccaggct  120
ccagggaagg ggctggaatg gatcggatgc attggtactg gtagtggtag cacttactac  180
gggagctggg cgaaaggccg attcaccatc tccaaaacct cgtcgaccac ggtgactctg  240
caaatgacca gtctgacagc cgcggacacg gccacctatt tctgtgtgag agggggctggt  300 tatagttctt ataggttgtg gggcccaggc accctggtca ccatctcctc a           351

<210> SEQ ID NO 191
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 191
ggattctcct tcagtagcag ctactgg                                     27

<210> SEQ ID NO 192
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 192
attggtactg gtagtggtag c                                           21

<210> SEQ ID NO 193
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 193
gtgagagggg ctggttatag ttcttatagg ttg                              33
```

<210> SEQ ID NO 194
<211> LENGTH: 330
<212> TYPE: DNA
<213> ORGANISM: Artificial sequence
<220> FEATURE:
<223> OTHER INFORMATION: Synthetic nucleic acid

<400> SEQUENCE: 194
gagctcgata tgacccagac accagcctcc gtgtctgaac ctgtgggagg cacagtcacc    60
atcaagtgcc aggccagtga aagcgttagc aactggttag cctggtatca gcagaaacca   120
gggcagcgtc ccaagctcct gatctatggt gcatccactc tggaatctgg ggtcccatcg   180
cggttcagcg gcagtggatc tgggacagag ttcactctca ccatcagcaa cctggagtgt   240
gccgatgctg ccacttacta ctgtcaacag ggttatgatt gggataatat cgataatgct   300
ttcggcggag ggaccgaggt ggtggtcaaa                                    330

<210> SEQ ID NO 195
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 195
gaaagcgtta gcaactgg                                                  18

<210> SEQ ID NO 196
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 196
caacagggtt atgattggga taatatcgat aatgct                              36

<210> SEQ ID NO 197
<211> LENGTH: 369
<212> TYPE: DNA
<213> ORGANISM: Artificial sequence
<220> FEATURE:
<223> OTHER INFORMATION: Synthetic nucleic acid

<400> SEQUENCE: 197
cagtcggtga aggagtccgg gggagacctg gtcaagcctg ggcatccct gacactcacc     60 tgcacagcct ctggattctc cttcattagc acctactgga tatgctgggt ccgccaggct   120
ccagggaagg ggctggagtt gatcgcatgc atttatactg gtggtagtgg tagcacttac   180
tacgcgagct gggcgaaagg ccgattcacc atctccaaaa cctcgtcgac cacggtgact   240
ctgcaactga acagtctgac agccgcggac acggccacct atttctgtgc gagagccctc   300
tatgttgatt atgttgatta tgattatata gatttgtggg gcccaggcac cctggtcacc   360
gtctcctca                                                           369

<210> SEQ ID NO 198
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 198

```
ggattctcct tcattagcac ctactgg                                               27

<210> SEQ ID NO 199
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 199
atttatactg gtggtagtgg tagcact                                               27

<210> SEQ ID NO 200
<211> LENGTH: 48
<212> TYPE: DNA
<213> ORGANISM: Artificial sequence
<220> FEATURE:
<223> OTHER INFORMATION: Synthetic nucleic acid

<400> SEQUENCE: 200
gcgagagccc tctatgttga ttatgttgat tatgattata tagatttg                        48

<210> SEQ ID NO 201
<211> LENGTH: 330
<212> TYPE: DNA
<213> ORGANISM: Artificial sequence
<220> FEATURE:
<223> OTHER INFORMATION: Synthetic nucleic acid

<400> SEQUENCE: 201
gagctcgatc tgacccagac accagcctcc gtggaggcag ctgtgggagg cacagtcacc           60
atcaagtgcc aggccagtga aacattggt agtagattag cctggtatca gcagaaacca          120
gggcagcctc ccaagctcct gatctatgct gcatccaatc tggcatctgg ggtctcatcg          180
cggttcaaag gcagtagatc tgggacacag ttcactctca ccatcagcga cctagagtgt          240
gccgatgctg ccatttacta ctgtcaatgt agttattatg gtagtactta tgttttggt           300 ttcggcggag ggaccgaggt ggaaatcaaa                                          330

<210> SEQ ID NO 202
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 202
gagaacattg gtagtaga                                                        18

<210> SEQ ID NO 203
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 203
caatgtagtt attatggtag tacttatgtt tttggt                                     36

<210> SEQ ID NO 204
<211> LENGTH: 360
<212> TYPE: DNA
<213> ORGANISM: Artificial sequence
<220> FEATURE:
```

<223> OTHER INFORMATION: Synthetic nucleic acid

<400> SEQUENCE: 204

```
gagcagtcgg tggaggagtc cgggggagac ctggtcaagc ctgggacatc cctgacactc    60
acttgtaaaa tgtctggatt ctccctcagt agcagctatt ggatatgctg ggtccgccag   120
gctccaggga agggactgga gtggatcgga tgcatcgata gtggtagtgt tggtatcact   180
tactacgcga cctgggcgaa aggccgattc accatctcca gaagcaccag cctaaacacg   240
gtgactctgc aaatgaccag tctgacaggc gcggacacgg ccatgtattt ctctgtgagg   300
catggtgata ttgggctttg gatttgtgg ggcccaggca ccctggtcac catctcctca   360
```

<210> SEQ ID NO 205
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 205

```
ggattctccc tcagtagcag ctattgg                                         27
```

<210> SEQ ID NO 206
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 206

```
atcgatagtg gtagtgttgg tatcact                                         27
```

<210> SEQ ID NO 207
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 207

```
tctgtgaggc atggtgataa ttgggctttg gatttg                               36
```

<210> SEQ ID NO 208
<211> LENGTH: 330
<212> TYPE: DNA
<213> ORGANISM: Artificial sequence
<220> FEATURE:
<223> OTHER INFORMATION: Synthetic nucleic acid

<400> SEQUENCE: 208

```
gagctcgtgc tgacccagac accagcctcc gtgtctgagc ctgtgggagg cacagtcacc    60
atcaagtgcc aggccagtca gagtatcaac agttggttag cctggtatca gcagaaacca   120
ggacagcctc ccaagctcct gatctacaag gcgtccactc tggcatctgg ggtcccatcg   180
cggttcagtg ccagtggatc tgggacagag ttcactctca ccatcaccgg cgtgcagtgc   240
gacgatgctg ccacttacta ctgtcaacat ggctatattc gtggtgatct tgataatgtt   300
ttcggcggag ggaccgaggt ggtggtcaaa                                     330
```

<210> SEQ ID NO 209
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 209
cagagtatca acagttgg                                                     18

<210> SEQ ID NO 210
<211> LENGTH: 36
<212> TYPE: DNA
<213> ORGANISM: Artificial sequence
<220> FEATURE:
<223> OTHER INFORMATION: Synthetic nucleic acid

<400> SEQUENCE: 210
caacatggct atattcgtgg tgatcttgat aatgtt                                 36

<210> SEQ ID NO 211
<211> LENGTH: 21
<212> TYPE: DNA
<213> ORGANISM: Artificial sequence
<220> FEATURE:
<223> OTHER INFORMATION: Synthetic single guide RNA

<400> SEQUENCE: 211
gaacgactag ttaggcgtgt a                                                 21

<210> SEQ ID NO 212
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 212
tgttactatc gcagccctgt                                                   20

<210> SEQ ID NO 213
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 213
gtaggtcccc ccgtgcactg                                                   20

<210> SEQ ID NO 214
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 214
cctgtgacct cagtgcacgg                                                   20

<210> SEQ ID NO 215
<211> LENGTH: 19
<212> TYPE: DNA
<213> ORGANISM: Artificial sequence
<220> FEATURE:
<223> OTHER INFORMATION: Synthetic single guide RNA

<400> SEQUENCE: 215
cttttgggat tacctgcgc                                                    19

<210> SEQ ID NO 216
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 216
aactggcact gggtcgcttt                                               20

<210> SEQ ID NO 217
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 217
taagacctac atcgccagcc                                               20

<210> SEQ ID NO 218
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 218
gaagaacttg caccagcgtc                                               20

<210> SEQ ID NO 219
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 219
gagacttcac actttccgtt                                               20

<210> SEQ ID NO 220
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 220
tacagtacta caactcaagc                                               20

<210> SEQ ID NO 221
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 221
cacgcagagc gcgtatgccc                                               20

<210> SEQ ID NO 222
<211> LENGTH: 20
<212> TYPE: DNA
<213> ORGANISM: Artificial sequence
<220> FEATURE:
<223> OTHER INFORMATION: Synthetic single guide RNA

<400> SEQUENCE: 222
tggcaacatc acccgctcca					20

<210> SEQ ID NO 223
<211> LENGTH: 120
<212> TYPE: PRT
<213> ORGANISM: Artificial sequence
<220> FEATURE:
<223> OTHER INFORMATION: Synthetic amino acid

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Cys Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asp Asn Trp Ala Leu Asp Leu Trp Gly Gln
            100                 105                 110

Gly Thr Leu Val Thr Val Ser Ser
        115                 120

<210> SEQ ID NO 224
<211> LENGTH: 11
<212> TYPE: PRT
<213> ORGANISM: Artificial sequence
<220> FEATURE:
<223> OTHER INFORMATION: Synthetic amino acid

<400> SEQUENCE: 224

Val Arg His Gly Asp Asn Trp Ala Leu Asp Leu
1               5                   10

<210> SEQ ID NO 225
<211> LENGTH: 120
<212> TYPE: PRT
<213> ORGANISM: Artificial sequence
<220> FEATURE:
<223> OTHER INFORMATION: Synthetic amino acid

<400> SEQUENCE: 225

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Cys Trp Val Arg Gln Ala Pro Gly Lys Gly Leu Glu Trp
        35                  40                  45

Val Ser Ser Ile Asp Ser Gly Ser Val Gly Ile Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

```
Tyr Cys Val Arg His Gly Asp Asn Trp Ala Leu Asp Leu Trp Gly Gln
            100                 105                 110

Gly Thr Leu Val Thr Val Ser Ser
        115                 120

<210> SEQ ID NO 226
<211> LENGTH: 120
<212> TYPE: PRT
<213> ORGANISM: Artificial sequence
<220> FEATURE:
<223> OTHER INFORMATION: Synthetic amino acid

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120

<210> SEQ ID NO 227
<211> LENGTH: 11
<212> TYPE: PRT
<213> ORGANISM: Artificial sequence
<220> FEATURE:
<223> OTHER INFORMATION: Synthetic amino acid

<400> SEQUENCE: 227

Ala Arg His Gly Asp Asn Trp Ala Leu Asp Leu
1               5                   10

<210> SEQ ID NO 228
<211> LENGTH: 120
<212> TYPE: PRT
<213> ORGANISM: Artificial sequence
<220> FEATURE:
<223> OTHER INFORMATION: Synthetic amino acid

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Val Ser Ser Ile Asp Ser Gly Ser Val Gly Ile Thr Tyr Tyr Ala Thr
    50                  55                  60

Trp Ala Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120

<210> SEQ ID NO 229
<211> LENGTH: 120
<212> TYPE: PRT
<213> ORGANISM: Artificial sequence
<220> FEATURE:
<223> OTHER INFORMATION: Synthetic amino acid

<400> SEQUENCE: 229

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Val Ile Asp Ser Gly Ser Val Gly Ile Thr Tyr Tyr Ala Thr
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120

<210> SEQ ID NO 230
<211> LENGTH: 120
<212> TYPE: PRT
<213> ORGANISM: Artificial sequence
<220> FEATURE:
<223> OTHER INFORMATION: Synthetic amino acid

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120

<210> SEQ ID NO 231
```

<211> LENGTH: 120
<212> TYPE: PRT
<213> ORGANISM: Artificial sequence
<220> FEATURE:
<223> OTHER INFORMATION: Synthetic amino acid

<400> SEQUENCE: 231

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Ser
            20                  25                  30

Tyr Trp Ile Ser Trp Val Arg Gln Ala Pro Gly Lys Gly Leu Glu Trp
        35                  40                  45

Ile Gly Ser Ile Asp Ser Gly Ser Val Gly Ile Thr Tyr Tyr Ala Thr
    50                  55                  60

Trp Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asp Asn Trp Ala Leu Asp Leu Trp Gly Gln
            100                 105                 110

Gly Thr Leu Val Thr Val Ser Ser
        115                 120

<210> SEQ ID NO 232
<211> LENGTH: 110
<212> TYPE: PRT
<213> ORGANISM: Artificial sequence
<220> FEATURE:
<223> OTHER INFORMATION: Synthetic amino acid

<400> SEQUENCE: 232

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
            100                 105                 110

<210> SEQ ID NO 233
<211> LENGTH: 7
<212> TYPE: PRT
<213> ORGANISM: Artificial sequence
<220> FEATURE:
<223> OTHER INFORMATION: Synthetic amino acid

<400> SEQUENCE: 233

Lys Ala Ser Thr Leu Ala Ser
1               5

<210> SEQ ID NO 234
<211> LENGTH: 11

```
<212> TYPE: PRT
<213> ORGANISM: Artificial sequence
<220> FEATURE:
<223> OTHER INFORMATION: Synthetic amino acid

<400> SEQUENCE: 234

His Gly Tyr Ile Arg Gly Asp Leu Asp Asn Val
1               5                   10

<210> SEQ ID NO 235
<211> LENGTH: 110
<212> TYPE: PRT
<213> ORGANISM: Artificial sequence
<220> FEATURE:
<223> OTHER INFORMATION: Synthetic amino acid

<400> SEQUENCE: 235

Asp Leu Val Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Ser Trp
            20                  25                  30

Leu Ala Trp Tyr Gln Gln Lys Pro Gly Lys Pro Lys Leu Leu Ile
        35                  40                  45

Tyr Lys Ala Ser Thr Leu Ala Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Val Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
                100                 105                 110

<210> SEQ ID NO 236
<211> LENGTH: 110
<212> TYPE: PRT
<213> ORGANISM: Artificial sequence
<220> FEATURE:
<223> OTHER INFORMATION: Synthetic amino acid

<400> SEQUENCE: 236

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Tyr Ile Arg Gly Asp
                85                  90                  95

Leu Asp Asn Val Phe Gly Gly Gly Thr Lys Val Glu Ile Lys
                100                 105                 110

<210> SEQ ID NO 237
<211> LENGTH: 110
<212> TYPE: PRT
<213> ORGANISM: Artificial sequence
<220> FEATURE:
<223> OTHER INFORMATION: Synthetic amino acid
```

<400> SEQUENCE: 237

| Asp | Ile | Gln | Met | Thr | Gln | Ser | Pro | Ser | Thr | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Ser | Ile | Asn | Ser | Trp |
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Lys | Ala | Ser | Thr | Leu | Ala | Ser | Gly | Val | Pro | Ser | Arg | Phe | Ser | Gly |
| | 50 | | | | | 55 | | | | | 60 | | | | |

| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |

| Asp | Asp | Phe | Ala | Thr | Tyr | Tyr | Cys | Gln | His | Gly | Tyr | Ile | Arg | Gly | Asp |
| | | | | 85 | | | | | 90 | | | | | 95 | |

| Leu | Asp | Asn | Val | Phe | Gly | Gly | Gly | Thr | Lys | Val | Glu | Ile | Lys |
| | | | 100 | | | | | 105 | | | | | 110 |

<210> SEQ ID NO 238
<211> LENGTH: 236
<212> TYPE: PRT
<213> ORGANISM: Homo sapiens

<400> SEQUENCE: 238

| Gly | Pro | Leu | Pro | Lys | Pro | Thr | Leu | Trp | Ala | Glu | Pro | Gly | Ser | Val | Ile |
| 1 | | | | 5 | | | | | 10 | | | | | 15 | |

| Ser | Trp | Gly | Asn | Ser | Val | Thr | Ile | Trp | Cys | Gln | Gly | Thr | Leu | Glu | Ala |
| | | | 20 | | | | | 25 | | | | | 30 | | |

| Arg | Glu | Tyr | Arg | Leu | Asp | Lys | Glu | Glu | Ser | Pro | Ala | Pro | Trp | Asp | Arg |
| | | | 35 | | | | | 40 | | | | | 45 | | |

| Gln | Asn | Pro | Leu | Glu | Pro | Lys | Asn | Lys | Ala | Arg | Phe | Ser | Ile | Pro | Ser |
| | | | 50 | | | | | 55 | | | | | 60 | | |

| Met | Thr | Glu | Asp | Tyr | Ala | Gly | Arg | Tyr | Arg | Cys | Tyr | Tyr | Arg | Ser | Pro |
| 65 | | | | | 70 | | | | | 75 | | | | | 80 |

| Val | Gly | Trp | Ser | Gln | Pro | Ser | Asp | Pro | Leu | Glu | Leu | Val | Met | Thr | Gly |
| | | | | 85 | | | | | 90 | | | | | 95 | |

| Ala | Tyr | Ser | Lys | Pro | Thr | Leu | Ser | Ala | Leu | Pro | Ser | Pro | Leu | Val | Thr |
| | | | 100 | | | | | 105 | | | | | 110 | | |

| Ser | Gly | Lys | Ser | Val | Thr | Leu | Leu | Cys | Gln | Ser | Arg | Ser | Pro | Met | Asp |
| | | | 115 | | | | | 120 | | | | | 125 | | |

| Thr | Phe | Leu | Leu | Ile | Lys | Glu | Arg | Ala | Ala | His | Pro | Leu | Leu | His | Leu |
| | | | 130 | | | | | 135 | | | | | 140 | | |

| Arg | Ser | Glu | His | Gly | Ala | Gln | Gln | His | Gln | Ala | Glu | Phe | Pro | Met | Ser |
| 145 | | | | | 150 | | | | | 155 | | | | | 160 |

| Pro | Val | Thr | Ser | Val | His | Gly | Gly | Thr | Tyr | Arg | Cys | Phe | Ser | Ser | His |
| | | | | 165 | | | | | 170 | | | | | 175 | |

| Gly | Phe | Ser | His | Tyr | Leu | Leu | Ser | His | Pro | Ser | Asp | Pro | Leu | Glu | Leu |
| | | | 180 | | | | | 185 | | | | | 190 | | |

| Ile | Val | Ser | Gly | Ser | Leu | Glu | Asp | Pro | Arg | Pro | Ser | Pro | Thr | Arg | Ser |
| | | | 195 | | | | | 200 | | | | | 205 | | |

| Val | Ser | Thr | Ala | Ala | Gly | Pro | Glu | Asp | Gln | Pro | Leu | Met | Pro | Thr | Gly |
| | | | 210 | | | | | 215 | | | | | 220 | | |

| Ser | Val | Pro | His | Ser | Gly | Leu | Arg | Arg | His | Trp | Glu |
| 225 | | | | | 230 | | | | | 235 | |

LILRB4 ANTIBODIES AND USES THEREOF

PRIORITY CLAIM

This application is a national phase application under 35 U.S.C. § 371 of International Application No. PCT/US2019/050727, filed Sep. 12, 2019, which claims benefit of priority to U.S. Provisional Application Ser. No. 62/730,715, filed Sep. 13, 2018, the entire contents of each of which are hereby incorporated by reference.

SEQUENCE LISTING

The sequence listing that is contained in the file named "UTFH_P0349WO_ST25", which is 4 KB (as measured in Microsoft Windows) and was created on Sep. 9, 2019, is filed herewith by electronic submission and is incorporated by reference herein.

BACKGROUND

1. Field

The present disclosure relates generally to the fields of medicine, oncology, and immunology. More particular, the disclosure relates to antibodies that bind to LILRBs and can treat cancers, including leukemia.

2. Description of Related Art

Acute myeloid leukaemia (AML) is the most common acute leukaemia of adults and a common pediatric cancer. Current treatment for AML involves intensive cytotoxic chemotherapy, often times followed by myeloablative conditioning and stem cell transplant. However, despite treatment, most patients relapse or succumb to disease within 5 years. To effectively treat AML, new molecular targets and therapeutic approaches must be identified. Recently, it has been shown that inhibitory leukocyte immunoglobulin-like receptors (LILRBs) and a related immunoreceptor tyrosine-based inhibitory motif (ITIM)-containing receptor, LAIR1, have tumour-promoting functions in various hematopoietic and solid cancer cells. ITIM-containing receptors are expressed on a wide range of immune cells and transduce signals by recruitment of phosphatases SHP-1, SHP-2, or SHIP, leading to negative regulation of immune cell activation. Similar to CTLA4 and PD-1, LILRBs are considered immune checkpoint factors.

LILRBs may inhibit activities of a number of immune cell types facilitating tumour immune escape. LILRB4 is expressed on monocytes, macrophages, and dendritic cells and can inhibit innate immunity in a cell-autonomous manner and suppress T cell activation through an indirect mechanism. LILRB4 is a specific marker for monocytic AML including refractory and relapsed disease. LILRB1-5 are primate and human specific, while there are two mouse orthologues: paired immunoglobulin-like receptor B (PirB) and gp49B1. The related immunoreceptor tyrosine-based inhibitory motif (ITIM)-containing receptor, LAIR1, has both human and mouse versions of the protein. Because of the limited value of mouse models and the fact that ligands for several LILRBs including LILRB4 are unknown, the biological function and clinical significance of these receptors remain poorly understood.

SUMMARY

Thus, in one aspect, the present disclosure provides an isolated monoclonal antibody or an antigen-binding fragment thereof that binds specifically to LILRB4. In certain embodiments, the antibody or antigen-binding fragment, when bound to LILRB4, modulates the activation of LILRB4. In certain embodiments, the antibody or antigen-binding fragment, when bound to LILRB4, activates LILRB4. In certain embodiments, the antibody or antigen-binding fragment, when bound to LILRB4, suppresses activation of LILRB4. In certain embodiments, the antibody or antigen-binding fragment, when bound to LILRB4, specifically blocks binding of ApoE to LILRB4.

In certain embodiments, the antibody or an antigen-binding fragment thereof comprising (a) a heavy chain (HC) variable region (VH) comprising the following complementary determining regions (CDRs): a heavy chain CDR (HC-CDR) 1 that is a CDR1 in SEQ ID NOS: 1, 8, 15, 22, 29, 36, 43, 50, 57, 64, 71, 78, 85, 92, 99, 223, 225, 226, 228, 229, 230 or 231, a HC-CDR2 that is a CDR2 in SEQ ID NOS: 1, 8, 15, 22, 29, 36, 43, 50, 57, 64, 71, 78, 85, 92, 99, 223, 225, 226, 228, 229, 230 or 231, and a HC-CDR3 that is a CDR3 in SEQ ID NOS: 1, 8, 15, 22, 29, 36, 43, 50, 57, 64, 71, 78, 85, 92, 99, 223, 225, 226, 228, 229, 230 or 231, and variants thereof wherein one or more of the HC-CDRs has one, two, or three amino acid substitutions, additions, deletions, or combinations thereof; and (b) a light chain (LC) variable region (VL) comprising the following CDRs: a light chain CDR (LC-CDR) 1 that is a CDR1 in SEQ ID NOS: 5, 12, 19, 26, 33, 40, 47, 54, 61, 68, 75, 82, 89, 96, 103, 232, 235, 236 or 237, a LC-CDR2 that is a CDR2 in SEQ ID NOS: 5, 12, 19, 26, 33, 40, 47, 54, 61, 68, 75, 82, 89, 96, 103, 232, 235, 236 or 237, and a LC-CDR3 that is a CDR3 in SEQ ID NOS: 5, 12, 19, 26, 33, 40, 47, 54, 61, 68, 75, 82, 89, 96, 103, 232, 235, 236 or 237, and variants thereof wherein one or more of the LC-CDRs has one, two, or three amino acid substitutions, additions, deletions, or combinations thereof. In certain embodiments, each CDR is defined in accordance with Kabat definition, the Chothia definition, the combination of Kabat definition and Chothia definition, the AbM definition, or the contact definition of CDR.

In certain embodiments, the antibody comprises the heavy chain variable region comprising: a HC-CDR1 having the amino acid sequence set forth in SEQ ID NO: 2, 9, 16, 23, 30, 37, 44, 51, 58, 65, 72, 79, 86, 93, or 100, a HC-CDR2 having the amino acid sequence set forth in SEQ ID NO: 3, 10, 17, 24, 31, 38, 45, 52, 59, 66, 73, 80, 87, 94, or 101, and a HC-CDR3 having the amino acid sequence set forth in SEQ ID NO: 4, 11, 18, 25, 32, 39, 46, 53, 60, 67, 74, 81, 88, 95, 102, 224 or 227.

In certain embodiments, the antibody comprises the light chain variable region comprising: a LC-CDR1 having the amino acid sequence set forth in SEQ ID NO: 6, 13, 20, 27, 34, 41, 48, 55, 62, 69, 76, 83, 90, 97, or 104, a LC-CDR2 having the amino acid sequence of SAS, KAS, GAS, ATS, DAS or AAS or the amino acid sequence set forth in SEQ ID NO: 233, and a LC-CDR3 having the amino acid sequence set forth in SEQ ID NOS: 7, 14, 21, 28, 35, 42, 49, 56, 63, 70, 77, 84, 91, 98, 105 or 234.

In certain embodiments, the antibody is characterized by clone-paired heavy chain and light chain having amino acid sequences at least about 70%, 80%, 90%, or 95% identity to the clone-paired sequences from FIGS. 28A-28C and 30A-30C. In certain embodiments, the antibody comprises a heavy chain variable region having the amino acid sequence set forth in SEQ ID NO: 1, 8, 15, 22, 29, 36, 43, 50, 57, 64, 71, 78, 85, 92, 99, 223, 225, 226, 228, 229, 230 or 231. In certain embodiments, the antibody comprises a light chain variable region having the amino acid sequence set forth in SEQ ID NO: 5, 12, 19, 26, 33, 40, 47, 54, 61, 68, 75, 82, 89, 96, 103, 232, 235, 236 or 237. In certain embodiments, the antibody characterized by clone-paired heavy chain and light chain having CDRs of 0, 1 or 2 amino acid differences from the CDRs in Tables 1 and 2.

In another aspect, the present disclosure provides an isolated monoclonal antibody or an antigen-binding fragment thereof, which competes for the same epitope with an antibody having clone-paired heavy and light chain CDR sequences from Tables 1 and 2. In certain embodiments, the antibody competes for the same epitope with an antibody having clone-paired heavy and light chain variable regions from FIGS. 28A-28C and 30A-30C.

In certain embodiments, the epitope bound by the antibody or antigen-binding fragment is located within the linker region between the D1 and D2 domain of human LILRB4. In certain embodiments, the epitope comprises at least one amino acid within one or more of the amino acid sequences of LILRB4 listed in Table 9. In certain embodiments, the epitope comprises at least one amino acid within one or more of the amino acid sequences selected from W18, G96, A97, Y98, S99, K100, Q122, S123, R124, S125, P126, H153 and Q154 of SEQ ID NO: 238 (D1 and D2 domains of human LILRB4 protein).

In certain embodiments, the isolated monoclonal antibody described herein is a chimeric, humanized, or human antibody. In certain embodiments, isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')2 fragment, or Fv fragment.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody and recovering the antibody.

In another aspect, there is provided a chimeric antigen receptor (CAR) protein comprising an antigen-binding fragment as provided herein.

In another aspect, there is provided an isolated nucleic acid that encodes a CAR protein as provided herein.

In another aspect, there is provided an engineered cell comprising the isolated nucleic acid as provided herein. In certain embodiments, the cell is a T cell, NK cell, or myeloid cell.

In another aspect, there is provided a method of treating or ameliorating the effects of a cancer in a subject. The method may comprise administering to the subject a therapeutically effective amount of the antibody or an antigen-binding fragment thereof or an engineered cell as provided herein. In certain embodiments, the cancer is acute myeloid leukemia. In certain embodiments, the antibody or an antigen-binding fragment thereof is administered intravenously, intra-arterially, intra-tumorally or subcutaneously. In certain embodiments, the antibody or an antigen-binding fragment thereof comprises an antitumor drug (e.g., a toxin, a radio-isotope, a cytokine, or an enzyme) linked thereto. In certain embodiments, the isolated monoclonal antibody or an antigen binding fragment thereof is conjugated to a liposome or nanoparticle.

In yet another aspect, there is provided a method of detecting a cancer cell or cancer stem cell in a sample or subject. In certain embodiments, the method comprises contacting a subject or a sample from the subject with the antibody or an antigen-binding fragment thereof as provided herein and detecting binding of said antibody to a cancer cell or cancer stem cell in said subject or sample. The sample can be a body fluid or biopsy. The sample can be blood, sputum, tears, saliva, mucous, serum, urine or feces. In certain embodiments, the detection comprises immunohistochemistry, flow cytometry, FACS, ELISA, RIA or Western blot. In certain embodiments, isolated monoclonal antibody or an antigen binding fragment thereof further comprises a label (e.g., a peptide tag, an enzyme, a magnetic particle, a chromophore, a fluorescent molecule, a chemo-luminescent molecule, or a dye). In certain embodiments, the isolated monoclonal antibody or an antigen binding fragment thereof is conjugated to a liposome or nanoparticle.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A illustrates the percentage of amino acid sequence identity among the D1 domain of LILRB and LILRA family members. FIG. 1B illustrates the phylogenetic tree for the D1 domain of LILRB and LILRA family members.

FIG. 2A, LILRB4 surface expression was quantified by flow cytometry analysis of samples from 105 patients. FIG. 2B, LILRB4 surface expression was compared on normal monocytes and neoplastic monocytes from the same AML patients (n=6). MFI: mean fluorescence intensity. FIG. 2C, Autologous T cells (pT, patient T cells) isolated from a patient with monocytic AML (AML #19) or allogeneic T cells (nT, normal T cells)

isolated from a healthy donor were incubated with irradiated LILRB4+ or LILRB4− (B4+ or B4−) primary leukemia cells from patient AML #19 (n=3 biologically independent samples, mean±s.e.m.). The absolute T cell numbers of different subsets ($CD3^+CD8^-CD4^-$, $CD3^+CD8^+CD4^+$, $CD3^+CD8^-CD4^+$, and $CD3^+CD8^+CD4^-$) are shown in different colors of the stacking bar graphs.

Figures 1A, 1B:
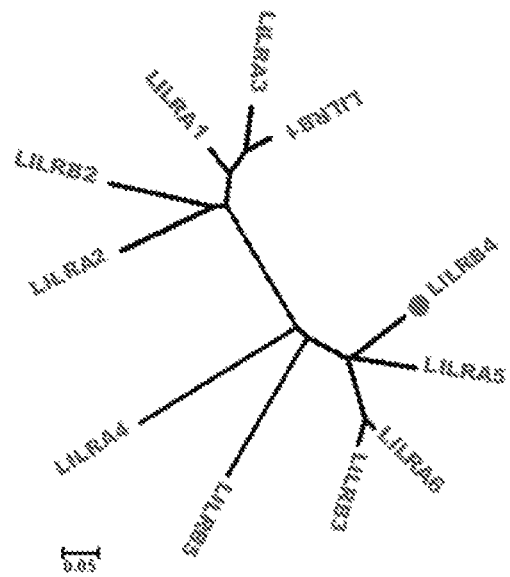
FIGS. 1A-1B illustrate the sequence conservation among LILRA and LILRB family members.
Figure 2A:
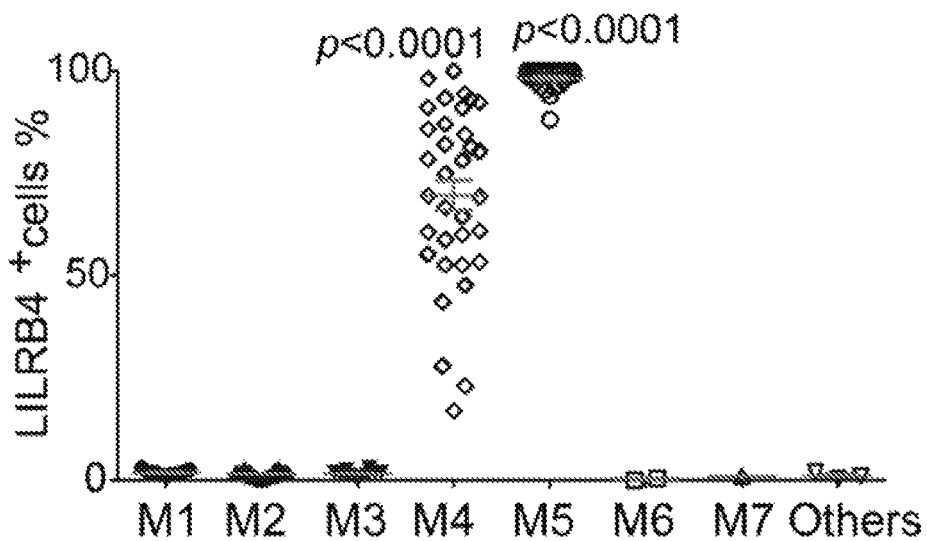
FIGS. 2A-2K illustrate that LILRB4 expressed on leukemia cells suppresses T cell proliferation.
Figure 2B:
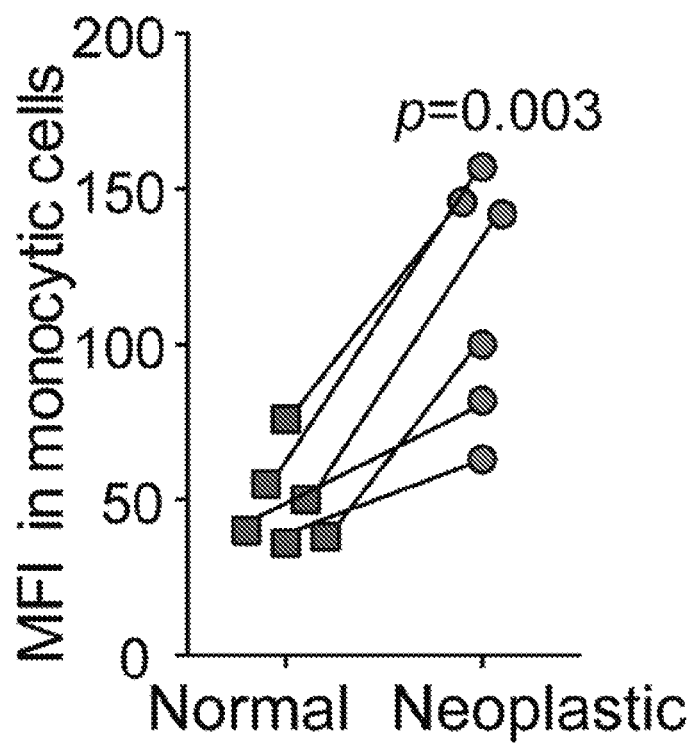
Figure 2C:
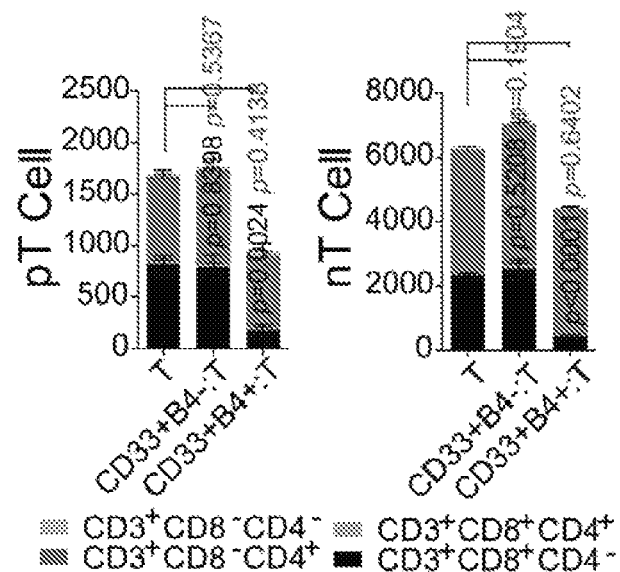
Figure 2D:
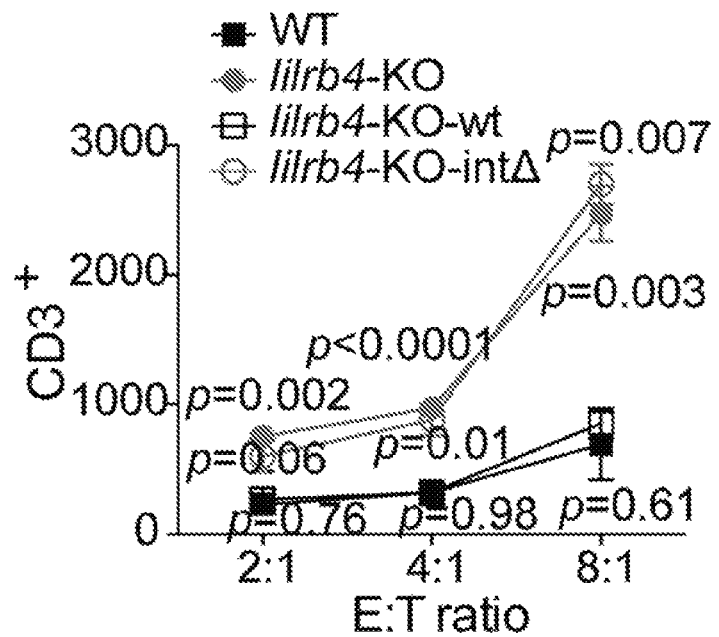
Figures 2E, 2F:
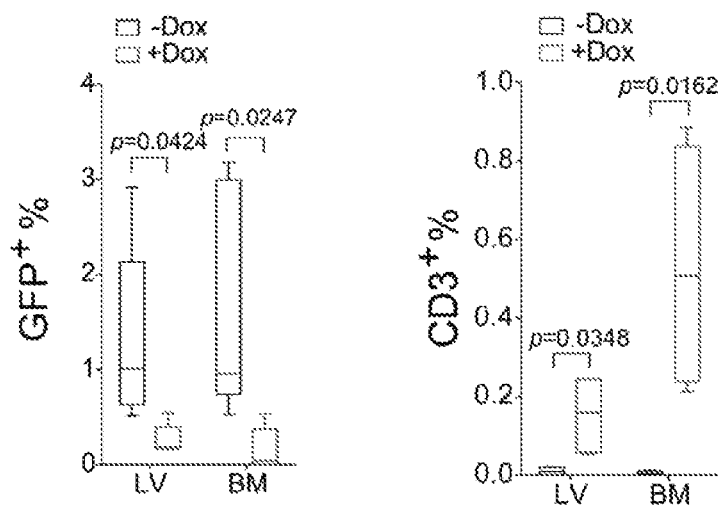
Figure 2G:
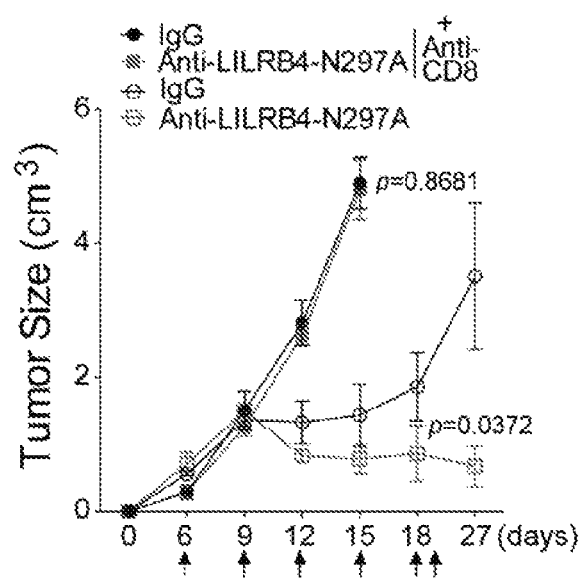
Figure 2H:
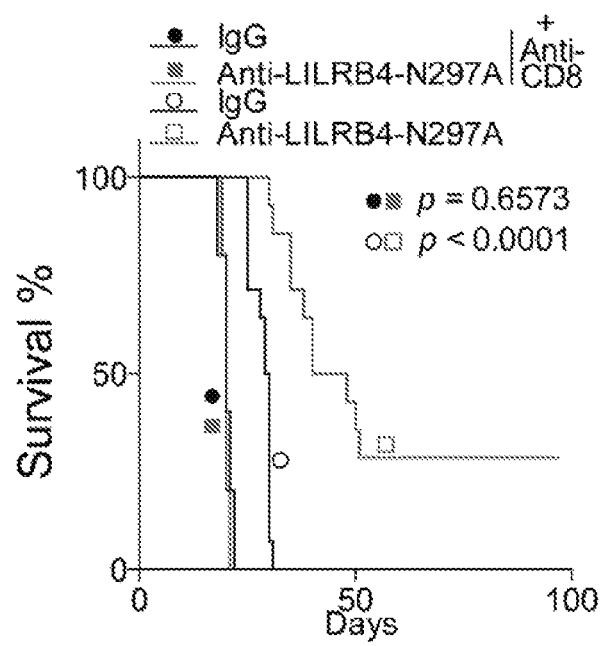
Figure 2I:
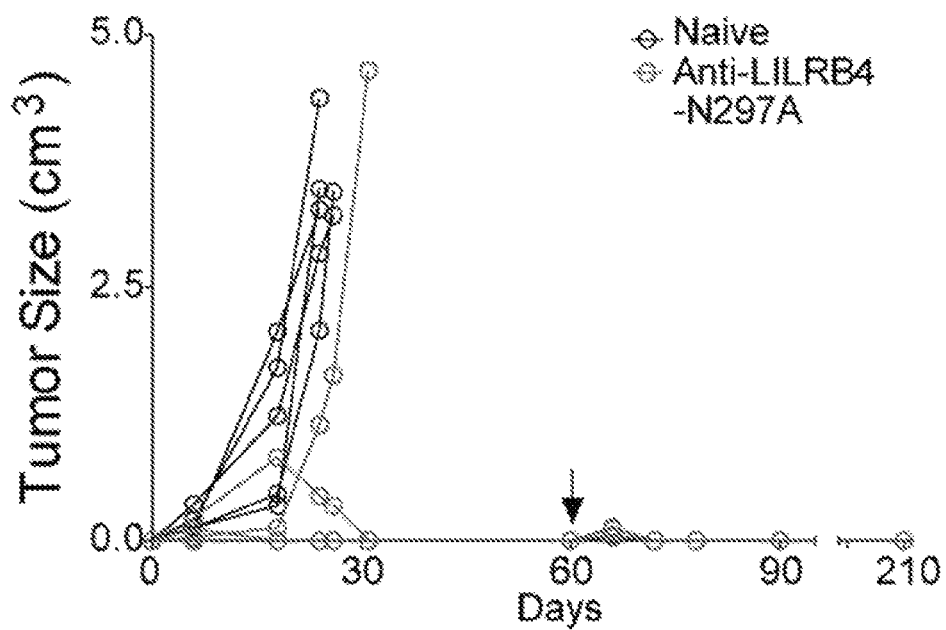
Figure 2J:
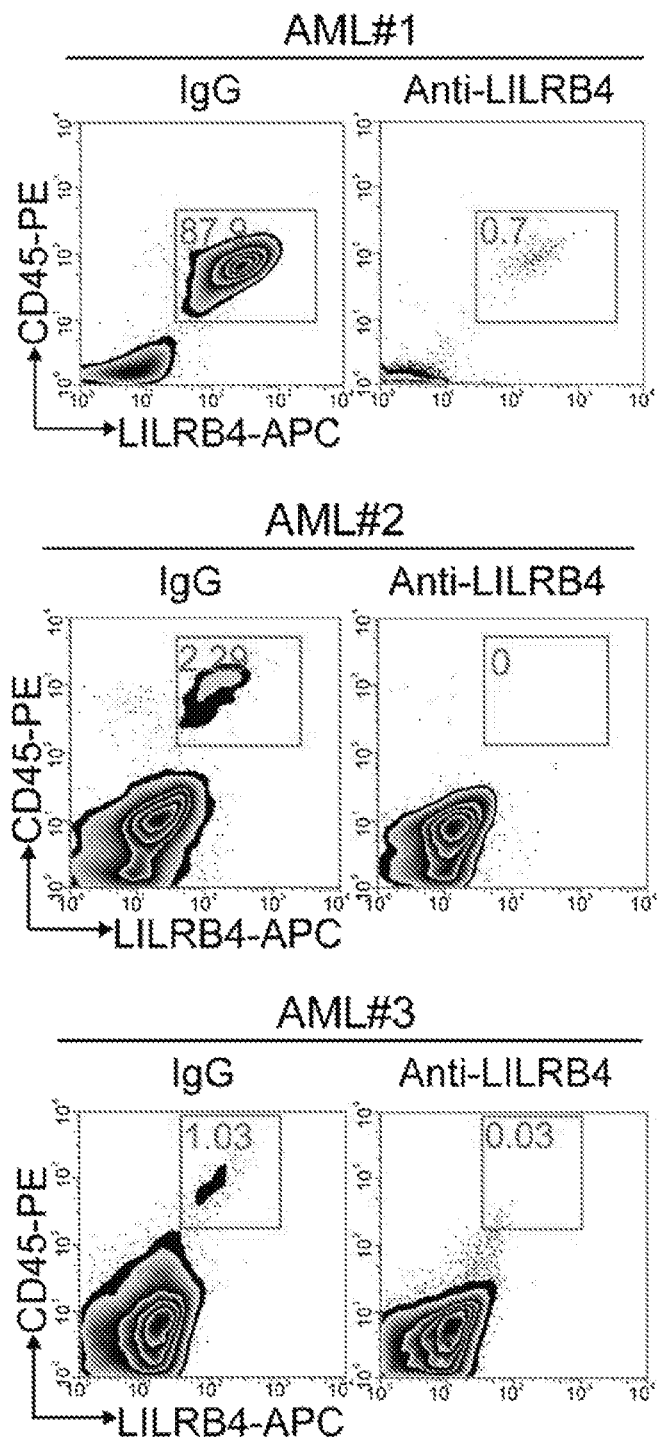
Figure 2K:
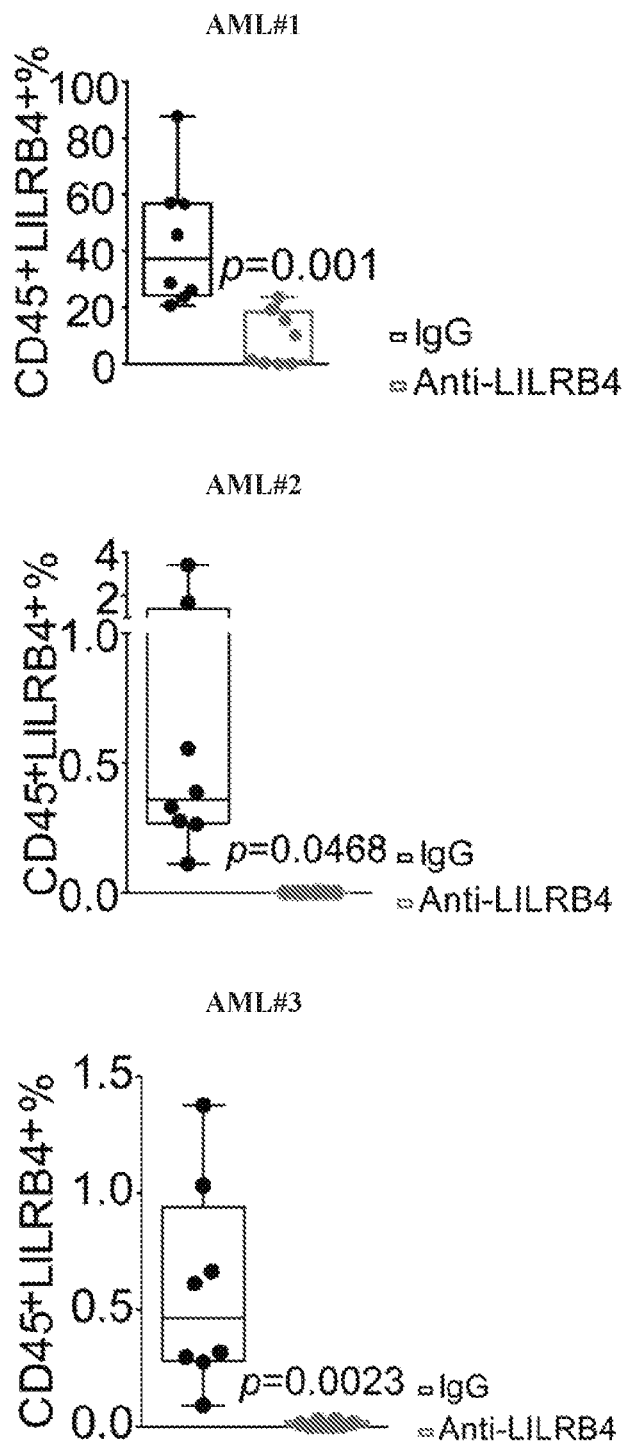

FIG. 2D, T cells (E: effector cells) isolated from healthy donors were incubated with indicated irradiated THP-1 cells (T: target cells) in cell-contact manner. The numbers of CD3+ T cells are shown at different E:T ratios. FIGS. 2E-2F, Engraftment of human T cells and i.v. transplanted Doxycycline (Dox)-inducible lilrb-knockout THP-1 cells ($GFP^+$) in NOD-SCID IL2Rγ-null (NSG) mice (n=5). LV, liver; BM, bone marrow. FIG. 2G, Tumor growth of subcutaneously implanted human LILRB4-expressing mouse AML C1498 cells (hlilrb4-C1498) in C57BL/6 mice with anti-LILRB4-N297A antibody or control antibody treatment (n=5), in the absence or presence of anti-CD8. FIG. 2H, Survival curve of subcutaneous hlilrb4-C1498-tumor-bearing mice (n=12). FIG. 2I, Adoptive transplantation of spleen cells from control mice or tumor-bearing mice that were cured by anti-LILRB4-N297A treatment (n=5). Tumor size was monitored as a function of time. Arrow indicates day of re-challenge with 3-times number of AML cells in mice that had eliminated leukemia (n=4). FIGS. 2J-2K, Representative flow plots and quantification of percent of $CD45^+$ $LILRB4^+$ cells in bone marrow from mice xenografted with human primary monocytic AML cells after treatment with anti-LILRB4 antibody or control IgG (n=8 biologically independent samples). Experiment repeated for 16 independent patient samples with similar results.

FIGS. 3A-3D show that LILRB4 promotes AML cell migration and infiltration. WT and lilrb4-KO THP-1 cells (GFP+) were used, with or without reconstitution of LILRB4 (wt) or LILRB4 lacking the intracellular domain (intΔ). The numbers of leukemia cells (GFP+) in bone marrow (BM), liver (LV), and spleen (SP) were determined by flow cytometry and normalized to the number in peripheral blood. FIG. 3A, Comparison of the short-term (20 hrs) infiltration of indicated WT or modified THP-1 cells in NSG mice (n=5). FIGS. 3B-3D, Comparison of the short-term (20 hrs) infiltration of human primary monocytic AML cells in NSG mice (n=5) after treatment with anti-LILRB4 antibody or IgG control. n.s., not significant; p values were from two-tailed student t-test.

Figure 4A:
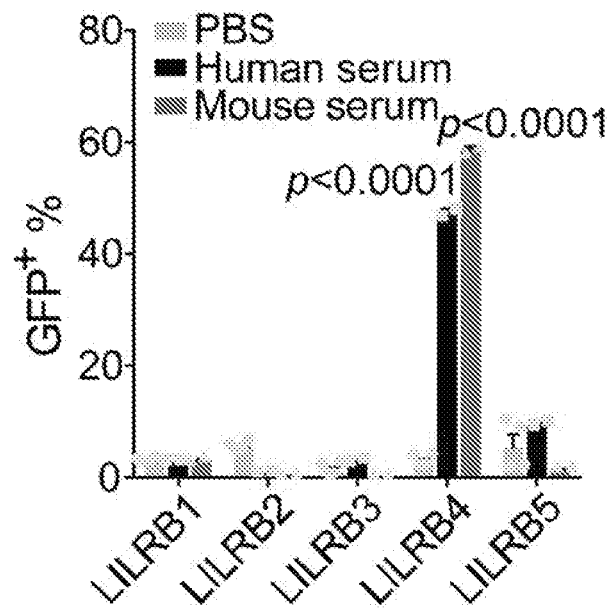
Figure 4B:
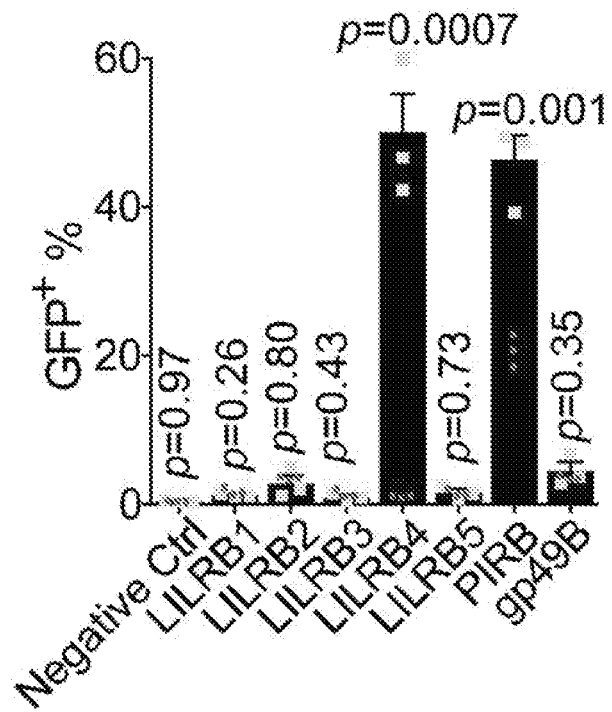
Figures 4C, 4D:
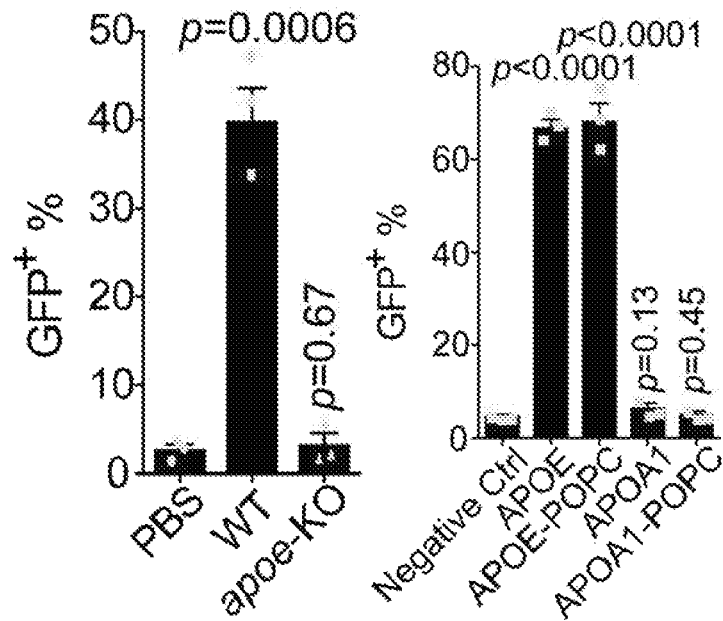
Figure 4E:
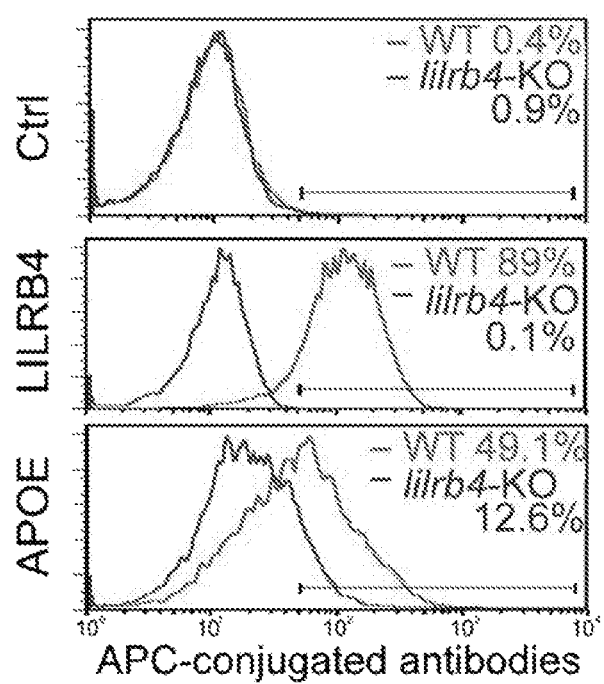
Figure 4F:
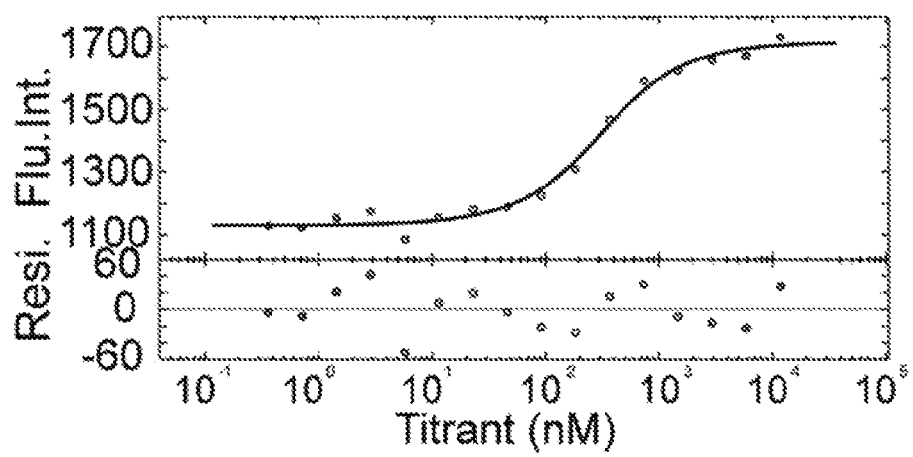
Figure 4G:
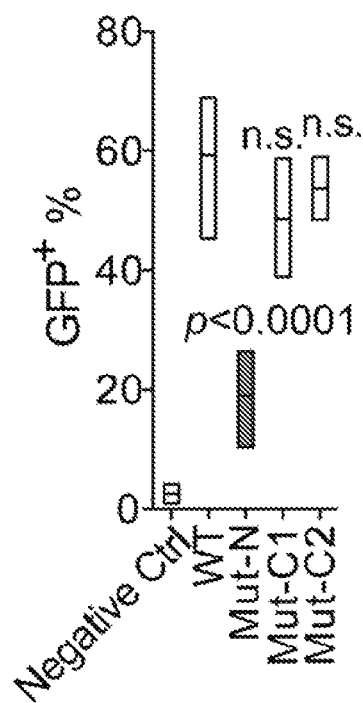
Figures 4K, 4L:
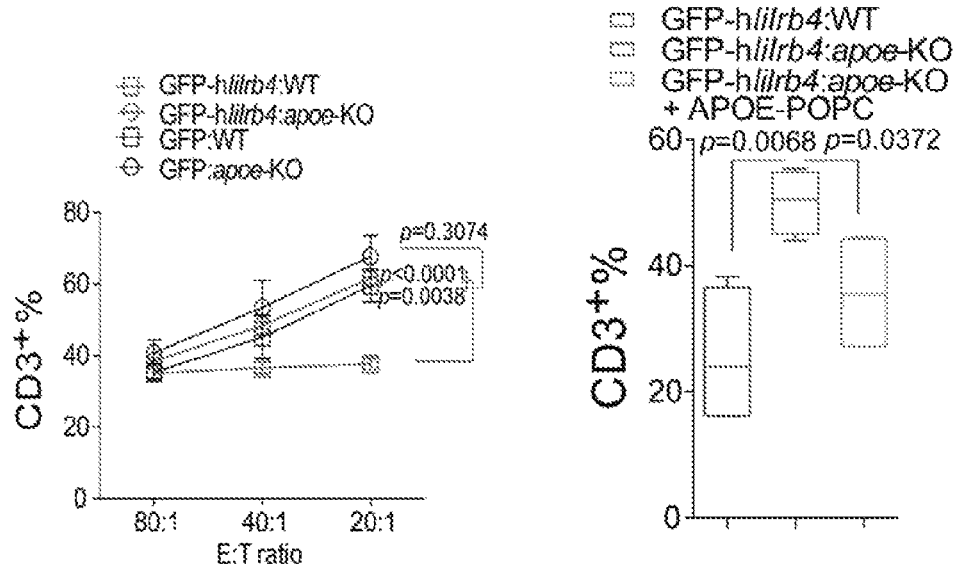
Figure 4M:
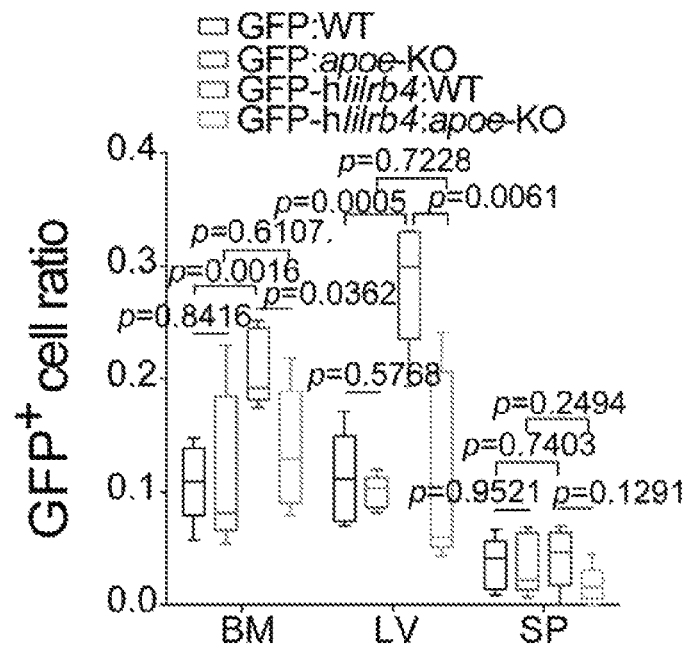

FIGS. 4A-4M show that APOE is an extracellular binding protein of LILRB4. FIG. 4A, Percentages of indicated LILRB reporter cells activated ($GFP^+$) in the presence of 10% human serum, 10% mouse serum, or PBS control. FIG. 4B, Percentages of indicated LILRB reporter cells activated by recombinant APOE (10 μg/ml). FIG. 4C, Percentages of LILRB4 reporter cells activated by 10% mouse serum collected from wild-type or apoe-knockout KO mice or PBS control. FIG. 4D, Percentages of LILRB4 reporter cells activated by 10 μg/ml of APOE, APOE-POPC, APOA1, or APOA1-POPC. FIG. 4E, Binding of His-tagged APOE to WT and lilrb4-KO THP-1 cells. FIG. 4F, Binding kinetics of human His-tagged APOE-3 to LILRB4-ECD were measured using microscale thermophoresis (MST). Upper panel: fluorescence intensity (Flu.Int.) plot and regression of the binding; down panel: the corresponding residuals (Resi.) versus fits plot. FIG. 4G, Percentages of LILRB4 reporter cells activated by WT and mutant APOE proteins. Mut-N, R142A/K143A/R145A/K146A/R147A/R150A; Mut-C1, deletion of residues 245-299; and Mut-C2, deletion of residues 279-299. FIG. 4H, Percentages of indicated LILRB4 mutant reporter cells activated by APOE proteins. Data on mutants that interfere with binding are highlighted in red in (FIGS. 4G-4H). FIG. 4I, T cells isolated from healthy donors were incubated with indicated irradiated THP-1 cells without (WT) or with lilrb4 or apoe gene knockout (lilrb4-KO, apoe-KO-1, apoe-KO-2). T cells were analyzed by flow cytometry after 7 days. FIGS. 4J-4L, C57bl/6 mouse spleen cells (as effector cells or E) were incubated with irradiated human lilrb4-expressing (GFP-hlilrb4) or control (GFP) C1498 cells (as target cells or T) at indicated E:T ratios. Cells were supplemented with 5% serum collected from WT or apoe-KO mice, cultured with anti-CD3/CD28-coated beads for 60 hours, and then stained with anti-CD3 antibody. Shown are representative flow plots from samples at E:T of 20:1 (FIG. 4J), percentages of $CD3^+$ T cells (FIG. 4K), and the effects of APOE-POPC rescue of apoe-KO serum (FIG. 4L). FIG. 4M, Forced expression of human lilrb4 in mouse leukemia C1498 cells increases leukemia cell infiltration in WT recipient mice but not in apoe-KO recipient mice (n=5). n.s., not significant; p values were from two-tailed student t-test.

Figure 5A:
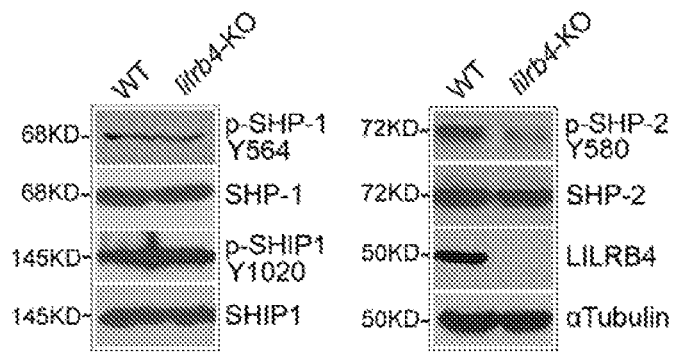
Figure 5B:
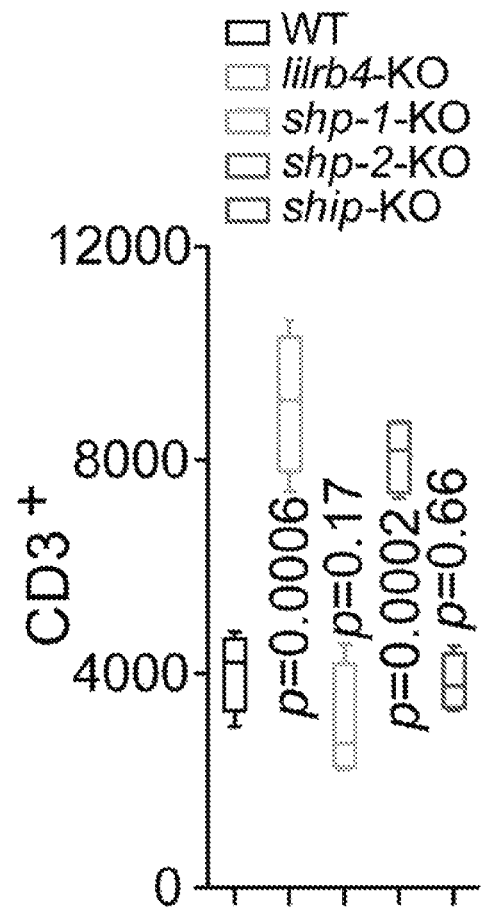
Figure 5C:
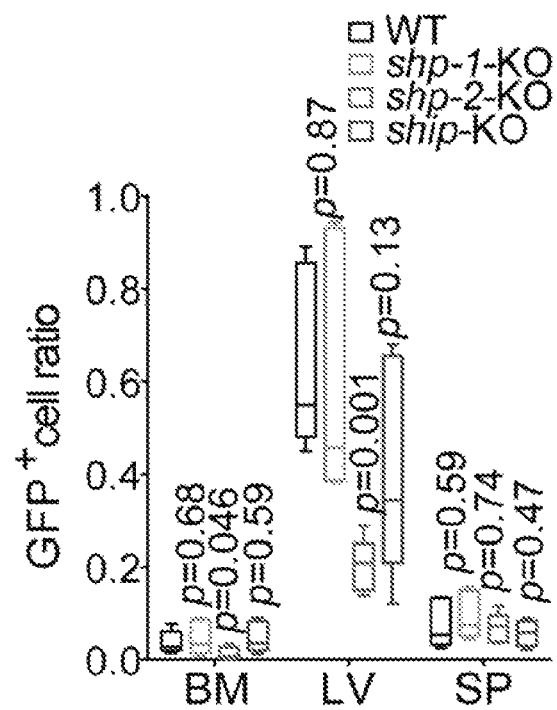
Figure 5D:
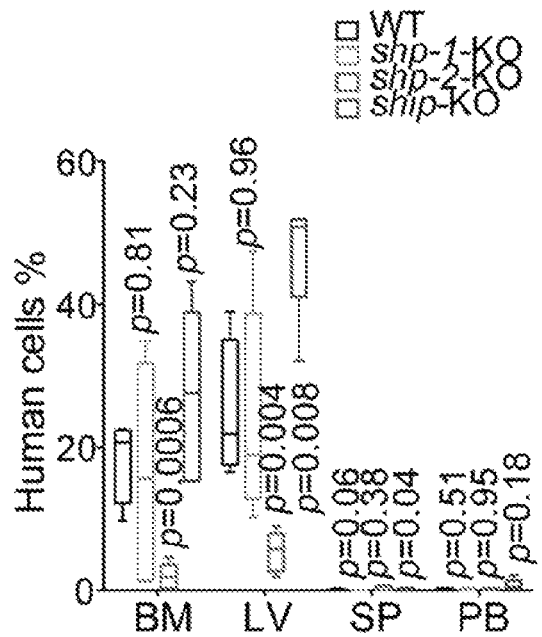
Figure 5E:
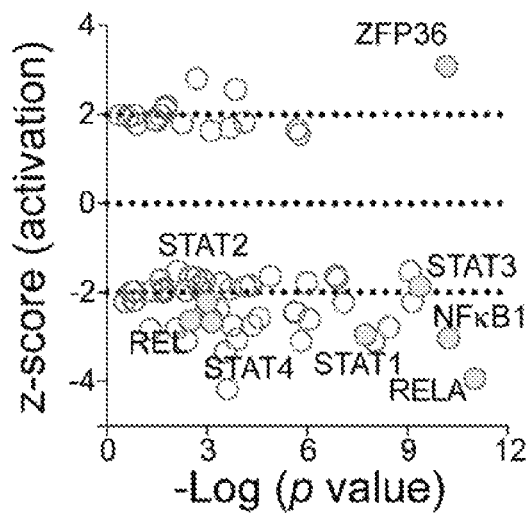
Figure 5F:
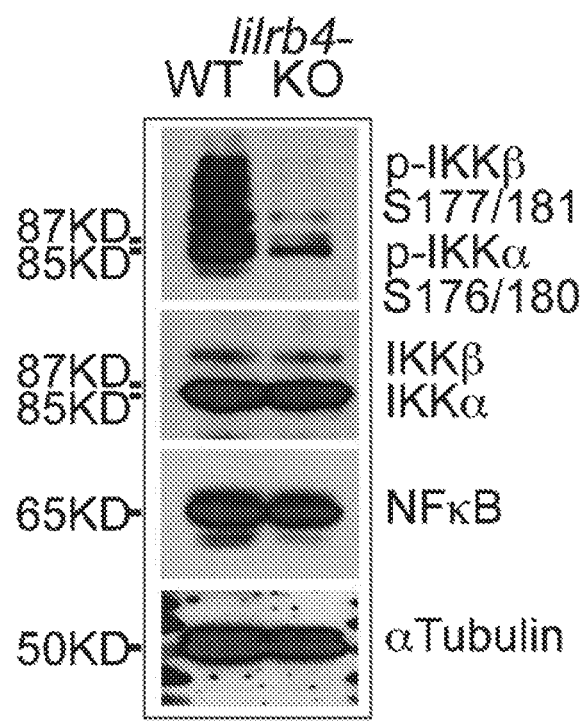
Figure 5G:
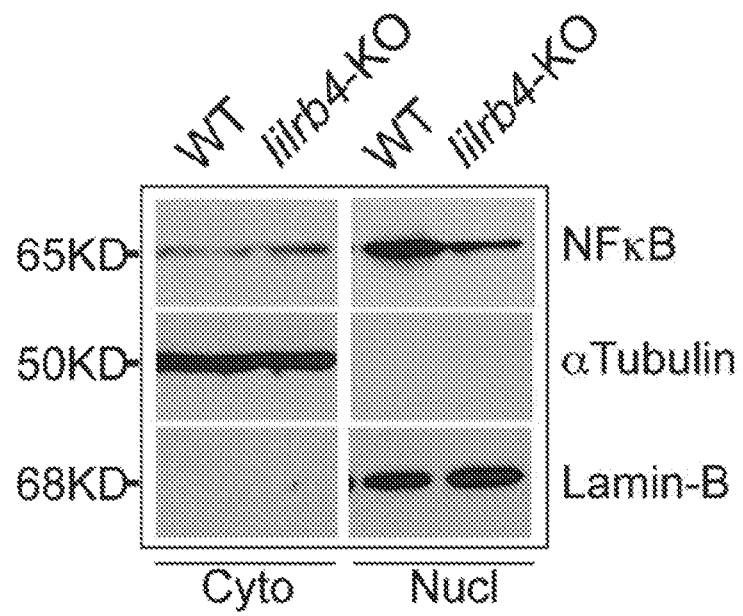
Figure 5H:
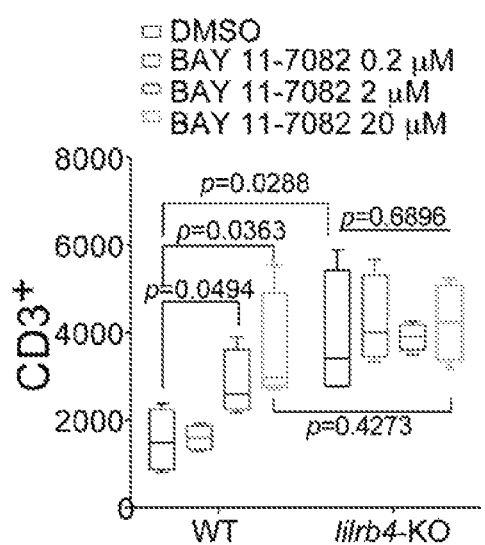
Figure 5I:
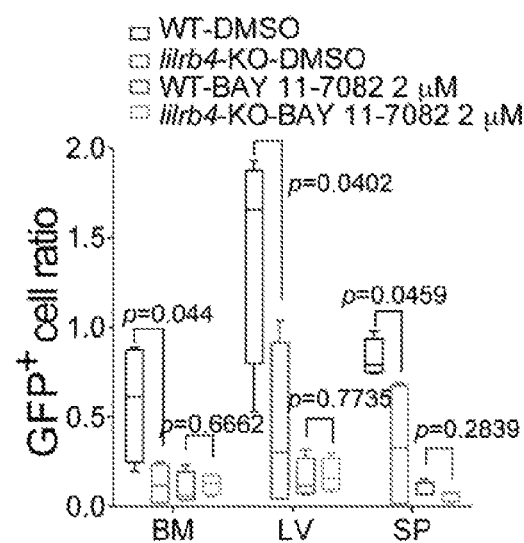
Figure 5J:
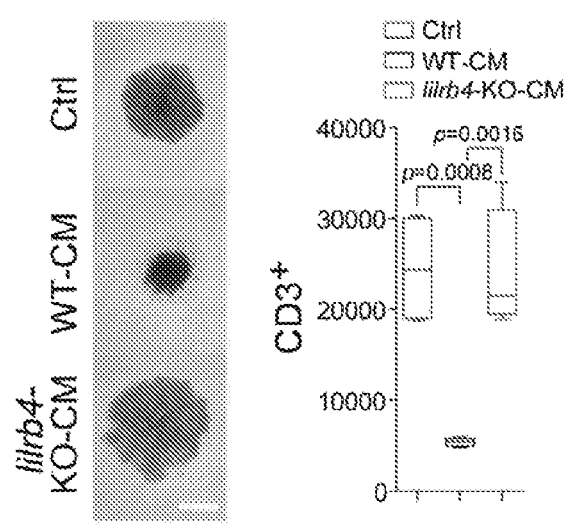
Figures 5K, 5L:
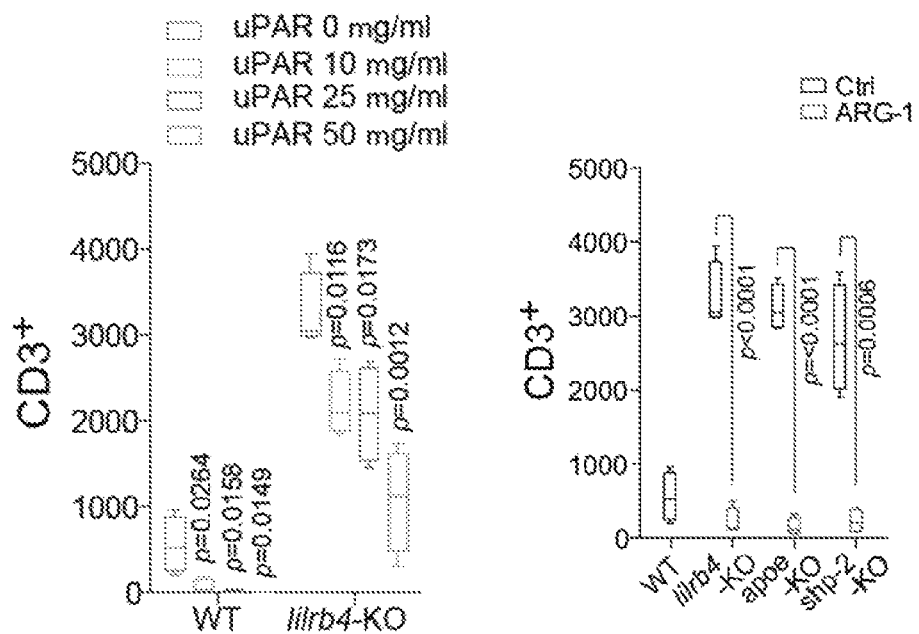
Figure 5M:
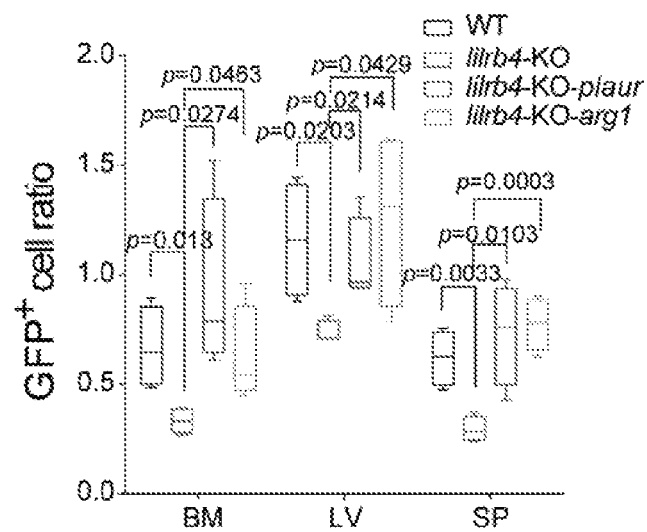

FIGS. 5A-5M show that LILRB4-mediated intracellular signaling controls AML cell migration and T cell suppression. FIG. 5A, Expression and phosphorylation of three phosphatases in wild-type and lilrb4-KO THP-1 cells. FIG. 5B, Primary T cells and irradiated indicated THP-1 cells were cultured in the lower and upper chambers respectively. T cells were analyzed by flow cytometry after 7 days. FIGS. 5C-5D, Knockout of shp-2 reduces THP-1 cell short-term and long-term infiltration in NSG mice (n=5). FIG. 5E, Upstream transcription factor analysis of RNA-seq data generated from lilrb4-KO and WT THP-1 cells. Yellow dots highlighted the transcription factors involved in JAK/STATs and NF-κB pathways. FIG. 5F, Decreased phosphorylation of IKKα/β in lilrb4-KO THP-1 cells. FIG. 5G, Decreased NFκB in the nuclear fraction in lilrb4-KO THP-1 cells. FIGS. 5H-5I, The NF-κB inhibitor reversed T cell suppression by WT THP-1 cells (FIG. 5H) and decreased infiltration of MV4-11 cells (FIG. 5I) in an LILRB4-dependent manner. FIG. 5J, T cells isolated from healthy donors were supplemented with 25% condition medium (CM) of WT or lilrb4-KO THP-1 cells. Representative cells were photographed (scale bar, 100 μm) and T cells were analyzed by flow cytometry. FIGS. 5K-5L, T cells were incubated with irradiated indicated THP-1 cells supplemented with indicated concentration of recombinant uPAR (uPA receptor, also known as Urokinase receptor) (FIG. 5K) or ARG-1 (Arginase-1) (FIG. 5L) proteins for 7 days and were analyzed by flow cytometry. FIG. 5M, Overexpression of uPAR (plaur) or ARG1 rescued infiltration defect of lilrb4-KO MV4-11 cells (n=5). n.s., not significant; p values were from two-tailed student t-test.

Figures 6A, 6B:
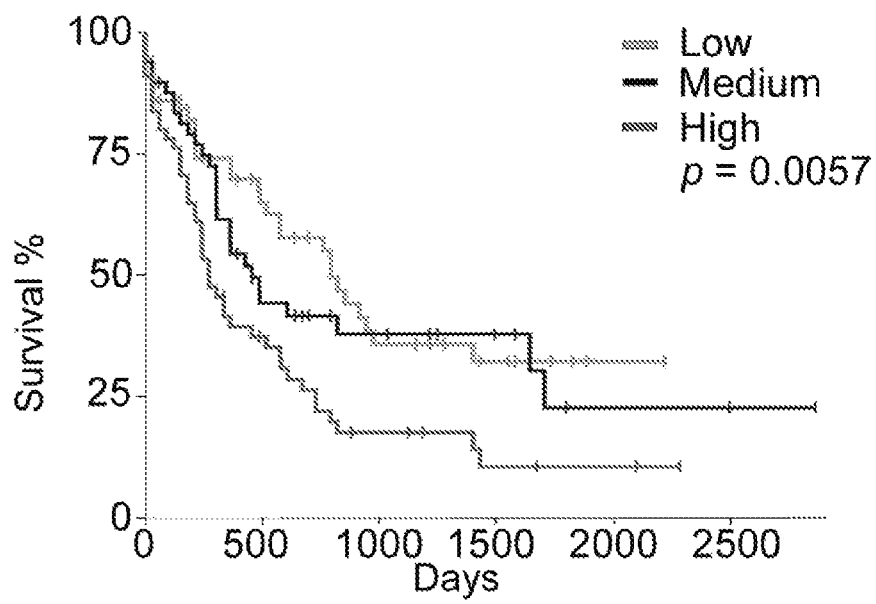
Figure 7A:
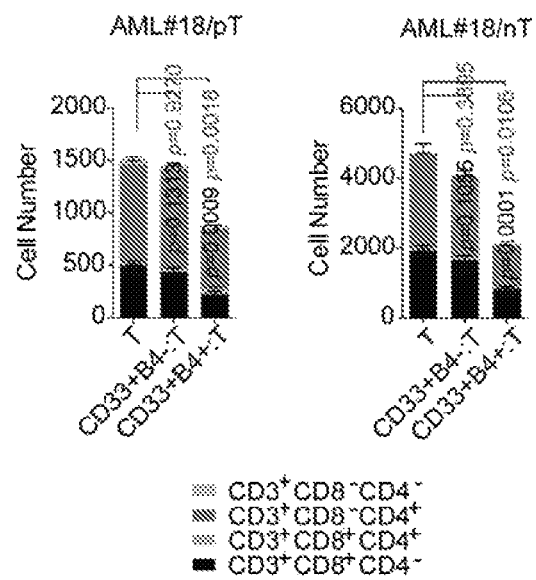
Figure 7B:
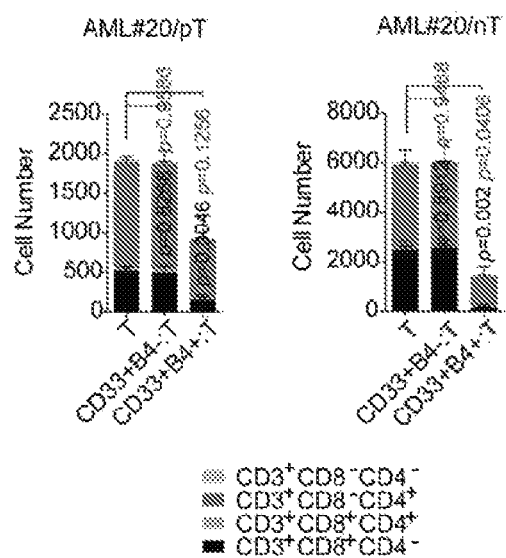

FIGS. 6A-6B show that LIRB4 expression in human AML patients and negatively correlated with patient overall survival. FIG. 6A, Analysis of correlations between lilrb4 mRNA level and the overall survival of AML patients (n=160) from the TCGA database. Low, n=57; Medium, n=48; High, n=55. FIG. 6B, A multivariable Cox regression analysis to assess the association, with adjustment for confounders that include age, cytogenetics, and PML-RAR mutation in TCGA database. The total sample size was 79. *,p<0.05 is considered as significant.

FIGS. 7A-7F shows that primary LILRB4-expressing AML cells suppress T cell proliferation. Autologous T cells isolated from individual monocytic AML or B-ALL patients were incubated with irradiated lilrb4-positive (B4+) or lilrb4-negative (B4-) primary leukemia cells from the same patients. pT, patient T cells. Allogeneic T cells isolated from healthy donors were incubated with irradiated lilrb4-positive or lilrb4-negative primary leukemia cells from indicated AML or B-ALL patients at an E:T of 10:1. nT, normal T cells. After culture with anti-CD3/CD28/CD137-coated beads and rhIL-2 for 14 days, T cells were stained with anti-CD3, anti-CD4, and anti-CD8 antibodies and analyzed by flow cytometry. p values in black indicate significance of $CD3^+CD8^+$ cells; p values in red indicate significance of $CD3^+CD4^+$ cells. n.s., not significant.

Figure 8A:
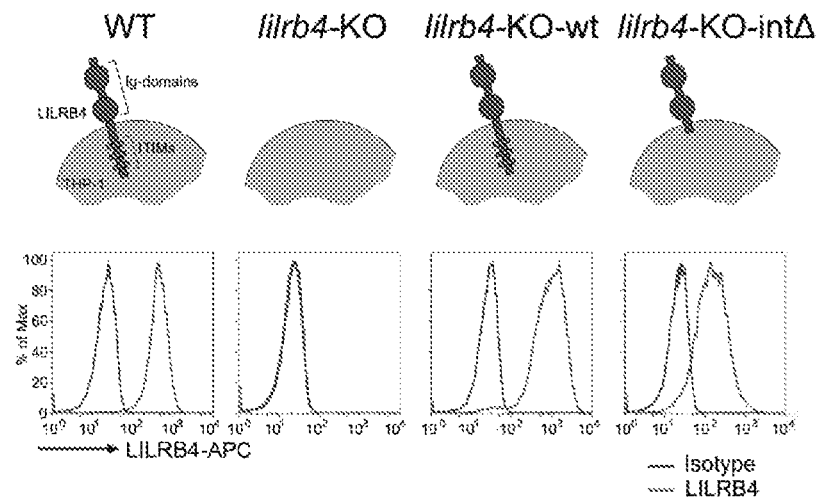
Figure 8B:
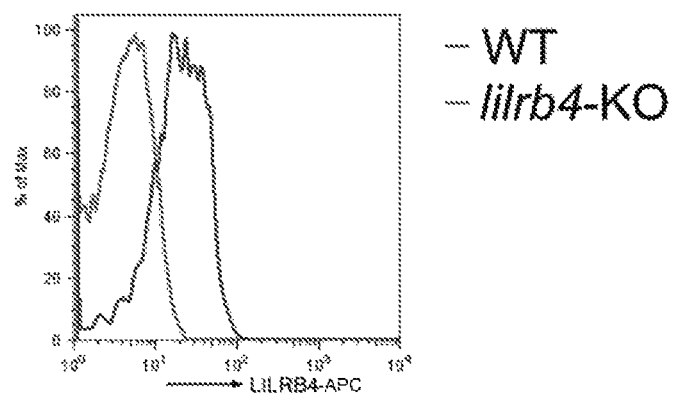
Figures 8C, 8D:
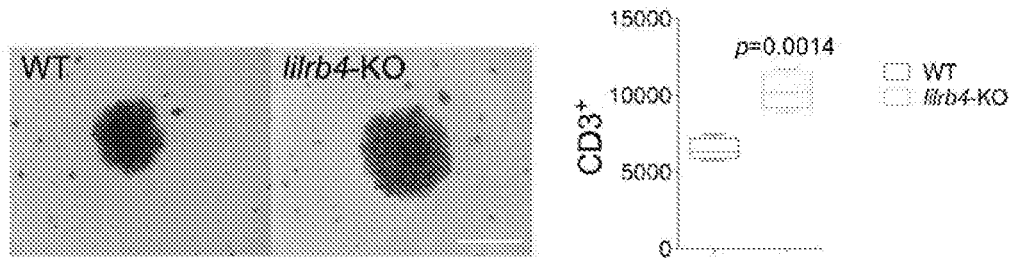
Figure 8E:
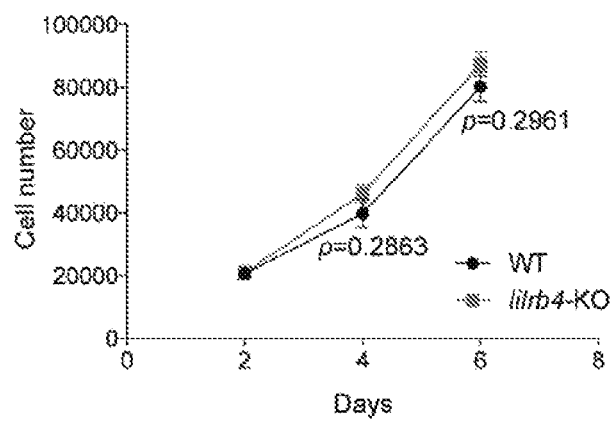
Figures 8F, 8G:
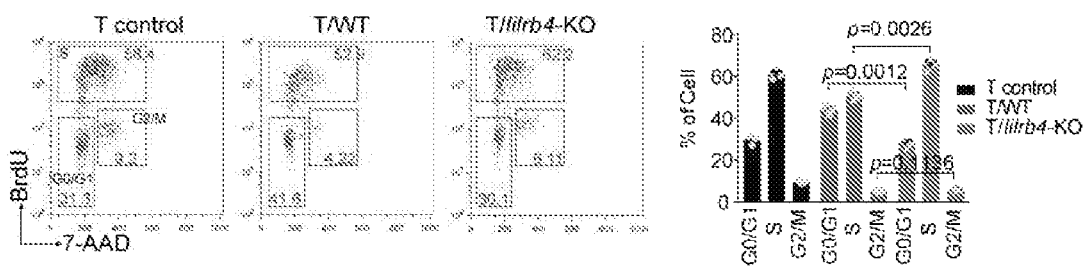
Figures 8H, 8I:
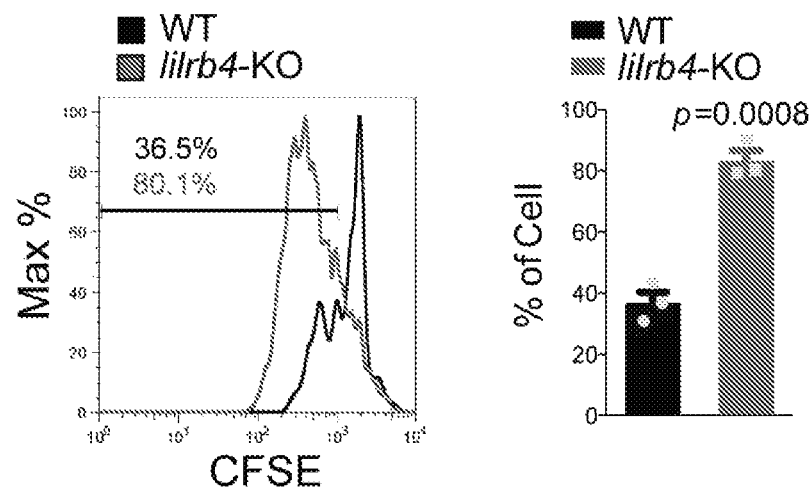
Figure 8J:
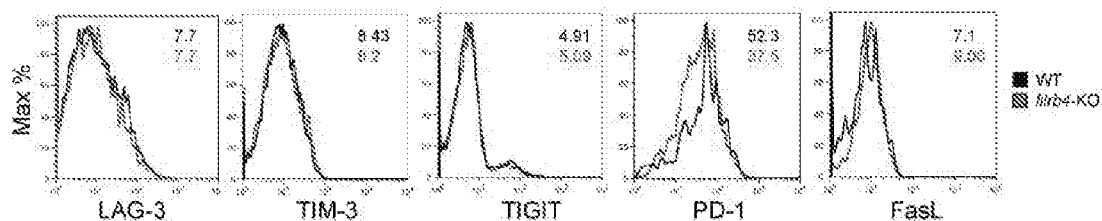
Figure 8K:
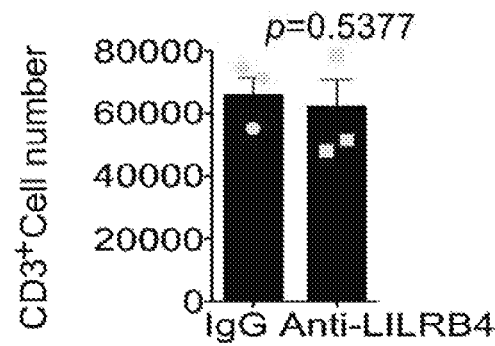
Figure 8L:
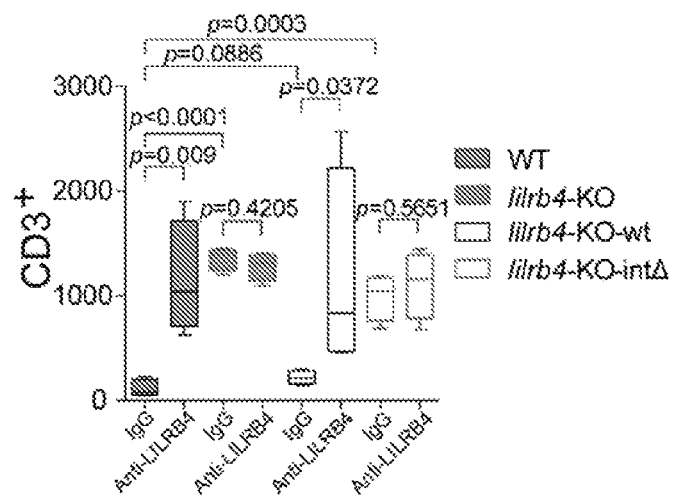
Figure 8M:
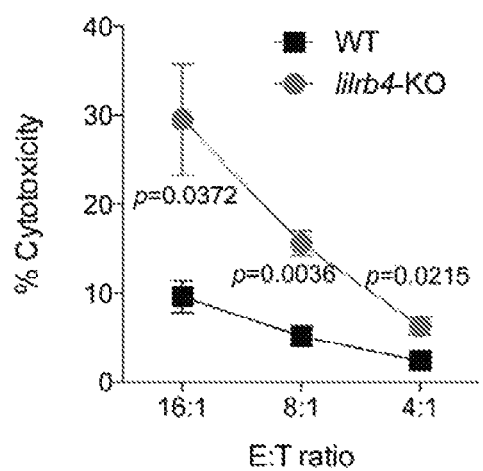

FIGS. 8A-8O show that LILRB4 suppresses T cell proliferation in vitro. FIG. 8A, Schematic of preparation of lilrb4-modulated THP-1 cells and examination of LILRB4 expression on the cell surfaces by flow cytometry. WT, THP-1 cells treated with scrambled control; lilrb4-KO, lilrb4-knockout THP-1 cells; lilrb4-KO-wt, forced expression of wild-type lilrb4 on lilrb4-KO THP-1 cells; lilrb4-KO-intΔ, forced expression of the intracellular domain-deleted mutant lilrb4 on lilrb4-KO THP-1 cells. FIG. 8B, Examination of LILRB4 expression on cell surface of lilrb4-KO MV4-11 cells by flow cytometry. FIGS. 8C-8D, Loss of lilrb4 on MV4-11 cells reduces T cell suppression. T cells isolated from healthy donors incubated in the lower chambers of a 96-well transwell plate with irradiated MV4-11 cells (E:T of 2:1) in the upper chamber separated by a membrane with 3 μm pores. After culture with anti-CD3/CD28-coated beads and rhIL-2 for 7 days, representative cells were photographed using an inverted microscope (scale bar, 100 μm) (FIG. 8C) and T cells were stained with anti-CD3 and analyzed by flow cytometry (FIG. 8D). n=3. FIG. 8E, Loss of lilrb4 on MV4-11 cells does not affect cell proliferation. FIGS. 8F-8G, T cells (E: effector cells) isolated from healthy donors were incubated with indicated irradiated THP-1 cells (T: target cells) without direct contact in transwells for 2 days. E:T=2:1. T cells were treated with BrdU for 30 mins followed by BrdU and 7-AAD staining for flow cytometry analysis. Representative flow cytometry plots are shown in FIG. 8F and the cell cycle status is summarized in FIG. 8G. T control, T cells were cultured without THP-1 cells. FIGS. 8H-8I, T cells (E: effector cells) isolated from healthy donors were stained with CFSE and incubated with indicated irradiated THP-1 cells (T: target cells) without direct contact in transwells for 2 days. A representative flow cytometry plot is shown in FIG. 8H and the percentages of proliferating T cells indicated by CFSE-low staining is shown in FIG. 8I. FIG. 8J, LILRB4 increases PD-1 expression on T cells in coculture of leukemia cells and T cells. T cells (E: effector cells) isolated from healthy donors were incubated with indicated irradiated THP-1 cells (T: target cells) in a non-contact manner for 5 days. E:T=2:1. T cells were stained with anti-LAG-3, anti-TIM-3, anti-TIGIT, anti-PD-1 and anti-FasL antibodies for flow cytometry analysis. Representative flow cytometry plots are shown and the mean of fluorescence intensities were calculated and shown in right-up corner (black, WT; red, KO). Experiments were performed three times with similar results. FIG. 8K, Anti-LILRB4 antibody had no effect on proliferation of T cells. The numbers of human primary T cells after 5 days treatment of IgG or anti-LILRB4 antibody in vitro are shown (n=3 biologically independent samples with mean and s.e.m.). FIG. 8L, Primary T cells and irradiated THP-1 cells (E:T ratio, 2:1) were placed to the lower chambers and upper chamber respectively and treated with 10 μg/ml control IgG or anti-LILRB4 antibodies. T cells were stained with anti-CD3 and analyzed by flow cytometry. FIG. 8M, Primary T cells stimulated with anti-CD3/CD28/CD137-coated beads were co-cultured with WT or lilrb4-KO-THP-1 cells with indicated E:T ratios for 4 hrs. Cytotoxicity of leukemia cells was determined by PI staining in flow cytometry analysis (n=3 biologically independent samples with mean and s.e.m.). FIGS. 8N-8O, $CD8^+$ T cells ($5 \times 10^4$ cells) stimulated with anti-CD3/CD28/CD137-coated beads were co-cultured with $5 \times 10^3$ THP-1 cells that stably express GFP and treated with 100 μg/ml anti-LILRB4 antibodies or control IgG for 5 days. n=4. Shown are quantification of $GFP^+$ leukemia cells (FIG. 8N, n=4 biologically independent samples), and secretion of IFNγ (FIG. 8O, n=3 biologically independent samples with mean and s.e.m.). n.s., not significant.

Figure 9B:
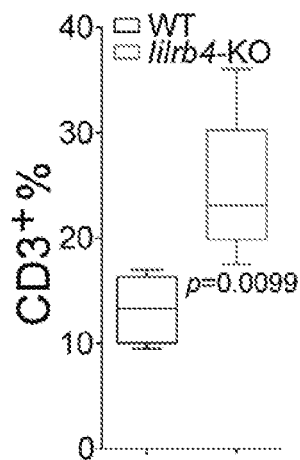
Figure 9C:
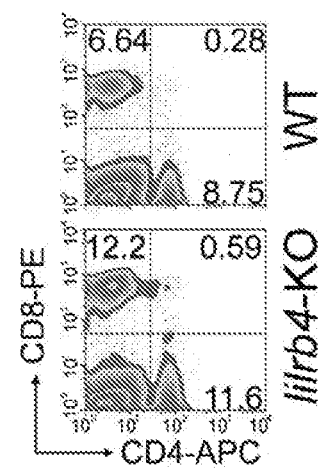
Figure 9D:
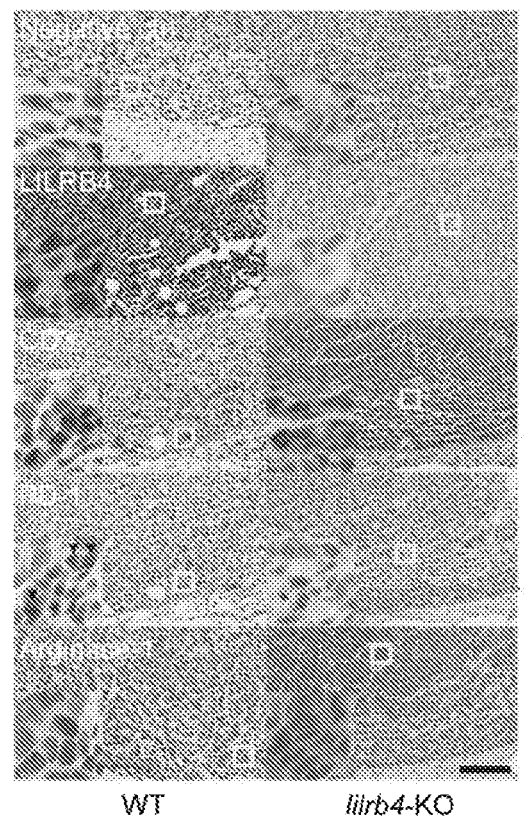
Figure 9E:
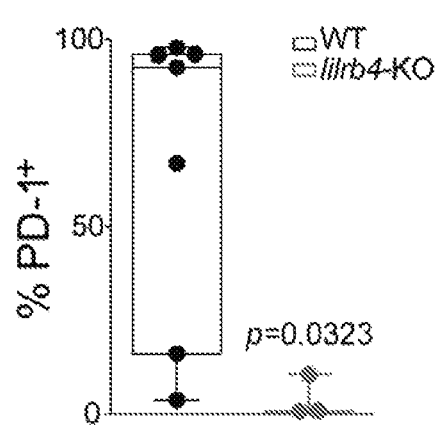
Figure 9F:
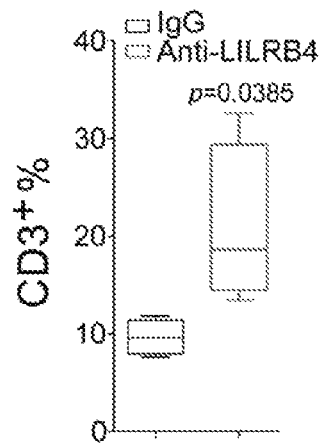
Figure 9G:
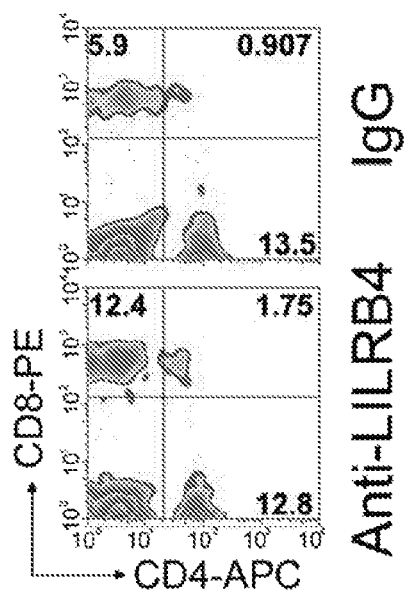
Figures 9H, 9I:
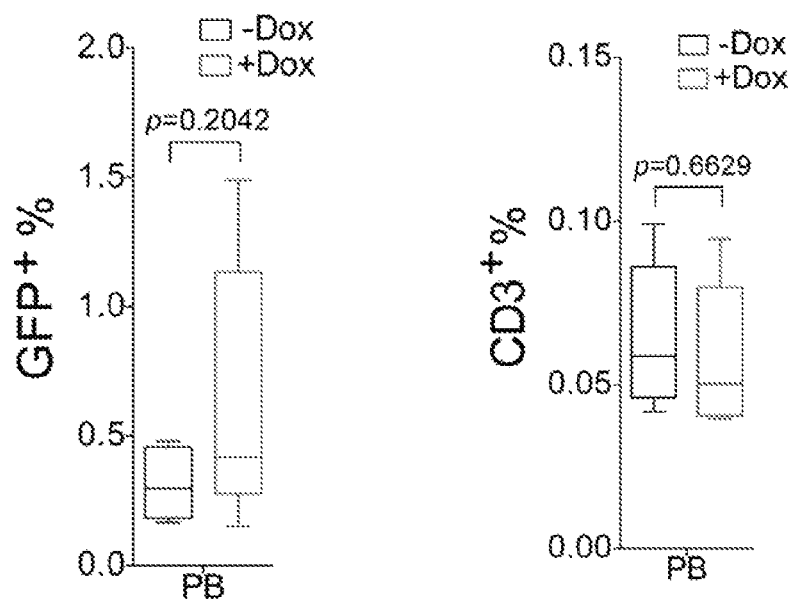
Figure 9J:
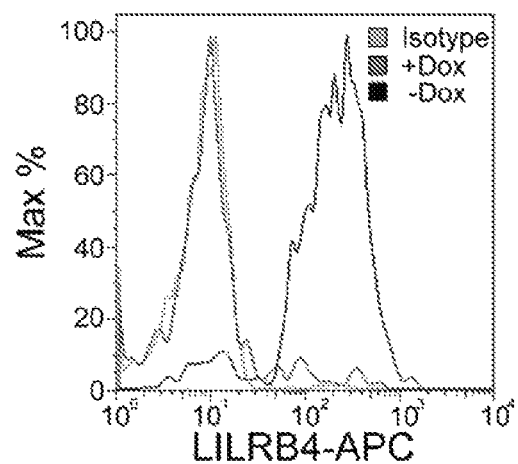

FIGS. 9A-9J show that inhibition of LILRB4 reduces leukemia development in humanized immunocompromised mice. FIGS. 9A-9C, WT or lilrb4-KO THP-1 cells ($3 \times 10^6$ cells/mouse) were subcutaneously implanted into hPBMC-repopulated NSG mice (WT, n=14 mice with mean and s.e.m.; lilrb4-KO, n=10 mice with mean and s.e.m.). Shown are tumor size (FIG. 9A), quantitation of $CD3^+$ at day 31 in peripheral blood of recipient mice (FIG. 9B) and representative flow plots showing $CD4^+$ and $CD8^+$ T cells (FIG. 9C). FIGS. 9D-9E, LILRB4 increases PD-1 expression on tumor-infiltrated T cells. WT or lilrb4-KO THP-1 cells were subcutaneously implanted in hPBMC-repopulated NSG mice. Three weeks after implantation, 7 out of 10 WT-group mice had large tumors and 3 out of 10 KO-group mice had tiny tumors. These tumors were dissected for immunohistochemistry and flow cytometry staining with anti-LILRB4, anti-CD3, anti-PD-1 or anti-Arginase-1 antibodies. FIG. 9D, Left corner images were magnified from the yellow highlighted regions. In CD3 and PD-1 staining images, orange dash lines indicate the tumor boundary. Black arrowheads indicate PD-1 positive cells. Scale bar, 100 μm. FIG. 9E, tumors were dissected and cells in tumor region were stained with anti-CD3 and anti-PD-1 antibodies for flow cytometry analysis. The percentages of PD-$1^+$ T cells (Ratio of PD-$1^+$ $CD3^+$ cells/$CD3^+$ cells) were calculated. FIGS. 9F-9G, THP-1 cells were transplanted into hPBMC-repopulated NSG mice, and mice were treated with control IgG or anti-LILRB4 antibody after 6 days (10 mg/kg; n=5). T cell numbers at day 26 in representative mice were also shown. FIGS. 9H-9I, Engraftment of human T cells and i.v. transplanted Doxycycline (Dox)-inducible lilrb4-knockout THP-1 cells ($GFP^+$) in NSG mice at day 7 before Dox administration (n=5). FIG. 9J, Representative flow plot shows LILRB4 was successfully deleted in engrafted leukemia cells in bone marrow of Dox-fed mouse at the endpoint. n.s., not significant.

Figures 10A, 10B:
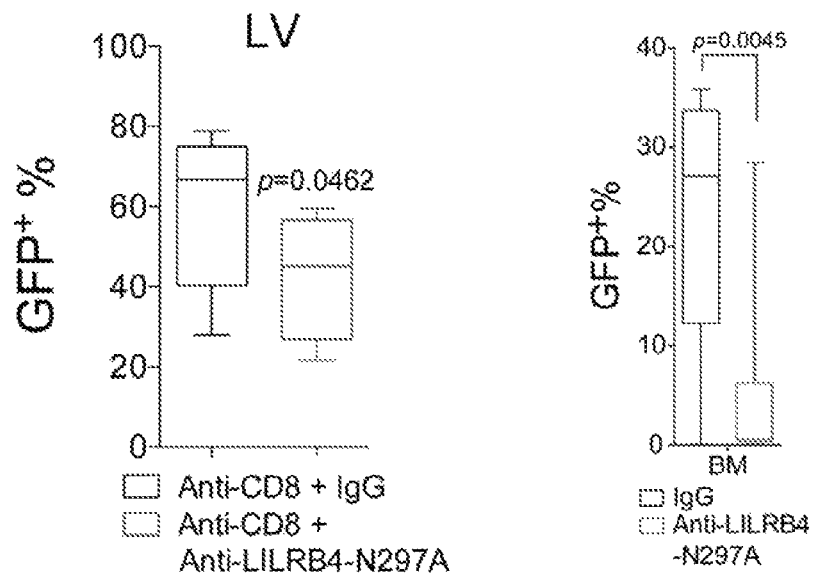
Figures 10C, 10D:
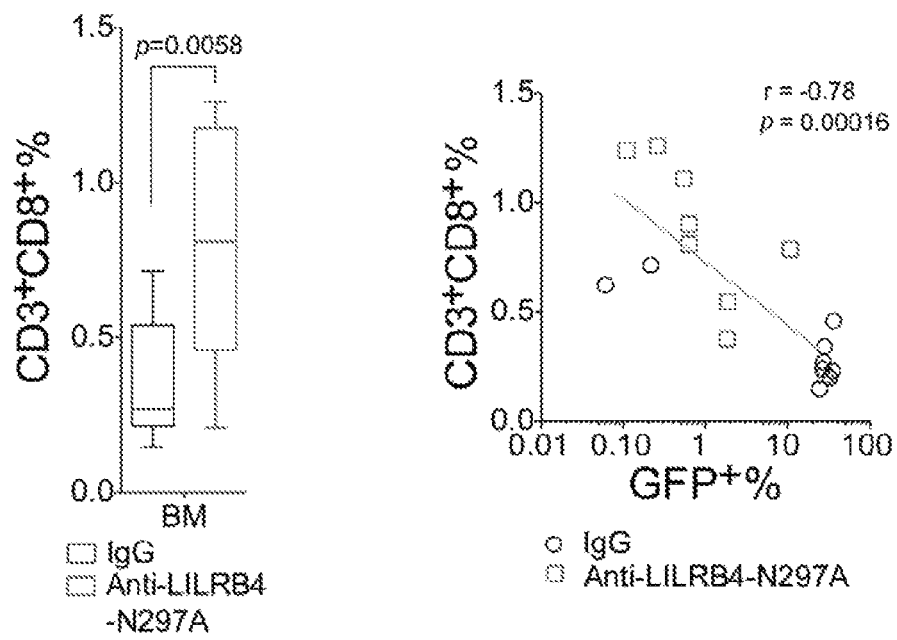

FIGS. 10A-10D show that anti-LILRB4 antibodies reduce leukemia development in syngeneic mice. FIG. 10A, mouse AML C1498 cells ($3 \times 10^6$ cells/mouse) that stably express LILRB4-IRES-GFP were s.c. implanted into C57bl/6 mice. Anti-LILRB4-N297A antibodies or control IgG were i.v. injected at 6, 9, 12, 15, 18, and 21 days post-implantation of tumor cells. Two groups of mice were treated with anti-CD8 antibodies at 3, 6, 9, and 12 days post-implantation of tumor cells to achieve $CD8^+$ T cell depletion. Anti-LILRB4 antibodies reduced the leukemia cells infiltrating into host tissues such as liver (LV, in FIG. 10A), even when $CD8^+$ cells were depleted (FIG. 10A). FIGS. 10B-10D, C57bl/6 mice were i.v. implanted with human LILRb4-expressing mouse AML C1498 cells ($3 \times 10^6$ cells/mouse) that express GFP. Anti-LILRB4-N297A antibodies (n=9 mice) or control IgG (n=9 mice) were i.v. injected at 6, 9, 12 15 and 18 days post-implantation of tumor cells. Anti-LILRB4 antibodies decreased the percentage of leukemia cells in bone marrow (BM) (FIG. 10B). Anti-LILRB4 antibodies increased $CD8^+$ T cells in bone marrow (FIG. 10C). The percentage of CD8+ T cells in bone marrow is significantly negatively correlated with the percentage of leukemia cells (FIG. 10D). n.s., not significant. All p values (except of FIG. 10D from Pearson's correlation) were from two-tailed student t-test.

Figure 11A:
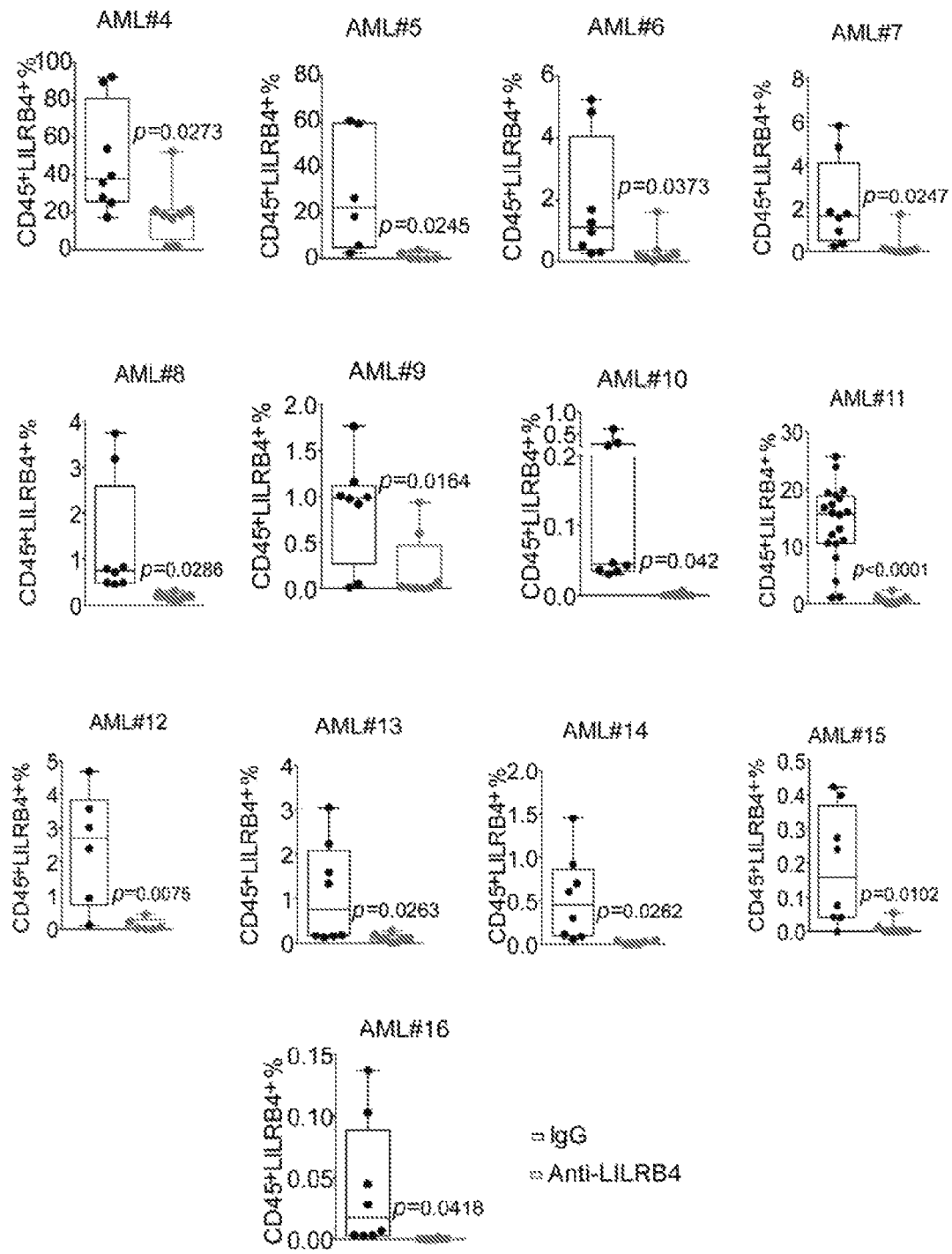
Figure 11B:
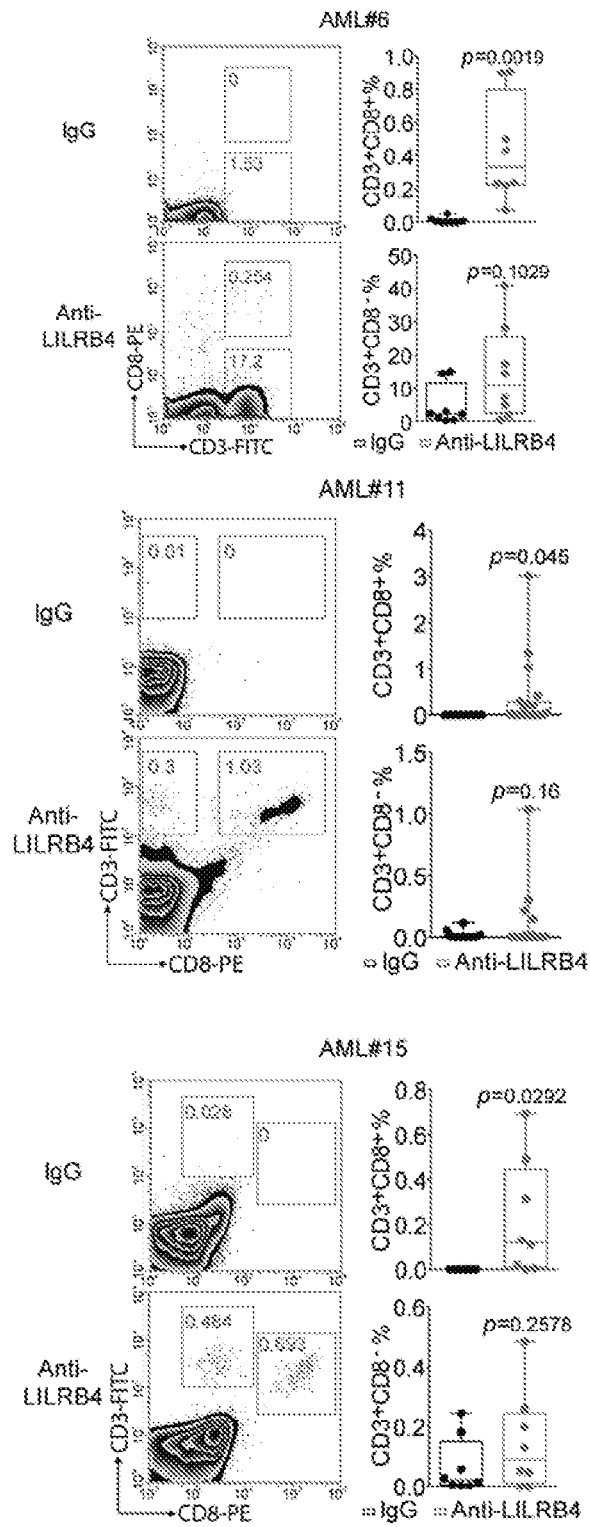

FIGS. 11A-11B show that anti-LILRB4 antibodies reduce leukemia development and restore autologous T cells in PDX mice. FIG. 11A, Primary peripheral blood or bone marrow mononuclear AML cells ($5\times10^6$-$1\times10^7$ cells/mouse) from each of sixteen human patients (three shown in FIGS. 2J-K) were injected into NSG mice followed by treatment with IgG or anti-LILRB4 antibody (10 mg/kg, twice a week by i. v. injection). Shown are percentages of human CD45+ LILRB4+ AML cells harvested from hematopoietic tissues including bone marrow, spleen, liver and peripheral blood at 2-4 months after transplantation as determined by flow cytometry. FIG. 11B, Shown are percentages of autologous human T cells harvested from hematopoietic tissues including bone marrow, spleen, liver and peripheral blood at 2~4 months after transplantation as determined by flow cytometry; and representative flow plots of CD3+CD8+ T cells in bone marrow of mice in three PDXs. n.s., not significant. n=8 biologically independent samples for all PDXs except for AML #11 which has n=20 biologically independent samples.

Figure 12A:
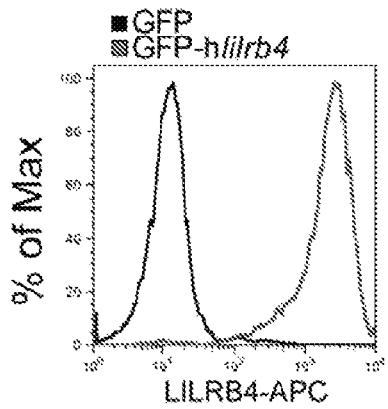
Figure 12B:
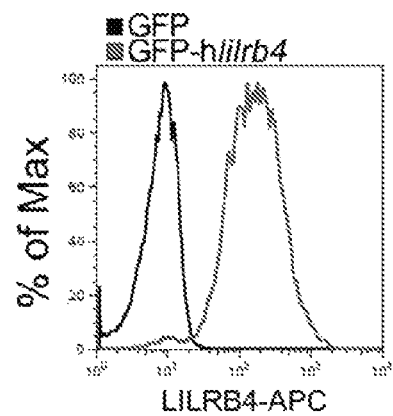
Figure 12C:
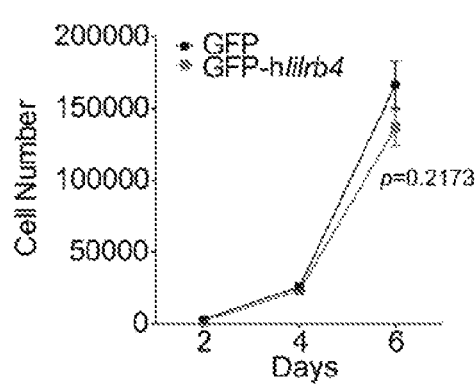
Figure 12D:
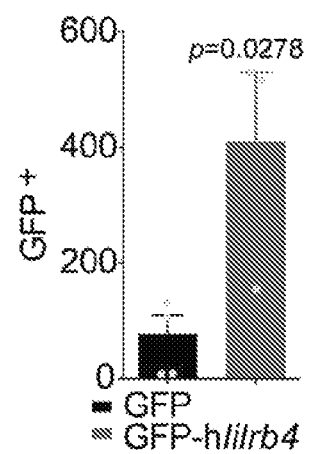
Figure 12E:
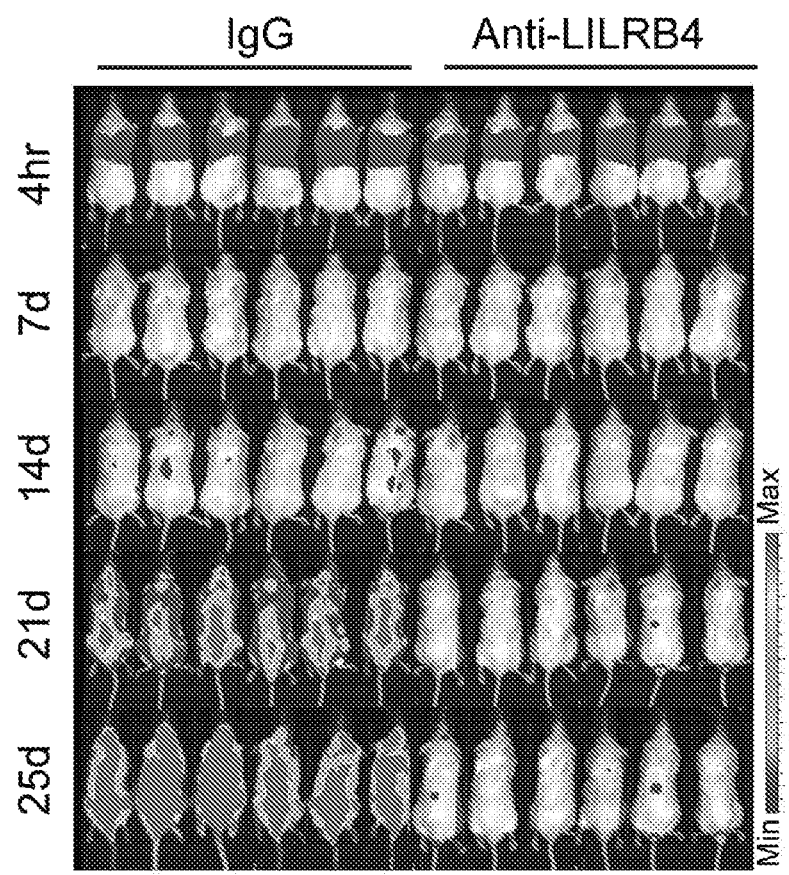
Figure 12F:
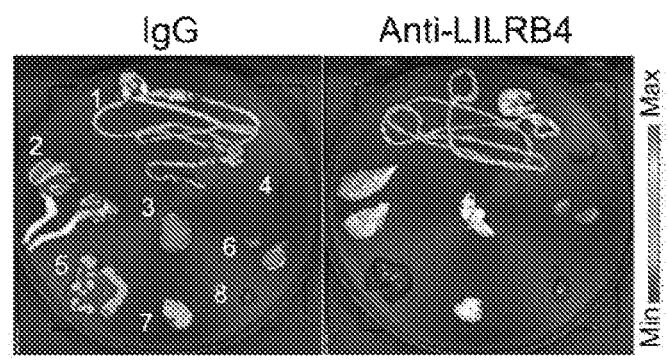
Figure 12G:
Figure 12H:
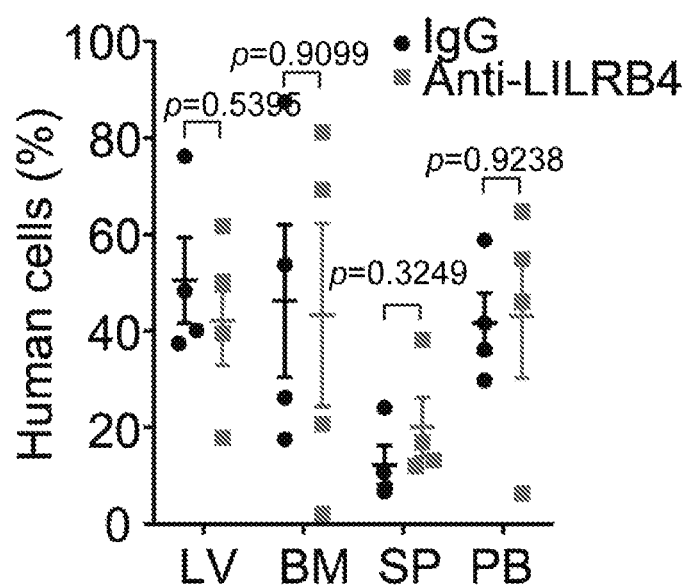
Figure 12I:
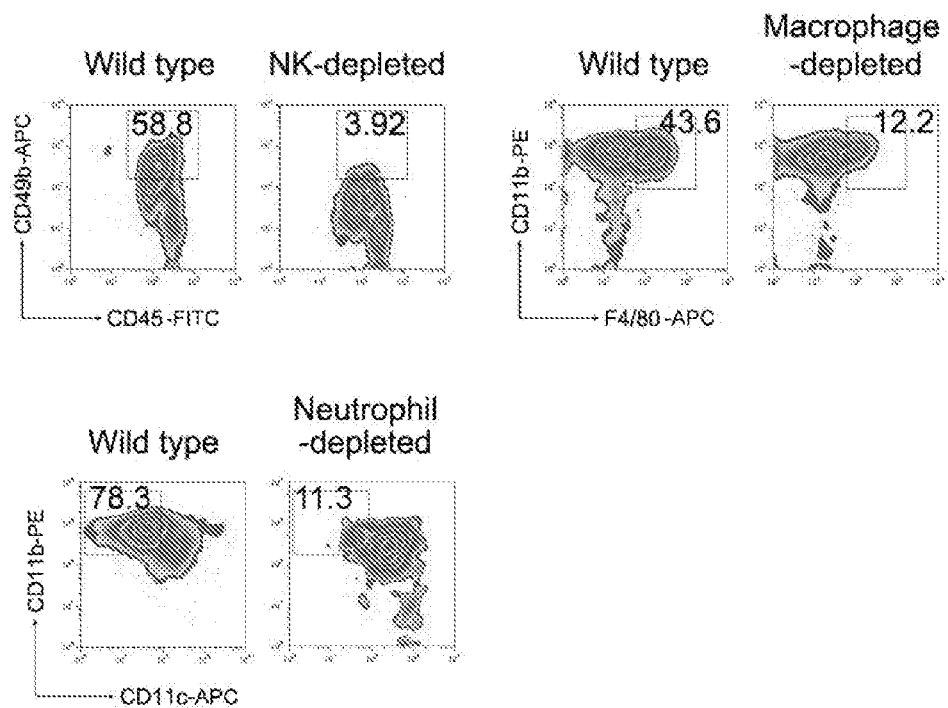
Figure 12J:
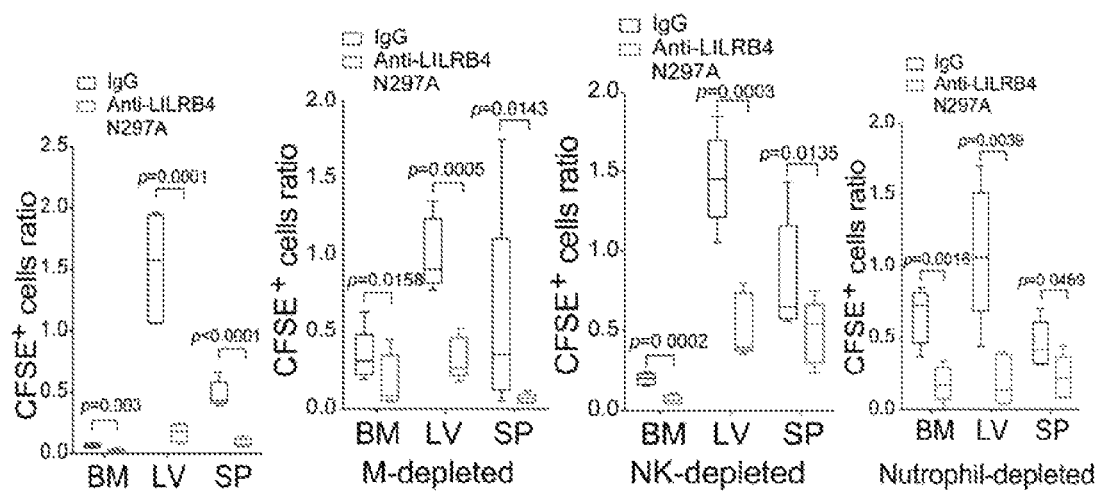

FIGS. 12A-12J show that LILRB4 promotes infiltration of AML cells. FIGS. 12A and 12B, Examination of human LILRB4 expression on mouse AML cells, C1498 (FIG. 12A) or WEHI-3 (FIG. 12B) that stably express lilrb4. FIG. 12C, Forced expression of LILRB4 did not affect cell proliferation of mouse AML cells such as WEHI-3 (n=3). FIG. 12D, Forced expression of human LILRB4 promoted transendothelial migration of mouse AML WEHI-3 cells (n=3). FIG. 12E, NSG mice (n=6) were injected with $1\times10^6$ THP-1 cells followed immediately by IgG or anti-LILRB4 antibody treatment and were monitored by bioluminescence imaging. FIGS. 12F-12G, Anti-LILRB4 antibodies decreased AML cells infiltration into internal organs. Mice were sacrificed at 21 days for ex vivo bioluminescence imaging of internal organs after transplantation of $1\times10^6$ luciferase-expressed THP-1 cells. Images of luminescence flux (radiance) from representative mice are shown (FIG. 12F). 1: GI tract; 2: legs; 3: lung; 4: spleen; 5: liver; 6: kidneys; 7: brain; 8: heart. Infiltrated leukemia cells formed tumor nodules in liver (FIG. 12G). FIG. 12H, Anti-LILRB4 antibodies did not have effect on LILRB4-negative cancer cells. LILRB4 is expressed on THP-1 and MV4-11 human AML cells but not on U937 cells. NSG mice were injected with U937 human AML cells, which do not express LILRB4, and then treated with anti-LILRB4 antibodies (FIG. 12H). IgG served as control antibodies. Mice were sacrificed at day 25 post-transplant for analysis of LV, BM, SP, and PB by flow cytometry. The presence of human AML cells was detected by anti-human CD45 antibody staining (n=3). FIG. 12I, Targeted immune cell populations were depleted in NSG mice. Representative flow cytometry plots demonstrating successful reduction of NK cell (CD45+CD49b+), macrophage (CD11b+F4/80+), and neutrophil (CD11b+CD11c−) frequency in NSG mice depleted of the respective immune cell subtype by treatment with anti-asialo GM1 antibodies, clodronate liposomes, and anti-Ly6G antibodies, respectively, compared to non-depleted (wild-type) NSG mice. FIG. 12J, CFSE-labeled MV4-11 cells ($5\times10^6$ per mouse) were injected into NSG mice in that respective innate immune cells were depleted, followed immediately by IgG or anti-LILRB4-N297A antibody treatment (n=5). Numbers of leukemia cells (CFSE positive) in LV, SP, and BM normalized to that in PB at 20 hr post-injection are shown. n.s., not significant.

Figure 13A:
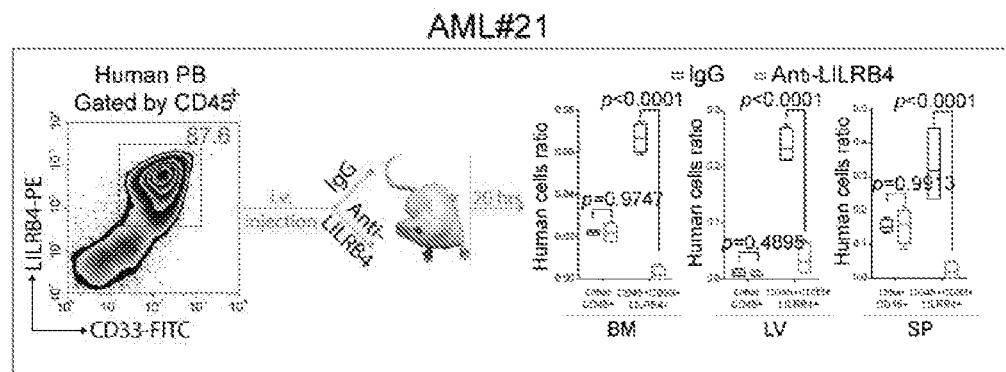
Figure 13B:
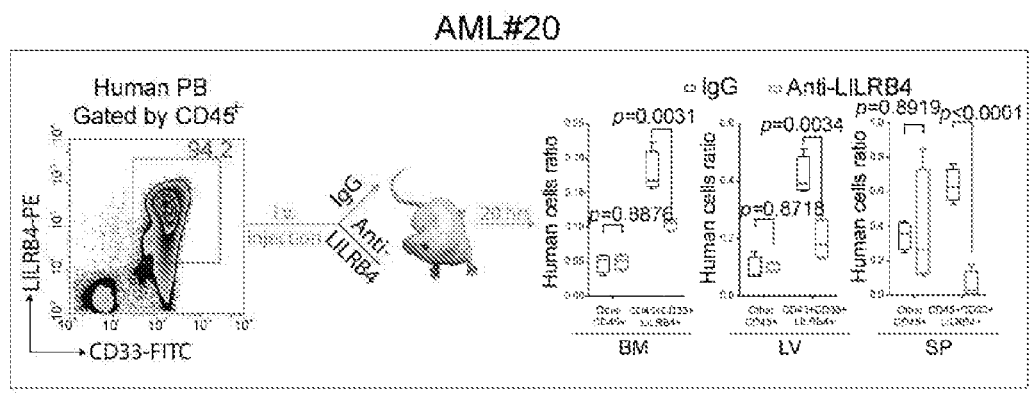
Figure 13C:
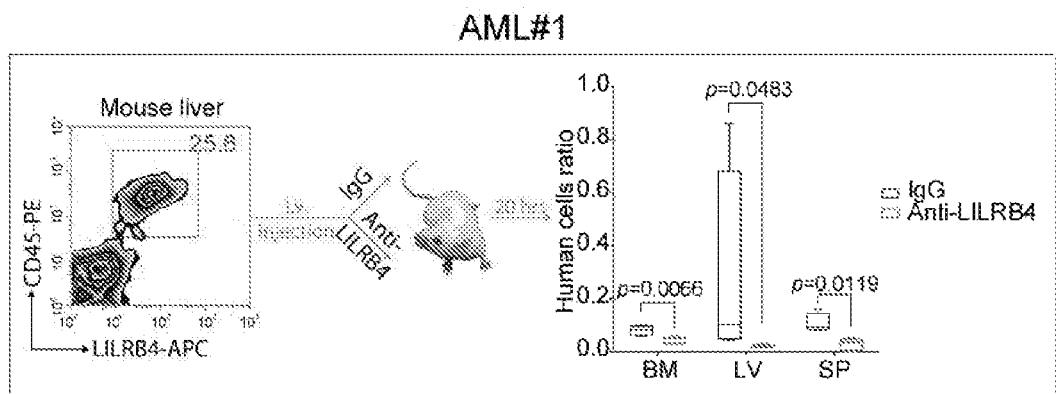

FIGS. 13A-13C show that anti-LILRB4 inhibits infiltration of primary AML cells. Comparison of infiltration of human primary monocytic AML cells in NSG mice (n=5) after treatment with anti-LILRB4 antibody or IgG control. FIGS. 13A-13B, Primary human peripheral blood mononuclear cells from monocytic AML patients were injected. FIG. 13C, Mouse liver cells with xenografted primary human monocytic AML cells (human CD45+LILRB4+ cells) were injected. n.s., not significant. All p values were from two-tailed student t-test.

FIGS. 14A-14G show that loss of APOE in AML cells restores T cell proliferation and suppresses AML cell migration in vitro. Examination of APOE expression in apoe-knockout THP-1 and MV4-11 cells by immunoblots (FIGS. 14A and 14C). Primary T cells and irradiated THP-1 or MV4-11 cells (E:T=2:1) were incubated in the lower and upper chambers respectively. T cells were photographed (FIGS. 14B and 14D, scale bar, 100 μm) and quantified by flow cytometry (FIG. 4I and FIG. 14E) after 7 days. FIGS. 14F-G, Loss of APOE suppresses transendothelial migration of human AML THP-1 and MV4-11 cells (n=4 biologically independent samples with mean and s.e.m.).

Figure 15A:
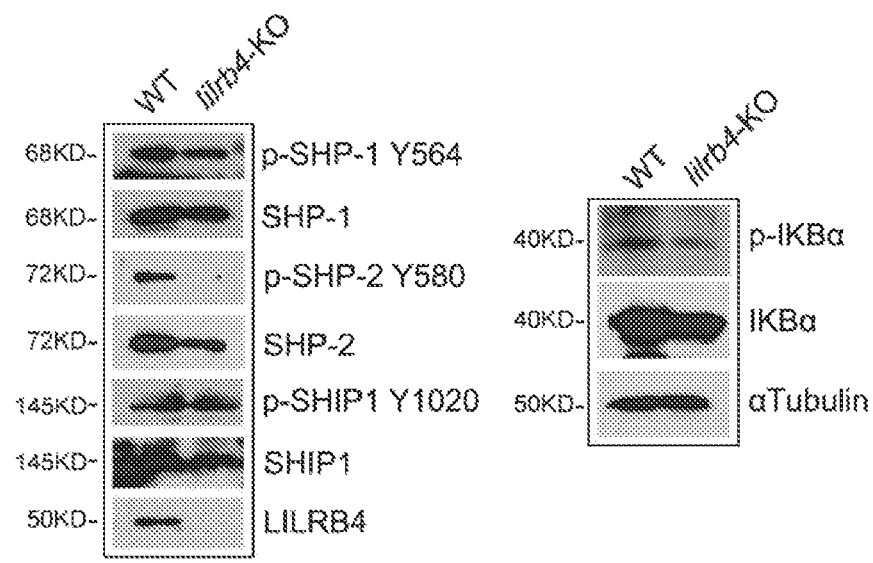
Figure 15B:
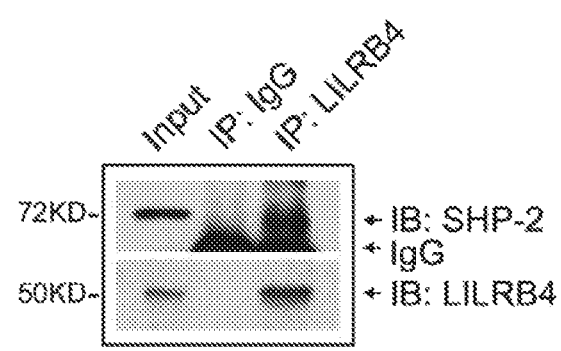
Figure 15C:
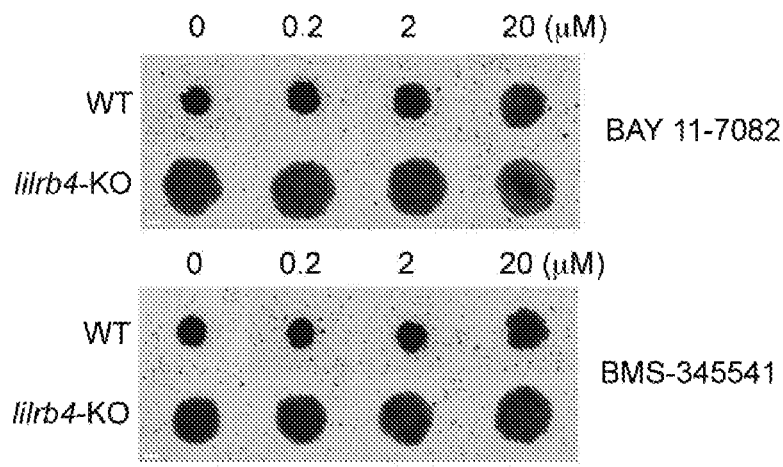
Figure 15D:
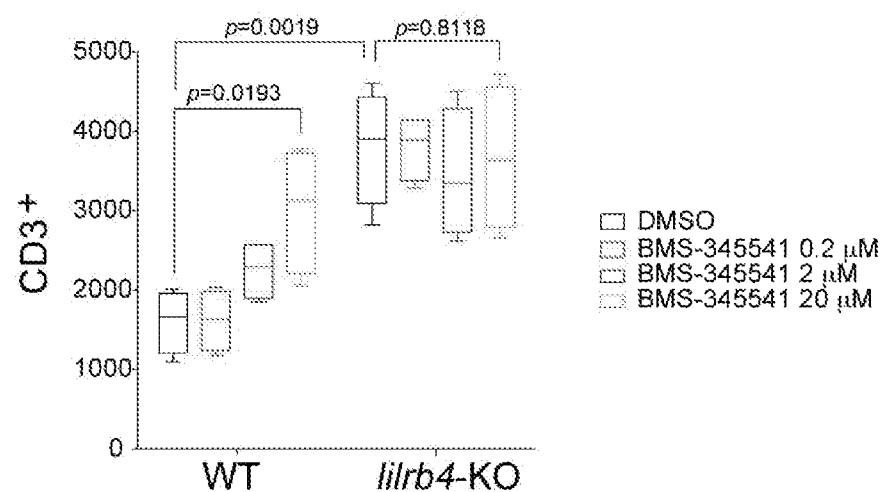

FIGS. 15A-15D show that LILRB4 upregulates phosphorylation of SHP-2 and NF-kB signaling. FIG. 15A, Phosphorylated SHP-2, phosphorylated IKB, uPAR, and ARG1 were down-regulated upon lilrb4-knockout (KO) in MV4-11 cells. FIG. 15B, Co-immunoprecipitation demonstrated LILRB4 interacts with SHP-2 in THP-1 cells. FIGS. 15C-15D, Two different NF-κB inhibitors restored T cell proliferation from the suppression by THP-1 cells in an LILRB4-dependent manner. THP-1 cells were pretreated with various doses of NF-κB inhibitors for 1 hr. Primary T cells and irradiated pretreated THP-1 cells (E:T=2:1) were cultured in the lower and upper chambers respectively. T cells were photographed (FIG. 15C, scale bar, 100 μm) and analyzed by flow cytometry (FIG. 15D) after 7 days. n.s., not significant.

Figure 16A:
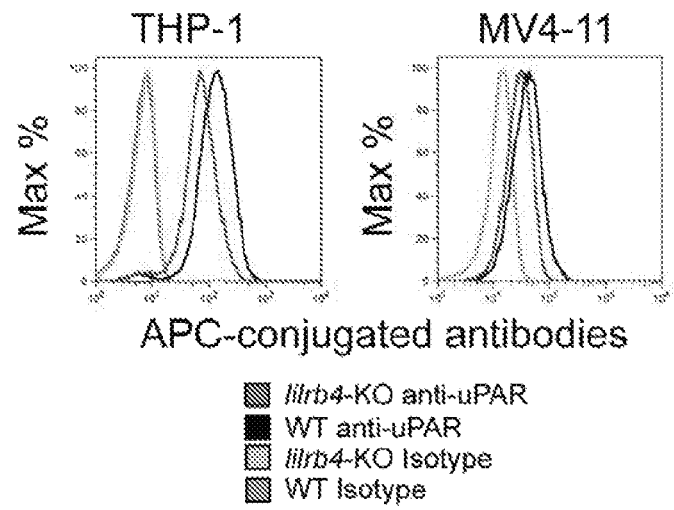
Figure 16B:
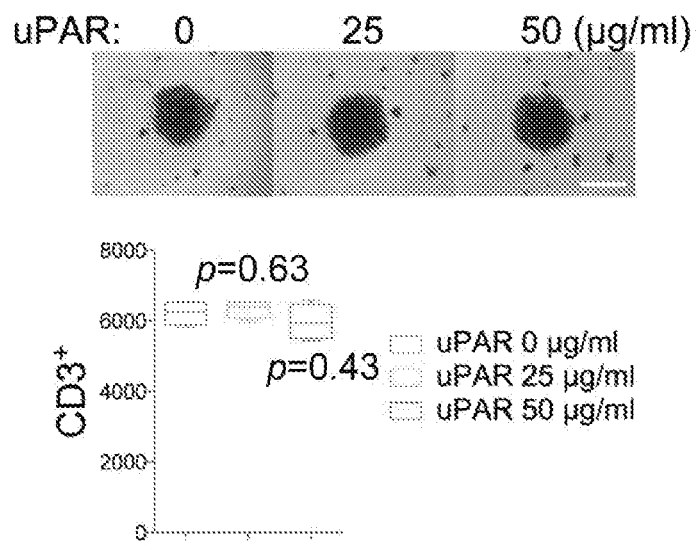
Figure 16C:
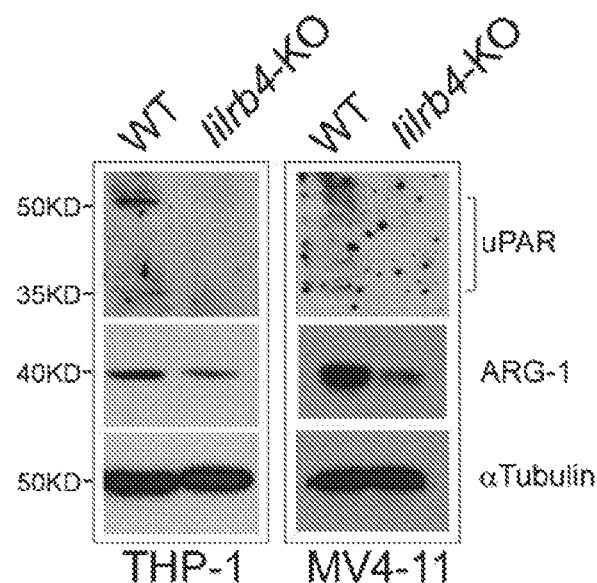
Figure 16D:
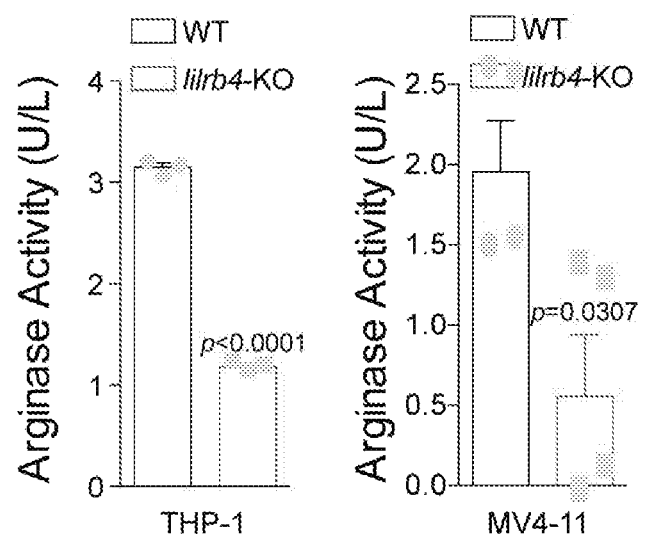
Figure 16E:
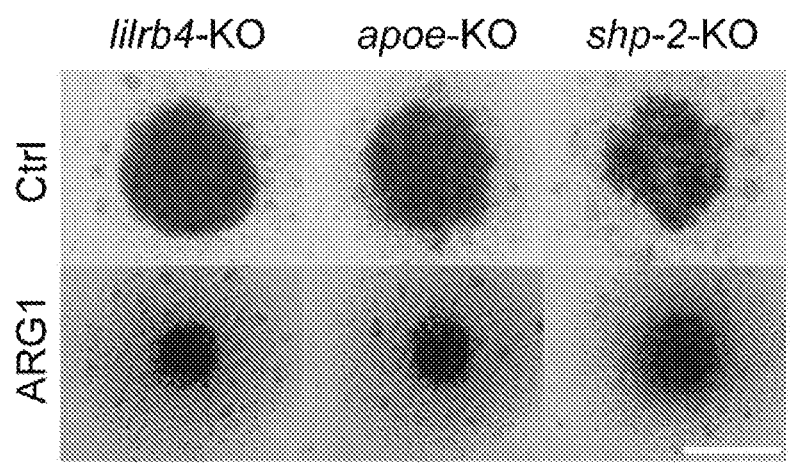
Figure 16F:
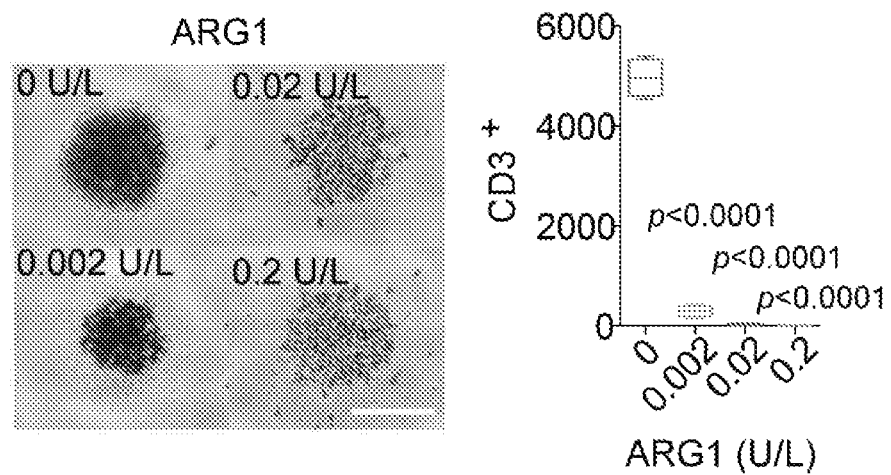
Figure 16G:
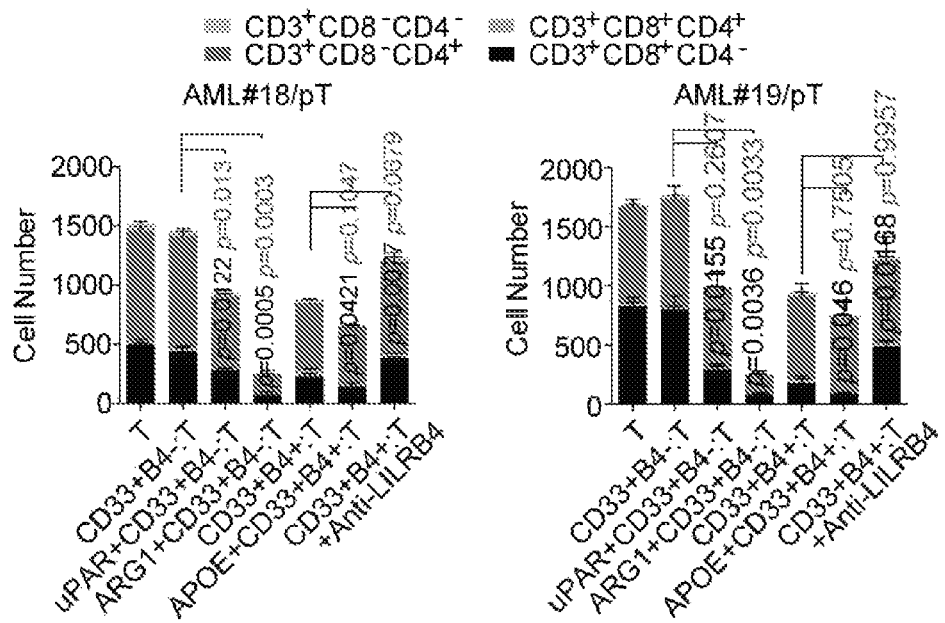
Figure 16H:
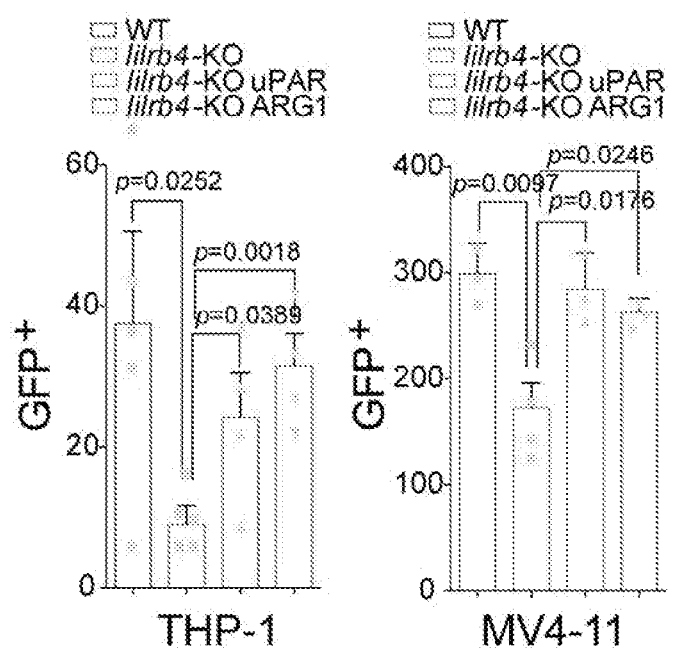

FIGS. 16A-16H show that LILRB4 upregulates uPAR and Arginase-1 to suppress T cell activity and promote leukemia migration. FIG. 16A, Surface uPAR was downregulated in lilrb4-knockout THP-1 and MV4-11 AML cells. FIG. 16B, T cells isolated from healthy donors were cultured with anti-CD3/CD28-coated beads and rhIL-2 and supplemented with indicated concentrations of uPAR proteins for 3 days (n=4 biologically independent samples). Representative cells were photographed using an inverted microscope and T cells were analyzed by flow cytometry. FIG. 16C, Expression of uPAR and Arginase-1 (ARG1) is downregulated in in lilrb4-knockout THP-1 and MV4-11 AML cells. FIG. 16D, Arginase activity as determined by a colorimetric method (DARG-100, BioAssay system) was decreased in condition medium of lilrb4-KO THP-1 and MV4-11 cells. FIG. 16E, Primary T cells and irradiated indicated THP-1 cells (E:T=2: 1) were incubated in the lower and upper chambers respectively and were supplemented with 0.002 U/L recombinant ARG1 proteins for 7 days. T cells were photographed. FIG. 16F, T cells isolated from healthy donors were cultured with anti-CD3/CD28-coated beads and rhIL-2 and supplemented with indicated concentrations of ARG1 proteins for 3 days (n=4 biologically independent samples). Representative cells were photographed using an inverted microscope and T cells were analyzed by flow cytometry. FIG. 16G, Autologous T cells isolated from individual monocytic AML patients were incubated with irradiated lilrb4-positive or lilrb4-negative primary leukemia cells from the same patients at an E:T of 10:1, supplemented with recombinant anti-LILRB4 antibodies, APOE-VLDL, uPAR or ARG1. pT, patient T cells. After culture with anti-CD3/CD28/CD137-coated beads and rhIL-2 for 14 days, T cells were stained with anti-CD3, anti-CD4, and anti-CD8 antibodies and analyzed by flow cytometry. FIG. 16H, Supplementation of recombinant uPAR or ARG1 to the medium rescued the decrease of transmigration ability of lilrb4-KO THP-1 or lilrb4-KO MV4-11 cells across endothelium (n=3). Scale bar, 100 µm. n.s., not significant. All p values were from two-tailed student t-test.

Figure 17A:
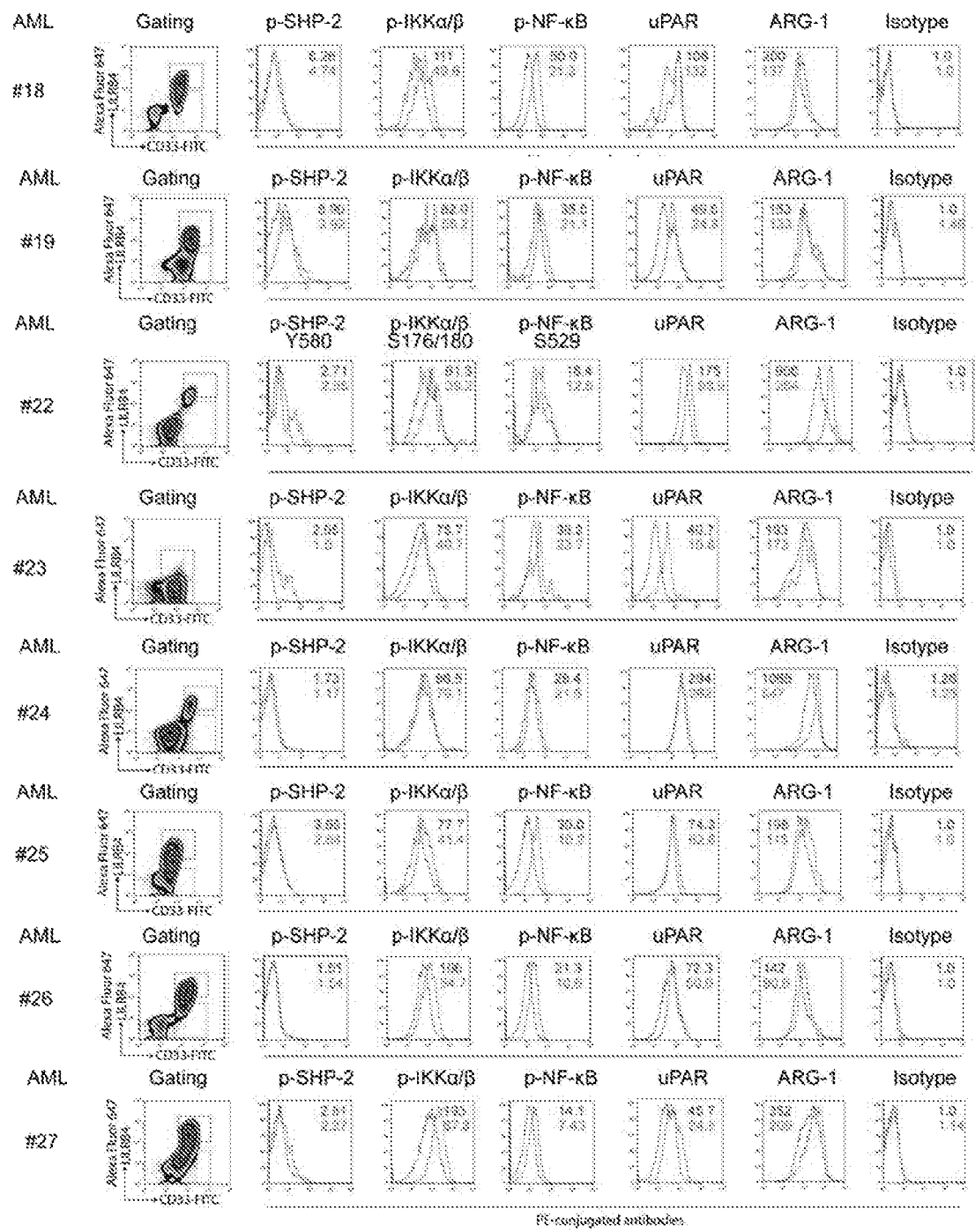
Figure 17B:
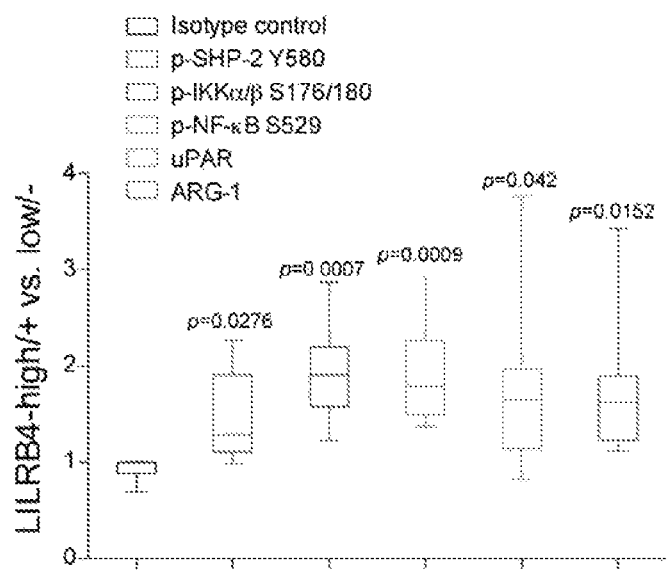

FIGS. 17A-17B show that the detection of SHP-2/NF-κB signaling and uPAR and Arginase-1 expression in primary human monocytic AML cells. FIG. 17A, LILRB4-positive or -high CD33$^+$ AML cells (box) and LILRB4-negative or -low CD33$^+$ AML cells (box) were gated for further intracellular staining of phosphorylated-SHP-2 at Y580, phosphorylated-IKKα/β at S176/S180, phosphorylated-NF-κB at S529, uPAR, and Arginase-1 (ARG1). Isotype IgG was used as negative controls. Red numbers indicate MFIs (mean fluorescence intensity) of LILRB4-positive or -high CD33$^+$ AML cells; blue numbers indicate MFIs of LILRB4-negative or -low CD33$^+$ AML cells. FIG. 17B, Quantification of individual staining in LILRB4-positive or -high CD33$^+$ AML cells versus in LILRB4-negative or low CD33$^+$ AML cells.

Figure 18:
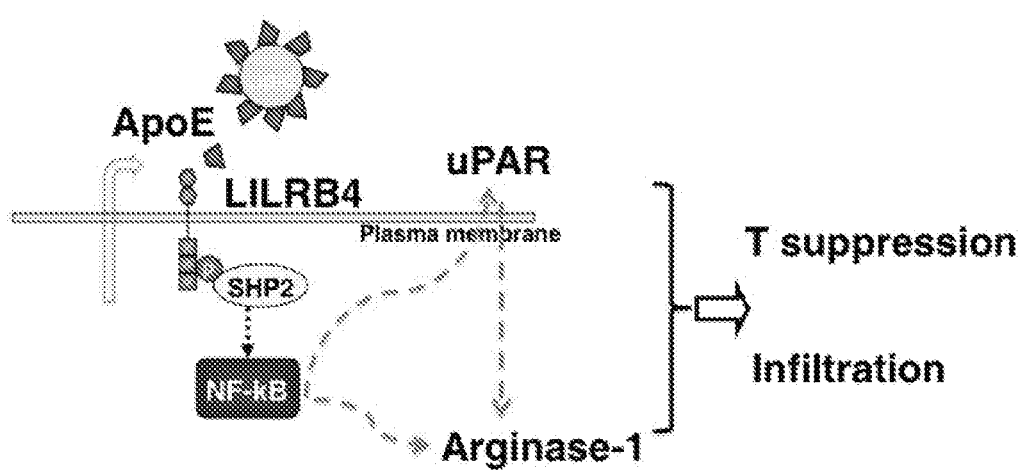

FIG. 18 shows the schematic for the mechanisms by which LILRB4 suppresses T cells and promotes leukemia infiltration.

Figure 19A:
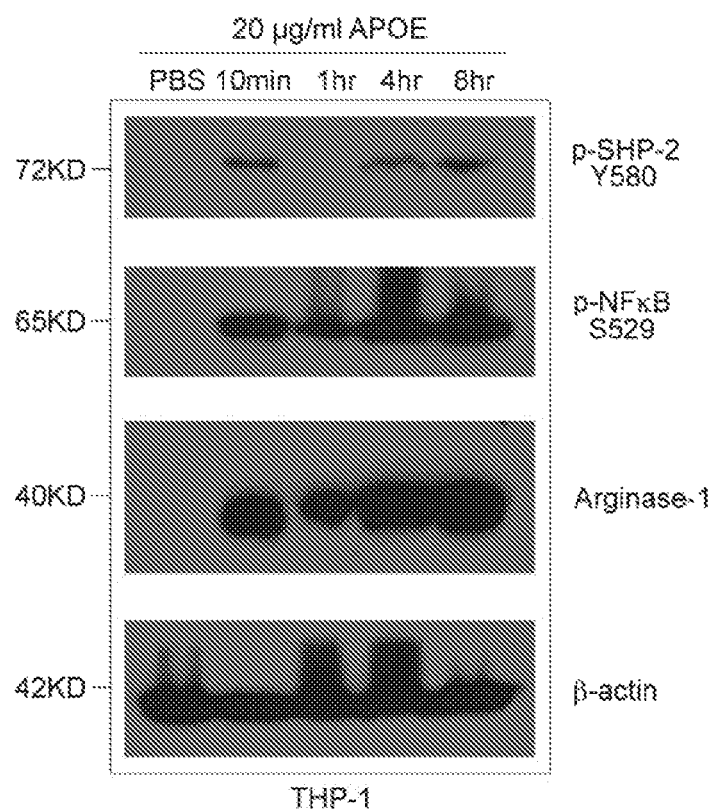
Figure 19B:
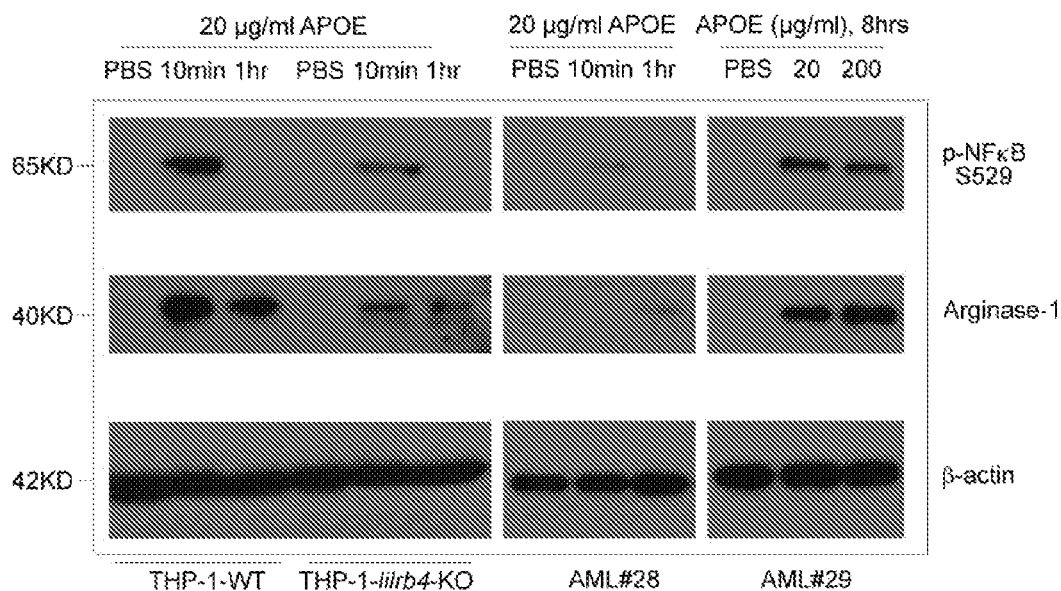
Figure 19C:
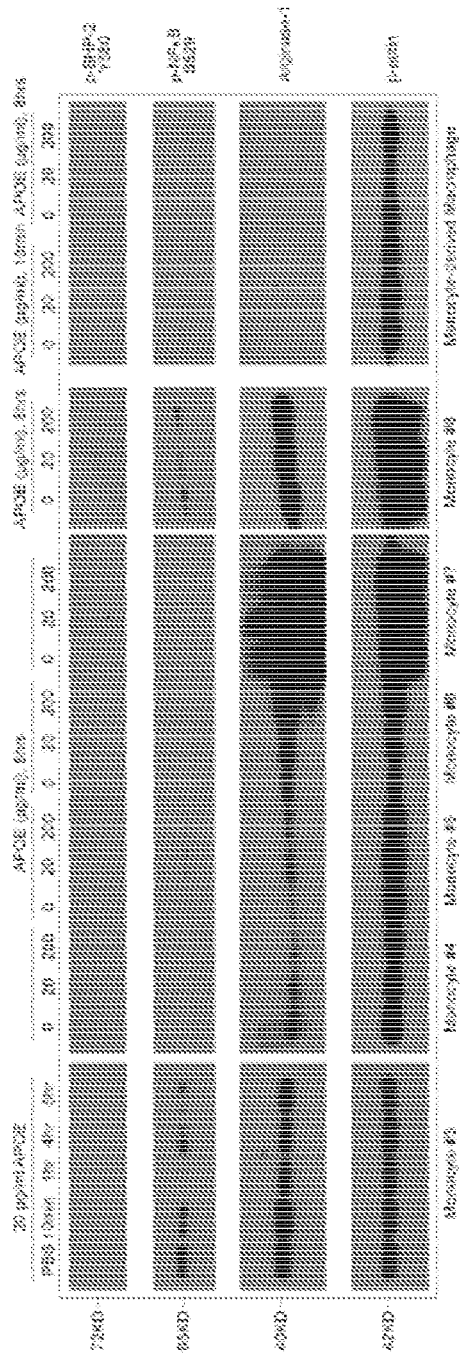

FIGS. 19A-19D show comparison of LILRB4 mediated intracellular signaling in leukemia cells and in normal hematopoietic cells. FIGS. 19A-19B, APOE activates LILRB4 intracellular signaling in leukemia cells. Indicated THP-1 cells and primary AML (M5) cells were serum starved overnight and then treated with the indicated concentration of human recombinant APOE protein for indicated time. Phospho-SHP-2, phosphor-NFκB, and Arginase-1 were examined by western blotting. FIG. 19C, the effect of APOE on normal monocytes or in vitro differentiated macrophages. Normal monocytes were isolated from health donors and macrophages were derived from these monocytes after one-week differentiation in vitro. Cells were serum starved overnight and then treated with indicated concentrations of human recombinant APOE protein for indicated time. Phospho-SHP-2, phosphor-NFκB, and Arginase-1 were examined by western blotting. FIG. 19D, APOE induces uPAR upregulation on AML cells but not in normal monocyte. Normal monocytes were isolated from health donors. Indicated primary AML cells and normal monocytes were serum starved overnight and then treated with 20 µg/ml human recombinant APOE protein for eight hours. Surface uPAR were examined by flow cytometry. Representative flow plots are shown and the mean fluorescence intensities were shown in right-up corner (black, PBS control; red, APOE treatment). Experiments were performed three times with similar results. p values were from two-tailed student t-test.

FIGS. 20A-20B show that anti-LILRB4 does not affect engraftment of normal hematopoietic cells. FIG. 20A, Comparison of LILRB4 surface expression on normal monocytes from two healthy donors and on WT and lilrb4-KO THP-1 cells. FIG. 20B, Anti-LILRB4 antibody did not affect homing ability of normal monocytes. Human normal monocytes (as shown in FIG. 20A) were isolated through CD14-positive selection. These isolated monocytes were pooled and stained by CFSE. After staining, monocytes (5×10$^6$ for each mouse) were injected into NSG mice followed immediately by antibody treatment, and then the mice (n=4) were sacrificed at 20 hrs after transplant. The number of CFSE$^+$ cells in liver, spleen, and bone marrow were normalized to that in peripheral blood as determined by flow cytometry.

Figure 21C:
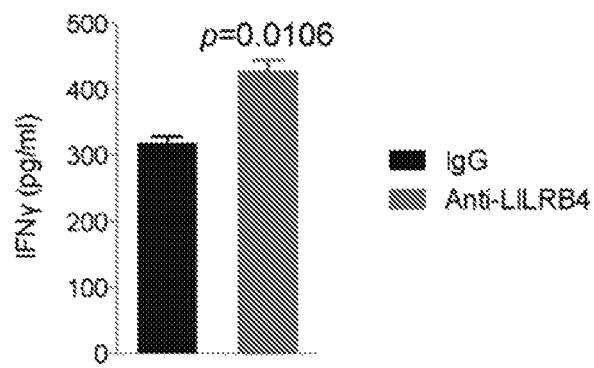

FIGS. 21A-21C show that LILRB4 expressed on MDSCs suppresses T cells. FIG. 21A, Peripheral blood mononuclear cells were isolated by ficoll density gradient centrifugation from 11 solid cancer patient blood samples from UTSW cohort. Surface expression of LILRB4 on MDSCs (CD14$^+$ HLA-DR$^{low-/-}$) was determined by flow cytometry. FIG. 21B, Autologous T cells were cultured with LILRB4-positive or negative MDSCs with indicated E:S ratio (E, effect T cells; S, MDSC suppressor cells) for 5 days in T cell culture media (RPMI-1640 media supplemented with 10% FBS, 30 U/ml human IL-2 and anti-CD3/CD28 Dynabeads at a bead-to-cell ratio of 1:1). Representative photographs of T cells were shown. FIG. 21C, Anti-LILRB4 increases IFNγ secretion from T cells in in-vitro myeloid derived suppressor cells (MDSCs)/T cell co-culture. T cells (E: effector cells; CD3+) and MDSCs (S: suppressor cells; HLA-DR$^{low-/-}$ CD14$^+$) were isolated from peripheral blood of melanoma patients. T cells were co-incubated with MDSCs for 5 days. E:S=2:1. The supernatant of culture media were collected and the level of IFNγ was determined by ELISA. Experiments were performed in triplicates.

Figure 22:
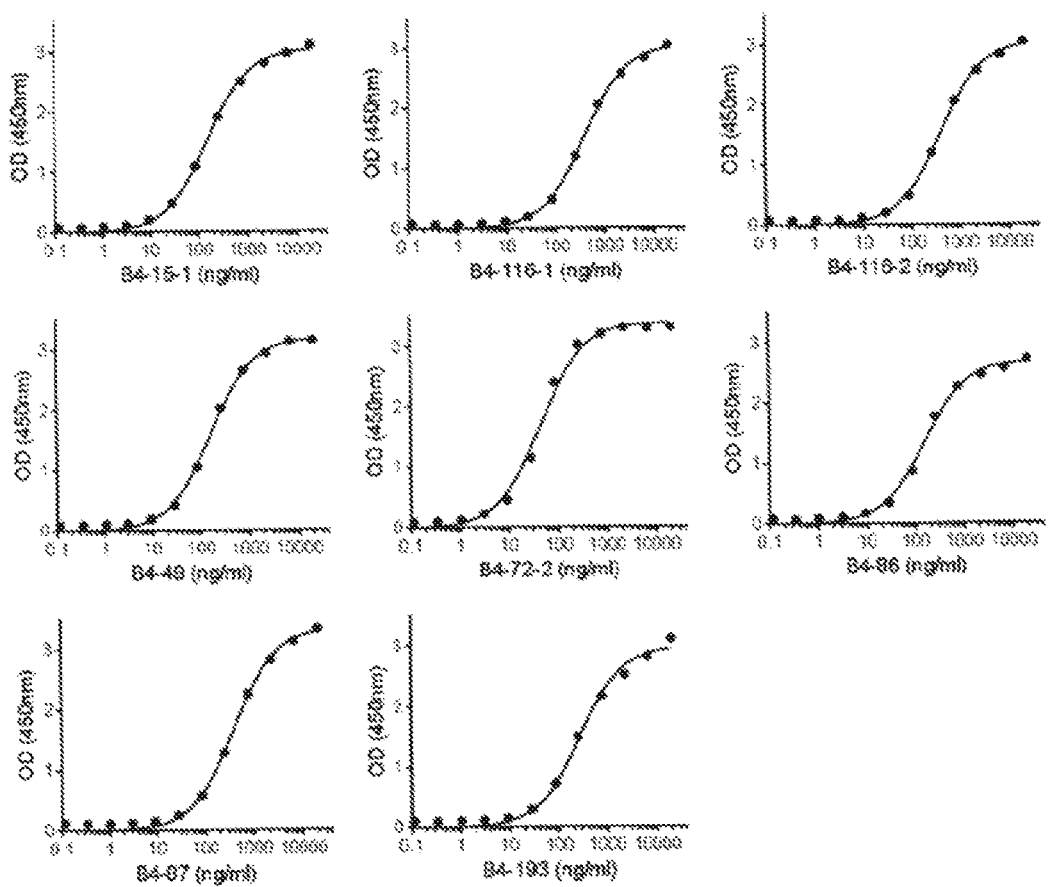

FIG. 22 illustrates the determination of exemplary LILRB4 monoclonal antibody (mAbs) binding to human LILRB4 ECD using a concentration titration (0-10 µg/ml) by ELISA. X axis indicates the antibody concentrations and Y-axis is binding signals in OD (450 nm). LILRB4 ECD recombinant protein was coated on high absorption 96-well plates. Serial diluted (3-fold) LILRB4 mAb was added to the coated/blocked and detected using goat anti-rabbit IgG F(ab)$_2$-conjugated HRP as secondary antibody. The titration curves were fitted using 4-parameter fitting curve using the GraphPad software for EC50 estimation.

Figure 23A:
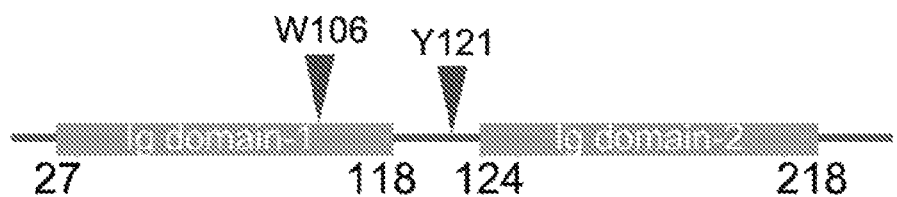
Figure 23B:
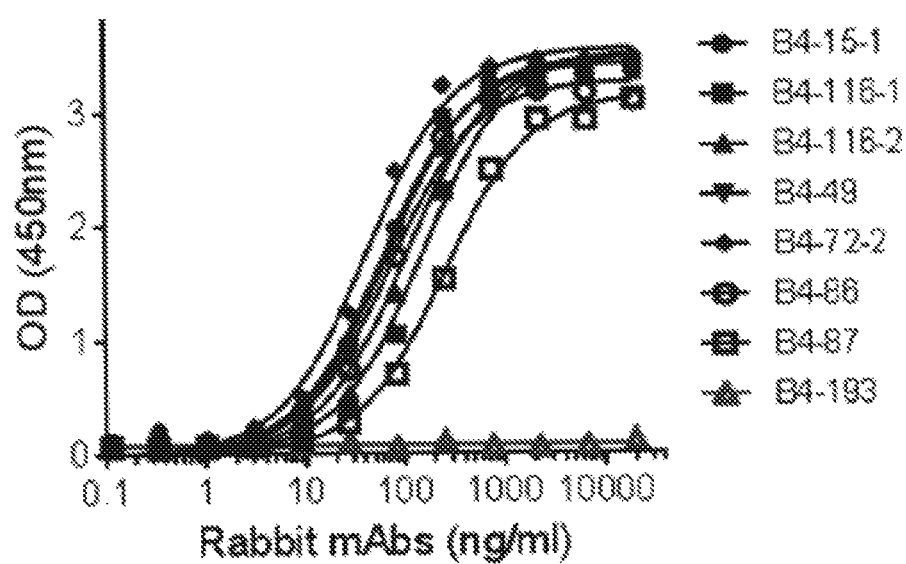

FIGS. 23A-23B. FIG. 23A is a schematic of the LILRB4 extracellular domain (ECD). Mutation of two residues, W106 and Y121, that significantly reduced activation of LILRB4 by APOE, are shown located in the first Ig domain and in the linker between two Ig domains, respectively. FIG. 23B illustrates the determination of exemplary LILRB4 mAbs binding to Ig domain-1 (D1 domain) of human LILRB4. X axis indicates the antibody concentrations and Y-axis is binding signals in OD (450 nm). LILRB4 D1 recombinant protein was coated on high absorption 96-well plates. Serial diluted (3-fold) LILRB4 mAb was added to the coated/blocked plates and detected using goat anti-rabbit IgG F(ab)$_2$-conjugated HRP as secondary antibody. D1 domain alone of LILRB4 is sufficient for binding by seven mAbs whereas D1 alone is not sufficient for binding by B4-193 (open triangle) in this assay.

Figure 24A:
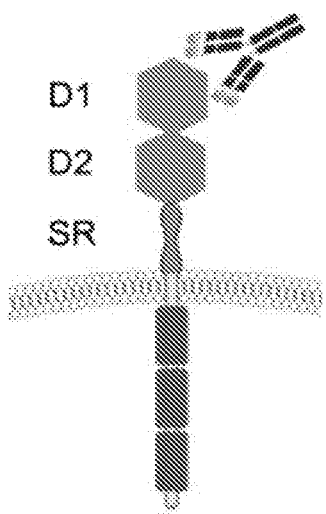
Figure 24B:
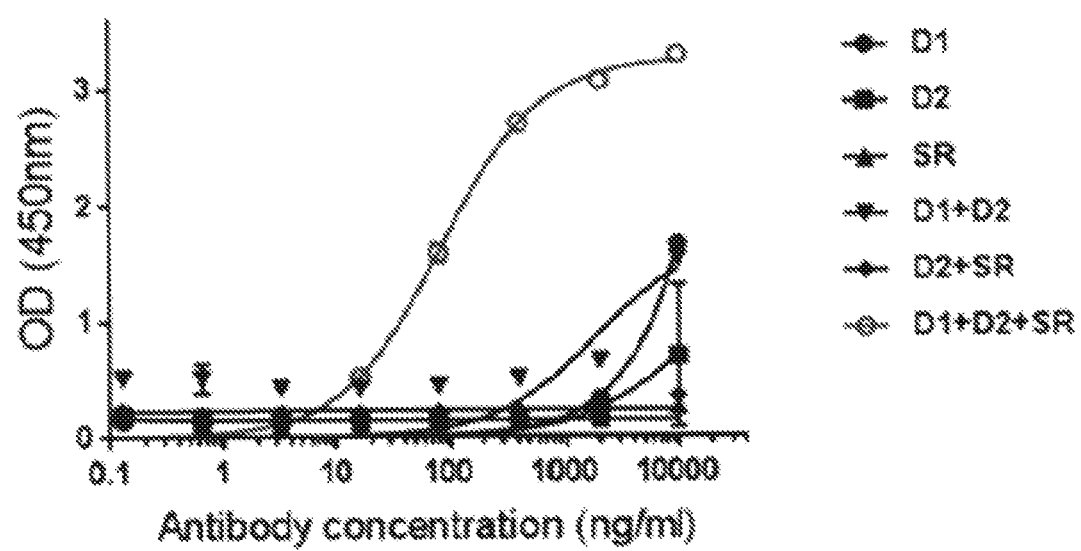

FIGS. 24A-24B. FIG. 24A is a schematic of the LILRB4 membrane protein. The Ig domain-1 (D1), Ig domain-2 (D2) and the stalk region (SR) in the extracellular domain are shown, along with an illustration of an antibody that recognizes the D1 domain. FIG. 24B illustrates the determination of the binding domains of B4-193. LILRB4 D1 domain (D1), D2 domain (D2), stalk region (SR), D1+D2, D2+SR and full-length ECD (D1+D2+SR) of human LILRB4 recombinant proteins were coated on high absorption 96-well plates. Serial diluted (3-fold) B4-193 were added to the coated/blocked plates and detected using goat anti-rabbit IgG F(ab)$_2$-conjugated HRP as secondary antibody. B4-193 only binds to full-length ECD of human LILRB4 in this assay.

Figure 25:
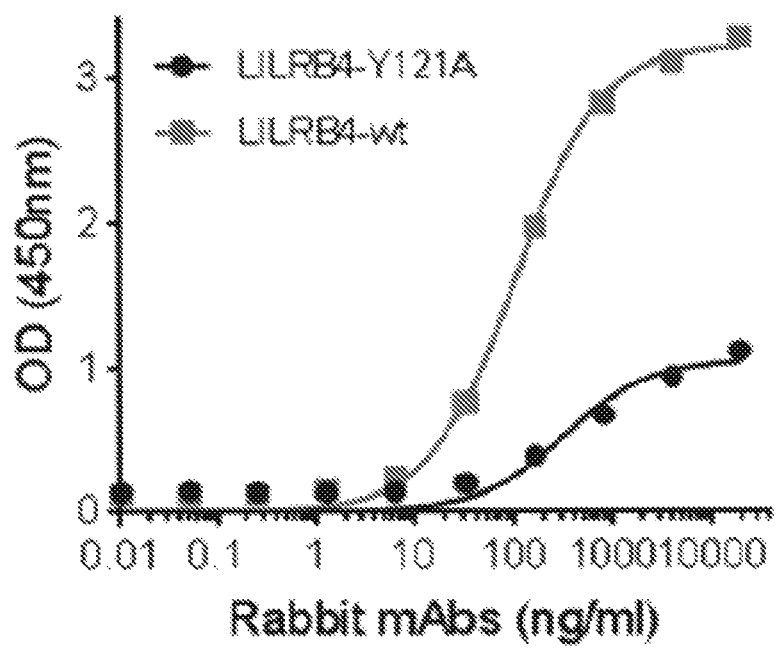

FIG. 25 illustrates the contribution of amino acid Y121 (tyrosine at the position 121. Please note that the numbering of Y at this position 121 is in the context of additional N-terminal sequence before D1; this position is the same as Y98 in SEQ ID No: 238 which starts at D1 without the preceding N-terminal sequence) on LILRB4 to the binding of B4-193. Wild-type and Y121A mutated human LILRB4 ECD recombinant proteins were coated on the high absorption 96-well plates. Serial diluted (3-fold) mAb B4-193 were added to the coated/blocked plates and detected using goat anti-rabbit IgG F(ab)$_2$-conjugated HRP as secondary antibody. The Y121A mutation of LILRB4 significantly decreased the binding of B4-193 to LILRB4.

Figures 26, 27:
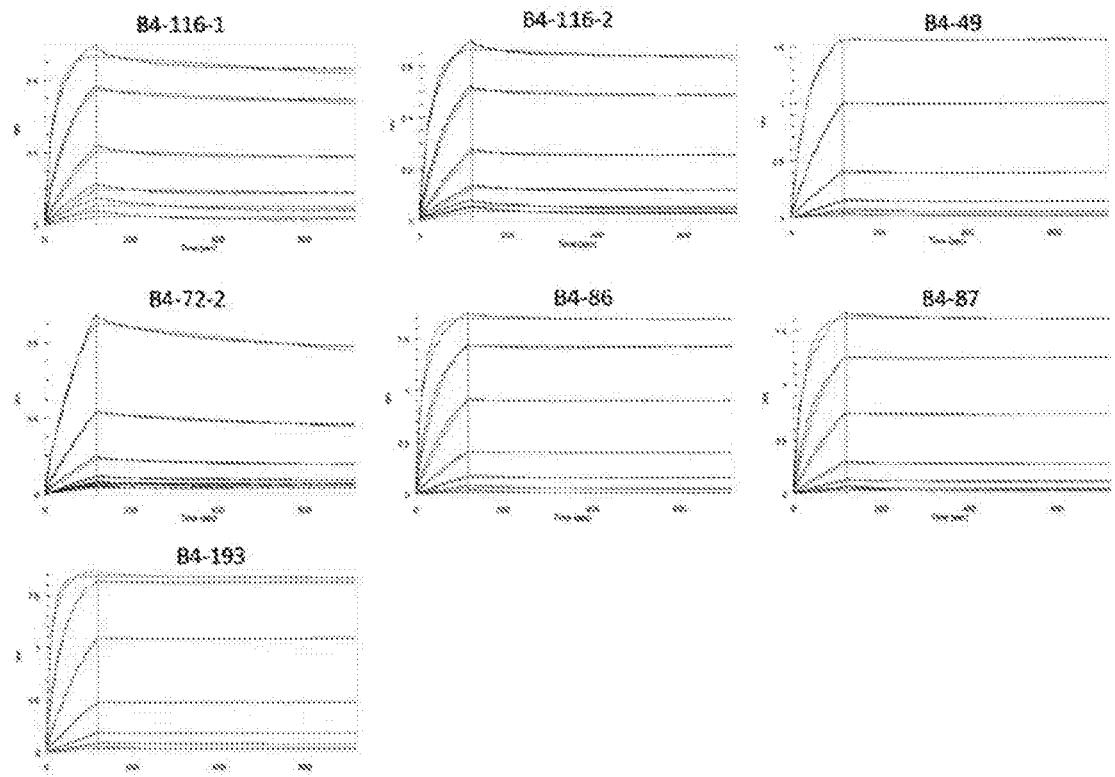

FIG. 26 illustrates the kinetic binding measurements (sensor-grams) for exemplary LILRB4 antibodies determined using Octet. Antibody at 30 µg/mL was loaded to the proteins A sensor for 4 min. Following a short baseline in kinetics buffer, the loaded sensors were exposed to a series of recombinant human LILRB4 concentrations (0.1-200 nM) and background subtraction was used to correct for sensor drifting. All experiments were performed with shaking at 1,000 rpm. Background wavelength shifts were measured from reference sensors that were loaded only with antibody. ForteBio's data analysis software was used to fit the data to a 1:1 binding model to extract an association rate and dissociation rate. The KD was calculated by the ratio koff/kon using ForteBio's data analysis software 7.0.

FIG. 27 illustrates the epitope binding of exemplary LILRB4 mAbs. Classical sandwich epitope binning experiments were performed in 8-channel Red96. First antibodies (40 ug/mL) were loaded onto protein A sensors for 4 min and remaining Fc-binding sites on the sensors were blocked with an irrelevant rabbit antibody (20 µg/ml) for 4 min, following by soaking the sensors in kinetics buffer for 10 sec. The sensors were then exposed to recombinant LILRB4 (25 µg/mL) for 4 min. Finally, the sensors were exposed to the second antibodies (40 µg/mL) for 4 min to check for the binding. Raw data was processed using ForteBio's data analysis software 7.0 and the antibody pairs were assessed for competitive binding. Additional binding by the second antibody indicates an unoccupied epitope (non-competitor "−"), while no binding indicates epitope blocking (competitor "+").

FIGS. 28A-28C illustrate the amino acid sequences of the heavy chain variable regions of exemplary LILRB4 antibodies.

FIGS. 29A-29C illustrate the nucleic acid sequences of the heavy chain variable regions of exemplary LILRB4 antibodies.

FIGS. 30A-30C illustrate the amino acid sequences of the light chain variable regions of exemplary LILRB4 antibodies.

FIGS. 31A-31C illustrate the nucleic acid sequences of the light chain variable regions of exemplary LILRB4 antibodies.

Figure 32:
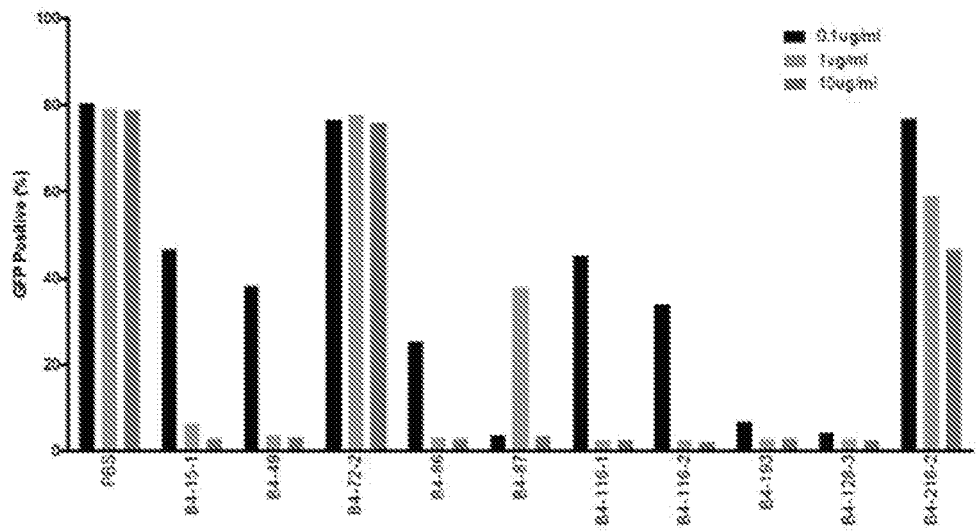

FIG. 32 illustrates the APOE-competition by exemplary anti-LILRB4 antibodies at different concentrations (0.1 µg/ml, 1 µg/ml and 10 µg/ml). Effective blocking of APOE activity is shown as reduced GFP positive (%) compared to the PBS control.

Figure 33:
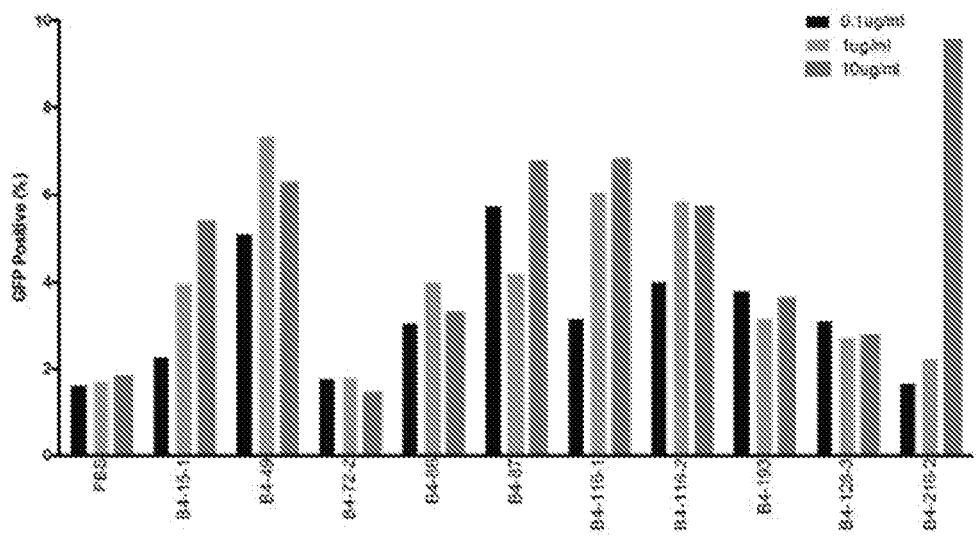

FIG. 33 illustrates the LILRB4-reporter cells/K562-co-culture with exemplary anti-LILRB4 antibodies at different concentrations (0.1 µg/ml, 1 µg/ml and 10 µg/ml). Potential agonistic antibodies may lead to relatively higher GFP positive (%) compared to the PBS control in this assay due to potential cross-linking of antibodies by the Fc receptors on K562 cells.

Figure 34:
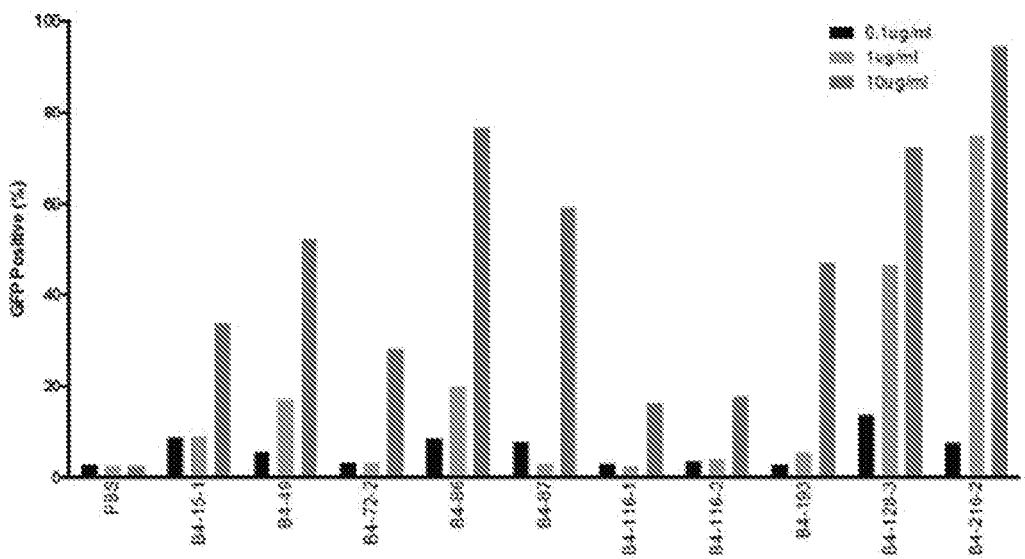

FIG. 34 illustrates the LILRB4-reporter cells treated with coated anti-LILRB4 antibodies at different concentrations (0.1 µg/ml, 1 µg/ml and 10 µg/ml). Antibodies recognizing the LILRB4 extracellular domain tend to register a positive GFP (%) signal compared to the PBS control, due to immobilization of antibodies on the plastic surface in this assay.

Figure 35:
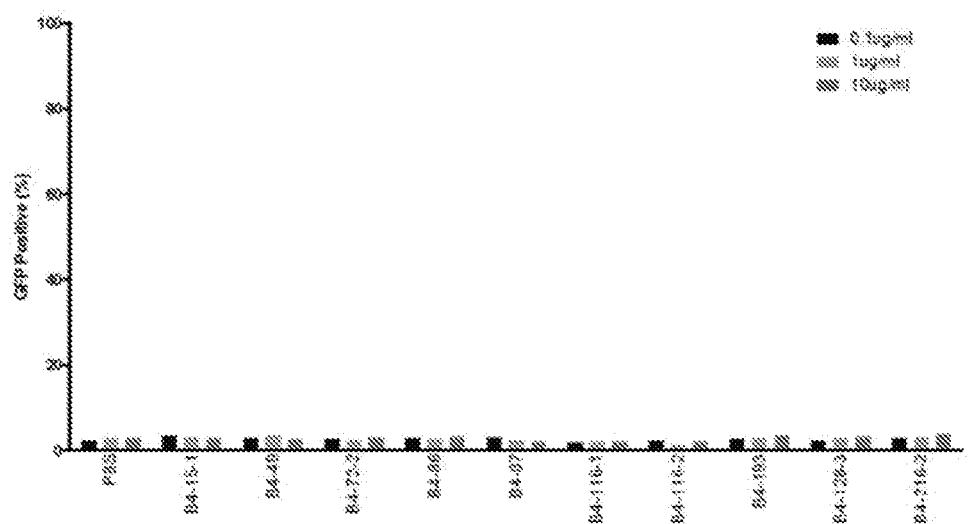

FIG. 35 illustrates the LILRB4-reporter cells treated with soluble anti-LILRB4 antibodies at different concentrations (0.1 µg/ml, 1 µg/ml and 10 µg/ml).

Figures 36, 37:
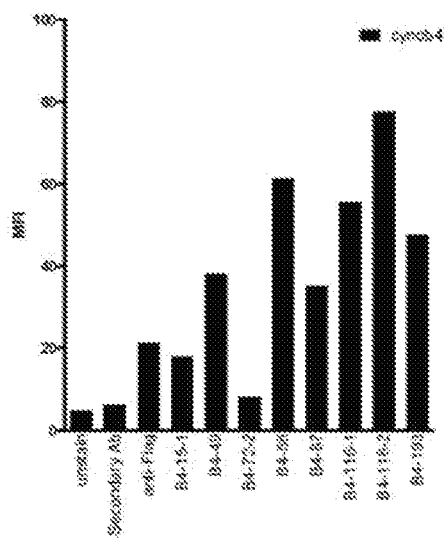

FIG. 36 illustrates the exemplary anti-LILRB4 antibodies binding to cynomolgus monkey LILRB4 (cynob4)-expressing CHO cells by flow cytometry.

FIG. 37 illustrates the cross-reactivity with LILRB family members, LILRA family members as well as cynomolgus monkey LILRB4 (cynoB4) by exemplary anti-LILRB4 antibodies. "+" indicates binding of an antibody with a particular recombinant protein.

Figure 38:
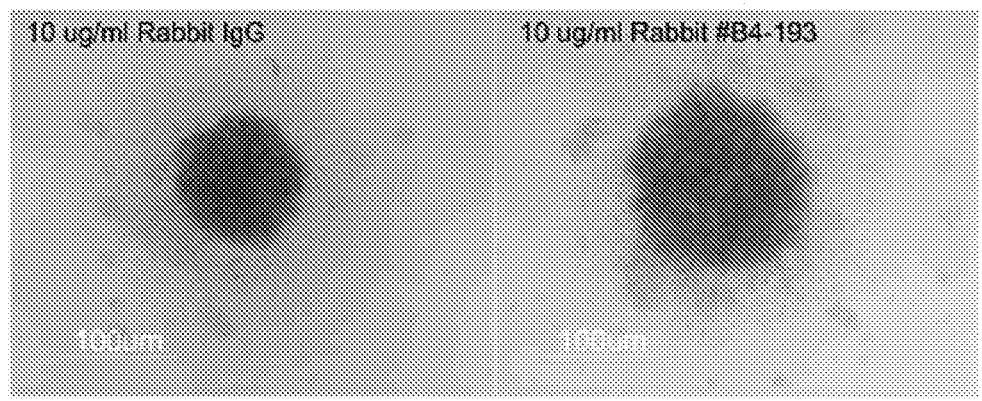

FIG. 38 illustrates that the exemplary anti-LILRB4 antibody Rabbit #B4-193 rescues T cell suppression by THP-1 cells.

Figure 39A:
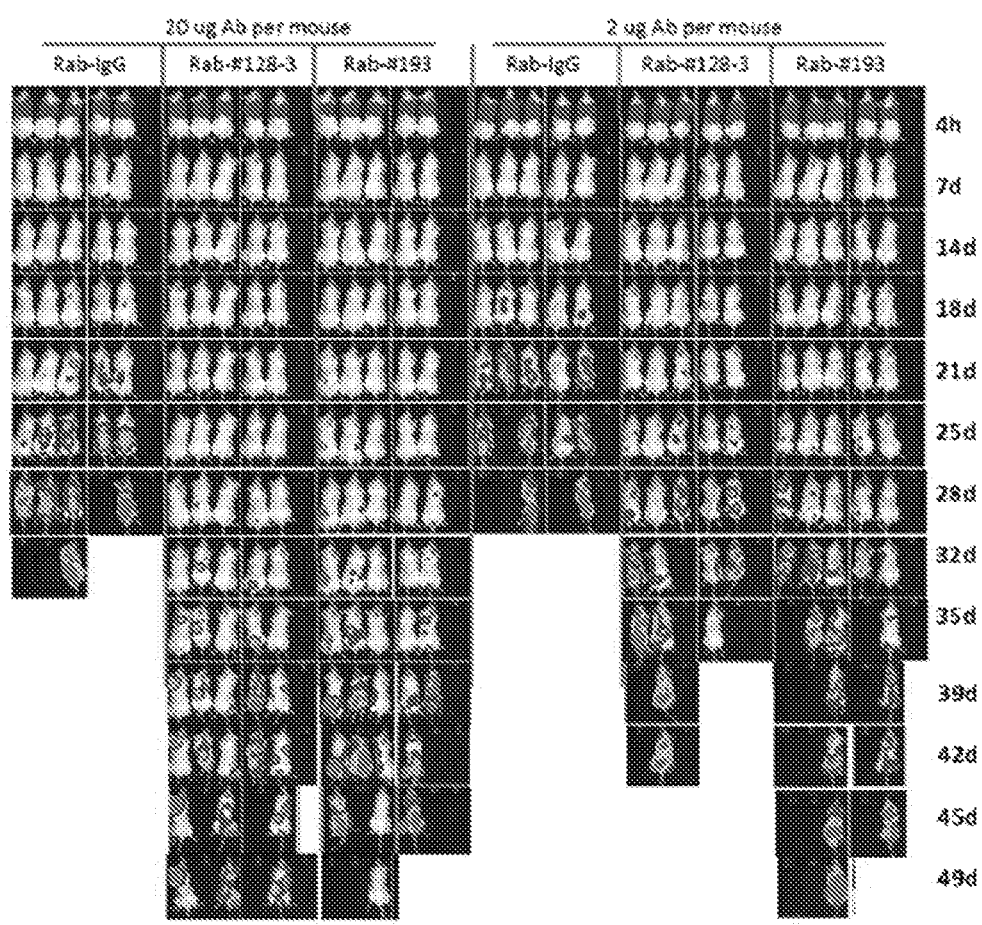
Figure 39B:
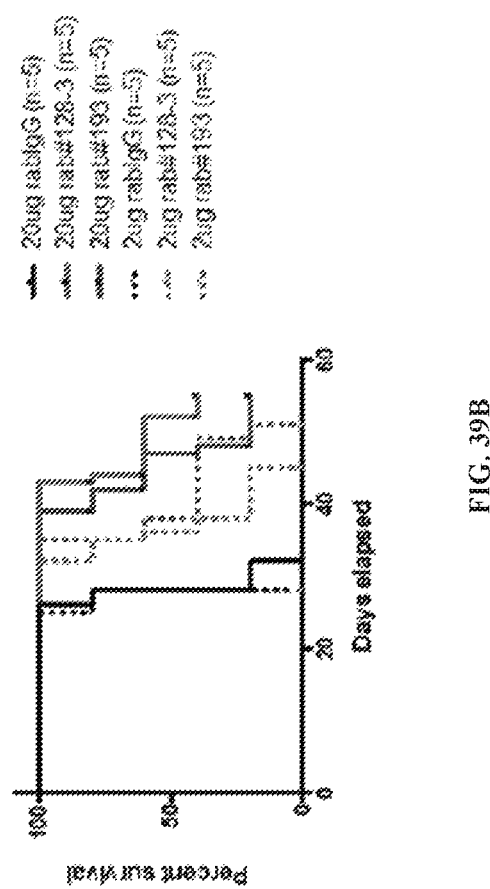
Figure 39C:
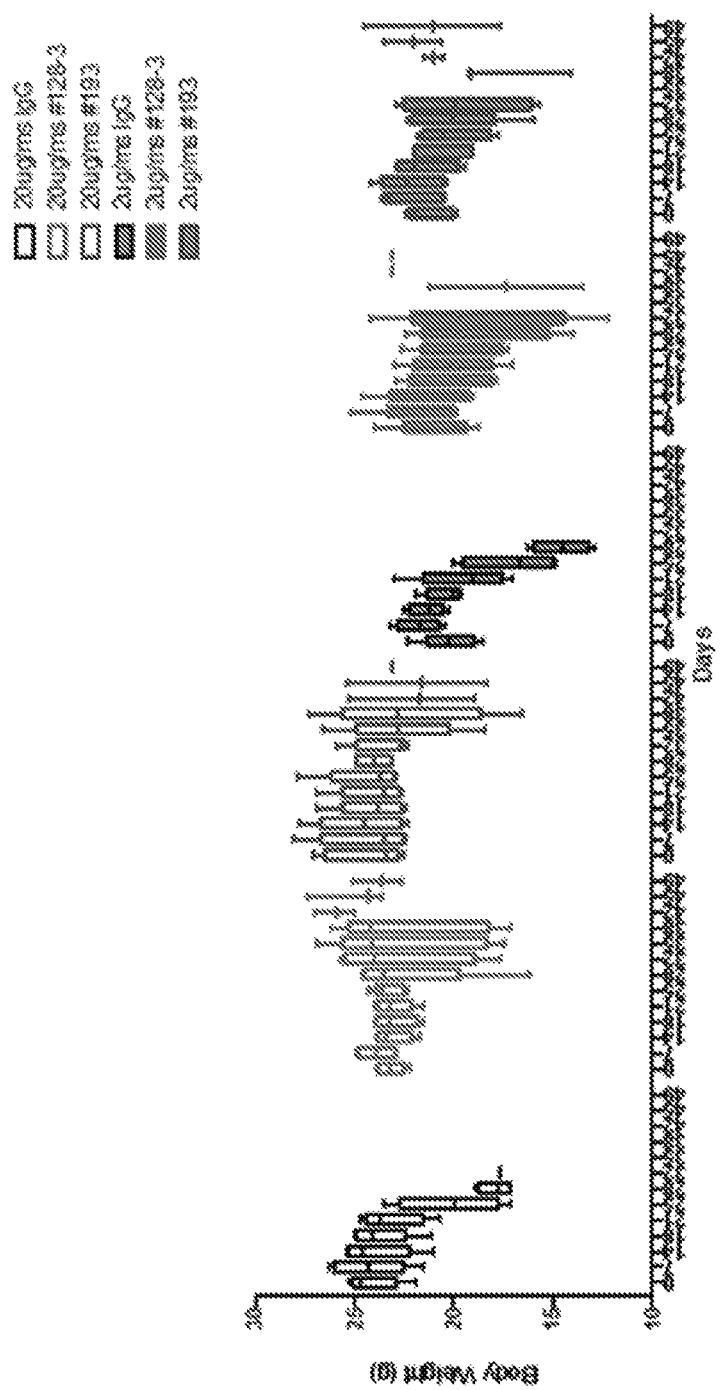

FIGS. 39A-39C illustrate that exemplary anti-LILRB4 antibodies Rab-#128-3 and Rab-#193 inhibit leukemia development in THP-1 xenograft mice.

Figure 40:
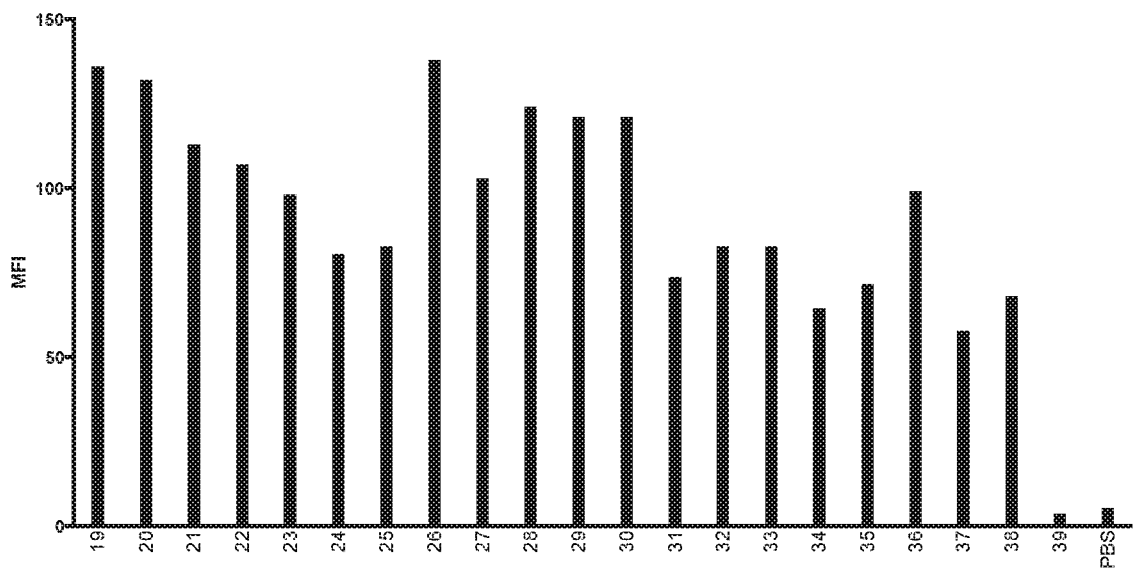

FIG. 40 illustrates the binding of h193 antibodies to human LILRB4 protein determined by flow cytometry. The number under each histogram bar refers to the specific recombinant humanized antibody shown in Table 8. Antibody 39 is an irrelevant antibody. Both Antibody 39 and PBS serve as negative controls.

Figure 41A:
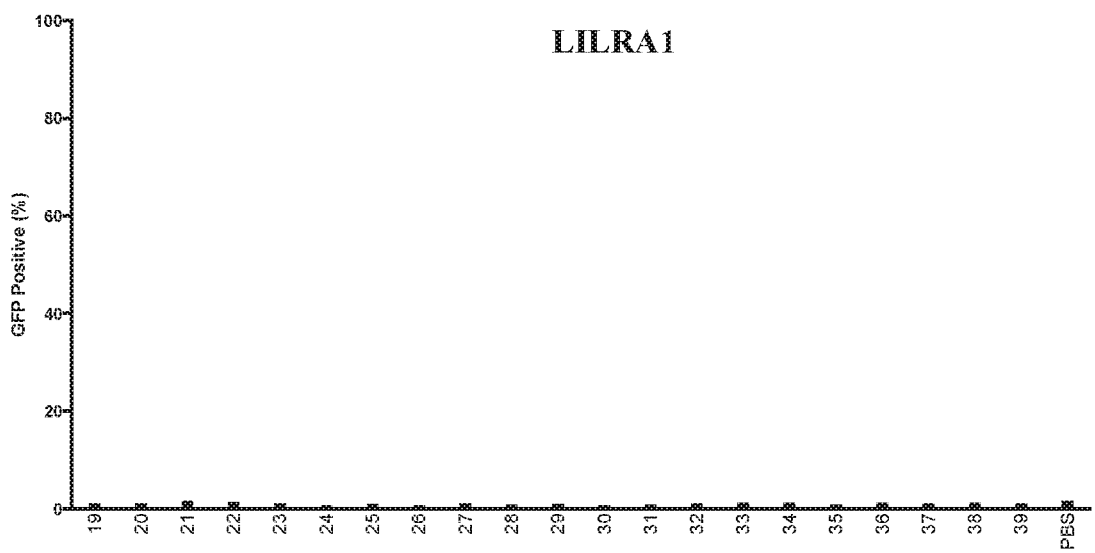
Figure 41B:
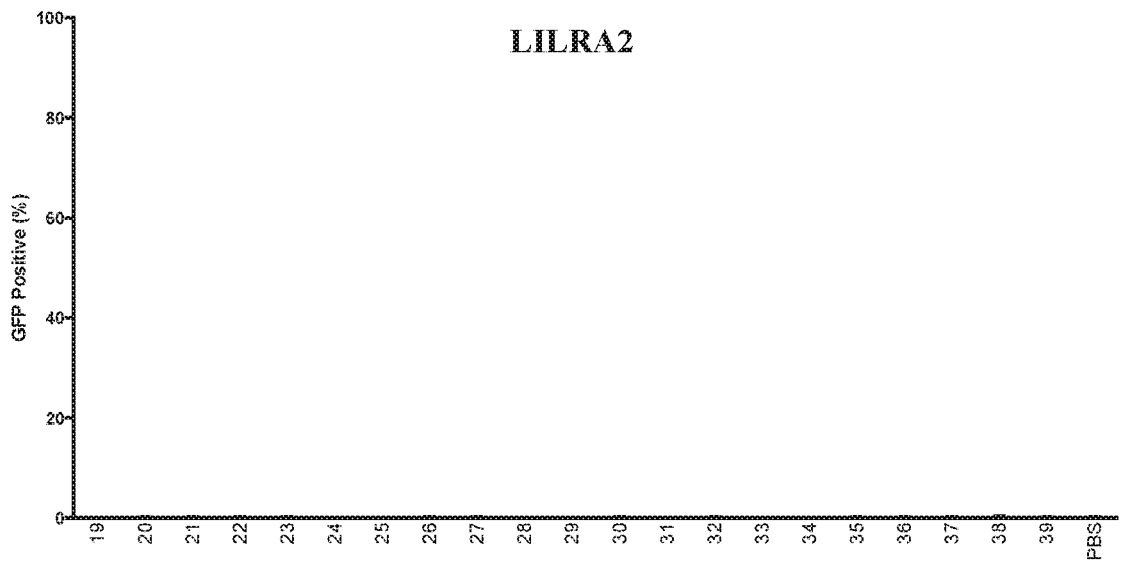
Figure 41C:
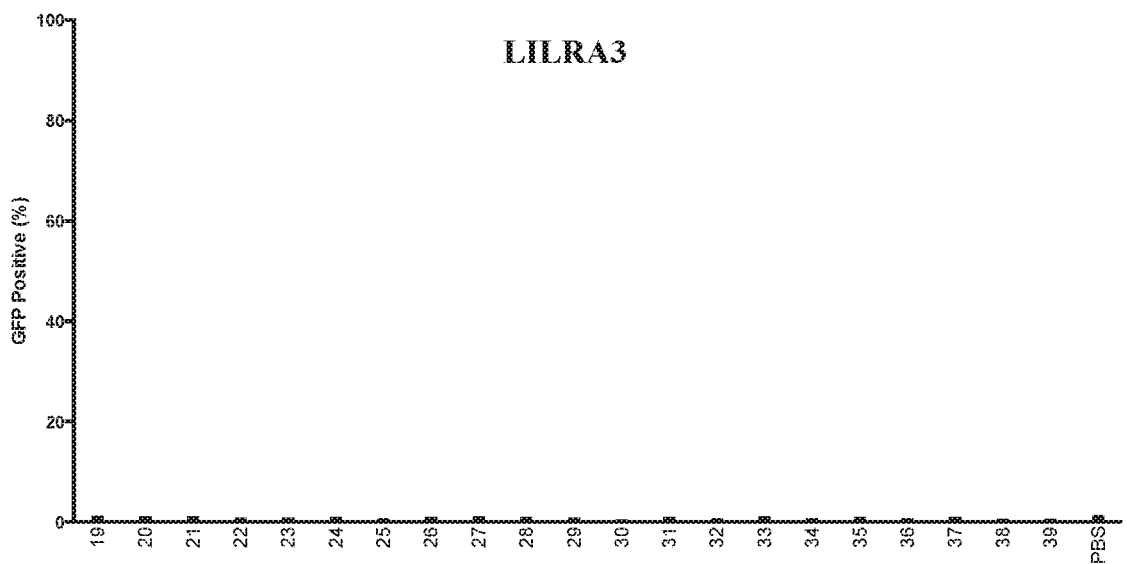
Figure 41D:
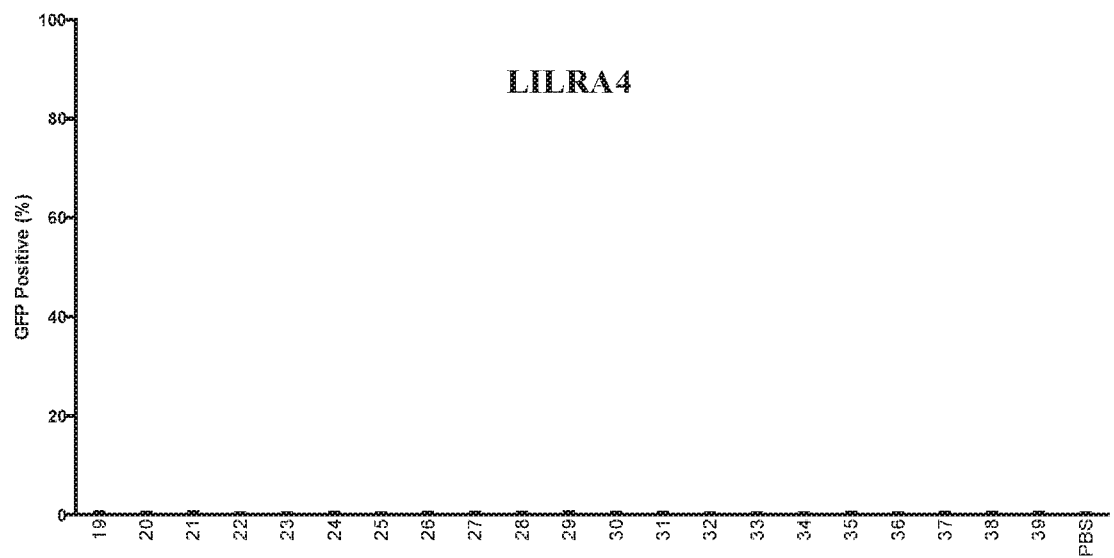
Figure 41E:
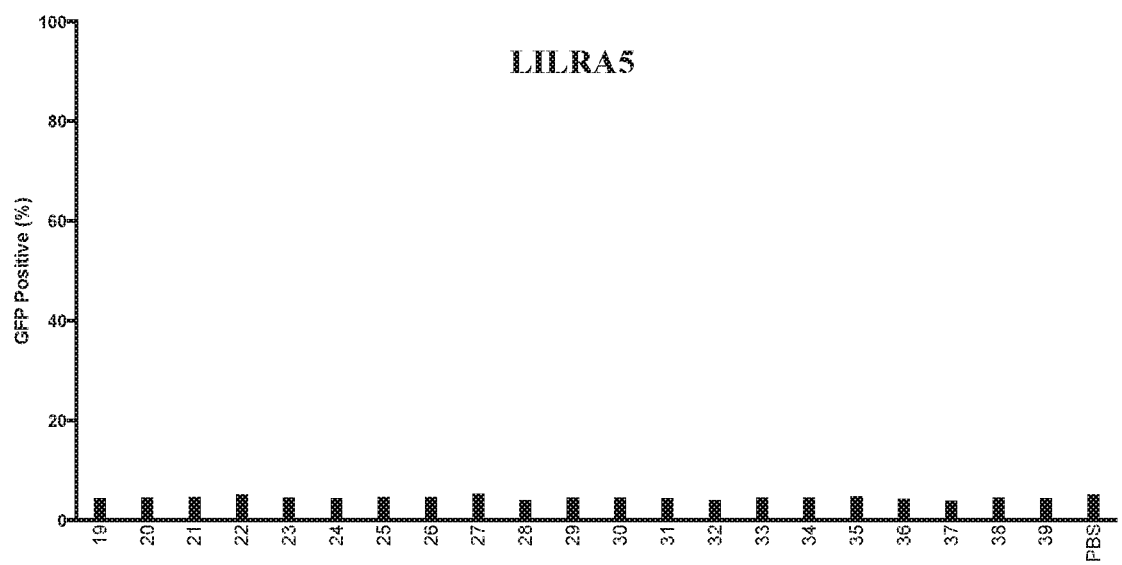
Figure 41F:
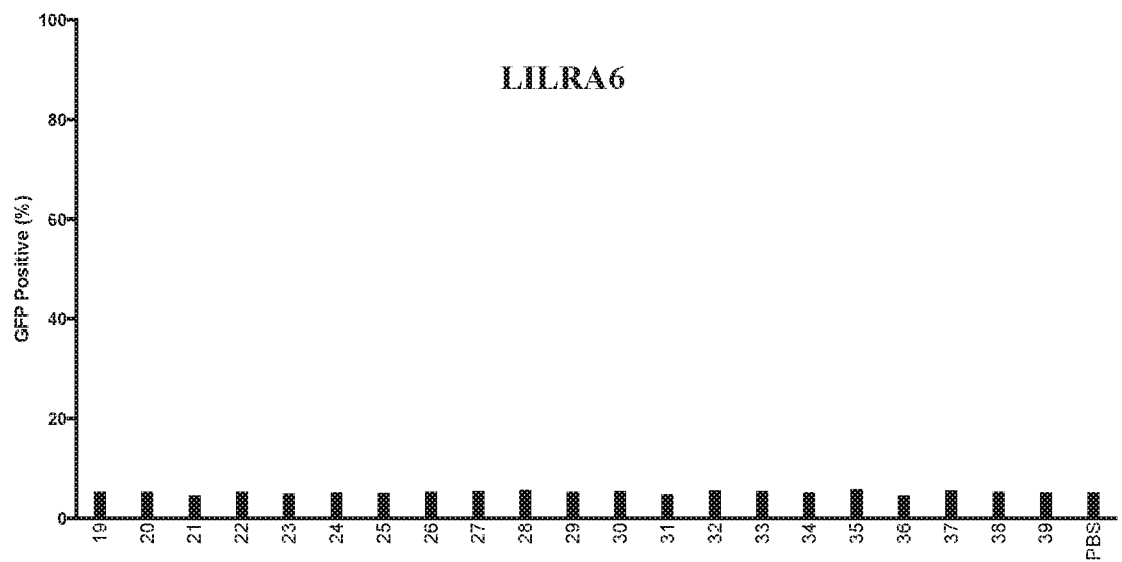
Figure 41G:
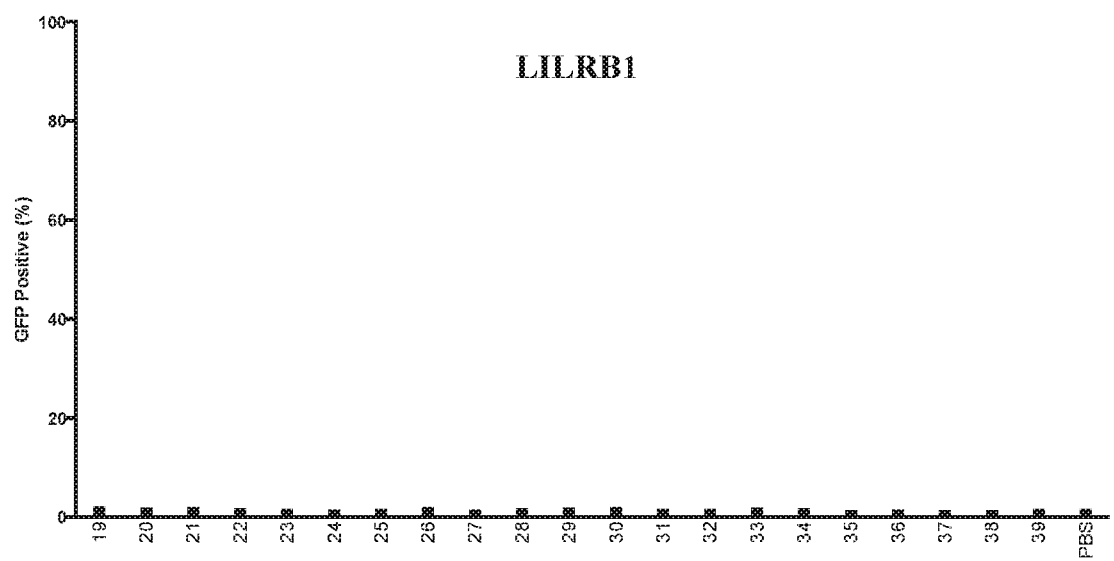
Figure 41H:
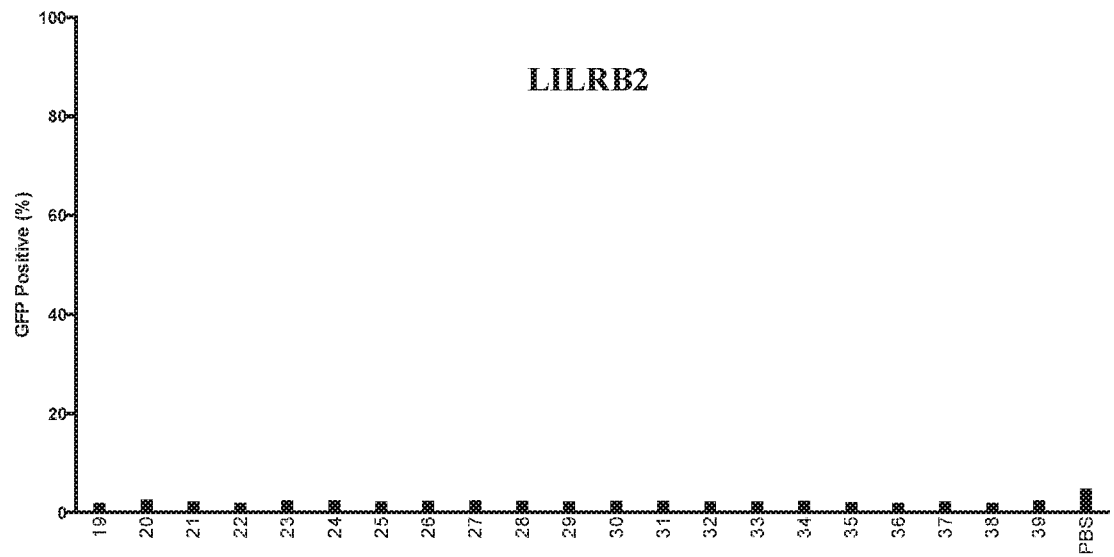
Figure 41I:
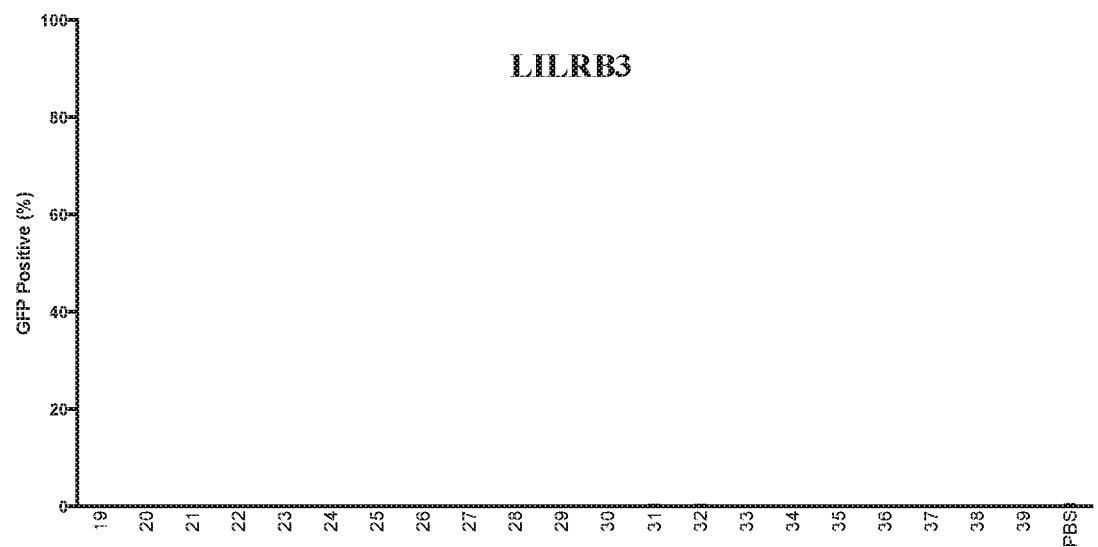
Figure 41J:
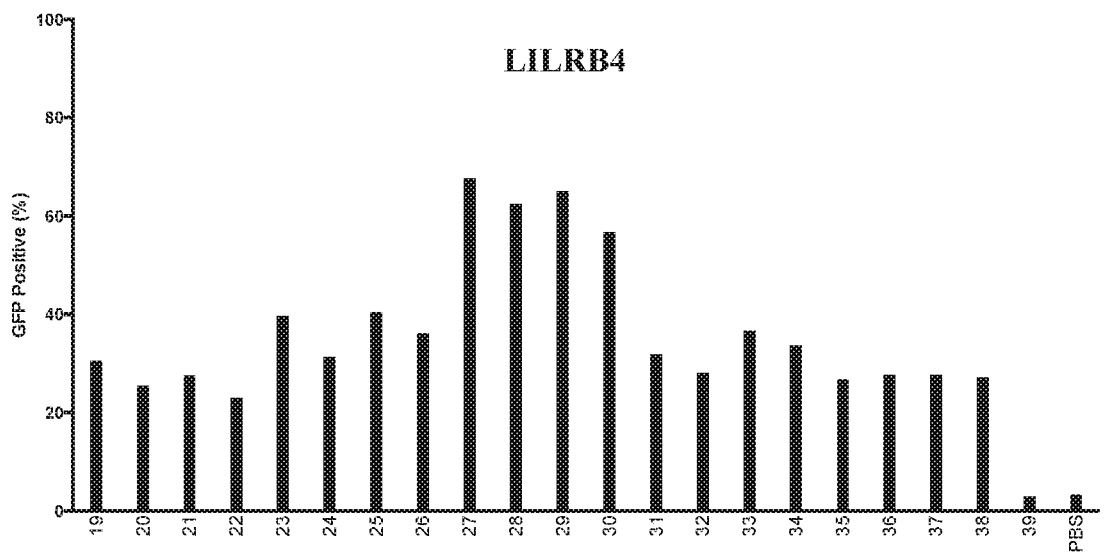
Figure 41K:
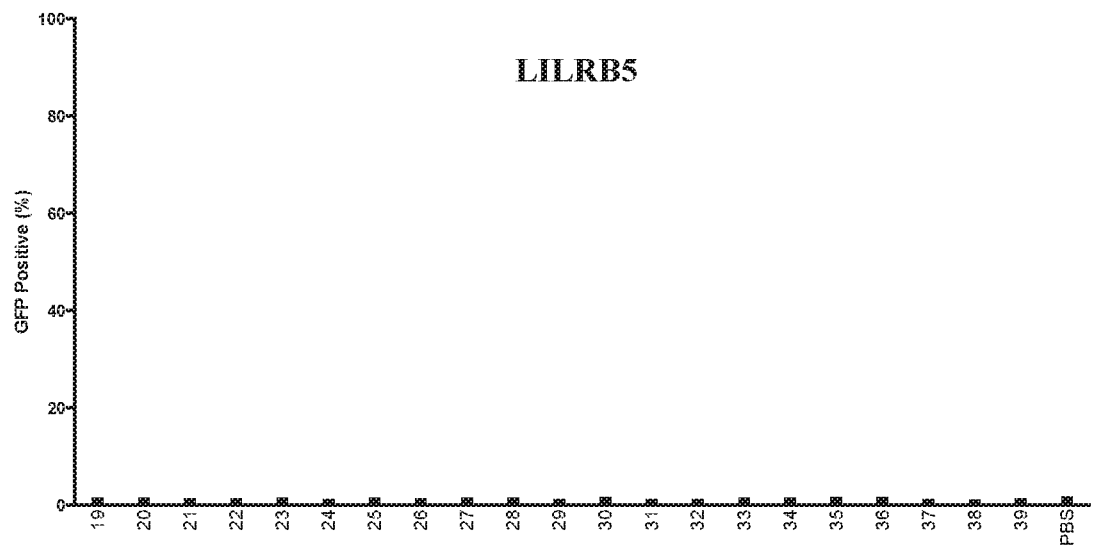
Figure 41L:
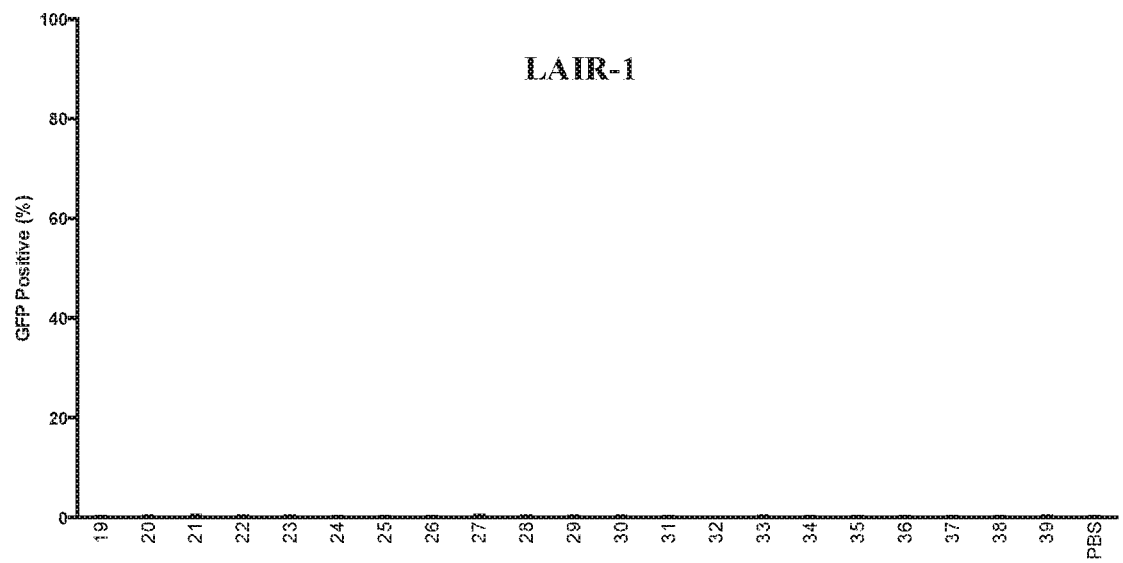
Figure 41M:
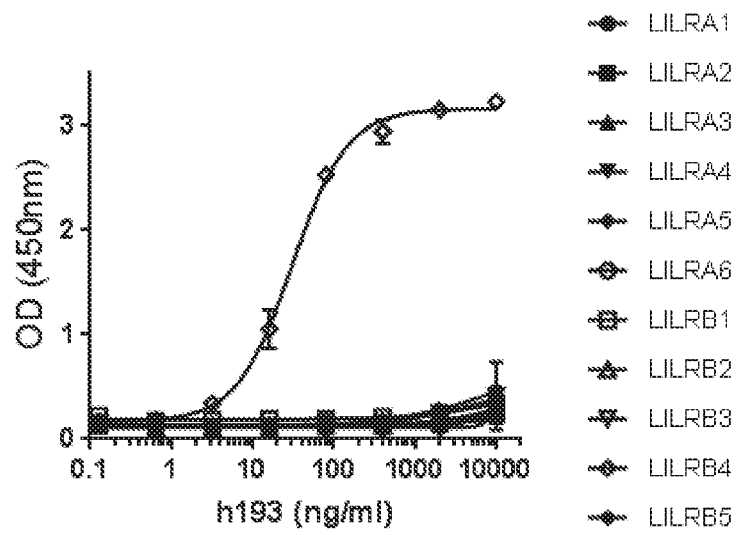

FIGS. 41A-41M illustrate specific binding of h193 antibodies to LILRB4 protein. FIGS. 41A-41L illustrate the specificity of h193 antibodies determined by LILR reporter assays, in which LILR reporter cells are added to the plates coated with h193 antibodies. The binding of h193 antibodies to the ECD of the LILR member on the surface of the reporter cells induced GFP signal. FIG. 41M illustrates the specificity of an exemplary h193 antibody determined by ELISA. LILRA and LILRB recombinant proteins were coated on high absorption 96-well plates. Serial diluted (5-fold) mAb h193 were added to the coated/blocked plates and detected using goat anti-human IgG F(ab)2 conjugated HRP as secondary antibody.

Figure 42:
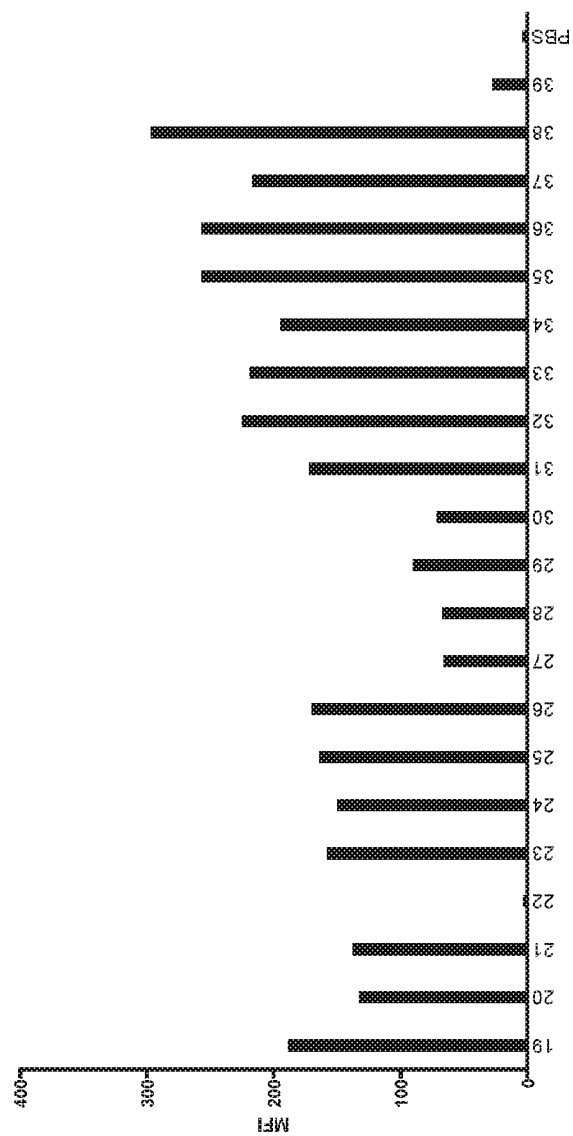

FIG. 42 illustrates binding of h193 antibodies to cynomolgus monkey LILRB4 determined by flow cytometry. The number under each histogram bar refers to the specific recombinant humanized antibody shown in Table 8. Antibody 39 is an irrelevant antibody. Both Antibody 39 and PBS serve as negative controls.

Figure 43A:
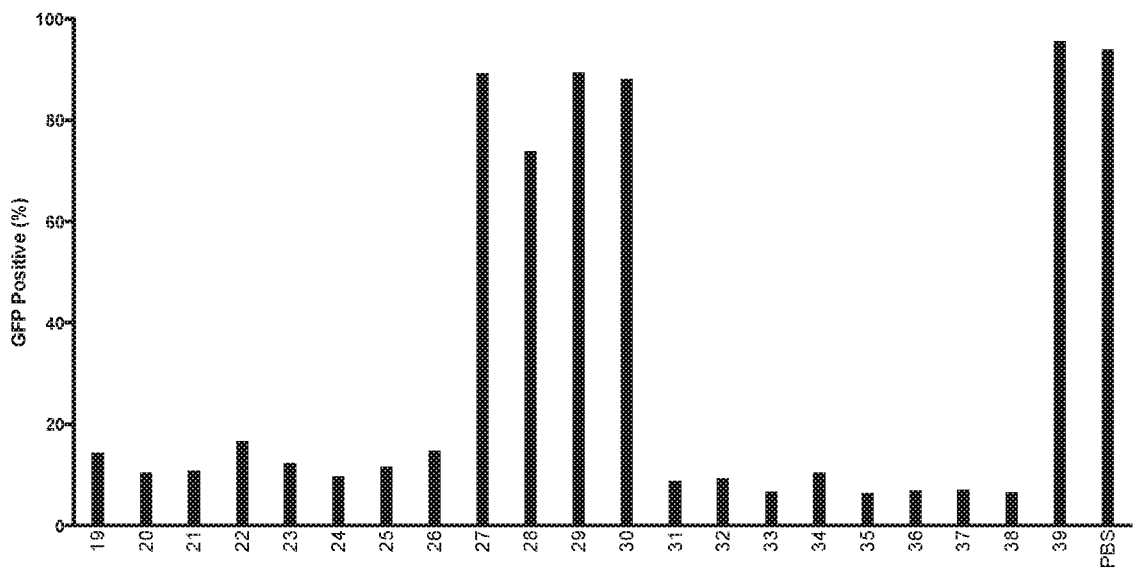
Figure 43B:
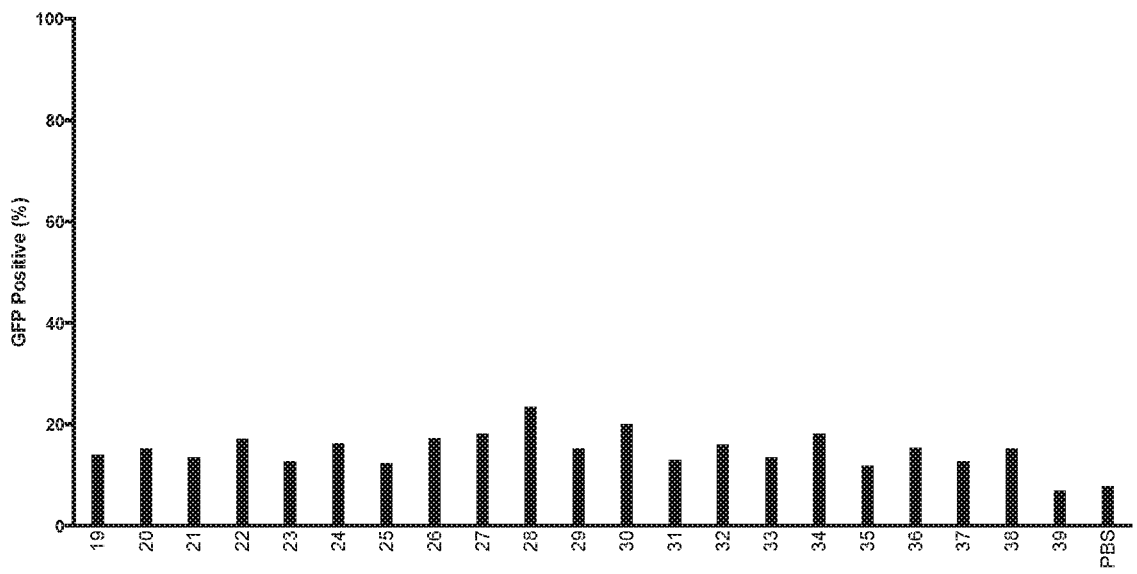
Figure 44A:
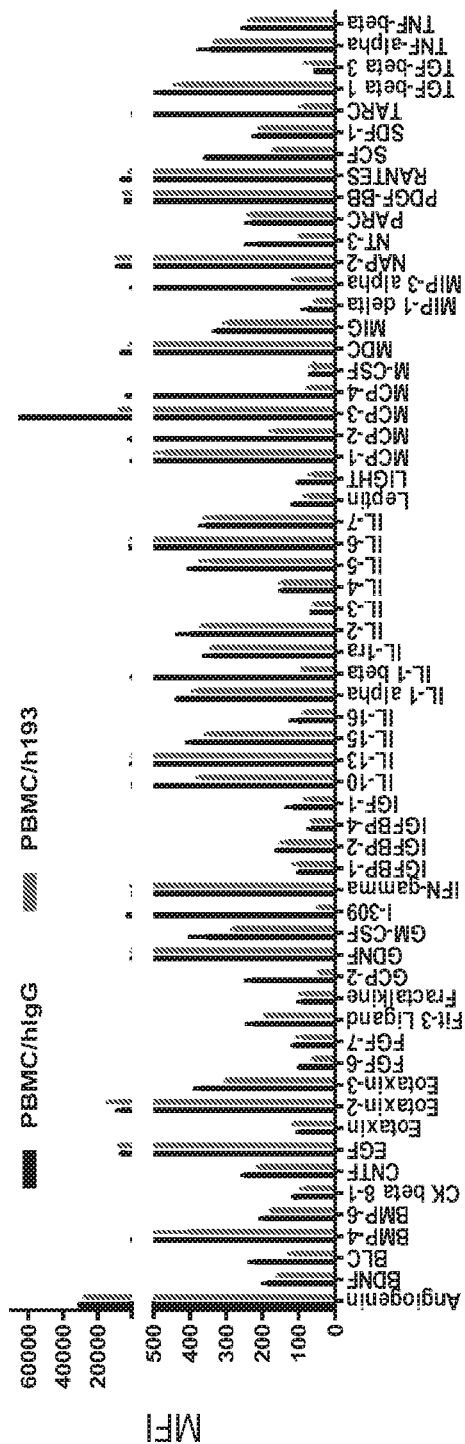
Figure 44B:
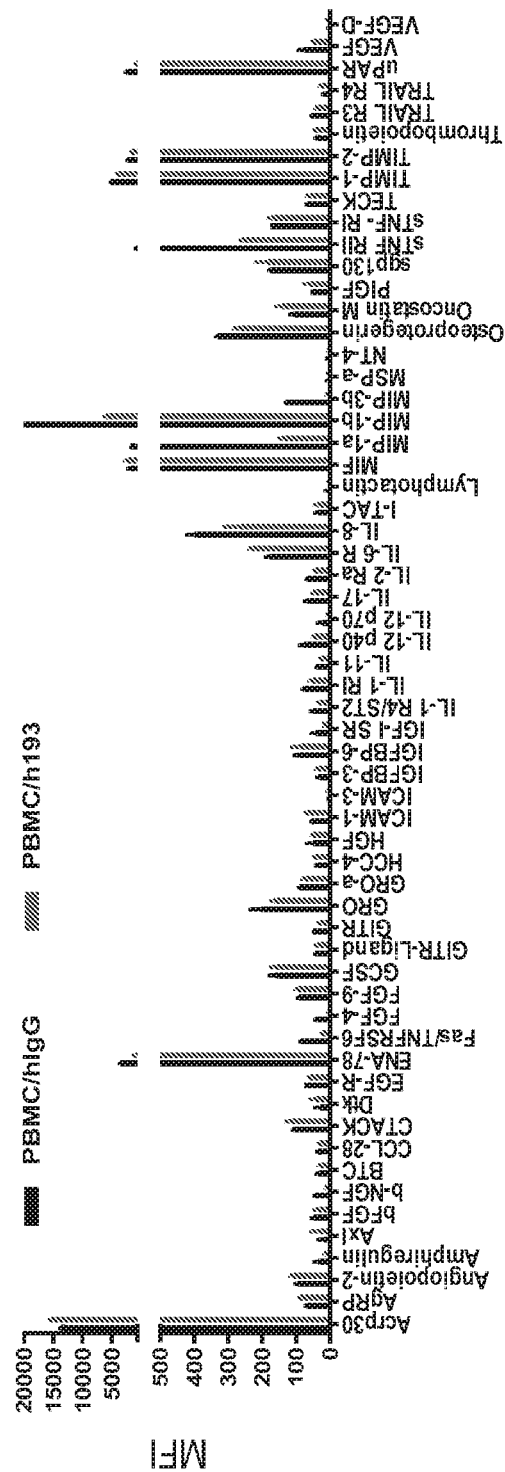
Figure 44C:
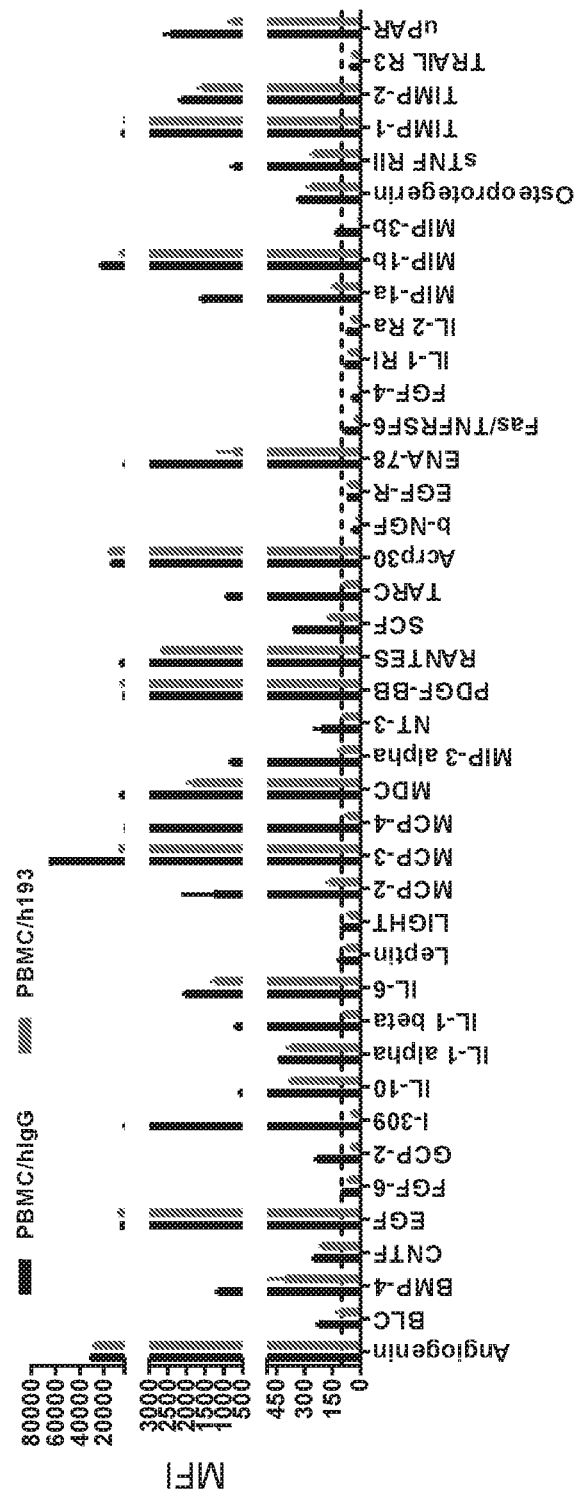
Figure 44D:
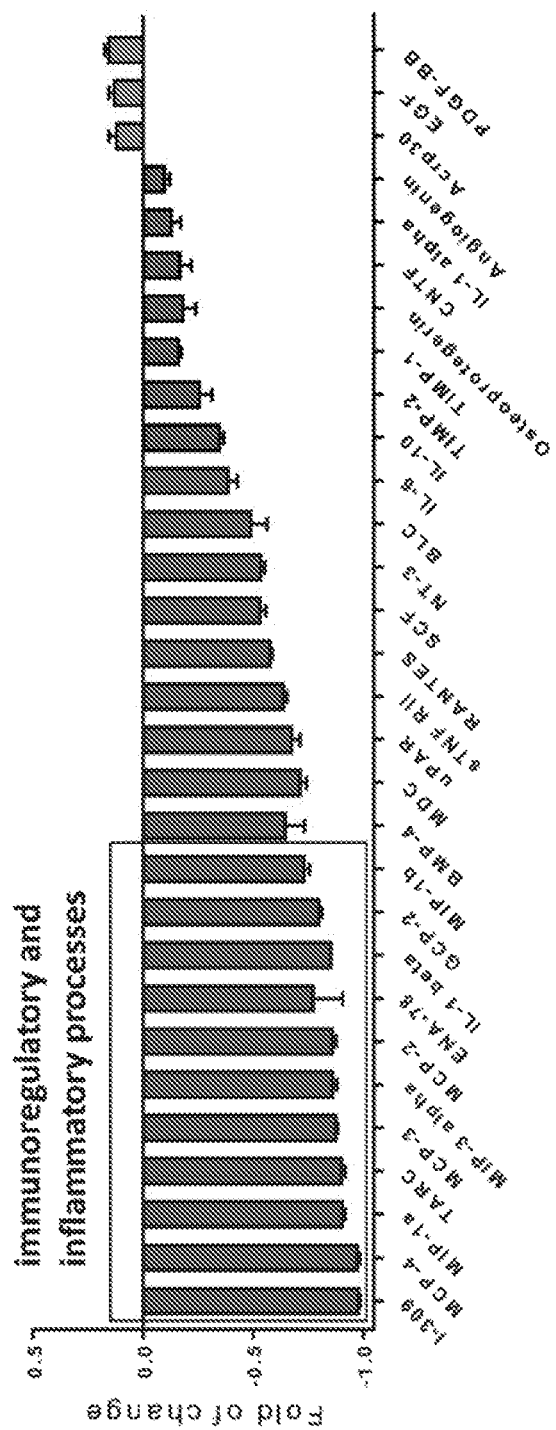
Figure 45A:
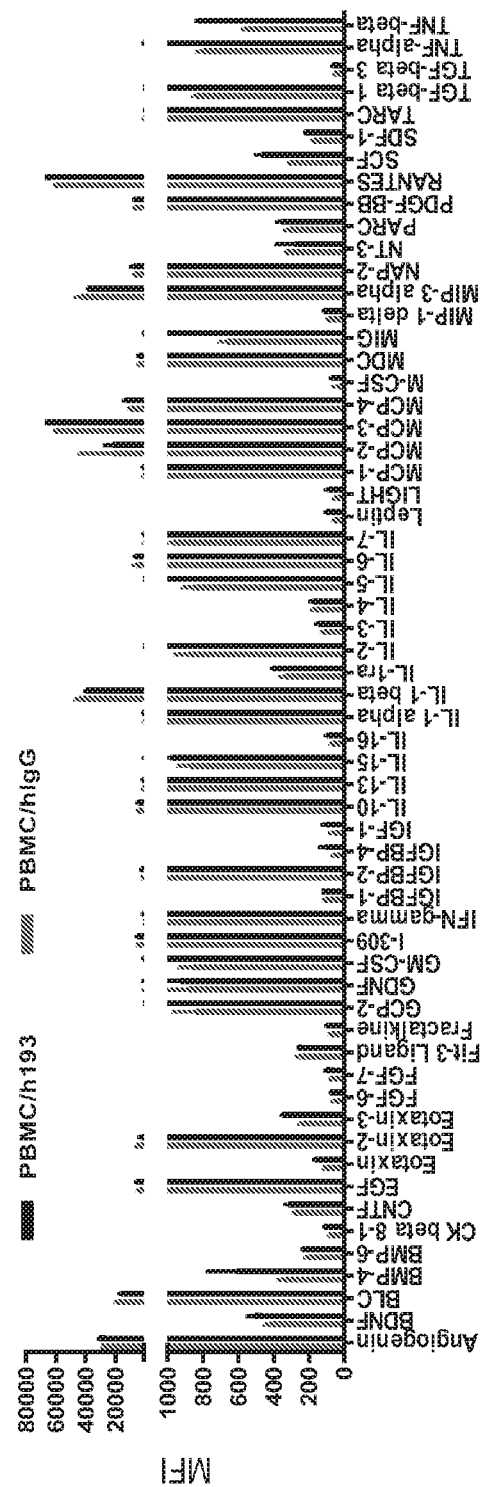
Figure 45B:
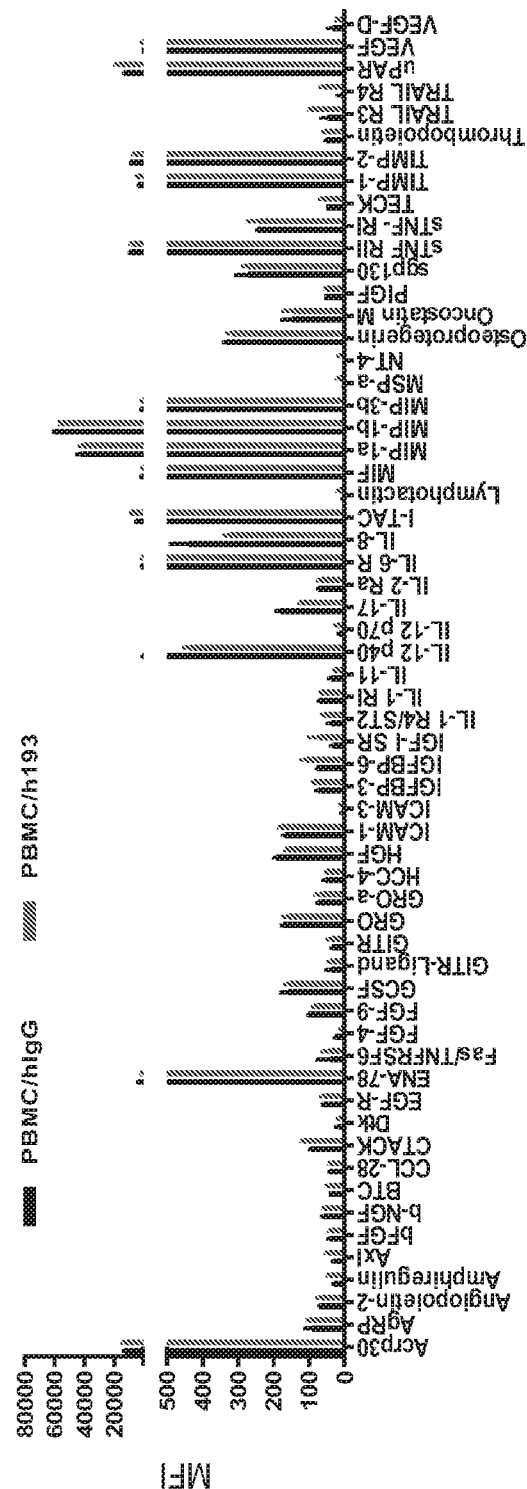
Figure 45C:
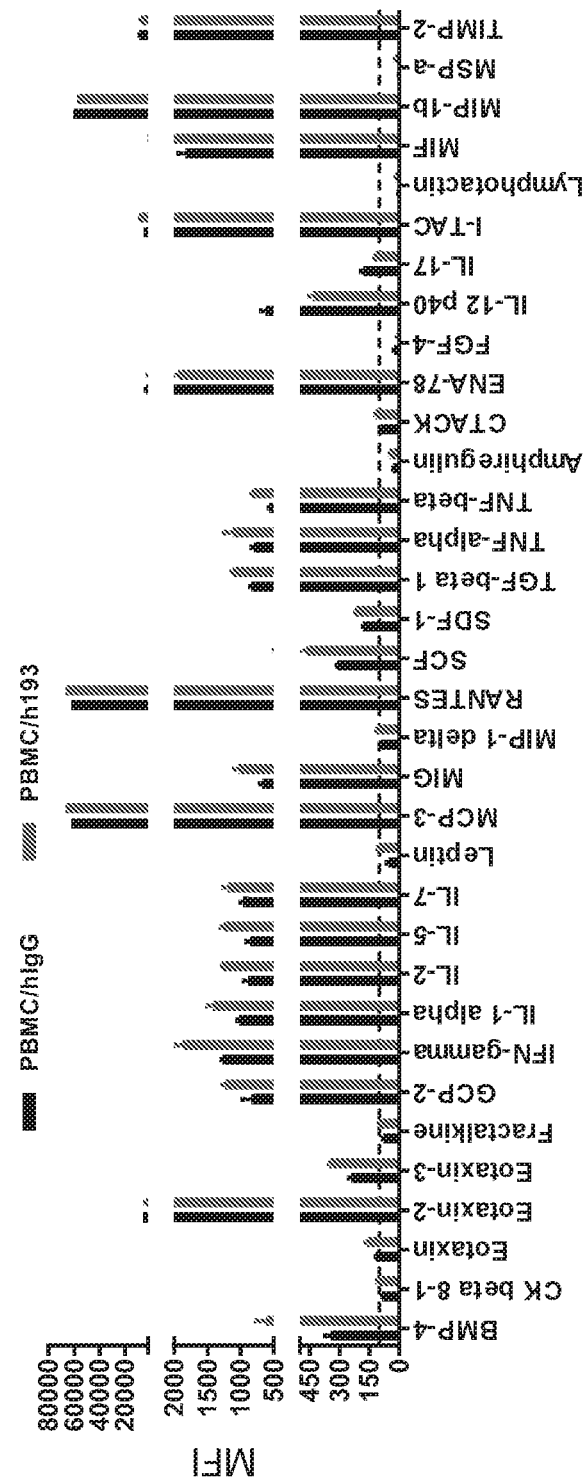
Figure 45D:
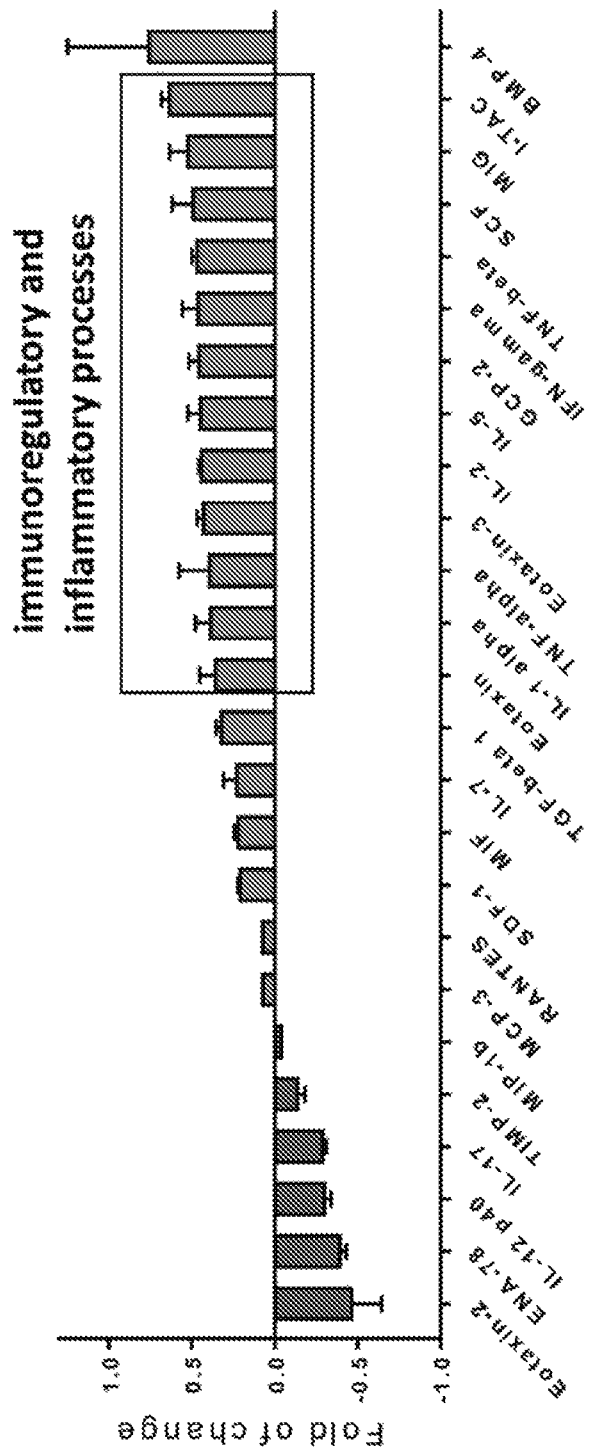
Figure 46A:
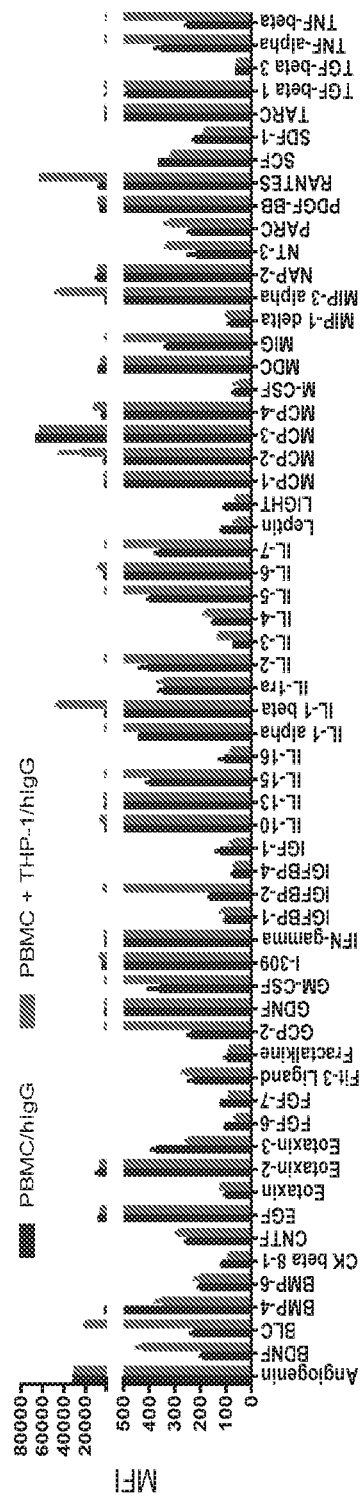
Figure 46B:
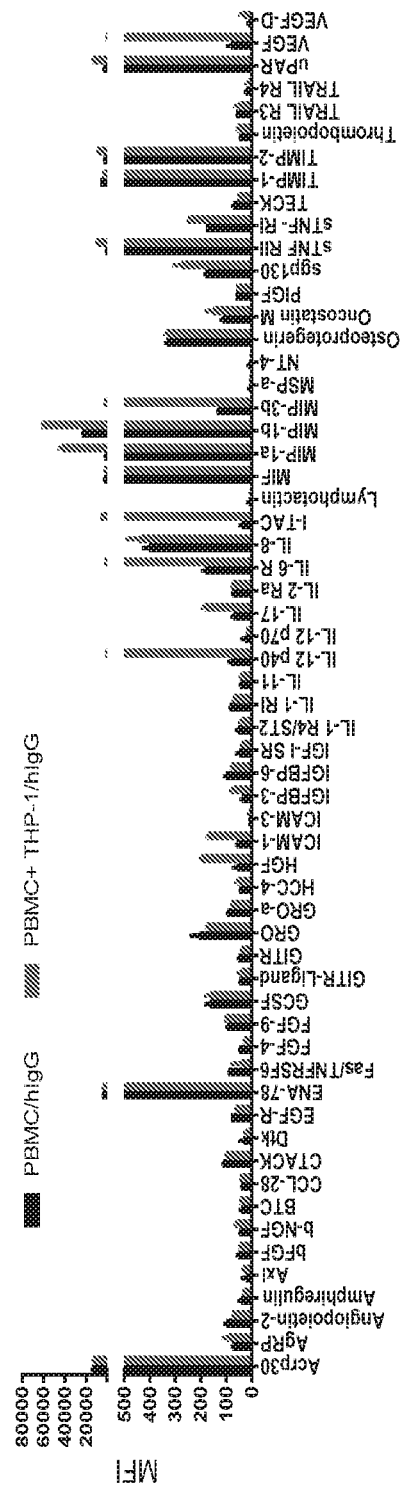
Figure 46C:
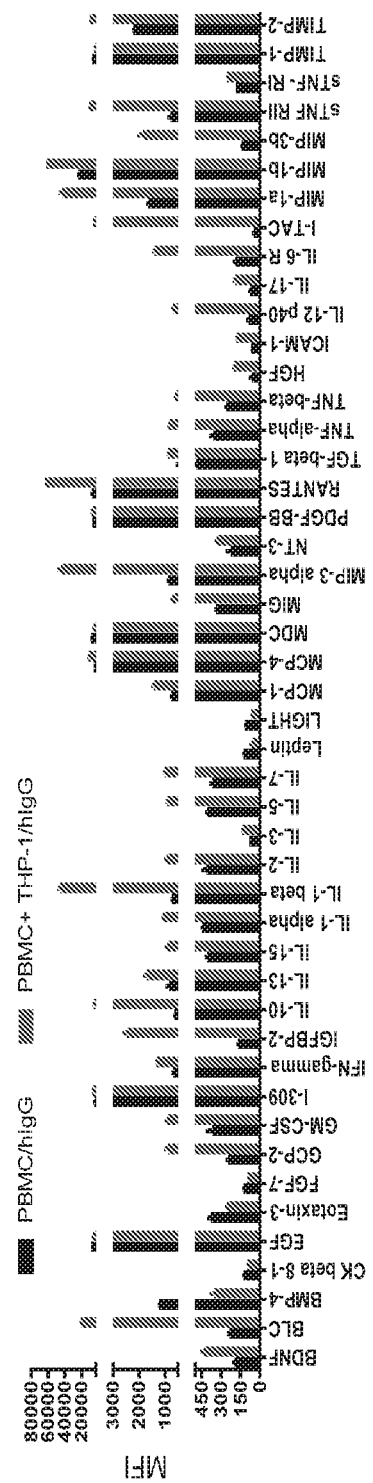
Figure 46D:
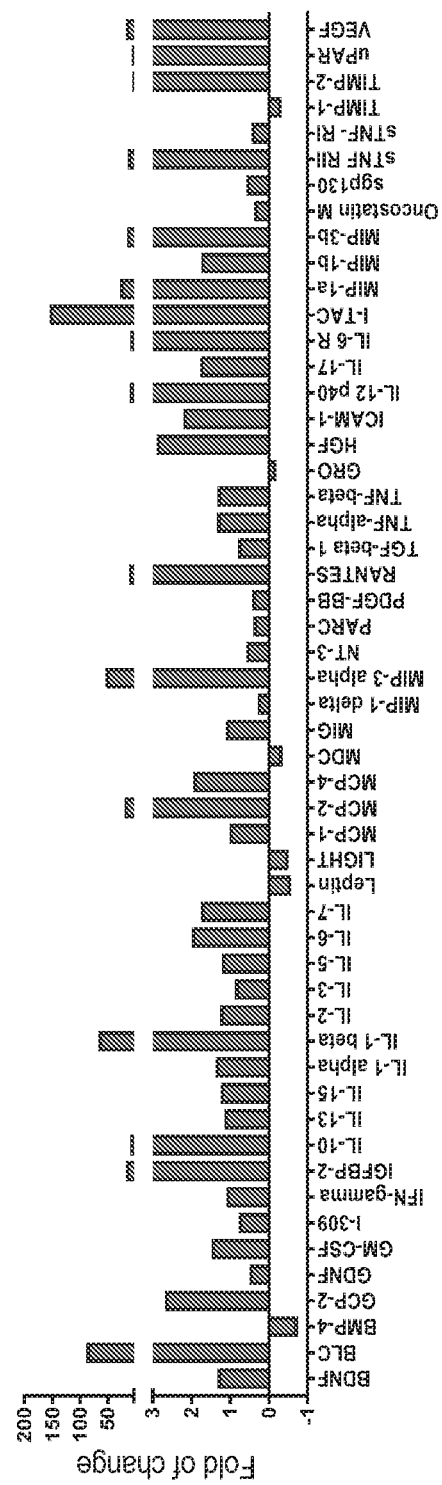

FIGS. 43A and 43B illustrates the effect of the h193 antibodies using ApoE competition assay (FIG. 43A) and K562 co-culture assay (FIG. 43B). The number under each histogram bar refers to the specific recombinant humanized antibody shown in Table 8. Antibody 39 is an irrelevant antibody. Both Antibody 39 and PBS serve as negative controls.

FIGS. 44A-44D illustrate the result of a cytokine array assay that measured the effect of h193 antibody in modulating cytokine secretion in PBMC (peripheral blood mononuclear cell).

FIGS. 45A-45D illustrate the result of a cytokine array assay that measured the effect of h193 antibody in modulating cytokine secretion in PBMC cells co-cultured with THP-1 cells.

FIGS. 46A-46D illustrate the result of a cytokine array assay that compared the cytokine secretion in the PBMC treated with human IgG and PBMC co-cultured with THP-1 cells treated with human IgG.

Figure 47:
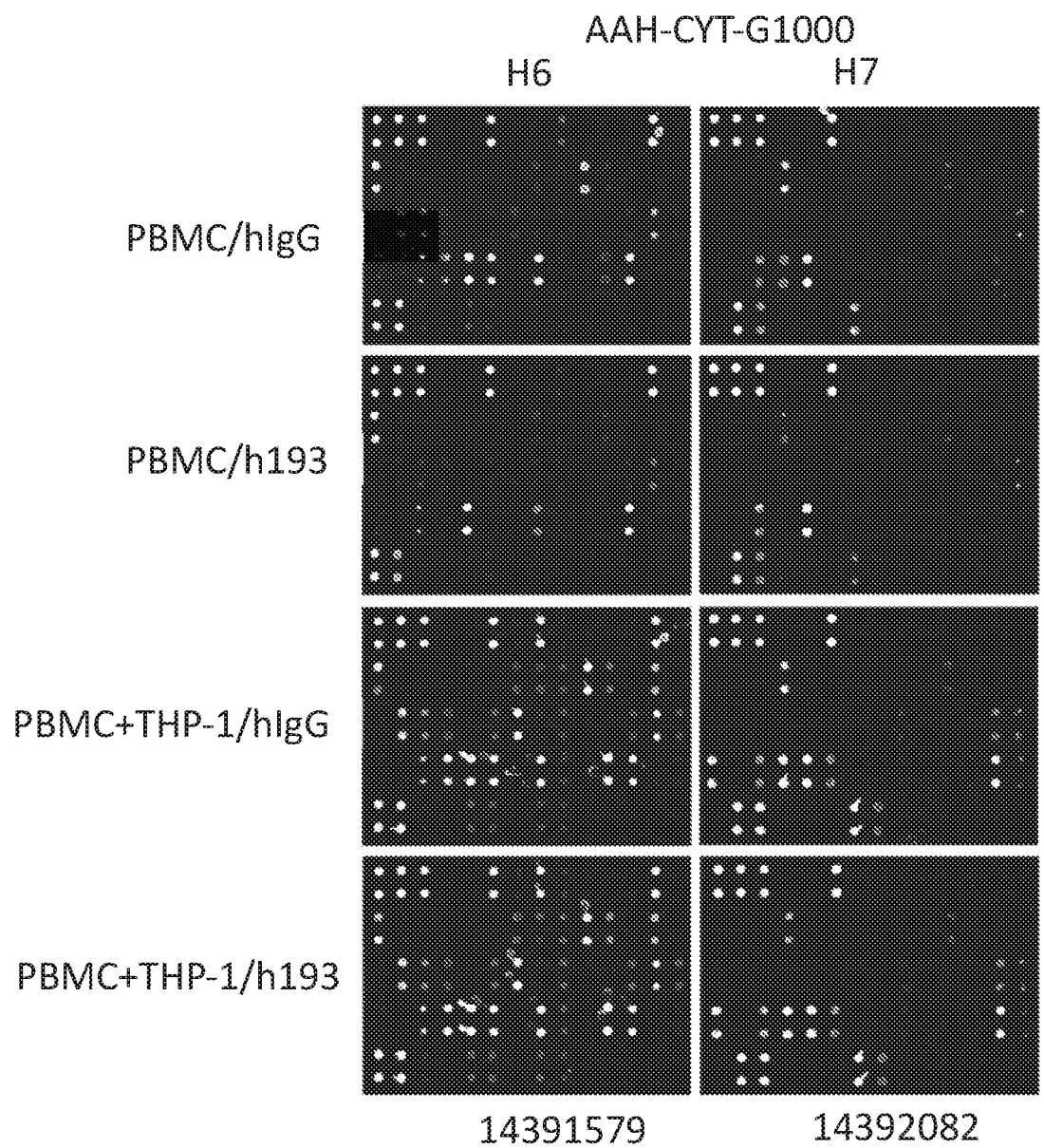

FIG. 47 shows exemplary images (in duplicate) of the cytokine array assay of FIGS. 44-46.

Figure 48:
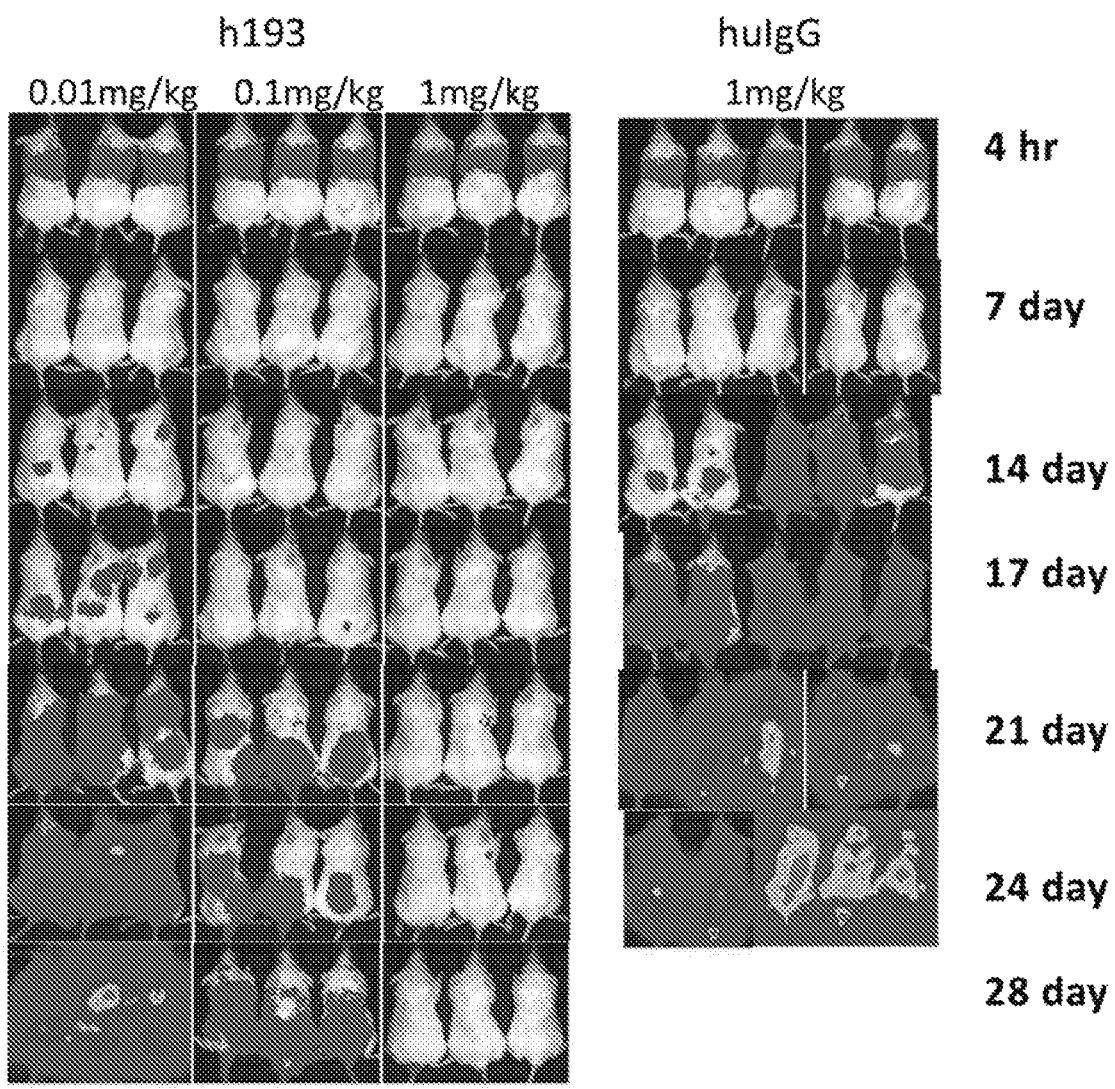

FIG. 48 illustrates that an exemplary h193 antibody suppressed leukemia development in a xenograft mouse model.

Figure 49A:
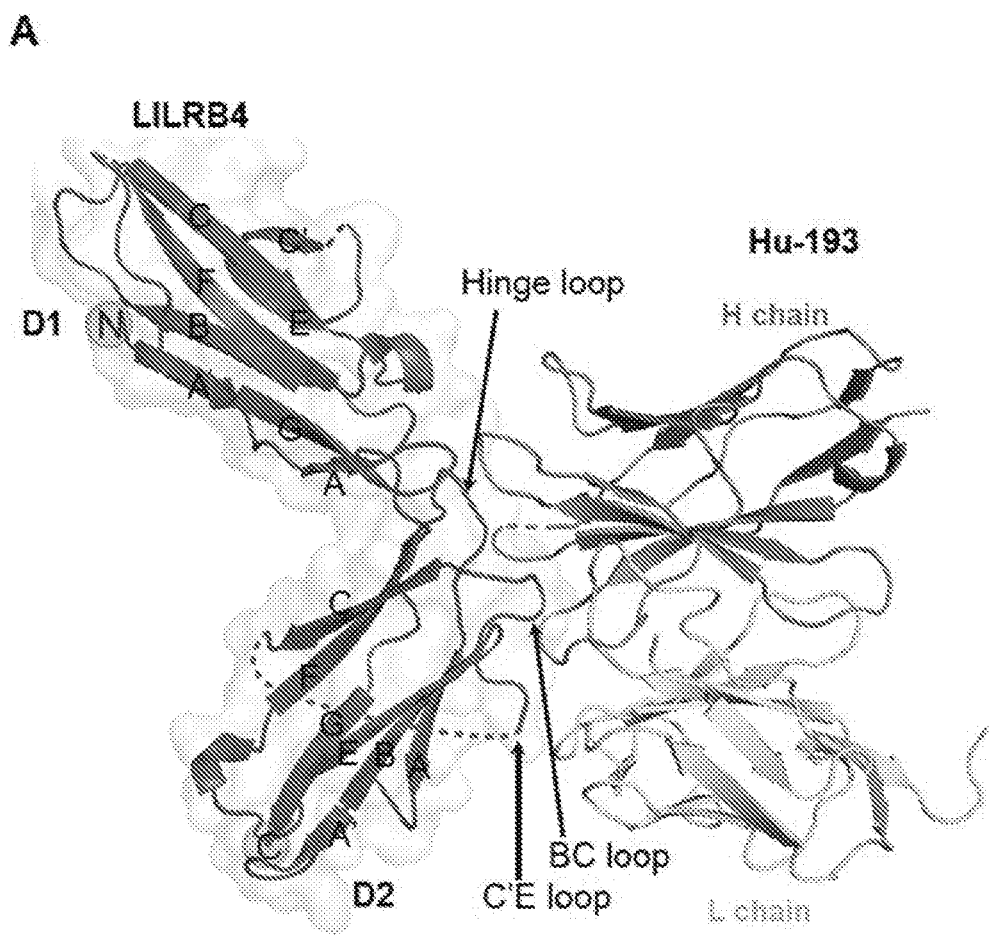
Figure 49B:
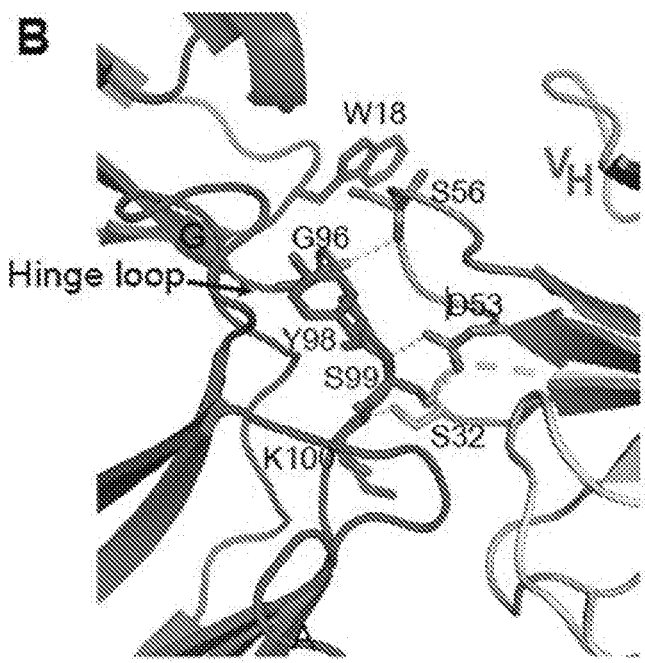
Figure 49C:
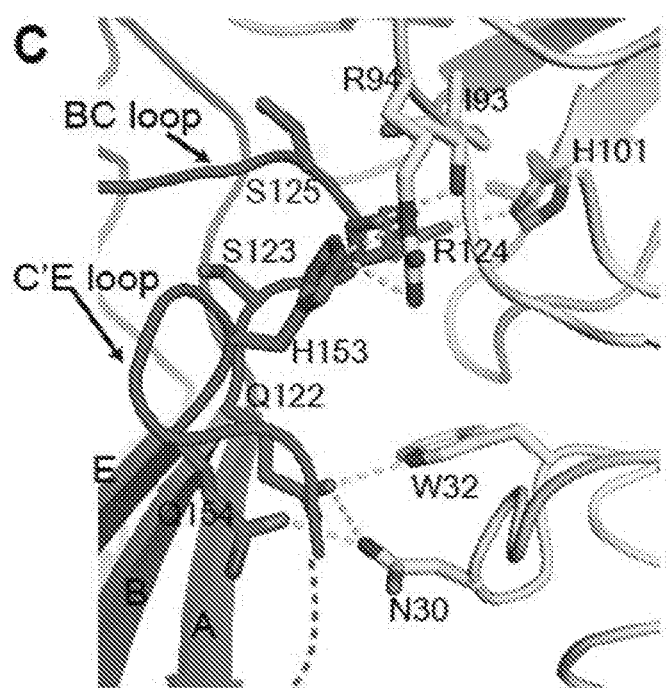
Figure 49D:
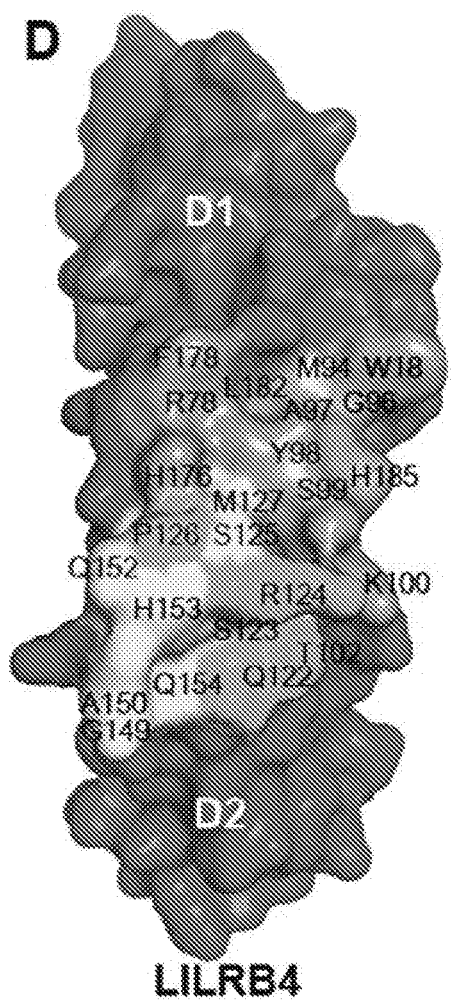

FIGS. 49A-49D illustrate the crystal structure of the complex of LILRB4 and h193. (FIG. 49A) The overall structure of LILRB4/h193 scFv complex is shown in a cartoon representation. The h193 binds to the D1D2 hinge loop, and the BC and C'E loops of the D2 domain of the LILRB4 molecule. The atomic interaction details of the heavy chain (FIG. 49B) and light chain (FIG. 49C) of the h193 binding to portions of LILRB4 are shown. Residues involved in the interactions are shown as sticks and labeled. Hydrogen bonds are shown as dashed lines. FIG. 49D, Binding surface of LILRB4 contacted by h193.

DESCRIPTION OF ILLUSTRATIVE EMBODIMENTS

The inventors have isolated a panel of novel monoclonal antibodies recognizing LILRB4 protein, an ITIM-containing receptor, which can be used for cancer treatment. LILRB4 is upregulated on some tumour cells especially leukemia cells and promotes tumour growth. The anti-human LILRB4 antibodies identified block LILRB4 signalling and can modulate immunity against cancer.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definition

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

An "antigen binding protein" ("ABP") as used herein means any protein that binds a specified target antigen. In the instant application, the specified target antigen is the LILRB protein or fragment thereof "Antigen binding protein" includes but is not limited to antibodies and antigen-binding fragment thereof. Peptibodies are another example of antigen binding proteins.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. In certain embodiments, the antigen-binding fragment is not derived from an antibody but rather is derived from a receptor. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies. In certain embodiments, the antigen-binding fragment is derived from a receptor and contains one or more mutations. In certain embodiments, the antigen-binding fragment does not bind to the natural ligand of the receptor from which the antigen-binding fragment is derived.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the LILRB4 specific antibodies of the present invention are specific to LILRB4. In some embodiments, the antibody that binds to LILRB4 has a dissociation constant (Kd) of ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$M, e.g., from $10^{-9}$M to $10^{-13}$ M).

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., LILRB or a fragment thereof). Numerous types of competitive binding assays can be used to determine if one antigen binding protein competes with another, for example: solid phase direct or indirect radio-immunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, and an alveolar macrophage; a cell from circular system or organ (e.g., myocardiocyte and pericyte); a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, and a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell; a cell from urinary system or organ (e.g., a podocyte, a juxtaglomerular cell, an intraglomerular mesangial cell, an extraglomerular mesangial cell, a kidney proximal tubule brush border cell, and a macula densa cell); and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

The term "chimeric antigen receptor" or "CAR" as used herein refers to an artificially constructed hybrid protein or polypeptide containing an antigen binding domain of an antibody (e.g., a single chain variable fragment (scFv)) linked to a domain or signaling, e.g., T-cell signaling or T-cell activation domains, that activates an immune cell, e.g., a T cell or a NK cell (see, e.g., Kershaw et al., supra, Eshhar et al., Proc. Natl. Acad. Sci. USA, 90(2): 720-724 (1993), and Sadelain et al., Curr. Opin. Immunol. 21(2): 215-223 (2009)). CARs are capable of redirecting the immune cell specificity and reactivity toward a selected target in a non-MHC-restricted manner, taking advantage of the antigen-binding properties of monoclonal antibodies. The non-MHC-restricted antigen recognition confers immune cells expressing CARs on the ability to recognize an antigen independent of antigen processing, thus bypassing a major mechanism of tumor escape. In addition, when expressed in T-cells, CARs advantageously do not dimerize with endogenous T-cell receptor (TCR) alpha and beta chains.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

Leukocyte immunoglobulin-like receptor subfamily B member 4 (LILRB4) is a protein that in humans is encoded by the LILRB4 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. The receptor can also function in antigen capture and presentation. It is thought to control inflammatory responses and cytotoxicity to help focus the immune response and limit autoreactivity. LILRB4 is also expressed in human gastric cancer cells and may enhance tumor growth. Multiple transcript variants encoding different isoforms have been found for this gene. LILRB4 has been shown to interact with PTPN6.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass LILRB antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a LILRB-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. Cancers

A. Cancers

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the tubulysin analogs described herein may be used to lead to decreased cell counts and as such can potentially be used to treat a variety of types of cancer lines. In some aspects, it is anticipated that the tubulysin analogs described herein may be used to treat virtually any malignancy. Here, the only requirement is the presence of LILRBs on the surface of the cancer cell, and in particular on the surface of cancer stem cells.

Cancer cells that may be treated according to the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

B. Acute Myeloid Leukemia

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified, but the specific cause is not clear. As an acute leukemia, AML progresses rapidly and is typically fatal within weeks or months if left untreated.

AML has several subtypes; treatment and prognosis varies among subtypes. Five-year survival varies from 15-70%, and relapse rate varies from 33-78%, depending on subtype. AML is treated initially with chemotherapy aimed at inducing a remission; patients may go on to receive additional chemotherapy or a hematopoietic stem cell transplant. Recent research into the genetics of AML has resulted in the availability of tests that can predict which drug or drugs may work best for a particular patient, as well as how long that patient is likely to survive.

Most signs and symptoms of AML are caused by the replacement of normal blood cells with leukemic cells. A lack of normal white blood cell production makes the patient susceptible to infections; while the leukemic cells themselves are derived from white blood cell precursors, they have no infection-fighting capacity. A drop in red blood cell count (anemia) can cause fatigue, paleness, and shortness of breath. A lack of platelets can lead to easy bruising or bleeding with minor trauma.

The early signs of AML are often vague and nonspecific and may be similar to those of influenza or other common illnesses. Some generalized symptoms include fever, fatigue, weight loss or loss of appetite, shortness of breath, anemia, easy bruising or bleeding, petechiae (flat, pin-head sized spots under the skin caused by bleeding), bone and joint pain, and persistent or frequent infections.

Enlargement of the spleen may occur in AML, but it is typically mild and asymptomatic. Lymph node swelling is rare in AML, in contrast to acute lymphoblastic leukemia. The skin is involved about 10% of the time in the form of leukemia cutis. Rarely, Sweet's syndrome, a paraneoplastic inflammation of the skin, can occur with AML.

Some patients with AML may experience swelling of the gums because of infiltration of leukemic cells into the gum tissue. Rarely, the first sign of leukemia may be the development of a solid leukemic mass or tumor outside of the bone marrow, called a chloroma. Occasionally, a person may show no symptoms, and the leukemia may be discovered incidentally during a routine blood test.

A number of risk factors for developing AML have been identified, including: other blood disorders, chemical exposures, ionizing radiation, and genetics.

"Preleukemic" blood disorders, such as myelodysplastic syndrome or myeloproliferative disease, can evolve into AML; the exact risk depends on the type of MDS/MPS. Exposure to anticancer chemotherapy, in particular alkylating agents, can increase the risk of subsequently developing AML. The risk is highest about three to five years after chemotherapy. Other chemotherapy agents, specifically epipodophyllotoxins and anthracyclines, have also been associated with treatment-related leukemia. These treatment-related leukemias are often associated with specific chromosomal abnormalities in the leukemic cells. Occupational chemical exposure to benzene and other aromatic organic solvents is controversial as a cause of AML. Benzene and many of its derivatives are known to be carcinogenic in vitro. While some studies have suggested a link between occupational exposure to benzene and increased risk of AML, others have suggested the attributable risk, if any, is slight. High amounts of ionizing radiation exposure can increase the risk of AML. A hereditary risk for AML appears to exist. Multiple cases of AML developing in a family at a rate higher than predicted by chance alone have been reported. Several congenital conditions may increase the risk of leukemia; the most common is probably Down syndrome, which is associated with a 10- to 18-fold increase in the risk of AML.

The first clue to a diagnosis of AML is typically an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made via examination of the peripheral blood smear when there are circulating leukemic blasts, a definitive diagnosis usually requires an adequate bone marrow aspiration and biopsy.

Marrow or blood is examined via light microscopy, as well as flow cytometry, to diagnose the presence of leukemia, to differentiate AML from other types of leukemia (e.g., acute lymphoblastic leukemia—ALL), and to classify the subtype of disease (see below). A sample of marrow or blood is typically also tested for chromosomal abnormalities by routine cytogenetics or fluorescent in situ hybridization. Genetic studies may also be performed to look for specific mutations in genes such as FMS-like tyrosine kinase 3 (FLT3), nucleophosmin, and KIT, which may influence the outcome of the disease.

Cytochemical stains on blood and bone marrow smears are helpful in the distinction of AML from ALL, and in subclassification of AML. The combination of a myeloperoxidase or Sudan black stain and a nonspecific esterase stain will provide the desired information in most cases. The myeloperoxidase or Sudan black reactions are most useful in establishing the identity of AML and distinguishing it from ALL. The nonspecific esterase stain is used to identify a monocytic component in AMLs and to distinguish a poorly differentiated monoblastic leukemia from ALL.

The diagnosis and classification of AML can be challenging and should be performed by a qualified hematopathologist or hematologist. In straightforward cases, the presence of certain morphologic features (such as Auer rods) or specific flow cytometry results can distinguish AML from other leukemias; however, in the absence of such features, diagnosis may be more difficult.

According to the widely used WHO criteria, the diagnosis of AML is established by demonstrating involvement of more than 20% of the blood and/or bone marrow by leukemic myeloblasts. The French-American-British (FAB) classification is a bit more stringent, requiring a blast percentage of at least 30% in bone marrow (BM) or peripheral blood (PB) for the diagnosis of AML. AML must be carefully differentiated from "preleukemic" conditions such as myelodysplastic or myeloproliferative syndromes, which are treated differently.

Because acute promyelocytic leukemia (APL) has the highest curability and requires a unique form of treatment, it is important to quickly establish or exclude the diagnosis of this subtype of leukemia. Fluorescent in situ hybridization performed on blood or bone marrow is often used for this purpose, as it readily identifies the chromosomal translocation [t(15;17)(q22;q12);] that characterizes APL. There is also a need to molecularly detect the presence of PML/RARA fusion protein, which is an oncogenic product of that translocation.

First-line treatment of AML consists primarily of chemotherapy and is divided into two phases: induction and post-remission (or consolidation) therapy. The goal of induction therapy is to achieve a complete remission by reducing the number of leukemic cells to an undetectable level; the goal of consolidation therapy is to eliminate any residual undetectable disease and achieve a cure. Hematopoietic stem cell transplantation is usually considered if induction chemotherapy fails or after a patient relapses, although transplantation is also sometimes used as front-line therapy for patients with high-risk disease.

All FAB subtypes except M3 are usually given induction chemotherapy with cytarabine (ara-C) and an anthracycline (most often daunorubicin). This induction chemotherapy regimen is known as "7+3" (or "3+7"), because the cytarabine is given as a continuous IV infusion for seven consecutive days while the anthracycline is given for three consecutive days as an IV push. Up to 70% of patients will achieve a remission with this protocol. Other alternative induction regimens, including high-dose cytarabine alone, FLAG-like regimens or investigational agents, may also be used. Because of the toxic effects of therapy, including myelosuppression and an increased risk of infection, induction chemotherapy may not be offered to the very elderly, and the options may include less intense chemotherapy or palliative care.

The M3 subtype of AML, also known as acute promyelocytic leukemia (APL), is almost universally treated with the drug all-trans-retinoic acid (ATRA) in addition to induction chemotherapy, usually an anthracycline. Care must be taken to prevent disseminated intravascular coagulation (DIC), complicating the treatment of APL when the promyelocytes release the contents of their granules into the peripheral circulation. APL is eminently curable, with well-documented treatment protocols.

The goal of the induction phase is to reach a complete remission. Complete remission does not mean the disease has been cured; rather, it signifies no disease can be detected with available diagnostic methods. Complete remission is obtained in about 50%-75% of newly diagnosed adults, although this may vary based on the prognostic factors described above. The length of remission depends on the prognostic features of the original leukemia. In general, all remissions will fail without additional consolidation therapy.

Even after complete remission is achieved, leukemic cells likely remain in numbers too small to be detected with current diagnostic techniques. If no further post-remission or consolidation therapy is given, almost all patients will eventually relapse. Therefore, more therapy is necessary to eliminate non-detectable disease and prevent relapse—that is, to achieve a cure.

The specific type of post-remission therapy is individualized based on a patient's prognostic factors (see above) and general health. For good-prognosis leukemias (i.e., inv(16), t(8;21), and t(15;17)), patients will typically undergo an additional three to five courses of intensive chemotherapy, known as consolidation chemotherapy. For patients at high risk of relapse (e.g., those with high-risk cytogenetics, underlying MDS, or therapy-related AML), allogeneic stem cell transplantation is usually recommended if the patient is able to tolerate a transplant and has a suitable donor. The best post-remission therapy for intermediate-risk AML (normal cytogenetics or cytogenetic changes not falling into good-risk or high-risk groups) is less clear and depends on the specific situation, including the age and overall health of the patient, the patient's personal values, and whether a suitable stem cell donor is available.

For patients who are not eligible for a stem cell transplant, immunotherapy with a combination of histamine dihydrochloride (Ceplene) and interleukin 2 (Proleukin) after the completion of consolidation has been shown to reduce the absolute relapse risk by 14%, translating to a 50% increase in the likelihood of maintained remission.

For patients with relapsed AML, the only proven potentially curative therapy is a hematopoietic stem cell transplant, if one has not already been performed. In 2000, the monoclonal antibody-linked cytotoxic agent gemtuzumab ozogamicin (Mylotarg) was approved in the United States for patients aged more than 60 years with relapsed AML who are not candidates for high-dose chemotherapy. This drug was voluntarily withdrawn from the market by its manufacturer, Pfizer in 2010. Since treatment options for relapsed AML are so limited, palliative care may be offered.

Patients with relapsed AML who are not candidates for stem cell transplantation, or who have relapsed after a stem cell transplant, may be offered treatment in a clinical trial, as conventional treatment options are limited. Agents under investigation include cytotoxic drugs such as clofarabine, as well as targeted therapies, such as farnesyl transferase inhibitors, decitabine, and inhibitors of MDR1 (multidrug-resistance protein). For relapsed acute promyelocytic leukemia (APL), arsenic trioxide has been tested in trials and approved by the U.S. FDA. Like ATRA, arsenic trioxide does not work with other subtypes of AML.

While acute myeloid leukemia is a curable disease, the chance of cure for a specific patient depends on a number of prognostic factors. The single most important prognostic factor in AML is cytogenetics, or the chromosomal structure of the leukemic cell. Certain cytogenetic abnormalities are associated with very good outcomes (for example, the (15:17) translocation in acute promyelocytic leukemia). About half of AML patients have "normal" cytogenetics; they fall into an intermediate risk group. A number of other cytogenetic abnormalities are known to associate with a poor prognosis and a high risk of relapse after treatment.

AML which arises from a pre-existing myelodysplastic syndrome (MDS) or myeloproliferative disease (so-called secondary AML) has a worse prognosis, as does treatment-related AML arising after chemotherapy for another previous malignancy. Both of these entities are associated with a high rate of unfavorable cytogenetic abnormalities.

In some studies, age >60 years and elevated lactate dehydrogenase level were also associated with poorer outcomes. As with most forms of cancer, performance status (i.e., the general physical condition and activity level of the patient) plays a major role in prognosis as well.

FLT3 internal tandem duplications (ITDs) have been shown to confer a poorer prognosis in AML. Treating these patients with more aggressive therapy, such as stem-cell transplantation in first remission, has not been shown to enhance long-term survival. ITDs of FLT3 may be associated with leukostasis. In 2012, the FLT3 inhibitor quizartinib showed positive phase II trial results in AML patients with FLT3-ITD mutations. In 2017, the FLT3 inhibitor Rydapt® (midostaurin, formerly PKC412) was approved by FDA for the treatment of newly diagnosed AML patients who are FLT3 mutation-positive (FLT3+), as detected by an FDA-approved test, in combination with chemotherapy.

Researchers are investigating the clinical significance of c-KIT mutations in AML. These are prevalent, and clinically relevant because of the availability of tyrosine kinase inhibitors, such as imatinib and sunitinib that can block the activity of c-KIT pharmacologically. Other genes being investigated as prognostic factors or therapeutic targets include CEBPA, BAALC, ERG, and NPMJ.

B. Chronic Myelomonocytic Leukemia (CMML)

CMML is a malignant hematopoietic stem cell disorder with clinical and pathological features of both a myeloproliferative neoplasm and a myelodysplastic syndrome. Patients may present with symptoms or complications resulting from a previously unrecognized cytopenia (e.g., infection, fatigue, dyspnea, petechiae, hemorrhage), skin lesions, or symptoms related to splenomegaly (e.g., early satiety, abdominal fullness). CMML is characterized by a peripheral blood monocytosis accompanied by bone marrow dysplasia. In the USA, approximately 2,000 new cases of CMML are diagnosed each year. Progression to AML occurs in 15 to 30% of cases (Swerdlow et al., 2017), and median survival is dismal across WHO prognostic subgroups, ranging from 10 to 48 months after the initial diagnosis. Only a HSCT is disease-modifying for CMML patients to a clinically-significant degree, other therapies, including cytoreductive and hypomethylating agents, offer symptomatic relief (Schuler et al., 2014). Therefore, there is an urgent need for new therapies to reduce the morbidity and prolong the survival of patients with CMML.

C. Acute Lymphoblastic Leukemia (ALL)

Acute lymphoblastic leukemia (ALL) or acute lymphoid leukemia is an acute form of leukemia, or cancer of the white blood cells, characterized by the overproduction of cancerous, immature white blood cells—known as lymphoblasts. In persons with ALL, lymphoblasts are overproduced in the bone marrow and continuously multiply, causing damage and death by inhibiting the production of normal cells—such as red and white blood cells and platelets—in the bone marrow and by infiltrating to other organs. ALL is most common in childhood with a peak incidence at 2-5 years of age, and another peak in old age.

The symptoms of ALL are indicative of a reduced production of functional blood cells, because the leukemia wastes the resources of the bone marrow, which are normally used to produce new, functioning blood cells. These symptoms can include fever, increased risk of infection (especially bacterial infections like pneumonia, due to neutropenia; symptoms of such an infection include shortness of breath, chest pain, cough, vomiting, changes in bowel or bladder habits), increased tendency to bleed (due to thrombocytopenia) and signs indicative of anemia including pallor, tachycardia (high heart rate), fatigue and headache.

About 6,000 cases are reported in the U.S. every year; statistics from other countries are difficult to come by, although it is known to be more common in the United States, Italy and Costa Rica. Cure is a realistic goal and is achieved in over 80% of affected children, although only 20-40% of adults can be cured. "Acute" refers to the relatively short time course of the disease to differentiate it from chronic lymphocytic leukemia, which has a potential time course of many years.

The symptoms are not specific to ALL but worsen to the point that medical help is sought. They result from the lack of normal and healthy blood cells because they are crowded out by malignant and immature leukocytes (white blood cells). Therefore, people with ALL experience symptoms from malfunctioning of their erythrocytes (red blood cells), leukocytes, and platelets. Laboratory tests that might show abnormalities include blood count tests, renal function tests, electrolyte tests, and liver enzyme tests.

The signs and symptoms of ALL are variable but follow from bone marrow replacement and/or organ infiltration, and include generalized weakness and fatigue, anemia, dizziness, frequent or unexplained fever and infection, weight loss and/or loss of appetite, excessive and unexplained bruising, bone pain, joint pain (caused by the spread of "blast" cells to the surface of the bone or into the joint from the marrow cavity), breathlessness, enlarged lymph nodes, liver and/or spleen, pitting edema (swelling) in the lower limbs and/or abdomen, and petechiae, which are tiny red spots or lines in the skin due to low platelet levels.

In general, cancer is caused by damage to DNA that leads to uncontrolled cellular growth and spreads throughout the body, either by increasing chemical signals that cause growth or by interrupting chemical signals that control growth. Damage can be caused through the formation of fusion genes, as well as the dysregulation of a proto-oncogene via juxtaposition of it to the promoter of another gene, e.g., the T-cell receptor gene. This damage may be caused by environmental factors such as chemicals, drugs or radiation, and occurs naturally during mitosis or other normal processes (although cells have numerous mechanisms of DNA repair that help to reduce this).

ALL is associated with exposure to radiation and chemicals in animals and humans. High level radiation exposure is a known risk factor for developing leukemia, as found by studies of survivors of atom bomb exposure in Hiroshima and Nagasaki. In animals, exposure to benzene and other chemicals can cause leukemia. Epidemiological studies have associated leukemia with workplace exposure to chemicals, but these studies are not as conclusive. Some evidence suggests that secondary leukemia can develop in individuals treated for other cancers with radiation and chemotherapy as a result of that treatment.

Diagnosing ALL begins with a medical history, physical examination, complete blood count, and blood smears. Because the symptoms are so general, many other diseases with similar symptoms must be excluded. Typically, the higher the white blood cell count the worse the prognosis. Blast cells are seen on blood smear in the majority of cases (blast cells are precursors (stem cells) to all immune cell lines). A bone marrow biopsy is conclusive proof of ALL. A lumbar puncture (also known as a spinal tap) will indicate if the spinal column and brain have been invaded.

Pathological examination, cytogenetics (in particular the presence of Philadelphia chromosome), and immunophenotyping establish whether myeloblastic (neutrophils, eosinophils, or basophils) or lymphoblastic (B lymphocytes or T lymphocytes) cells are the problem. RNA testing can establish how aggressive the disease is; different mutations have been associated with shorter or longer survival. Immunohistochemical testing may reveal TdT or CALLA antigens on the surface of leukemic cells. TdT is a protein expressed early in the development of pre-T and pre-B cells, whereas CALLA is an antigen found in 80% of ALL cases and also in the "blast crisis" of CML. Medical imaging (such as ultrasound or CT scanning) can find invasion of other organs commonly the lung, liver, spleen, lymph nodes, brain, kidneys, and reproductive organs.

The earlier acute lymphocytic leukemia is detected, the more effective the treatment. The aim is to induce a lasting remission, defined as the absence of detectable cancer cells in the body (usually less than 5% blast cells in the bone marrow). Treatment for acute leukemia can include chemotherapy, steroids, radiation therapy, intensive combined treatments (including bone marrow or stem cell transplants), and growth factors.

Chemotherapy is the initial treatment of choice. Most ALL patients will receive a combination of different treatments. There are no surgical options, due to the body-wide distribution of the malignant cells. In general, cytotoxic chemotherapy for ALL combines multiple antileukemic drugs in various combinations. Chemotherapy for ALL consists of three phases: remission induction, intensification, and maintenance therapy.

As the chemotherapy regimens can be intensive and protracted (often about 2 years in case of the GMALL UKALL, HyperCVAD or CALGB protocols; for ALL about 3 years, 2 months for males on COG protocols; 2 years, 2 months for females—longer for males, as testicles are a potential reservoir), many patients have an intravenous catheter inserted into a large vein (termed a central venous catheter or a Hickman line), or a Portacath, a cone-shaped port with a silicone nose that is surgically planted under the skin, usually near the collar bone, and the most effective product available, due to low infection risks and the long-term viability of a portacath.

Radiation therapy (or radiotherapy) is used on painful bony areas, in high disease burdens, or as part of the preparations for a bone marrow transplant (total body irradiation). Radiation in the form of whole-brain radiation is also used for central nervous system prophylaxis, to prevent recurrence of leukemia in the brain. Whole-brain prophylaxis radiation used to be a common method in treatment of children's ALL. Recent studies showed that CNS chemotherapy provided results as favorable but with less developmental side-effects. As a result, the use of whole-brain radiation has been more limited. Most specialists in adult leukemia have abandoned the use of radiation therapy for CNS prophylaxis, instead using intrathecal chemotherapy.

For some subtypes of relapsed ALL, aiming at biological targets such as the proteasome, in combination with chemotherapy, has given promising results in clinical trials. Selection of biological targets on the basis of their combinatorial effects on the leukemic lymphoblasts can lead to clinical trials for improvement in the effects of ALL treatment. In ongoing clinical trials, a CD19-CD3 bi-specific monoclonal murine antibody—Blinatumomab, is showing great promise.

Chimeric antigen receptors (CARs) have been developed as a promising therapy for ALL. This technology uses a single chain variable fragment (scFv) designed to recognize the cell surface marker CD19 as a method of treating ALL. CD19 is a molecule found on all B-cells and can be used as a means of distinguishing the potentially malignant B-cell population in the patient. In this therapy, mice are immunized with the CD19 antigen and produce anti-CD19 antibodies. Hybridomas developed from the mouse spleen cells fused to a myeloma cell line can be developed as a source for the cDNA encoding the CD19 specific antibody. The cDNA is sequenced and the sequence encoding the variable heavy and variable light chains of these antibodies are cloned together using a small peptide linker. This resulting sequence encodes the scFv. This can be cloned into a transgene encoding what will become the endodomain of the CAR. There are varying arrangements of subunits used as the endodomain but they generally consist of the hinge region that attaches to the scFv, a transmembrane region, the intracellular region of a costimulatory molecule such as CD28, and the intracellular domain of CD3-zeta containing ITAM repeats. Other sequences frequently included are: 4-1bb and OX40. The final transgene sequence, containing the scFv and endodomain sequences is then inserted into immune effector cells that are obtained from the patient and expanded in vitro. In previous trials these have been a type of T-cell capable of cytotoxicity. Inserting the DNA into the effector cell can be accomplished by several methods. Most commonly, this is done using a lentivirus which encodes the transgene. Pseudotyped, self-inactivating lentiviruses have been shown to be an effective method for the stable insertion of a desired transgene into the target cell genomic DNA. Other methods include electroporation and transfection, but these are limited in their efficacy as transgene expression will diminish over time. The gene-modified effector cells are then transplanted back into the patient. Typically, this process is done in conjunction with a conditioning regiment such as cyclophosphamide which has been shown to potentiate the effects of infused T-cells. This effect has been attributed to the creation of an immunologic space niche. The process as a whole results in an effector cell, typically a T-cell that can recognize a tumor cell antigen in a major histocompatibility complex independent manner and initiate a cytotoxic response.

D. Chronic Lymphoblastic Leukemia (CLL)

B-cell chronic lymphocytic leukemia (B-CLL), also known as chronic lymphoid leukemia (CLL), is the most common type of leukemia (a type of cancer of the white blood cells) in adults. CLL affects B cell lymphocytes, which originate in the bone marrow, develop in the lymph nodes, and normally fight infection by producing antibodies. In CLL, B cells grow out of control and accumulate in the bone marrow and blood, where they crowd out healthy blood cells. CLL is a stage of small lymphocytic lymphoma (SLL), a type of B-cell lymphoma, which presents primarily in the lymph nodes. CLL and SLL are considered the same underlying disease, just with different appearances. CLL is a disease of adults. Most (>75%) people newly diagnosed with CLL are over the age of 50, and the majority are men. However, in rare cases, it can occur in teenagers and occasionally in children. Some of these may relate to an inherited predisposition.

Most people are diagnosed without symptoms as the result of a routine blood test that returns a high white blood cell count, but, as it advances, CLL results in swollen lymph nodes, spleen, and liver, and eventually anemia and infections. Early CLL is not treated, and late CLL is treated with chemotherapy and monoclonal antibodies.

DNA analysis has distinguished two major types of CLL, with different survival times. CLL that is positive for the marker ZAP-70 has an average survival of 8 years, while CLL negative for ZAP-70 has an average survival of more than 25 years. Many patients, especially older ones, with slowly progressing disease can be reassured and may not need any treatment in their lifetimes.

Most people are diagnosed without symptoms as the result of a routine blood test that returns a high white blood cell count. Less commonly, CLL may present with enlarged lymph nodes without a high white blood cell count or no evidence of the disease in the blood. This is referred to as small lymphocytic lymphoma. In some individuals the disease comes to light only after the neoplastic cells overwhelm the bone marrow resulting in anemia producing tiredness or weakness.

CLL is usually first suspected by the presence of lymphocytosis, an increase in a type of white blood cell, on a complete blood count (CBC) test. This frequently is an incidental finding on a routine physician visit. Most often the lymphocyte count is greater than 4000 cells per microliter (µl) of blood but can be much higher. The presence of a lymphocytosis in an elderly individual should raise strong suspicion for CLL, and a confirmatory diagnostic test, in particular flow cytometry, should be performed unless clinically unnecessary.

The diagnosis of CLL is based on the demonstration of an abnormal population of B lymphocytes in the blood, bone marrow, or tissues that display an unusual but characteristic pattern of molecules on the cell surface. This atypical molecular pattern includes the coexpression of cells surface markers cluster of differentiation 5 (CD5) and cluster of differentiation 23 (CD23). In addition, all the CLL cells within one individual are clonal, that is, genetically identical. In practice, this is inferred by the detection of only one of the mutually exclusive antibody light chains, kappa or lambda, on the entire population of the abnormal B cells. Normal B lymphocytes consist of a stew of different antibody-producing cells, resulting in a mixture of both kappa and lambda expressing cells. The lack of the normal distribution of kappa and lambda producing B cells is one basis for demonstrating clonality, the key element for establishing a diagnosis of any B cell malignancy (B cell non-Hodgkin lymphoma).

The combination of the microscopic examination of the peripheral blood and analysis of the lymphocytes by flow cytometry to confirm clonality and marker molecule expression is needed to establish the diagnosis of CLL. Both are easily accomplished on a small amount of blood. A flow cytometer is an instrument that can examine the expression of molecules on individual cells in fluids. This requires the use of specific antibodies to marker molecules with fluorescent tags recognized by the instrument. In CLL, the lymphocytes are genetically clonal, of the B cell lineage (expressing marker molecules cluster of differentiation 19 (CD19) and CD20), and characteristically express the marker molecules CD5 and CD23. These B cells resemble normal lymphocytes under the microscope, although slightly smaller, and are fragile when smeared onto a glass slide, giving rise to many broken cells, which are called "smudge" or "smear" cells.

The Matutes's CLL score allows the identification of a homogeneous subgroup of classical CLL, that differs from atypical/mixed CLL for the five markers' expression (CD5, CD23, FMC7, CD22 and immunoglobulin light chain) Matutes's CLL scoring system is very helpful for the differential diagnosis between classical CLL and the other B cell chronic lymphoproliferative disorders, but not for the immunological distinction between mixed/atypical CLL and mantle cell lymphoma (MCL malignant B cells). Discrimination between CLL and MCL can be improved by adding non-routine markers such as CD54 and CD200. Among routine markers, the most discriminating feature is the CD20/CD23 mean fluorescence intensity ratio. In contrast, FMC7 expression can surprisingly be misleading for borderline cases.

Staging, determining the extent of the disease, is done with the Rai staging system or the Binet classification (see details) and is based primarily on the presence of a low platelet or red cell count. Early stage disease does not need to be treated.

CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes).

Initial CLL treatments vary depending on the exact diagnosis and the progression of the disease, and even with the preference and experience of the health care practitioner. Dozens of agents are used for CLL therapy. An initial treatment regimen that contains fludarabine, cyclophosphamide, and rituximab (known as FCR) has demonstrated higher overall response rates and complete response rates.

A study carried out by the researchers at the University of Pennsylvania used genetically modified T cells to attack cells that expressed the CD19 protein to fight the disease. In 2013, the researchers announced that 26 of 59 patients had achieved complete remission and that the original patient had remained tumor-free.

Leukemia is rarely associated with pregnancy, affecting only about 1 in 10,000 pregnant women. Treatment for chronic lymphocytic leukemias can often be postponed until after the end of the pregnancy. If treatment is necessary, then giving chemotherapy during the second or third trimesters is less likely to result in pregnancy loss or birth defects than treatment during the first trimester.

While generally considered incurable, CLL progresses slowly in most cases. Many people with CLL lead normal and active lives for many years—in some cases for decades. Because of its slow onset, early-stage CLL is, in general, not treated since it is believed that early CLL intervention does not improve survival time or quality of life. Instead, the condition is monitored over time to detect any change in the disease pattern.

The decision to start CLL treatment is taken when the patient's clinical symptoms or blood counts indicate that the disease has progressed to a point where it may affect the patient's quality of life. Clinical "staging systems" such as the Rai 4-stage system and the Binet classification can help to determine when and how to treat the patient. Determining when to start treatment and by what means is often difficult; studies have shown there is no survival advantage to treating the disease too early. The National Cancer Institute Working Group has issued guidelines for treatment, with specific markers that should be met before it is initiated.

Combination chemotherapy regimens are effective in both newly diagnosed and relapsed CLL. Combinations of fludarabine with alkylating agents (cyclophosphamide) produce higher response rates and a longer progression-free survival than single agents: FC (fludarabine with cyclophosphamide); FR (fludarabine with rituximab); FCR (fludarabine, cyclophosphamide, and rituximab); and CHOP (cyclophosphamide, doxorubicin, vincristine and prednisolone).

Although the purine analogue fludarabine was shown to give superior response rates to chlorambucil as primary therapy, there is no evidence early use of fludarabine improves overall survival, and some clinicians prefer to reserve fludarabine for relapsed disease.

Chemoimmunotherapy with FCR has shown to improve response rates, progression-free survival and overall survival in a large randomized trial in CLL patients selected for good physical fitness. This has been the first clinical trial demonstrating that the choice of a first line therapy can improve the overall survival of patients with CLL. Alkylating agents approved for CLL include bendamustine and cyclophosphamide.

Targeted therapy attacks cancer cells at a specific target, with the aim of not harming normal cells. Monoclonal antibodies, such as alemtuzumab (directed against CD52), and rituximab and ofatumumab (directed against CD20), are used in CLL. Tyrosine kinase inhibitor therapy can also be used in CLL. In February 2014, the FDA granted ibrutinib approval to treat chronic lymphocytic leukemia. Ibrutinib is a Bruton's tyrosine kinase (BTK) inhibitor. In July 2014, the FDA and EMA granted idelalisib approval to treat different types of leukemia. Idelalisib is a PI3K inhibitor that targets the PI3Kδ pathway. It is taken orally.

Autologous stem cell transplantation, using the recipient's own cells, is not curative. Younger individuals, if at high risk for dying from CLL, may consider allogeneic hematopoietic stem cell transplantation (HSCT). Myeloablative (bone marrow killing) forms of allogeneic stem cell transplantation, a high-risk treatment using blood cells from a healthy donor, may be curative, but treatment-related toxicity is significant. An intermediate level, called reduced-intensity conditioning allogeneic stem cell transplantation, may be better tolerated by older or frail patients.

"Refractory" CLL is a disease that no longer responds favorably to treatment. In this case, more aggressive therapies, including lenalidomide, flavopiridol, and bone marrow (stem cell) transplantation, are considered. The monoclonal antibody, alemtuzumab (directed against CD52), may be used in patients with refractory, bone marrow-based disease.

Complications include Richter's syndrome, hypogammaglobulinemia leading to recurrent infection, warm autoimmune hemolytic anemia in 10-15% of patients, transformation to high grade lymphoma. Chronic lymphocytic leukemia may transform into Richter's syndrome, the development of fast-growing diffuse large B cell lymphoma, prolymphocytic leukemia, Hodgkin's lymphoma, or acute leukemia in a patient who has chronic lymphocytic leukemia. Its incidence is estimated to be around 5 percent in patients with CLL.

Gastrointestinal (GI) involvement can rarely occur with chronic lymphocytic leukemia. Some of the reported manifestations include intussusception, small intestinal bacterial contamination, colitis and others. Usually, GI complications with CLL occur after Richter transformation. There have been two case reports to date of GI involvement in chronic lymphocytic leukemia without Richter's transformation.

III. Monoclonal Antibodies and Production Thereof

The monoclonal antibodies described herein can be prepared using standard methods, followed by screening, characterization and functional assessment. Variable regions can be sequenced and then subcloned into a human expression vector to produce the chimeric antibody genes, which are then expressed and purified. These chimeric antibodies can be tested for antigen binding, signaling blocking, and in xenograft experiments.

A. General Methods

It will be understood that monoclonal antibodies binding to LILRB4 will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

1. Antibodies to LILRB4

Antibodies or antigen-binding fragments thereof according to the present disclosure may be defined, in the first instance, by their binding specificity, which in this case is for LILRB4. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to LILRB4. In some embodiments, when bound to LILRB4, such antibodies modulate the activation of LILRB4. In certain embodiments, the antibody or antigen-binding fragment, when bound to LILRB4, activates LILRB4. In certain embodiments, the antibody or antigen-binding fragment, when bound to LILRB4, suppresses activation of LILRB4. In certain embodiments, the antibody or antigen-binding fragment, when bound to LILRB4, can specifically interfere with, block or reduce the interaction between ApoE and LILRB4. In certain embodiments, the antibody or antigen-binding fragment provided herein is capable of inhibiting ApoE-mediated activity of LILRB4. In certain embodiments, the antibodies or antigen-binding fragments provided herein specifically or selectively bind to human LILRB4.

In some embodiments, the antibodies or antigen-binding fragments bind specifically to human LILRB4 and/or substantially inhibits binding of human LILRB4 to ApoE by at least about 20%-40%, 40-60%, 60-80%, 80-85%, or more (for example, by an assay as disclosed in the Example). In some embodiments, the antibody or antigen-binding fragment has a Kd of less (binding more tightly) than $10^{-7}$, $10^{-8}$, $10^{-9}$, $10^{-10}$, $10^{-11}$, $10^{-12}$, $10^{-13}$M. In some embodiments, the antibody or antigen-binding fragment has an IC50 for blocking the binding of ApoE to LILRB4 of less than 1 uM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some embodiments, the antibodies or antigen-binding fragments provided herein having clone-paired CDR's from the heavy chains illustrated in FIGS. 28A-28C and light chains as illustrated in FIGS. 30A-30C. Such antibodies may be produced by the clones discussed below in the Examples section using methods described herein. In certain embodiments, each CDR is defined in accordance with Kabat definition, the Chothia definition, the combination of Kabat definition and Chothia definition, the AbM definition, or the contact definition of CDR. In certain embodiments, the antibody or antigen-binding fragment is characterized by clone-paired heavy and light chain CDR sequences from Tables 1 and 2.

In certain embodiments, the antibodies may be defined by their variable sequence, which include additional "framework" regions. The antibody is characterized by clone-paired heavy chain and light chain amino acid sequences from FIGS. 28A-28C and FIGS. 30A-30B. Furthermore, the antibodies sequences may vary from these sequences, particularly in regions outside the CDRs. For example, the amino acids may vary from those set out above by a given percentage, e.g., 80%, 85%, 90%, 91%, 92%, 93%, 94%, 95%, 96%, 97%, 98% or 99% homology, or the amino acids may vary from those set out above by permitting conservative substitutions (discussed below). Each of the foregoing apply to the amino acid sequences of FIGS. 28A-28C and FIGS. 30A-30C. In another embodiment, the antibody derivatives of the present disclosure comprise VL and VH domains having up to 0, 1, 2, 3, 4, 5, 6, 7, 8, 9, 10 or more conservative or non-conservative amino acid substitutions, while still exhibiting the desired binding and functional properties.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (C1q) of the classical complement system. Thus, the term "antibody" includes intact immunoglobulins of types IgA, IgG, IgE, IgD, IgM (as well as subtypes thereof), wherein the light chains of the immunoglobulin may be of types kappa or lambda. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., $2^{nd}$ ed. Raven Press, N.Y. (1989).

The present disclosure further comprises nucleic acids which hybridize to nucleic acids encoding the antibodies disclosed herein. In general, the nucleic acids hybridize under moderate or high stringency conditions to nucleic acids that encode antibodies disclosed herein and also encode antibodies that maintain the ability to specifically bind to an LILRB4. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., MOLECULAR CLONING: A LABORATORY MANUAL, $3^{rd}$ ed., Cold Spring Harbor Press, Cold Spring Harbor, N.Y. 2001). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

TABLE 1

Heavy chain CDR sequences, amino acids

| Antibody/Chain | HCDR1 | SEQ ID NO: | HCDR2 | SEQ ID NO: | HCDR3 | SEQ ID NO: |
|---|---|---|---|---|---|---|
| B4-15-1 | GFTINSAH | 2 | STTGGPS | 3 | ARDGPGNNIDMDL | 4 |
| B4-15-2 | GIDLTNYA | 9 | ITGSSNT | 10 | ASNPDSHNANGV | 11 |
| B4-116-1 | GFSFSSTYC | 16 | IHGVSTNNR | 17 | ARSTDYEWGLSL | 18 |
| B4-116-2 | GFSFSSTYC | 23 | IHGVSTNNR | 24 | ARSTDYEWGLSL | 25 |
| B4-116-3 | GFSLSNNG | 30 | IYVGSGTT | 31 | ARGFGVGDWQEWFFDL | 32 |
| B4-116-4 | GFSLSNNG | 37 | IYVGSGTT | 38 | ARGFGVGDWQEWFFDL | 39 |
| B4-55-1 | GFSLSSYA | 44 | IGTGTTT | 45 | VRNDVYWAFNL | 46 |
| B4-55-2 | GFSLSSYA | 51 | IGTGTTT | 52 | VRNDVYWAFNL | 53 |
| B4-19 | GFSISTYA | 58 | IGTGGSA | 59 | ARNDIYWAFGL | 60 |
| B4-49 | GFDFSSSGW | 65 | IYSGRSGST | 66 | ARALYVDYVDYDYIDL | 67 |
| B4-72-1 | GFSLSSYY | 72 | INTGGSA | 73 | ARGWSRGDL | 74 |
| B4-72-2 | GFSLSSYY | 79 | INTGGSA | 80 | ARGWSRGDL | 81 |
| B4-86 | GFSFSSSYW | 86 | IGTGSGS | 87 | VRGAGYSSYRL | 88 |
| B4-87 | GFSFISTYW | 93 | IYTGGSGST | 94 | ARALYVDYVDYDYIDL | 95 |
| B4-193 | GFSLSSSYW | 100 | IDSGSVGIT | 101 | SVRHGDNWALDL | 102 |
| h193-H1 | GFSLSSSYW | 100 | IDSGSVGIT | 101 | VRHGDNWALDL | 224 |
| h193-H2 | GFSLSSSYW | 100 | IDSGSVGIT | 101 | VRHGDNWALDL | 224 |
| h193-H3 | GFSLSSSYW | 100 | IDSGSVGIT | 101 | ARHGDNWALDL | 227 |
| h193-H4 | GFSLSSSYW | 100 | IDSGSVGIT | 101 | ARHGDNWALDL | 227 |
| h193-H5 | GFSLSSSYW | 100 | IDSGSVGIT | 101 | ARHGDNWALDL | 227 |
| h193-H6 | GFSLSSSYW | 100 | IDSGSVGIT | 101 | ARHGDNWALDL | 227 |
| h193-H7 | GFSLSSSYW | 100 | IDSGSVGIT | 101 | ARHGDNWALDL | 227 |

TABLE 2

Kappa light chain CDRs, amino acid sequences

| Antibody/Chain | LCDR1 | SEQ ID NO: | LCDR2 | SEQ ID NO: | LCDR3 | SEQ ID NO: |
|---|---|---|---|---|---|---|
| B4-15-1 | QNRGGS | 6 | SAS | na | QSTIYSISDIGA | 7 |
| B4-15-2 | QSVYDNN | 13 | SAS | na | QSYGITNKNNYNS | 14 |
| B4-116-1 | ESIGSR | 20 | KAS | na | QCAGQSSTWA | 21 |
| B4-116-2 | ESIGSR | 27 | KAS | na | QCAGQSSTWA | 28 |
| B4-116-3 | ESISNY | 34 | KAS | na | QAYWGTSTMA | 35 |
| B4-116-4 | ESISNY | 41 | KAS | na | QAYWGTSTMA | 42 |
| B4-55-1 | QSVVNNNA | 48 | KAS | na | QGGYYIGISDYP | 49 |
| B4-55-2 | QSVVNNNA | 55 | KAS | na | QGGYYIGISDYP | 56 |
| B4-19 | EGIRNW | 62 | GAS | na | QGGVYSSSIYGYP | 63 |
| B4-49 | QSTGIR | 69 | ATS | na | QYSYYGSSYVFD | 70 |
| B4-72-1 | ESVDNW | 76 | DAS | na | LGVFHDGINNA | 77 |
| B4-72-2 | QNVYDDDT | 83 | DAS | na | LGVFHDGINNA | 84 |
| B4-86 | ESVSNW | 90 | GAS | na | QQGYDWDNIDNA | 91 |
| B4-87 | ENIGSR | 97 | AAS | na | QCSYYGSTYVFG | 98 |
| B4-193 | QSINSW | 104 | KAS | na | QHGYIRGDLDNV | 105 |
| h193-K1 | QSINSW | 104 | KASTLAS | 233 | HGYIRGDLDNV | 234 |
| h193-K2 | QSINSW | 104 | KASTLAS | 233 | HGYIRGDLDNV | 234 |
| h193-K3 | QSINSW | 104 | KASTLAS | 233 | HGYIRGDLDNV | 234 |

TABLE 2-continued

Kappa light chain CDRs, amino acid sequences

| Antibody/Chain | LCDR1 | SEQ ID NO: | LCDR2 | SEQ ID NO: | LCDR3 | SEQ ID NO: |
|---|---|---|---|---|---|---|
| h193-K4 | QSINSW | 104 | KASTLAS | 233 | HGYIRGDLDNV | 234 |

TABLE 3

Sequence ID Nos for LILRB4 antibodies

| Antibody | Heavy Chain Variable Region (CDR1, CDR2, CDR3) A.A. SEQ ID NO. | Light Chain Variable Region (CDR1, CDR2, CDR3) A.A. SEQ ID NO. | Heavy Chain Variable Region (CDR1, CDR2, CDR3) N.A. SEQ ID NO. | Light Chain Variable Region (CDR1, CDR2, CDR3) N.A. SEQ ID NO. |
|---|---|---|---|---|
| B4-15-1 | 1 (2, 3, 4) | 5 (6, SAS, 7) | 106 (107, 108, 109) | 110 (111, tctgcatcc, 112) |
| B4-15-2 | 8 (9, 10, 11) | 12 (13, SAS, 14) | 113 (114, 115, 116) | 117 (118, tctgcatcc, 119) |
| B4-116-1 | 15 (16, 17, 18) | 19 (20, KAS, 21) | 120 (121, 122, 123) | 124 (125, aaggcatcc, 126) |
| B4-116-2 | 22 (23, 24, 25) | 26 (27, KAS, 28) | 127 (128, 129, 130) | 131 (132, aaggcatcc, 133) |
| B4-116-3 | 29 (30, 31, 32) | 33 (34, KAS, 35) | 134 (135, 136, 137) | 138 (139, aaggcatcc, 140) |
| B4-116-4 | 36 (37, 38, 39) | 40 (41, KAS, 42) | 141 (142, 143, 144) | 145 (146, aaggcatcc, 147) |
| B4-55-1 | 43 (44, 45, 46) | 47 (48, KAS, 49) | 148 (149, 150, 151) | 152 (153, aaggcttcc, 154) |
| B4-55-2 | 50 (51, 52, 53) | 54 (55, KAS, 56) | 155 (156, 157, 158) | 159 (160, aaggcttcc, 161) |
| B4-19 | 57 (58, 59, 60) | 61 (62, GAS, 63) | 162 (163, 164, 165) | 166 (167, ggtgcatcc, 168) |
| B4-49 | 64 (65, 66, 67) | 68 (69, ATS, 70) | 169 (170, 171, 172) | 173 (174, gctacatcc, 175) |
| B4-72-1 | 71 (72, 73, 74) | 75 (76, DAS, 77) | 176 (177, 178, 179) | 180 (181, gatgcatcc, 182) |
| B4-72-2 | 78 (79, 80, 81) | 82 (83, DAS, 84) | 183 (184, 185, 186) | 187 (188, gatgcatcc, 189) |
| B4-86 | 85 (86, 87, 88) | 89 (90, GAS, 91) | 190 (191, 192, 193) | 194 (195, ggtgcatcc, 196) |
| B4-87 | 92 (93, 94, 95) | 96 (97, AAS, 98) | 197 (198, 199, 200) | 201 (202, gctgcatcc, 203) |
| B4-193 | 99 (100, 101, 102) | 103 (104, KAS, 105) | 204 (205, 206, 207) | 208 (209, aaggcgtcc, 210) |

TABLE 4

Sequence ID Nos for humanized 193 (h193) antibody heavy chains

| Heavy Chain | Variable Region (CDR1, CDR2, CDR3) A.A. SEQ ID NO. |
|---|---|
| h193-H1 | 223 (100, 101, 224) |
| h193-H2 | 225 (100, 101, 224) |
| h193-H3 | 226 (100, 101, 227) |
| h193-H4 | 228 (100, 101, 227) |
| h193-H5 | 229 (100, 101, 227) |
| h193-H6 | 230 (100, 101, 227) |
| h193-H7 | 231 (100, 101, 227) |

TABLE 5

Sequence ID Nos for humanized 193 (h193) antibody light chains

| Light Chain | Variable Region (CDR1, CDR2, CDR3) A.A. SEQ ID NO. |
|---|---|
| h193-K1 | 232 (104, 233, 234) |
| h193-K2 | 235 (104, 233, 234) |
| h193-K3 | 236 (104, 233, 234) |
| h193-K4 | 237 (104, 233, 234) |

2. Exemplary Epitopes and Competing Antigen Binding Proteins

In another aspect, the present disclosure provides epitopes to which anti-LILRB4 antibodies bind.

In some embodiments, epitopes that are bound by the antibodies described herein are useful. In certain embodiments, an epitope provided herein can be utilized to isolate antibodies or antigen binding proteins that bind to LILRB4. In certain embodiments, an epitope provided herein can be utilized to generate antibodies or antigen binding proteins which bind to LILRB4. In certain embodiments, an epitope or a sequence comprising an epitope provided herein can be utilized as an immunogen to generate antibodies or antigen binding proteins that bind to LILRB4. In certain embodiments, an epitope described herein or a sequence comprising an epitope described herein can be utilized to interfere with biological activity of LILRB4.

In some embodiments, antibodies or antigen-binding fragments thereof that bind to any of the epitopes are particularly useful. In some embodiments, an epitope provided herein, when bound by an antibody, modulates the biological activity of LILRB4. In some embodiments, an epitope provided herein, when bound by an antibody, activates LILRB4. In some embodiments, an epitope provided herein, when bound by an antibody, suppress the activation of LILRB4. In some embodiments, an epitope provided herein, when bound by an antibody, block the interaction between ApoE and LILRB4.

In some embodiments, the domain(s)/region(s) containing residues that are in contact with or are buried by an antibody can be identified by mutating specific residues in LILRB4 and determining whether the antibody can bind the mutated LILRB4 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In another aspect, the present disclosure provides antigen-binding proteins that compete with one of the exemplified antibodies or antigen-binding fragment binding to the epitope described herein for specific binding to LILRB4. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the heavy and light chain variable regions and CDRs included in Tables 1 and 2. In certain embodiments, the epitope is located within the linker region between the D1 and D2 domain of human LILRB4. In certain embodiments, the epitope comprises at least one amino acid within one or more of the amino acid sequences listed in Table 9. In certain embodiments, the epitope comprises at least one amino acid within one or more of the amino acid sequences selected from W18, G96, A97, Y98, S99, K100, Q122, S123, R124, S125, P126, H153 and Q154 of SEQ ID NO: 238 (D1 and D2 domains of human LILRB4 protein).

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full-length IgG antibodies may be generated by subcloning heavy and light chain Fv DNAs from the cloning vector into an IgG plasmid vector, transfected into 293 Freestyle cells or CHO cells, and antibodies collected a purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody.

The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328. In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as Lemna (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyl-transferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase α-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (See for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3 GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3 GlcNAc2; GalGlcNAc2Man3 GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man5GlcNAc2(Fuc), GlcNAcMan5 GlcNAc2(Fuc), Man3 GlcNAc2(Fuc), GlcNAcMan3GlcNAc2(Fuc), GlcNAc2Man3 GlcNAc2 (Fuc), GalGlcNAc2Man3 GlcNAc2 (Fuc), Gal2GlcNAc2Man3GlcNAc2(Fuc), NANAGal2GlcNAc2Man3GlcNAc2(Fuc), and NANA2Gal2GlcNAc2Man3GlcNAc2(Fuc); in an α1,3-linkage or α1,4-linkage fucose to produce a glycoform selected from the group consisting of GlcNAc(Fuc)Man5GlcNAc2, GlcNAc(Fuc)Man3GlcNAc2, GlcNAc2(Fuc1-2)Man3GlcNAc2, GalGlcNAc2(Fuc1-2)Man3 GlcNAc2, Gal2GlcNAc2(Fuc1-2)Man3GlcNAc2, NANA-Gal2 GlcNAc2 (Fuc1-2)Man3GlcNAc2, and NANA2Gal2GlcNAc2(Fuc1-2)Man3GlcNAc2; or in an α1,2-linkage fucose to produce a glycoform selected from the group consisting of Gal(Fuc)GlcNAc2Man3 GlcNAc2, Gal2(Fuc1-2)GlcNAc2Man3GlcNAc2, NANAGal2 (Fuc1-2)GlcNAc2Man3 GlcNAc2, and NANA2Gal2 (Fuc1-2) GlcNAc2Man3 GlcNAc2.

In further aspects, the antibodies comprise high mannose N-glycans, including but not limited to, Man8GlcNAc2, Man7GlcNAc2, Man6GlcNAc2, Man5GlcNAc2, Man4GlcNAc2, or N-glycans that consist of the Man3GlcNAc2 N-glycan structure. In further aspects of the above, the complex N-glycans further include fucosylated and non-fucosylated bisected and multiantennary species. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

V. Treatment of Cancer

A. Formulation and Administration

The present disclosure provides pharmaceutical compositions comprising anti-LILRB antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Cell Therapies

In another aspect, the present disclosure provides immune cells which express a chimeric antigen receptor (CAR). In some embodiment, The CAR comprises an antigen-binding fragment provided herein. In an embodiment, the CAR protein includes from the N-terminus to the C-terminus: a leader peptide, an anti-LILRB4 heavy chain variable domain, a linker domain, an anti-LILRB4 light chain variable domain, a human IgG1-CH2-CH3 domain, a spacer region, a CD28 transmembrane domain, a 4-1BB intracellular costimulatory signaling and a CD3 ζ intracellular T cell signaling domain.

Also provided are methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy.

The immune cells may be T cells (e.g., regulatory T cells, CD4+ T cells, CD8+ T cells, or gamma-delta T cells), NK cells, invariant NK cells, NKT cells, or macrophages. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from healthy human subjects, healthy volunteers, or healthy donors. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible. To be rendered subject-compatible, allogeneic cells can be treated to reduce immunogenicity.

The immune cells can be genetically engineered to express antigen receptors such as engineered TCRs and/or chimeric antigen receptors (CARs). For example, the host cells (e.g., autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook et al., supra; and Ausubel et al., CURRENT PROTOCOLS IN MOLECULAR BIOLOGY, Greene Publishing Associates and John Wiley & Sons, N Y, 1994. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

C. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-DC-HIL antibody or the other therapy will be desired. Various combinations may be employed, where the antibody is "A," and the other therapy is "B," as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene) and interleukin 2 (Proleukin) after the completion of consolidation therapy, gemtuzumab ozogamicin (Mylotarg) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are one or more drugs selected from the group consisting of a topoisomerase inhibitor, an anthracycline, a topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inihbitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

VI. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Antibody conjugates are also preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (0' Shannessy et al., 1987). This approach has been reported to produce diagnostically and therapeutically promising antibodies which are currently in clinical evaluation.

VII. Immunodetection Methods

In still further embodiments, the present disclosure concerns immunodetection methods for binding, purifying, removing, quantifying and otherwise generally detecting LILRB-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LILRBs also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing LILRB-related cancers and contacting the sample with a first antibody in accordance with the present disclosure, as the case may be, under conditions effective to allow the formation of immunocomplexes.

These methods include methods for detecting or purifying LILRBs or LILRB-related cancer cells from a sample. The antibody will preferably be linked to a solid support, such as in the form of a column matrix, and the sample suspected of containing the LILRB-related cancer cells will be applied to the immobilized antibody. The unwanted components will be washed from the column, leaving the LILRB-expressing cells immunocomplexed to the immobilized antibody, which is then collected by removing the organism or antigen from the column.

The immunobinding methods also include methods for detecting and quantifying the amount of LILRB-related cancer cells or related components in a sample and the detection and quantification of any immune complexes formed during the binding process. Here, one would obtain a sample suspected of containing LILRB-related cancer cells and contact the sample with an antibody that binds LILRBs or components thereof, followed by detecting and quantifying the amounts of immune complexes formed under the specific conditions. In terms of antigen detection, the biological sample analyzed may be any sample that is suspected of containing LILRB-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LILRBs. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the LILRB-related cancer cells is added to the wells. After binding and washing to remove non-specifically bound immune complexes, the bound antigen may be detected. Detection may be achieved by the addition of another anti-LILRB antibody that is linked to a detectable label. This type of ELISA is a simple "sandwich ELISA." Detection may also be achieved by the addition of a second anti-LILRB4 antibody, followed by the addition of a third antibody that has binding affinity for the second antibody, with the third antibody being linked to a detectable label.

In another exemplary ELISA, the samples suspected of containing the LILRB4-related cancer cells are immobilized onto the well surface and then contacted with the anti-LILRB4 antibodies of the disclosure. After binding and washing to remove non-specifically bound immune complexes, the bound anti-LILRB4 antibodies are detected. Where the initial anti-LILRB4 antibodies are linked to a detectable label, the immune complexes may be detected directly. Again, the immune complexes may be detected using a second antibody that has binding affinity for the first anti-LILRB4 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, the present disclosure concerns immunodetection kits for use with the immunodetection methods described above. As the antibodies may be used to detect LILRB-related cancer cells, the antibodies may be included in the kit. The immunodetection kits will thus comprise, in suitable container means, a first antibody that binds to an LILRB, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of LILRBs, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

5. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mice. C57 BL/6J and NOD-SCID IL2Rγ null (NSG) mice were purchased from and maintained at the animal core facility of University of Texas Southwestern Medical Center (UTSW). Apoe-Knockout (apoe-KO,Apoe$^{tm1Unc}$) mice as previously described[31] were purchased from the Jackson Laboratory. Animal work has been approved and conducted under the oversight of the UT Southwestern Institutional Animal Care and Use Committee (IACUC). For each experiment, the same sex and age-matched (4-8 weeks) mice were used and randomly allocated to each group; and for tumor size measurement and in vivo lumina imaging experiments, treatment conditions of the mice were blinded. The minimum number of mice in each group was calculated based on results from the prior relevant studies. For the subcutaneous tumor model, the tumor size was calculated by (width×width×length) cm³. The maximal tumor measurement permitted by UTSW IACUC is 2 cm in diameter of tumor.

Cell culture. 293T cells were cultured in Dulbecco's modified Eagle's medium (DMEM) supplemented with 10% fetal bovine serum (FBS) at 37° C. in 5% CO2 and the normal level of $O_2$. Human umbilical vein/vascular endothelium cells (HUVECs) (ATCC, CRL-1730) were cultured in endothelial cell growth medium plus growth factor, cytokines and supplements (EGM-BulletKit, Lonza) at 37° C. in 5% CO2 and the normal level of $O_2$. Human monocytic AML cells, THP-1 (ATCC, TIB-202), MV4-11 (ATCC, CRL-9591), and U937 (ATCC, CRL-1593.2), and mouse AML cells, WEHI-3 (ATCC, TIB-68), were cultured in Roswell Park Memorial Institute (RPMI) 1640 supplemented with 10% FBS at 37° C. in 5% CO2 and the normal level of 02. Mouse AML cells, C1498 (ATCC, TIB-49) were cultured in DMEM supplemented with 10% FBS at 37° C. in 5% CO2 and the normal level of 02. All cell lines were routinely tested using a mycoplasma-contamination kit (R&D Systems).

Primary human leukemia cells. Primary human AML and B-ALL samples were obtained from the tissue banks at UTSW. Informed consent was obtained under a protocol reviewed and approved by the Institutional Review Board at UTSW. The UTSW cohort included 105 AML patients representative of AML subtypes by the French-American-British (FAB) classification, acute myeloblastic leukemia with minimal maturation (M1, n=9), acute myeloblastic leukemia with maturation (M2, n=34), acute promyelocytic leukemia (M3, n=10), acute myelomonocytic leukemia (M4, n=34), acute monocytic leukemia (M5, n=25), acute erythroid leukemia (M6, n=2), and acute megakaryoblastic leukemia (M7, n=1) and patients with undifferentiated leukemia (AUL; n=1) and transient myeloproliferative disorder (TAM; n=2). Samples were frozen in FBS with 10% DMSO and stored in liquid nitrogen.

Human normal monocytes and macrophages. Human normal monocytes (CD14$^+$ cells) were isolated by the AutoMACS Pro Separation System (Miltenyi Biotech, Auburn, CA) from the mononuclear cells fraction of normal peripheral blood. Briefly, buffy coat was purchased from Interstate Blood Bank (Memphis, TN) and the mononuclear cell layer was separated by Ficoll Hypaque (Ser. No. 17/144, 003, GE Lifesciences) density gradient separation. Mononuclear cells were treated with red blood cell lysis buffer to remove red blood cells and then incubated with CD14 microbead-conjugated antibody (130-050-201, Miltenyi Biotech, Auburn, CA) for 15 min at 4° C. CD14 positive cells were then isolated using the positive selection program according to the manufacturer's protocol. One million CD14$^+$ cells were plated in macrophage culture media, Iscove's modified Dulbecco's medium (IMDM) (12440053, Thermo fisher) supplemented with 10% human AB serum (MT35060CI, Fisher Scientific), 1% NEAA (11-140-050, Fisher), 2 μM L-alanine-L-glutamine (SH3003402, Fisher), per each well of a 6-well plate and cultured for 7 days. After incubation, most of the cells were adherent to the plastic surface and stained positive for CD14 and other markers specific for macrophages.

TCGA analyses. Data were obtained from the TCGA acute myeloid leukemia database (version: Aug. 16, 2016). The patients were classified into AML subtypes (FAB classification) M0 (undifferentiated acute myeloblastic leukemia) (n=16), M1 (n=42), M2 (n=39), M3 (n=16), M4 (n=35), M5 (n=18), M6 (n=2), M7 (n=3); two cases were not classified by subtype. The mRNA levels of indicated genes were determined by RNA-seq (polyA+IlluminaHiSeq). RESM-normalized counts are reported, and data were analyzed and visualized with UCSC Xena (xena.ucsc.edu). For analysis of overall survival, 160 patients with available survival data were separated into three groups based on whether they had high, moderate, or low gene expression and then analyzed by Xena Kaplan Meier plot (xena.ucsc.edu/survival-plots).

Flow cytometry. Primary antibodies including anti-human CD45-PE (BD Pharmingen, HI30, 1:100), CD45-FITC (BD Pharmingen, HI30, 1:100), CD45-APC (BD Pharmingen, HI30, 1:100), anti-human CD34-FITC (BD Pharmingen, 55582, 1:100), anti-human CD19-PE (eBioscience, HIB19, 1:100), anti-human CD20-PE (BD Pharmingen, 555623, 1:100), anti-human CD11b-APC (eBioscience, ICRF44, 1:100), anti-human LILRB4-APC (eBioscience, ZM4.1, 1:100), anti-human LILRB4-PE (Biolegend, ZM4.1, 1:100), anti-human CD14-APC (eBioscience, 61D3, 1:100), anti-human CD33-APC (Biolegend, P67.6, 1:100), anti-human CD4-APC (eBioscience, RPA-T4, 1:100), anti-human CD3-FITC (BioLegend, HIT3α, 1:100), anti-human CD3-Pacific blue (BD Pharmingen, SP34-2, 1:100) anti-human CD8-PE (BD Pharmingen, 555367, 1:100), anti-human CD28-APC (eBioscience, CD28.2, 1:100), anti-human CD40L-APC (eBioscience, 24-31, 1:100), anti-human PD1-APC (Biolegend, EH12.2H7, 1:100), anti-human TIM3-APC (eBioscience, F38-2E2, 1:100), anti-human TIGIT-APC (eBioscience, MBSA43, 1:100), anti-human LAG3-APC (eBioscience, 3DS223H, 1:100), anti-human FasL-PE (eBioscience, 24-31, 1:100), anti-uPAR-APC (Biolegend, VIMS, 1:100), anti-mouse CD3-APC (BioLegend, 17A2, 1:200), anti-mouse CD8a-PE (BioLegend, 53-6.7, 1:200), anti-mouse CD45-PE (BD Pharmingen, 30-F11, 1:200), anti-mouse CD49b-APC (eBioscience, DXS, 1:200), anti-mouse CD49f-PE (eBioscience, GoH3, 1:200), anti-mouse CD11b-APC (BioLegend, M1/71, 1:200), anti-mouse CD11b-PE (BioLegend, M1/71, 1:200), anti-mouse CD11c-APC (eBioscience, N418, 1:200), anti-mouse F4/80-APC (BioLegend, BM8, 1:200), anti-His-tag-APC (R&D systems, AD1.1.10, 1:400), and IgG isotype-control-APC (eBioscience, P3.6.2.8.1, 1:400) antibodies were used. Cells were run on either Calibur for analysis or FACSAria for analysis and sorting. Flow data were analysed by Flowjo software. For analysis of human hematopoietic engraftment in NSG mice, a previously published protocol was followed. PI staining was used to exclude dead cells in analysis and sorting. For intracellular staining, the inventors followed the two-step protocol for fixation/methanol from eBioscience. Briefly, human primary AML cells were stained for the surface expression of LILRB4 (anti-LILRB4-Alexa Fluor 647, Biolegend, ZM4.1, 1:100) and CD33 (anti-human CD33-FITC, Biolegend, HIM3-4, 1:100) and fixable cell viability dye eFluor 450 (Bioscience, Cat #65-0863-14, 1:100) followed by fixation (IC fixation buffer, eBioscience, Cat #00-8222) and methanol treatment. After that, cells were stained for intracellular antigens by anti-p-SHP-2 (Y580)-PE (Cell signaling, Cat #13328S, 1:100), anti-pIKKα/β (S176/180) (16A6) (Cell signaling, Cat #2697, 1:100), anti-NFκB (S529)-PE (eBioscience, B33B4WP, 1:100), anti-uPAR-PE (Biolegend, VIMS, 1:100), anti-Arginase-1 (D4E3M) (Cell signaling, Cat #93668, 1:100), rabbit IgG Isotype control-PE (Cell signaling, Cat #5742, 1:100), mouse IgG Isotype control-PE (eBioscience, m2a-15F8, 1:100) and anti-rabbit IgG-PE (Jackson Immunoresearch Lab, Cat #111-116-144, 1:400) for flow cytometry analysis.

Virus construction and infection. For retrovirus packaging, plasmid constructs XZ201-IRES-GFP and XZ201-human lilrb4 (hlilrb4)-IRES-GFP were mixed with PCL-ECO (2:1), followed by transfection into 293T cells using Lipofectamine 2000 (Invitrogen). For lentivirus packaging, CRISPER/Cas-9 based gRNA (guide RNA) constructs and other constructs for gene overexpression including—pLentiLox3.7-luciferase-IRES-GFP, ZsGreen-hlilrb4 and ZsGreen-hlilrb4-intΔ, pLVX-p/aur-IRES-tdTomato, pLVX-arg1-IRES-tdTomato were mixed with psPAX2 and pMD2.G (Addgene) at a ratio of 4:3:1 and transfected into 293T cells using Lipofectamine 2000 (Invitrogen). Virus-containing supernatant was collected 48-72 hrs post-transfection and used for infection as described previously.

CRISPR/Cas9-based gene knockout in AML cells. Human AML cells were infected with doxycycline-inducible Cas9-expressing lentivirus (pCW-Cas9, Addgene 50661). After 1 µg/ml puromycin selection, the survived cells were infected with sgRNA-expressing lentivirus, produced by the plasmid modified from pSLQ1651 (Addgene 51024) by replacing the puro-mcherry with GFP for sorting. Scramble control sgRNA (sgRNA 5'-GAACGACTAGT-TAGGCGTGTA-3' (SEQ ID NO: 211)), lilrb4 targeting sgRNA (sgRNA1 5'-TGTTACTATCGCAGCCCTGT-3' (SEQ ID NO: 212); sgRNA2 5'-GTAGGTCCCCCCGTGCACTG-3' (SEQ ID NO: 213); sgRNA3 5'-CCTGTGACCTCAGTGCACGG-3' (SEQ ID NO: 214)), apoe targeting sgRNA (sgRNA1 5'-CTTTTGG-GATTACCTGCGC-3' (SEQ ID NO: 215); sgRNA2 5'-AACTGGCACTGGGTCGCTTT-3' (SEQ ID NO: 216)), shp-1 targeting sgRNA (sgRNA1 5'-TAAGACCTA-CATCGCCAGCC-3' (SEQ ID NO: 217); sgRNA2 5'-GAAGAACTTGCACCAGCGTC-3' (SEQ ID NO: 218)), shp-2 targeting sgRNA (sgRNA1 5'-GAGACTT-CACACTTTCCGTT-3' (SEQ ID NO: 219); sgRNA2 5'-TA-CAGTACTACAACTCAAGC-3' (SEQ ID NO: 220)), ship targeting sgRNA (sgRNA1 5'-CACGCAGAGCGCGTATGCCC-3' (SEQ ID NO: 221); sgRNA2 5'-TGGCAACATCACCCGCTCCA-3' (SEQ ID NO: 222)) which were designed by an online tool (crispr.mit.edu), were cloned into the sgRNA plasmid, individually. After treated with 1 µg/ml doxycycline (Sigma, Cat #PHR1789) for 1 week, these cells were staining with anti-LILRB4 antibody and the LILRB4 negative cells were sorted as lilrb4-knockout cells. For apoe-, shp-1-, shp-2- and ship-knockout cells, GFP+cells were sorted into a 96-well plate as single cell per well. After cell expanded, knockout cells were verified by western blotting. For in vivo induction of CRISPR/Cas9 to achieve gene knockout, the inventors fed mice with doxycycline as described. Briefly, 7 days after Cas9/lilrb4-sgRNA-transfected THP-1 cell implantation, mice were treat with 2 mg/mouse of doxycycline via gavage daily for 5 days to achieve Cas9 expression in engrafted leukemia cells. The knockout was validated by flow cytometry.

Leukemia cell and T cell co-culture assay. In the co-culture assay, human T cells ($5\times10^4$ per well) isolated from health donor peripheral blood (PB009-1-0, AllCells) were mixed with irradiated (28 Gy) indicated human leukemia cells in a U-bottom 96 well-plate. For non-contact co-culture of T cells with leukemia cells, leukemia cells were cultured in the upper chamber of transwell inserts (pore size, 3 µM, #09-761-80, Thermo Fisher) in U-bottom 96 well-plate. T cells isolated from healthy donors were placed in the lower chambers of a 96-well transwell plate. Irradiated indicated leukemia cells (E:T ratio=2:1 if not indicated) were added to the upper chambers and treated with indicated antibodies, proteins and reagents. After culture with anti-CD3/CD28-coated beads (11161D, Thermo Fisher) and 50 U/ml rhIL-2 for 5-7 days, representative cells were photographed using an inverted microscope, and T cells were stained with anti-CD3 antibodies and analyzed by flow cytometry.

For primary AML or B-ALL samples, patient leukemia cells were sorted as $CD33^+$ and $CD19^+$ for AML and B-ALL, respectively. These leukemia cells were cultured with autologous $CD3^+$ T cells from the same patient or allogeneic T cells from health donor (E:T ratio=2:1). After culture with anti-CD3/CD28-coated beads (11161D, Thermo Fisher) and 50 U/ml rhIL-2 for 14 days, representative cells were photographed using an inverted microscope, and T cells were stained with anti-CD3, anti-CD4 and anti-CD8 antibodies and analyzed by flow cytometry.

For cytotoxicity assay, human $CD8^+$ T cells ($5\times10^4$ per well) isolated from PBMCs of a healthy donor were stimulated with anti-CD3/CD28/CD137-coated beads (11163D, Thermo Fisher) for 2 days in a 96-well plate. Then, indicated $5×10^3$ leukemia cells and 50 to 500 µg/ml anti-LILRB4 antibodies or control IgG were added. Cell numbers were determined on day 7 in triplicate wells. Or indicated leukemia cells in indicated E:T ratios were cultured with T cells for 4-6 hrs in triplicate wells. Anti-CD3 and anti-CD8 were used to detect human CTL cells; indicated live THP-1 cells were positive for GFP and negative for PI. Cell supernatants from co-cultures of stimulated CTL cells and THP-1 cells treated with anti-LILRB4 or IgG were used to examine cytokine production using human cytokine arrays (AAH-CYT-6, RayBiotech).

For mouse leukemia/T cells co-culture, spleen cells from wild-type C57bl/6 were co-cultured with $2.5×10^4$ irradiated (28 Gy) mouse leukemia C1498 cells in a U-bottom 96 well-plate for 60 hrs. Anti-CD3/CD28-coated beads (11452D, Thermo Fisher), 50 U/ml recombinant human IL-2, and 5% serum from wild-type C57bl/6 mice or that from apoe-KO mice were added to the medium. In some experiments, 50 µg/ml lipid-bound APOE proteins (APOE-POPC) were added to the medium. The lipidation of APOE recombinant protein was conducted as described.

Transendothelial migration assays. To measure the ability of AML cells to migrate through endothelial cells, $3×10^5$ HUVEC cells were cultured on the transwell membrane (pore size is 8 µm). After 3 days, $1×10^5$ indicated leukemia cells were seeded in the upper chamber. In indicated experiments, leukemia cells were treated with antibodies or proteins in the upper chamber. After 18 h, cells in lower chamber were counted.

Short-term infiltration assay of leukemia cells and homing assay of hematopoietic stem/progenitor cells (HSPCs). Cells ($5×10^6$ cells per mouse) were injected intravenously into NSG mice. Animals were treated with 10 mg/kg of anti-LILRB4 antibodies or control IgG immediately after injection of leukemia cells. Mice were sacrificed after 20 hrs. Peripheral blood, bone marrow, liver, and spleen were harvested, and single-cell suspensions were examined by flow cytometry. CFSE, GFP or indicated markers such as anti-human CD45 and anti-human CD33 was used to detect target leukemia cells in indicated experiments. Numbers of leukemia cells in recipient liver, spleen, and bone marrow are reported as a ratio relative to cell numbers in peripheral blood.

To test the infiltration ability of mouse leukemia cells, $5×10^6$ C1498-GFP-hLILRB4 cells or C1498-GFP were injected intravenously into wild-type C57BL/6J or APOE-null mice. Mice were sacrificed after 20 h. GFP was used to detect leukemia cells by flow cytometry. The number of leukemia cells in recipient liver, spleen, and bone marrow were normalized to numbers in peripheral blood and are reported as a ratio.

To test HSPCs homing ability, $1×10^7$ human cord blood mononuclear cells were injected intravenously into an NSG mouse. Mice were treated with 10 mg/kg of anti-LILRB4 antibodies or control IgG immediately after injection of mononuclear cells and were sacrificed after 20 hrs. Anti-human CD45 and anti-human CD34 were used to detect human HSPCs by flow cytometry. Similarly, to test the infiltration ability of normal human monocytes, $5×10^6$ CD14-positive selected monocyte from health donor PBMC were labeled by CFSE and injected intravenously into an NSG mouse. Mice were treated with 10 mg/kg of anti-LILRB4 antibodies or control IgG immediately after injection of monocytes and were sacrificed after 20 hrs. CFSE-positive cells were analyzed by flow cytometry.

Innate immune cell depletion. NK cell depletion was done by i.p. injection of 50 µl anti-asialo GM1 antibodies (CL8955, Cedarlane) 3 days before leukemia cell implantation, which resulted in >90% depletion of CD45+CD49b+ NK cells in the circulation of NSG mice. Macrophages were depleted by treating NSG mice with clodronate (dichloromethylene bisphosphonate) liposomes (SKU8909, Clodrosome) (200 µl of stock solution 3 days before leukemia cell implantation), resulting in >70% depletion of CD45+CD11b+F4/80+ macrophages in the circulation of NSG mice. NSG mice were rendered neutropenic by i.p. injection of 200 µg anti-Ly-6G mAb (BP0075-1, Bioxcell) on days −3, −2, −1, and 0 post leukemia cell implantation, resulting in >80% depletion of $CD45.1^+CD11b^+CD11\ c^-$ neutrophils in the circulation of NSG mice.

Human AML xenograft. Xenografts were performed essentially as described[2,3,6,7]. Briefly, 6-8 week-old NSG mice were used for transplantation. $1×10^6$ human leukemia cells were resuspended in 200 µl PBS for each mouse i.v. injection. Mice were immediately given 10 mg/kg of anti-LILRB4 antibodies or control IgG intravenously. Three to four weeks after transplantation, the peripheral blood, bone marrow, spleen, and liver were assessed for the engraftment. Leukemia growth was monitored over time by luminescence imaging (Max, $3×10^8$ p/sec/cm²/sr; Min, $5×10^6$ p/sec/cm²/sr). For survival curve experiments, the death of mice was recorded when the moribund animals were euthanized. For primary patient-derived xenograft (PDX), each NSG mouse was given 5 to $10×10^6$ human primary peripheral blood or bone marrow mononuclear cells, which contain leukemia cells and other normal compartments such as normal hematopoietic stem progenitor cells and autologous T cells, via tail-vein injection. Mice were immediately given 10 mg/kg of anti-LILRB4 antibodies or control IgG intravenously and were treated twice a week until euthanization. For AML #11, mice were given 10 mg/kg of anti-LILRB4 antibodies or control IgG intravenously 7 days after leukemia cell implantation and were treated twice a week until euthanization. Leukemia growth was monitored over time by flow cytometry of human cells in peripheral blood. More than 1% of human leukemia cells in mouse tissue were considered successful engraftment of primary AML cells. One to four months after transplantation, the peripheral blood, bone marrow, spleen, and liver were assessed for the engraftment.

For the hPBMC-humanized model, $1×10^7$ human PBMCs were injected intravenously into each NSG mouse. Three weeks after implantation, mice had 30 to 50% engraftment of human T cells. At 3 weeks post-implantation, $1×10^6$ human AML THP-1 cells, including wild-type, lilrb4-KO THP-1 cells or THP-1 cells stably express luciferase (THP-1-Luc-GFP cells), were subcutaneously implanted. Mice were immediately given 10 mg/kg of anti-LILRB4 antibodies or control IgG intravenously and were treated twice a week until euthanization. Tumor growth was monitored over time by luminescence imaging (Max, $1×10^8$ p/sec/cm²/sr; Min, $5×10^6$ p/sec/cm²/sr). Tumor sizes were determined by caliper measure (width×width×length). For inducible lilrb4-knockout experiment, $1×10^6$ Cas9/lilrb4-sgRNA-transfected THP-1 cells were injected in each NSG mouse by i. v., immediately followed by i. v. injection of $0.5×10^6$ isolated human normal T cells from health donors. 7 days after THP-1 and T cell implantation, mice were treated with 2 mg/mouse of doxycycline via gavage daily for 5 days to achieve Cas9 expression in engrafted THP-1 cells. At 3 weeks post-implantation, the peripheral blood, bone marrow, spleen, and liver were assessed for the engraftment.

For the human Cord blood (hCB)-xenograft model, $2 \times 10^4$ human CD34+ hCB cells were injected intravenously into each NSG mouse. Six weeks after implantation, mice had 10 to 50% engraftment of human cells. $1 \times 10^6$ THP-1 cells that stably express luciferase (THP-1-Luc-GFP cells) were intravenously implanted. Mice were immediately given 10 mg/kg of anti-LILRB4 antibodies or control IgG intravenously. Tumor growth was monitored over time by luminescence imaging (Max, $1 \times 10^8$ p/sec/cm$^2$/sr; Min, $5 \times 10^6$ p/sec/cm$^2$/sr). Lineages of human normal blood cells were analyzed by flow cytometry.

Mouse AML allograft. The procedure of mouse AML allograft was similar to that of human AML xenograft. Briefly, 6-8 week-old wild-type C57bl/6 mice were used for transplantation. $1 \times 10^6$ mouse leukemia cells expressing human LILRB4 were resuspended in 200 µl PBS for each mouse intravenously or subcutaneously implantation. Mice were given 10 mg/kg of anti-LILRB4-N297A antibodies or control IgG intravenously 7 days after leukemia cell implantation and were treated twice a week until euthanization. Three weeks after transplantation, the peripheral blood, bone marrow, spleen, and liver were assessed for the engraftment. For subcutaneously implant mice, tumor sizes were determined by caliper measure (width×width×length). For survival curve experiments, the death of mice was recorded when the moribund animals were euthanized. For CD8+T depletion, 10 mg/kg anti-CD8 antibodies (YTS 169.4.2, Bioxcell) were i.v. injected 3 days after leukemia cell implantation and were treated for additional two time every 3 days. To determine whether anti-LILRB4 antibody treatment generates tumor-specific memory T cells against the tumor or against LILRB4, the inventors conducted adoptive transfer of spleen cells ($5 \times 10^6$/mouse) from anti-LILRB4 treated mice into normal recipient C57bl/6 mice. Four out of five transplanted mice rejected the control C1498-GFP mouse leukemia cells, and these mice were not susceptible to rechallenge with 3-fold higher numbers ($3 \times 10^6$/mouse) of C1498-GFP leukemia cells. While none of 5 mice with adoptive transfer of spleen cells from naïve mice reject the control C1498-GFP mouse leukemia cells.

Chimeric receptor reporter assay. A stable chimeric receptor reporter cell system was constructed as described to test the ability of a ligand to bind to the ECD of individual LILRBs, PirB, gp49B1 and LILRB4 site mutants and to trigger the activation or inhibition of the chimerically fused intracellular domain of paired immunoglobulin-like receptor (3, which signals through the adaptor DAP-12 to activate the NFAT promoter. If an agonist or antagonist binds the ECD and activates or suppresses the chimeric signaling domain, an increase or decrease, respectively, in GFP expression is observed. A competition assay was used to screen LILRB4 blocking antibodies. Briefly, APOE proteins (CI02, Novoprotein; 10 µg/ml) or human AB serum (10%, diluted in PBS) were pre-coated on 96-well plate at 37° C. for 3 hrs. After two washes with PBS, $2 \times 10^4$ LILRB4 reporter cells were seeded in each well; meanwhile, indicated anti-LILRB4 antibodies were added into culture media. After 16 hrs, the percentage of GFP+ reporter cells was analyzed by flow cytometry. The threshold of activation is 2 times of negative control treatment.

Fast protein liquid chromatography (FPLC) and Mass Spectrum. 10% human AB serum in PBS was loaded onto a 16/60 Superdex 200 gel filtration column and eluted with PBS and 2 mM EDTA. Eighty Fractions (40 ml) were collected, and each fraction (0.5 ml) was analyzed by chimeric receptor reporter assay. The active fractions (#26-30) were loaded onto PAGE-gel and processed to LC-MS/MS analysis (Orbitrap Elite) for protein identification in UTSW proteomics core. Recombinant or purified proteins used for validation were ZA2G (MBS145455, MyBioSource), AMBP (13141-H08H1, Sino Biological Inc), TTHY (12091-H08H, Sino Biological Inc), PEDF (11104-H08H, Sino Biological Inc), A2MG (MBS173010, MyBioSource), HEMO (MBS143111, MyBioSource), ANGT (MBS173525, MyBioSource), A1AT (MBS173006, MyBioSource), S100A9 (pro-814, Prospecbio), HORN (EBP08267, Biotrend USA), VTDB (CSB-EP009306HU, Biotrend USA), LRG1 (pro-141, Prospecbio), A1BG (RPE570Hu01, Cloud-Clone Corp), CRSP3 (RD172262100, BioVendor), APOA1 (16-16-120101-LEL, Athens Research & Technology), APOA2 (16-16-120102, Athens Research & Technology), APOA4 (16-16-120104, Athens Research & Technology), APOB (16-16-120200, Athens Research & Technology), APOC1 (16-16-120301, Athens Research & Technology), APOC2 (16-16-120302, Athens Research & Technology), APOC3 (16-16-120303, Athens Research & Technology), hAPOE (16-16-120500, Athens Research & Technology), mAPOE (CJ05, Novoprotein), APOE2 (350-12, Peprotech), APOE3 (350-02, Peprotech), APOE4 (350-04, Peprotech), PODXL2 (1524-EG-050, R&D systems), CD44 (12211-H08H, Sino Biological Inc), HCK (PV6128, Thermo Fisher), VEGFR3 (10806-H08H, Sino Biological Inc), NRG3 (16071-HO8H, Sino Biological Inc), PI16 (H00221476-P01, Novusbio), hMAG (8940-MG-050, R&D systems), mMAG (8580-MG-100, R&D systems), CNTF (303-CR-050, R&D systems), ANGPTL-7 (914-AN-025/CF, R&D systems), integrin-α1β1 (7064-AB-025, R&D systems), integrin-α2β1 (5698-AB-050, R&D systems), integrin-α2β3 (7148-AB-025, R&D systems), integrin-α3β1 (2840-A3-050, R&D systems), integrin-α4β1 (5668-A4-050, R&D systems), integrin-α4β7 (5397-A3-050, R&D systems), integrin-α5β1 (3230-A5-050, R&D systems), integrin-α5β3 (3050-AV-050, R&D systems), integrin-α5β5 (2528-AV-050, R&D systems), integrin-α5β6 (CT039-H2508H, Sino Biological Inc), mintegrin-α5β6 (CT051-M2508H, Sino Biological Inc), integrin-α5β8 (4135-AV-050, R&D systems), integrin-α6β4 (5497-A6-050, R&D systems), integrin-α8β1 (CT016-H2508H, Sino Biological Inc), integrin-α9β1 (5438-A9-050, R&D systems), integrin-α10β1 (5895-AB-050, R&D systems), integrin-α11β1 (6357-AB-050, R&D systems), integrin-αEβ7 (5850-A3-050, R&D systems), integrin-αXβ2 (CT017-H2508H, Sino Biological Inc) and normal mouse serum (NS03L, Millipore sigma).

Bio-layer interferometry. Binding interaction analyses between LILRB4-Fc with APOE2, APOE3, and APOE4 were performed on the Octet RED96 (ForteBio, Pall Corporation). All interaction studies were performed with the protein A dip-and-read biosensors (ForteBio). All binding experiments were performed using the Octet Red and kinetics buffer at 30° C. LILRB4-Fc coated biosensors (25 µg/ml LILRB4-Fc was loaded for 420 s) were washed in kinetics buffer before monitoring of association (300 s) and dissociation (600 s) of APOEs. Background wavelength shifts were measured from reference sensors that were loaded only with LILRB4-Fc.

Surface plasmon resonance (SPR). Biacore 2000 and CM5 chips were used to analyze binding of recombinant APOEs to the LILRB4 extracellular domain fused to hFc, using a method as previously described[2]. Recombinant protein A (Pierce) was pre-immobilized in two flow cells using the amine-coupling kit from GE. LILRB4-hFc was injected into one of the flow cells to be captured by the protein A. Each binding sensorgram from the sample flow cell, containing a captured LILRB4-hFc, was corrected for the protein A coupled cell control. Following each injection of an antigen solution, which induced the binding reaction, and the dissociation period during which the running buffer was infused, the protein A surface was regenerated by the injection of the regeneration solution containing 10 mM $Na_3PO_4$ (pH 2.5) and 500 mM NaCl. All captured LILRB4-hFc, with and without APOE bound, was completely removed, and another cycle begun. All measurements were performed at 25° C. with a flow rate of 30 µL/min.

Microscale thermophoresis (MST). MST experiments were performed on a Monolith NT.115 system (NanoTemper Technologies) using 80% LED and 20% IR-laser power. Laser on and off times were set at 30 s and 5 s, respectively. Recombinant LILRB4-ECD protein (SinoBio) was labeled with 4488-NHS (NanoTemper Technologies) and applied at a final concentration of 5.9 nM. A two-fold dilution series was prepared for unlabeled His-APOE (CI06, Novoprotein) in PBS, and each dilution point was similarly transferred to LILRB4-ECD solution. The final concentrations of His-APOE ranged from 0.36 nM to 12 µM. Samples were filled into standard-treated capillaries (NanoTemper Technologies) for measurement.

Western blotting and co-immunoprecipitation. Whole cells were lysed in Laemmli sample buffer (Sigma-Aldrich) supplemented with protease inhibitor cocktail (Roche Diagnostics). Samples were separated on SDS-PAGE gels (Bio-Rad) and transferred on nitrocellulose membranes (Bio-Rad) for protein detection. Primary antibodies including Anti-SHP-1 (Cell signaling, 3759, 1:1000), anti-phospho-SHP-1 Tyr564 (Cell signaling, 8849, 1:500), anti-phospho-SHP-1 Tyr564 (Invitrogen, PA537708, 1:500), anti-SHP-2 (Cell signaling, 3397, 1:1000), anti-phospho-SHP-2 Tyr580 (Cell signaling, 3703, 1:500), anti-SHIP1 (Cell signaling, 2727, 1:1000), anti-phospho-SHIP1 Tyr1020 (Cell signaling, 3941, 1:500), anti-NFκB p65 (Cell signaling, 8242, 1:1000), anti-IKKα (Cell signaling, 11930, 1:1000), anti-IKKβ (Cell signaling, 8943, 1:1000), anti-phospho-IKKα/β Ser176/180 (Cell signaling, 2697, 1:500), anti-IκBα (Cell signaling, 4814, 1:1000), anti-phospho-IκBα Ser32 (Cell signaling, 2859, 1:500), anti-Lamin-B2 (Cell signaling, 12255, 1:1000) and anti-Arginase-1 (Cell signaling, 9819, 1:1000), anti-uPAR (Invitrogen, MON R-4-02, 1:500), anti-LILRB4 (Santa cruz, sc-366213, 1:200), anti-APOE (Creative diagnostics, DCABH-2367, 1:250), anti-β-actin (Sigma-Aldrich, A2066, 1:1000) and anti-α-tubulin (Sigma-Aldrich, MABT205, 1:1000), as well as horseradish peroxidase (HRP) conjugated secondary antibodies (Cell signaling, 7074, 1:1,000, and 7076, 1:1,000) and chemiluminescent substrate (Invitrogen), were used. Specific cellular compartment fractionations were carried out using the NE-PER nuclear/cytoplasmic extraction kit (Thermo fisher, 78833) or the plasma membrane protein extraction kit (Abcam, ab65400). Proteins from plasma membrane fraction were further incubated with anti-LILRB4 antibodies and dynabeads protein A (Thermo fisher, 10001D) for further immunoprecipitation and western blotting.

Immunohistochemistry. Hematoxylin staining and immunostaining were performed on paraffin sections of tumors. Antibodies used were against LILRB4 (lab produced, 1:100), CD3 (Abcam, ab16669, 1:100), PD-1 (Thermo Fisher, J116, 14-9989-82, 1:100) and Arginase-1 (Cell signaling, 9819S, 1:100). The images were visualized using the Hamamatsu NanoZoomer 2.0-HT (Meyer instruments Inc., Houston, TX) and viewed in NPDview2 software (Hamamatsu, Japan).

Cytokine antibody array and arginase activity assay. To examine the secreted protein from leukemia cells, condition media were applied to a human cytokine antibody array (AAH-CYT-1000, RayBio) for the semi-quantitative detection of 120 human proteins. Image J (NIH) was used for quantification. Arginase activity was determined in condition media of indicated leukemia cells by a QuantiChrom Arginase assay kit (DARG-100, BioAssay system).

RNA-seq analysis. RNA was purified from sorted cells with Qiagen RNeasy Mini Kit and then reverse-transcribed with SuperScript III Reverse Transcriptase (Invitrogen) according to the manufacturer's instructions. RNA-seq was performed at the UTSW Genomics and Microarray Core Facility. The cDNA was sonicated using a Covaris S2 ultrasonicator, and libraries were prepared with the KAPA High Throughput Library Preparation Kit. Samples were end-repaired, and the 3' ends were adenylated and barcoded with multiplex adapters. PCR-amplified libraries were purified with AmpureXP beads and validated on the Agilent 2100 Bioanalyzer. Before being normalized and pooled, samples were quantified by Qubit (Invitrogen) and then run on an Illumina Hiseq 2500 instrument using PE100 SBS v3 reagents to generate 51-bp single-end reads. Before mapping, reads were trimmed to remove low-quality regions in the ends. Trimmed reads were mapped to the human genome (HM19) using TopHat v2.0.1227 with the UCSC iGenomes GTF file from Illumina.

Methods for data normalization and analysis are based on the use of "internal standards" that characterize some aspects of the system's behavior, such as technical variability, as presented elsewhere. Genes with logy (fold change) >2, P<0.01 and RPKM>0.1 were deemed to be significantly differentially expressed between the two conditions and were used for pathway analysis and upstream transcription factor analysis. Pathway analysis was conducted using the DAVID (david.ncifcrf.gov/tools.jsp). Upstream transcription-factor analysis was conducted using QIAGEN's Ingenuity tool (world-wide-web at ingenuity.com/).

Molecular docking of LILRB4 with APOE. Docking of LILRB4 with APOE was performed on ZDOCKpro module of the Insight II package. The general protocol for running ZDOCK includes two consecutive steps of calculation described as geometry search and energy search, running in program ZDOCK and RDOCK, respectively. LILRB4 crystal structure (3P2T) and APOE3 structure (2L7B) were obtained from PDB database. Top 50 ZDOCK poses were submitted to RDOCK refinement. Poses with high score both in ZDOCK and RDOCK were selected as candidate complex for LILRB4/APOE interaction analysis.

Statistical analyses. Representative data from four independent experiments or indicated independent samples are presented as dot plots (means±s.e.m.) or as box-and-whisker plots (median values (line), 25th-75th percentiles (box outline) and minimum and maximum values (whiskers)). Statistical significance for two samples-comparison was calculated by two-tailed Student's t-test. Statistical significance for survival was calculated by the log-rank test. The multivariate analysis of TCGA data was analyzed by Cox regression. The difference was considered statistically significant if p<0.05. n.s., not significant; p values are represented as precise values. The Pearson's correlation analyses were performed with the RStudio software (the R Foundation).

Preparation of the LILRB4 and h193 complex. The DNA encoding the extracellular domain of LILRB4 (residues 1-196 of the mature protein) was cloned in the vector pET21a (Novagen) with NdeI and XhoI restriction sites and expressed in *E. coli* strain BL21 (DE3) (Novagen). The bacteria were cultivated in LB medium containing the corresponding antibiotics (100 µg/ml ampicillin) in a shaker incubator at 37° C. Expression was induced by adding 1 mM isopropyl β-D-1-thiogalactopyranoside (IPTG) when the culture reached an $OD_{600}$ of 0.8-1.0, and then the culture was continued for 4-6 h before harvest. Centrifuged cells were suspended in PBS buffer (20 mM $Na_3PO_4$, 280 mM NaCl, 6 mM KCl, pH 7.4), and were disrupted using a homogenizer (JNBIO, China). The inclusion bodies of the recombinant proteins were purified and refolded as described with some modifications. Briefly, aliquots of inclusion body were dropwise diluted in an agitating refolding buffer (100 mM Tris-HCl, 2 mM EDTA, 400 mM L-arginine, 0.5 mM oxidized glutathione and 5 mM reduced glutathione, pH 8.0) for 8 h at 4° C. The refolded protein was concentrated and buffer-exchanged using an Amicon 8400 concentrator to the solution containing 20 mM Tris-HCl and 50 mM NaCl, pH 8.0. Subsequently the proteins were further purified by gel-filtration chromatography in the same exchanged buffer aforementioned on a HiLoad® 16/60 Superdex® 75 PG column (GE Healthcare). The eligible peak fractionated proteins were concentrated for further study or crystallization. h193-scFv was constructed as VL-(GGGGS)4-VH and cloned into the vector pET21a (Novagen) with NdeI and XhoI restriction sites. The scFv was over expressed in *Escherichia coli* as inclusion bodies and subsequently refolded and purified as described above as the LILRB4 protein. The LILRB4 and h193-scFv were then mixed together at a molar ratio of 1:2 and incubated for 1 h on ice. The LILRB4 and h193-scFv complex was further purified by HiLoad® 16/60 Superdex® 75 PG (GE Healthcare) chromatography to purify the LILRB4/Hu193-scFv complex from any excess LILRB4.

Crystallization of the LILRB4/h193 complex. The LILRB4/h193-scFv complex crystals were grown by vapor diffusion in sitting drops. A total of 1 µl of complex protein solution at 5 mg/ml or 10 mg/ml was mixed with an equal volume of reservoir solution. Crystals were grown in 1% w/v Tryptone, 0.05 M HEPES sodium pH 7.0, 20% w/v Polyethylene glycol 3,350 at 18° C. Crystals were frozen in liquid nitrogen in reservoir solution supplemented with 17% glycerol (vol/vol) as a cryoprotectant. X-ray diffraction data were collected at 100 K and indexed, integrated and scaled with HKL2000. The complex structure was solved by the molecular replacement method using Phaser from the CCP4 program suite, with the structures of LILRB4 (PDB: 3P2T) and the antibody (PDB: 4OQT) as the search models, respectively. Initial restrained rigid-body refinement and manual model building were performed using REFMAC5 and COOT, respectively, and were further refined using Phenix.

Example 2

LILRB4 expressed on leukemia cells suppresses T cell proliferation. To identify novel mechanisms for AML development and immune regulation, the inventors analyzed the relationship between gene expression of known co-stimulating and co-inhibitory receptors and the overall survival of AML patients as documented in the TCGA database. The protein expression, and the expression of the mRNA encoding leukocyte immunoglobulin-like receptor B4 (LILRB4), an immune inhibitory receptor restrictively expressed on monocytic cells (Kang et al., 2016; Hirayasu and Arase, 2015; Trowsdale et al., 2015) and monocytic AML cells (FAB M4 and M5 AML subtypes) (Dobrowolska et al., 2013) ranked on the top of the list for negative correlation with AML patient survival (FIGS. 2A and 6A). Importantly, LILRB4 protein levels were higher on the surface of neoplastic monocytes than that of normal monocytes (FIG. 2B).

A previous study reported that the extracellular domain of LILRB4 inhibited T cell activities (Vlad et al., 2010). To test whether LILRB4 expressed on AML cells has T cell-suppressive function, the inventors co-cultured LILRB4-positive leukemia cells, LILRB4-negative leukemia cells, or normal hematopoietic cells with either autologous T cells or T cells from healthy donors. Only LILRB4-positive monocytic AML cells significantly suppressed T cell proliferation (FIGS. 2C and 7A-7F). The inventors then deleted lilrb4 from human monocytic AML THP-1 and MV4-11 cells and found that the T cell suppressive ability of AML cells was significantly reduced upon lilrb4 knockout (lilrb4-KO) and was restored by forced expression of wild-type lilrb4 (as lilrb4-KO-wt), but not by a mutant lilrb4 with deleted intracellular domain (as lilrb4-KO-intΔ) (FIGS. 2D and 8A-8E). Moreover, when wild-type THP-1 cells and human T cells were cultured in separate transwells, LILRB4-mediated T cell inhibition was also observed and was able to be rescued by anti-LILRB4 blocking antibodies (FIGS. 8F-8L). Blocking LILRB4 resulted in increase of cytotoxicity T cells, decreased AML cells, and increased T cell cytokine releasing (FIGS. 8M-8O). These in vitro data suggest that, instead of the extracellular domain (Vlad et al., 2010), the intracellular signaling of LILRB4 in AML cells is required for suppression of T cell activity.

Next, the inventors used humanized mouse xenograft models and an immunocompetent mouse model to investigate LILRB4 function in immune checkpoint blockade. Subcutaneous implantation of THP-1 cells, but not the lilrb4-KO THP-1 cells, resulted in AML development in human T cell reconstituted mice, which was blocked by anti-LILRB4 treatment (Mosier et al., 1988) (FIGS. 9A-9G). Doxycycline-induced LILRB4 deletion in an established disseminated leukemia model in humanized mice also impaired leukemia development and restored T cells (FIGS. 2E-2F and 9H-9J). In addition, the inventors subcutaneously implanted human LILRB4-expressing mouse C1498 AML cells (hlilrb4-C1498) into C57BL/6 mice to establish a syngeneic immunocompetent mouse model. To exclude the anti-tumor effects from Fc effector functions, the inventors treated tumor-bearing mice with anti-LILRB4 with the Fc glycosylation site N297A mutation (Ha et al., 2011). LILRB4 blockade effectively lowered tumor burden and prolonged survival; depleting $CD8^+$ T cells eliminated the anti-tumor effects of the anti-LILRB4 antibody (FIGS. 2G-2H). These results suggest that the tumor-supportive effect of LILRB4 depends on host T cell inhibition. The anti-LILRB4 antibody treatment generated tumor-specific memory T cells (FIG. 2I). Similar results were obtained in disseminated hlilrb4-C1498 syngeneic mouse model (FIGS. 10A-10D). Finally, the blockade of LILRB4 significantly reduced leukemia development in primary human monocytic AML-derived xenografts (FIGS. 2J-2K) and increased the numbers of engraftable autologous human T cells. Together, the in vitro and in vivo results indicate that LILRB4 signaling in monocytic AML cells suppresses T cell-mediated anti-tumor immunity.

LILRB4 promotes AML cell migration and infiltration. One of the characteristic features of monocytic AML is enhanced extramedullary infiltration of tumor cells (Straus et al., 1980). The inventors observed that the antibody blockade of LILRB4 results in significant decrease of leukemic infiltration into internal organs, including bone marrow, liver, and brain. Although anti-LILRB4 antibody treatment did not reduce the size of subcutaneous C1498 tumors in C57BL/6 mice depleted of CD8+ T cells (FIG. 2G), treatment with anti-LILRB4 antibody did lead to decreased leukemia cell infiltration into liver (FIG. 10A). The inventors hypothesized that, in addition to T cell inhibition, LILRB4 promotes leukemia infiltration. To test this hypothesis, the inventors performed transendothelial migration and homing assays and monitored leukemia infiltration relative to LILRB4 expression on leukemia cells. Human AML THP-1 cells depleted of LILRB4 had lower transendothelial migration in vitro than cells that expressed LILRB4. Deletion of lilrb4 reduced homing and engraftment of AML cells to hematopoietic organs, resulting in prolonged survival of xenografted mice and delayed body weight loss. In contrast, forced expression of human LILRB4 in mouse AML C1498 or WEHI-3 cells had the opposite effects (FIGS. 12A-12D). Antibody-mediated LILRB4 blockade showed the same effect as lilrb4 knockout in LILRB4-expressing AML cells (FIGS. 12E-12G). This effect was depended on LILRB4 expression and its intracellular signaling in leukemia cells but not the Fc effector functions of the antibody (FIGS. 3A and 12H-12J). Furthermore, LILRB4 blockade reduced infiltration ability of primary monocytic AML cells (FIGS. 3B-3D and 13A-13C). The results are concordant with previous studies showing that the frequency of circulating LILRB4+ AML blasts is significantly lower than that of the LILRB4− AML blasts (Dobrowolska et al., 2013) and that LILRB4+ chronic lymphocytic leukemia cells are associated with lymphoid tissue involvement (Colovai et al., 2007). Bone marrow, liver, and brain to which LILRB4+ AML cells tend to migrate are known to have certain immune privileges (Crispe et al., 2006; Carson et al., 2006; Fujisaki et al., 2001). Thus, LILRB4-mediated migration, which supports enhanced extramedullary infiltration of monocytic AML cells, may also contribute to immune evasion.

APOE is an extracellular binding protein of LILRB4. The anti-LILRB4 antibody blockade of immune inhibitory and migration functions of AML cells suggests that those functions of LILRB4 are ligand dependent. Integrin-$\alpha_v\beta_3$, was previously identified as the ligand for gp49B1, the mouse LILRB4 orthologue (Castells et al., 2001). However, different integrin-$\alpha\beta$ complexes did not activate human LILRB4 reporter cells. Surprisingly, human serum and mouse serum were capable of activating the LILRB4 reporter but not reporters for other LILRBs (FIG. 4A). Through protein liquid chromatography fractionation followed by reporter assays and mass spectrometry, the inventors identified APOE that specifically activated the reporters of LILRB4 and mouse PirB (FIG. 4B). The serum from wild-type but not APOE-null mice activated the LILRB4 reporter (FIG. 4C). In addition, both liposome-reconstituted APOE protein (APOE-POPC) and lipid-free APOE activated LILRB4 reporter cells (FIG. 4D). The binding of APOE to THP-1 cells was significantly decreased by lilrb4-KO (FIG. 4E). The specific binding of recombinant APOE to LILRB4 was confirmed using microscale thermophoresis (MST), surface plasmon resonance (SPR), and bio-layer interferometry (Octet). The dissociation constant was 210 nM as determined by MST (FIG. 4F). Mutagenesis studies showed that the N-terminal domain of APOE, and P35 and W106 in the first Ig-domain and Y121 in the linker region between two Ig-domains of LILRB4 are critical for APOE-mediated activation of LILRB4 (FIGS. 4G-4H).

The finding that APOE activates the immune inhibitory receptor LILRB4 is in agreement with the well-documented immune-suppressive function of APOE (Grainger et al., 2004; Ali et al., 2005). To determine whether T cell suppressive activity of LILRB4 depends on APOE, the inventors examined proliferation of T cells co-cultured with control or apoe-knockout human AML cells. AML cells deficient in APOE restored proliferation of T cells and suppressed migration of leukemia cells (FIGS. 4I and 14). Moreover, the percentage of T cells in co-culture was significantly lower when the LILRB4-ectopically-expressing C1498 cells were treated with wild-type mouse serum compared to those treated with apoe-knockout mouse serum (FIGS. 4J-4K). Addition of liposome-reconstituted APOE to co-culture of mouse spleen cells and LILRB4-expressing AML cells decreased the T cell percentage (FIG. 4L). Furthermore, expression of LILRB4 significantly increased C1498 cells infiltrating to bone marrow and liver in wild-type mice but not in APOE-null recipients (FIG. 4M). These data indicate that APOE activates LILRB4 on human monocytic AML cells to suppress T cell proliferation and support AML cell migration.

LILRB4-mediated intracellular signaling controls AML cell migration and T cell suppression. The inventors sought to identify the signaling downstream of LILRB4 required for T cell suppression and leukemia infiltration. Phosphatases SHP-1, SHP-2, and SHIP can be recruited to the intracellular domain of LILRB (Kang et al., 2016). The level of phosphorylation of SHP-2 but not of SHP-1 or SHIP was lower in lilrb4-KO AML cells than in wild-type cells (FIGS. 5A and 15A). Loss of SHP-2, but not loss of SHP-1 or SHIP, reversed T cell suppression by THP-1 cells (FIGS. 5B and 15B), and decreased short-term and long-term infiltration of THP-1 cells (FIGS. 5C-5D). The results suggest that SHP-2 is a mediator of LILRB4 signaling.

The Ingenuity Pathway Analysis showed that the activity of key transcription factors NFkB1 and RELA in the NF-κB pathway (DiDonato et al., 2012), which is positively regulated by SHP-2 (You et al., 2001), were most significantly inhibited by loss of lilrb4 (FIG. 5E). Consistently, the phosphorylation of IKKα/β and levels of nuclear NF-κB were decreased in lilrb4-KO AML cells (FIGS. 5F-5G and 15A). Inhibition of NF-κB signaling restored T cell suppression and reduced AML cell infiltration in a LILRB4-dependent manner (FIGS. 5H-5I and 15C-15D). Therefore the effects of LILRB4 activation are mediated through the NF-κB pathway, which is particularly robust in monocytic AML among AML subtypes (Baumgartner et al., 2002).

Consistent with the result that AML cells inhibit T cell proliferation in transwells (FIG. 2D), the conditioned medium from wild-type THP-1 cells suppressed T cell activity but that medium from lilrb4-KO cells did not (FIG. 5J). Among proteins that were higher present in the conditioned medium of WT THP-1 cells than the lilrb4-KO counterparts (FIG. 16A), uPAR is highly expressed by monocytic AML cells (Bene et al., 2004). uPAR, an NF-κB target, is well known to promote cancer invasion, metastasis, survival, and angiogenesis (Su et al., 2016; Wang et al., 2000). The addition of recombinant uPAR decreased proliferation of T cells co-cultured with lilrb4-KO THP-1 cells in a dose-dependent manner (FIG. 5K). This activity of uPAR was likely mediated by downstream effectors in AML cells because uPAR does not effectively decrease T cell proliferation directly (FIG. 16B).

The expression of Arginase-1 (ARG1), like uPAR, was significantly lower in lilrb4-KO AML cells than in wild-type cells (FIGS. 16C-16D). ARG1 is up-regulated by uPAR-mediated signaling and inhibits T cell proliferation (Hu et al., 2014; Ilkovitch and Lopez, 2009), and can be elevated by APOE (Baitsch et al., 2011) and NF-κB (Hagemann et al., 2008) for immune-suppressive functions. The inventors hypothesized that ARG1 is a key downstream effector of LILRB4-NF-kB-uPAR signaling. ARG1 can be secreted by AML cells to inhibit T cell activity[27]. Recombinant ARG1 decreased T cell proliferation in the co-culture with lilrb4-KO, apoe-KO, and shp-2-KO AML or primary AML cells (FIGS. 5L and 16E-16G). In addition, addition and overexpression of either uPAR or ARG1 rescued the migration ability of lilrb4-KO AML cells in vitro and in vivo, respectively (FIGS. 16H and 5M). Together, the results indicate that LILRB4/SHP-2/NF-κB/uPAR/ARG1 is a signaling pathway in monocytic AML cells (FIGS. 17-18) that suppresses immune activity and supports leukemia migration.

Targeting LILRB4 may not only lead to specific attack of monocytic AML cells, but also reactivate multiple immune cell types including T cells and perhaps monocytes/macrophages (Kang et al., 2016). Importantly, because LILRB4 is restrictively expressed on normal monocytic cells (Kang et al., 2016) in which the LILRB4 signaling may differ from that in leukemia cells (FIG. 19) and LILRB4 blockade did not significantly interfere normal hematopoietic function (FIGS. 20A-20B), LILRB4 targeting may have minimal toxicity. Finally, LILRB4 is also expressed on certain other types of cancers and myeloid-derived suppressor cells, tolerogenic dendritic cells, and tumor-associated macrophages (Kang et al., 2016; de Goeje et al., 2015; Chang et al., 2002; Suciu-Foca et al., 2007). Targeting LILRB4 may thus enable combination of immunotherapy and targeted therapy in cancer treatment.

The inventors also found that LILRB4 is expressed on myeloid-derived suppressor cells (MDSCs) isolated form solid cancer patients (FIG. 21A). The expression of LILRB4 is positively correlated with autologous T cell suppressive ability of MDSCs (FIG. 21B). The inventors performed anti-LILRB4 treatment in MDSC/T cell co-culture and found that anti-LILRB4 treatment increased IFNγ secretion of co-cultured T cells (FIG. 21C).

Example 3

The inventors then generated a batch of rabbit monoclonal antibodies (mAbs) against human LILRB4 extracellular domain (ECD). The amino acid and nucleic acid sequences of the heavy chain and light chain variable regions of exemplary LILRB4 antibodies are shown in FIGS. 28A-28C, 29A-29C, 30A-30C and 31A-31C. The ELISA binding results for eight exemplary LILRB4 mAbs binding to LILRB4 ECD are shown in FIG. 22 and Table 6. The kinetic binding measurements (sensor-grams) for exemplary LILRB4 antibodies determined using Octet are shown in FIG. 26 and Table 7.

As illustrated in FIG. 23A, the LILRB4 ECD has two Ig domains D1 and D2. Two residues, W106 and Y121, whose mutations significantly reduced activation of LILRB4 by APOE, are located in the first Ig domain D1 and in the linker or hinge region between two Ig domains, respectively. As shown in FIG. 23B, among the eight exemplary mAbs binding to LILRB4 ECD, seven mAbs except B4-193 bind to the D1 domain of LILRB4.

TABLE 6

$EC_{50}$ of LILRB4 antibodies binding to human LILRB4 assayed by ELISA

| Antibody | EC50 (nM) |
|---|---|
| B4-15-1 | 0.99 |
| B4-116-1 | 2.58 |

TABLE 6-continued $EC_{50}$ of LILRB4 antibodies binding to human LILRB4 assayed by ELISA

| Antibody | EC50 (nM) |
|---|---|
| B4-116-2 | 1.7 |
| B4-49 | 1.01 |
| B4-72-2 | 0.29 |
| B4-86 | 1.02 |
| B4-87 | 2.54 |
| B4-193 | 1.81 |

TABLE 7

Kinetic binding constants for LILRB4 antibodies determined using Octet biosensor chip

| Antibody | Kd | Kon | Koff | $R^2$ |
|---|---|---|---|---|
| B4-116-1 | 8.20E-10 | 2.31E+05 | 1.89E-04 | 0.9972 |
| B4-116-2 | 4.95E-10 | 2.05E+05 | 1.01E-04 | 0.9983 |
| B4-49 | 2.33E-11 | 1.11E+05 | 2.58E-06 | 0.834 |
| B4-87 | 2.38E-10 | 7.04E+04 | 1.68E-05 | 0.9991 |
| B4-86 | 3.44E-10 | 7.96E+04 | 2.74E-05 | 0.9992 |
| B4-72-2 | 3.73E-09 | 4.26E+04 | 1.59E-04 | 0.6988 |
| B4-193 | 1.33E-10 | 1.31E+05 | 1.74E-05 | 0.9997 |

The inventors then determined the binding domains of B4-193 using LILRB4 D1 domain (D1), D2 domain (D2), stalk region (SR), D1+D2, D2+SR and full-length ECD (D1+D2+SR) of human LILRB4 recombinant proteins. As shown in FIG. 24B, B4-193 only binds to full-length ECD of human LILRB4 in this particular ELISA assay.

The inventors then determined the contribution of amino acid Y121 on LILRB4 to the binding of B4-193 using wild-type and Y121A mutated human LILRB4 ECD recombinant proteins. As shown in FIG. 25, the Y121A mutation of LILRB4 significantly decreased the binding of B4-193 to LILRB4.

The inventors measured the effects of the exemplary LILRB4 mAbs in modulating LILRB4 activity using the APOE-competition assay (FIG. 32), the LILRB4-reporter cells/K562-co-culture assay (FIG. 33), and the LILRB4-reporter cell assay (FIGS. 34 and 35).

The inventors also tested the cross-reactivity with LILRB family members, LILRA family members as well as cynomolgus monkey LILRB4 (cynoB4) by exemplary anti-LILRB4 antibodies (FIGS. 36 and 37).

As shown in FIG. 38, the exemplary anti-LILRB4 antibody B4-193 rescues T cell suppression by THP-1 cells.

As shown in FIGS. 39A-39C, the exemplary anti-LILRB4 antibodies 128-3 and B4-193 inhibit leukemia development in THP-1 xenograft mice without significant adverse effect on the mouse body weight.

Example 4

The inventors further generated a group of humanized anti-LILRB4 antibodies based on B4-193. The amino acid sequences of the heavy chain and light chain variable region of humanized B4-193 antibodies (h193) and CDRs thereof are shown in FIGS. 28B-28C, 30B-30C, Tables 4 and 5. The inventors measured the binding of the h193 antibodies to human LILRB4 using flow cytometry, ELISA and Octet assays, the results of which are shown in FIG. 40 and Table 8.

TABLE 8 h193 antibodies bind to human LILRB4

| Antibody No. (shown in FIGS. 40-43) | Heavy Chain (H) | Light Chain (K) | ELISA EC50 (ng/ml) | ELISA EC50 (nM) | Octet Kd (M) | Octet Kon (1/Ms) | Octet Koff (1/s) |
|---|---|---|---|---|---|---|---|
| 19 | H3 | K1 | 293.8 | 1.96 | 2.03E−09 | 1.45E+05 | 2.94E−04 |
| 20 | H3 | K2 | 272.1 | 1.81 | 1.67E−09 | 1.50E+05 | 2.50E−04 |
| 21 | H3 | K3 | 218.8 | 1.46 | 2.16E−09 | 1.45E+05 | 3.13E−04 |
| 22 | H3 | K4 | 221.7 | 1.48 | 2.39E−09 | 1.51E+05 | 3.61E−04 |
| 23 | H4 | K1 | 461.4 | 3.07 | 5.83E−09 | 1.25E+05 | 7.31E−04 |
| 24 | H4 | K2 | 466.5 | 3.11 | 4.41E−09 | 1.35E+05 | 5.95E−04 |
| 25 | H4 | K3 | 523.8 | 3.49 | 4.98E−09 | 1.28E+05 | 6.38E−04 |
| 26 | H4 | K4 | 435.5 | 2.9 | 5.30E−09 | 1.38E+05 | 7.33E−04 |
| 27 | H5 | K1 | >1000 | >6 | / | / | / |
| 28 | H5 | K2 | >1000 | >6 | / | / | / |
| 29 | H5 | K3 | >1000 | >6 | / | / | / |
| 30 | H5 | K4 | >1000 | >6 | / | / | / |
| 31 | H6 | K1 | 314.3 | 2.09 | 2.61E−09 | 1.44E+05 | 3.76E−04 |
| 32 | H6 | K2 | 261.5 | 1.74 | 2.38E−09 | 1.52E+05 | 3.62E−04 |
| 33 | H6 | K3 | 320 | 2.13 | 2.33E−09 | 1.48E+05 | 3.45E−04 |
| 34 | H6 | K4 | 343.8 | 2.29 | 2.39E−09 | 1.60E+05 | 3.81E−04 |
| 35 | H7 | K1 | 161.7 | 1.08 | 1.05E−09 | 1.41E+05 | 1.48E−04 |
| 36 | H7 | K2 | 144.6 | 0.96 | 1.01E−09 | 1.43E+05 | 1.44E−04 |
| 37 | H7 | K3 | 162.7 | 1.08 | 9.84E−10 | 1.43E+05 | 1.40E−04 |
| 38 | H7 | K4 | 183.3 | 1.22 | 9.49E−10 | 1.46E+05 | 1.39E−04 |

The inventors also tested the cross-reactivity with LILRB family members, LILRA family members as well as cynomolgus monkey LILRB4 (cynoB4) by h193 antibodies (FIGS. 41A-41M and 42). The results showed that h193 antibodies does not cross-react with LILRA family members or LILRB family members except LILRB4. H193 antibodies can also bind to cynomolgus monkey LILRB4 protein to different extent.

The inventors further measured the antagonistic and agonistic effect of the h193 antibodies using ApoE competition assay and K562 co-culture assay. As shown in FIGS. 43A (ApoE competition assay) and 43B (K562 cell co-culture assay), most h193 antibodies inhibited the LILRB4 activity induced by ApoE.

The inventors also measured the effects of h193 antibody in modulating cytokine release using a cytokine array assay (FIGS. 44-47). In short, human PBMC ($1.5 \times 10^6$ cells/ml) were treated with h193 antibody (20 ug/ml) for 48 hours and then subject to the cytokine array to measure the level of 120 cytokines. In another assay, human PBMC were co-cultured with THP-1 cells ($0.3 \times 10^6$ cells/ml) before treated with h193 antibody. Human IgG were used as a negative control. As shown in FIGS. 44A-44D, h193 antibody treatment decreased secretion of certain immunoregulatory and inflammatory process cytokines in PBMC only. As shown in FIGS. 45A-45D, h193 antibody treatment increased secretion of certain immunoregulatory and inflammatory process cytokines in PBMC co-cultured with THP-1 cells.

In a xenograft mouse model, h193 antibody suppressed leukemia development (FIG. 48).

Example 5

This example illustrates the molecular basis of the interaction between LILRB4 and h193 antibody through crystallization of LILRB4/h193 complex. The D1 and D2 domains of LILRB4 and the single chain Fv fragment (scFv) of h193 antibody were expressed as inclusion bodies in *E. coli*, and obtained the soluble proteins by in vitro refolding method, respectively. The LILRB4-D1D2/h193 scFv complex was subsequently prepared for crystal screening and the complex structure was determined by molecular replacement at a resolution of 2.0 Å.

The overall structure reveals that the h193 antibody mainly binds to the linker region between D1 and D2 of LILRB4 (FIG. 49A). The antibody utilizes both heavy chain ($V_H$) and light chain ($V_L$) to interact with LILRB4, involving in all three CDR loops in the h193 antibody $V_H$ and $V_L$ regions except CDR2 loop in $V_L$ (FIG. 49A and Table 9). In particular, the h193 antibody binds to the D1D2 hinge loop, and the BC and C'E loops of the D2 domain of LILRB4 molecule. Residues K100, G96 and S99 in the hinge loop of LILRB4 D1 and D2 domain forms three hydrogen bonds with residues both in HCDR1 (S32) and HCDR2 (S59 and D53) regions (FIG. 49B), while residue R124 in the BC loop of the D2 domain not only interacts with residue H101 from HCDR3 in $V_H$ by forming two hydrogen bonds, but also contributes one hydrogen bond with residues 193 (LCDR3) in $V_L$ (FIG. 49C). In addition, H153 in the BC loop of LILRB4-D2 contacts with R94 of HCDR3 loop by forming two hydrogen bonds (FIG. 49C). Residues Q122 in the BC loop of LILRB4-D2 and Q154 in the C'E loop form three hydrogen bonds with residues W32 and N30 from LCDR1 loop (FIG. 49C). Taken together, the three loops of LILRB4 are targeted by h193 antibody through series contacts including multiple hydrogen bond interactions. Notably, residues Q122 and H153, contributing important contacts with h193 antibody binding, is unique in LILRB4 among all LILRs molecules. This may contribute to the specific binding of h193 antibody to LILRB4.

TABLE 9

Interaction between h193 and LILRB4

| | h193 | LILRB4 | Contacts |
|---|---|---|---|
| Heavy Chain | S31 | H285 | 2 |
| | S32 | K100, H185, S99 | 12(1), 2, 7 |
| | Y33 | S99 | 4 |
| | W34 | R124, S125, S99 | 13, 4, 3 |
| | D53 | A97, Y98, S99 | 1, 5, 12(2) |
| | S54 | S99 | 3 |
| | G55 | G96, A97, Y98, S99 | 2, 5, 5, 2 |

TABLE 9-continued

Interaction between h193 and LILRB4

| | h193 | LILRB4 | Contacts |
|---|---|---|---|
| | S56 | W18, M94, G96, A97, Y98 | 5, 2, 7(1), 13(1), 1 |
| | V57 | F178, L182, E67, A97, Y98 | 3, 1, 4, 10(1), 3 |
| | G58 | A97 | 1 |
| | I59 | S125, M127, Y98 | 2, 1, 4 |
| | Y61 | S125, P126, H176 | 4, 5, 2 |
| | H101 | R124 | 12(2) |
| | G102 | R124 | 6(1) |
| | D103 | K100, R124 | 1, 1 |
| | W105 | T102, Q122, S123, R124 | 3, 7, 9, 35 |
| | | | Total contacts: 224 |
| Light | S28 | G149 | 2 |
| Chain | N30 | Q122, G149, Q154 | 3(1), 2, 5(1) |
| | W32 | T102, Q122 | 1, 10(1) |
| | G91 | R124 | 3 |
| | Y92 | Q122, R124, H153 | 1, 6, 11 |
| | I93 | R124, S125, P126, H153 | 10(1), 5, 4, 1 |
| | R94 | P126, A150, Q152, H153 | 4, 1, 5, 13(2) |
| | | | Total contacts: 87 |

Numbers represent the number of atom-to-atom contacts between the antibody residues and the LILRB4 residues, which were analyzed by the Contact program in CCP4 suite (the distance cutoff is 4.5 Å).

Numbers in the parentheses represent the number of hydrogen bonds between the antibody residues and the LILRB4 residues.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1 Curran, E. K., Godfrey, J. & Kline, J. Mechanisms of Immune Tolerance in Leukemia and Lymphoma. *Trends Immunol*, doi:10.1016/j.it.2017.04.004 (2017).

2 Kang, X. et al. Inhibitory leukocyte immunoglobulin-like receptors: Immune checkpoint proteins and tumor sustaining factors. *Cell Cycle* 15, 25-40, doi:10.1080/15384101.2015.1121324 (2016).

3 Hirayasu, K. & Arase, H. Functional and genetic diversity of leukocyte immunoglobulin-like receptor and implication for disease associations. *Journal of human genetics*, doi: 10.1038/jhg.2015.64 (2015).

4 Trowsdale, J., Jones, D. C., Barrow, A. D. & Traherne, J. A. Surveillance of cell and tissue perturbation by receptors in the LRC. *Immunol Rev* 267, 117-136, doi:10.1111/imr.12314 (2015).

5 Dobrowolska, H. et al. Expression of immune inhibitory receptor ILT3 in acute myeloid leukemia with monocytic differentiation. *Cytometry B Clin Cytom* 84, 21-29, doi: 10.1002/cyto.b.21050 (2013).

6 Vlad, G. et al. Membrane and soluble ILT3 are critical to the generation of T suppressor cells and induction of immunological tolerance. *Int Rev Immunol* 29, 119-132, doi:10.3109/08830180903281185 (2010).

7 Mosier, D. E., Gulizia, R. J., Baird, S. M. & Wilson, D. B. Transfer of a functional human immune system to mice with severe combined immunodeficiency. *Nature* 335, 256-259, doi:10.1038/335256a0 (1988).

8 Ha, S. et al. Isolation and characterization of IgG1 with asymmetrical Fc glycosylation. *Glycobiology* 21, 1087-1096, doi:10.1093/glycob/cwr047 (2011).

9 Straus, D. J. et al. The acute monocytic leukemias: multidisciplinary studies in 45 patients. *Medicine (Baltimore)* 59, 409-425 (1980).

10 Colovai, A. I. et al. Expression of inhibitory receptor ILT3 on neoplastic B cells is associated with lymphoid tissue involvement in chronic lymphocytic leukemia. *Cytometry B Clin Cytom* 72, 354-362, doi:10.1002/cyto.b.20164 (2007).

11 Crispe, I. N. et al. Cellular and molecular mechanisms of liver tolerance. *Immunol Rev* 213, 101-118, doi:10.1111/j.1600-065X.2006.00435.x (2006).

12 Carson, M. J., Doose, J. M., Melchior, B., Schmid, C. D. & Ploix, C. C. CNS immune privilege: hiding in plain sight. *Immunol Rev* 213, 48-65, doi:10.1111/j.1600-065X.2006.00441.x (2006).

13 Fujisaki, J. et al. In vivo imaging of Treg cells providing immune privilege to the haematopoietic stem-cell niche. *Nature* 474, 216-219, doi:10.1038/nature10160 (2011).

14 Castells, M. C. et al. gp49B1-alpha(v)beta3 interaction inhibits antigen-induced mast cell activation. *Nat Immunol* 2, 436-442, doi:10.1038/87749 (2001).

15 Grainger, D. J., Reckless, J. & McKilligin, E. Apolipoprotein E modulates clearance of apoptotic bodies in vitro and in vivo, resulting in a systemic proinflammatory state in apolipoprotein E-deficient mice. *J Immunol* 173, 6366-6375 (2004).

16 Ali, K., Middleton, M., Pure, E. & Rader, D. J. Apolipoprotein E suppresses the type I inflammatory response in vivo. *Circ Res* 97, 922-927, doi:10.1161/01.res.0000187467.67684.43 (2005).

17 DiDonato, J. A., Mercurio, F. & Karin, M. NF-kappaB and the link between inflammation and cancer. *Immunol Rev* 246, 379-400, doi:10.1111/j.1600-065X.2012.01099.x (2012).

18 You, M., Flick, L. M., Yu, D. & Feng, G. S. Modulation of the nuclear factor kappa B pathway by Shp-2 tyrosine phosphatase in mediating the induction of interleukin (IL)-6 by IL-1 or tumor necrosis factor. *J Exp Med* 193, 101-110 (2001).

19 Baumgartner, B. et al. Increased IkappaB kinase activity is associated with activated NF-kappaB in acute myeloid blasts. *Leukemia* 16, 2062-2071, doi:10.1038/sj.leu.2402641 (2002).

20 Bene, M. C. et al. CD87 (urokinase-type plasminogen activator receptor), function and pathology in hematological disorders: a review. *Leukemia* 18, 394-400, doi: 10.1038/sj.leu.2403250 (2004).

21 Su, S. C., Lin, C. W., Yang, W. E., Fan, W. L. & Yang, S. F. The urokinase-type plasminogen activator (uPA) system as a biomarker and therapeutic target in human malignancies. *Expert Opin Ther Targets* 20, 551-566, doi:10.1517/14728222.2016.1113260 (2016).

22 Wang, Y. et al. Identification of a novel nuclear factor-kappaB sequence involved in expression of urokinase-type plasminogen activator receptor. *Eur J Biochem* 267, 3248-3254 (2000).

23 Hu, J. et al. uPAR induces expression of transforming growth factor beta and interleukin-4 in cancer cells to promote tumor-permissive conditioning of macrophages. *Am J Pathol* 184, 3384-3393, doi:10.1016/j.ajpath.2014.08.003 (2014).

24 Ilkovitch, D. & Lopez, D. M. Urokinase-mediated recruitment of myeloid-derived suppressor cells and their suppressive mechanisms are blocked by MUC1/sec. *Blood* 113, 4729-4739, doi:10.1182/blood-2008-08-176438 (2009).

25 Baitsch, D. et al. Apolipoprotein E induces antiinflammatory phenotype in macrophages. *Arterioscler Thromb Vasc Biol* 31, 1160-1168, doi:10.1161/atvbaha.111.222745 (2011).

26 Hagemann, T. et al. "Re-educating" tumor-associated macrophages by targeting NF-kappaB. *J Exp Med* 205, 1261-1268, doi:10.1084/jem.20080108 (2008).

27 Mussai, F. et al. Acute myeloid leukemia creates an arginase-dependent immunosuppressive microenvironment. *Blood* 122, 749-758, doi:10.1182/blood-2013-01-480129 (2013).

28 de Goeje, P. L. et al. Immunoglobulin-like transcript 3 is expressed by myeloid-derived suppressor cells and correlates with survival in patients with non-small cell lung cancer. *Oncoimmunology* 4, e1014242, doi:10.1080/2162402x.2015.1014242 (2015).

29 Chang, C. C. et al. Tolerization of dendritic cells by T(S) cells: the crucial role of inhibitory receptors ILT3 and ILT4. *Nat Immunol* 3, 237-243, doi:10.1038/ni760 (2002).

30 Suciu-Foca, N. et al. Soluble Ig-like transcript 3 inhibits tumor allograft rejection in humanized SCID mice and T cell responses in cancer patients. *J Immunol* 178, 7432-7441 (2007).

31 Piedrahita, J. A., Zhang, S. H., Hagaman, J. R., Oliver, P. M. & Maeda, N. Generation of mice carrying a mutant apolipoprotein E gene inactivated by gene targeting in embryonic stem cells. *Proc Natl Acad Sci USA* 89, 4471-4475 (1992).

32 Zheng, J. et al. Inhibitory receptors bind ANGPTLs and support blood stem cells and leukaemia development. *Nature* 485, 656-660, doi:10.1038/nature11095 (2012).

33 Kang, X. et al. The ITIM-containing receptor LAIR1 is essential for acute myeloid leukaemia development. *Nat Cell Biol* 17, 665-677, doi:10.1038/ncb3158 (2015).

34 Deng, M. et al. A motif in LILRB2 critical for Angptl2 binding and activation. *Blood* 124, 924-935, doi:10.1182/blood-2014-01-549162 (2014).

35 Zheng, J. et al. Ex vivo expanded hematopoietic stem cells overcome the MHC barrier in allogeneic transplantation. *Cell Stem Cell* 9, 119-130, doi:10.1016/j.stem.2011.06.003 (2011).

36 Lu, Z. et al. Fasting selectively blocks development of acute lymphoblastic leukemia via leptin-receptor upregulation. *Nat Med* 23, 79-90, doi:10.1038/nm.4252 (2017).

37 Zhang, C. C., Kaba, M., Iizuka, S., Huynh, H. & Lodish, H. F. Angiopoietin-like 5 and IGFBP2 stimulate ex vivo expansion of human cord blood hematopoietic stem cells as assayed by NOD/SCID transplantation. *Blood* 111, 3415-3423, doi:blood-2007-11-122119 [pii] 10.1182/blood-2007-11-122119 [doi] (2008).

38 Zheng, J., Huynh, H., Umikawa, M., Silvany, R. & Zhang, C. C. Angiopoietin-like protein 3 supports the activity of hematopoietic stem cells in the bone marrow niche. *Blood* 117, 470-479, doi:10.1182/blood-2010-06-291716 (2011).

39 Cawthorne, C., Swindell, R., Stratford, I. J., Dive, C. & Welman, A. Comparison of doxycycline delivery methods for Tet-inducible gene expression in a subcutaneous xenograft model. *J Biomol Tech* 18, 120-123 (2007).

40 Denisov, I. G., Grinkova, Y. V., Lazarides, A. A. & Sligar, S. G. Directed self-assembly of monodisperse phospholipid bilayer Nanodiscs with controlled size. *J Am Chem Soc* 126, 3477-3487, doi:10.1021/ja0393574 (2004).

41 Swerdlow, S., Campo, E., Harris, N. L., Jaffe, E. S., Pileri, S. A., Stein, H., Thiele, J., Arber, D., Hasserjian, R., and Le Beau, M. (2017). WHO classification of tumors of haematopoietic and lymphoid tissues (WHO).

42 Schuler, E., Schroeder, M., Neukirchen, J., Strupp, C., Xicoy, B., Kundgen, A., Hildebrandt, B., Haas, R., Gattermann, N., and Germing, U. (2014). Refined medullary blast and white blood cell count based classification of chronic myelomonocytic leukemias. Leuk Res 38, 1413-1419.

What is claimed is:

1. An isolated monoclonal antibody or an antigen-binding fragment thereof comprising:
   (a) a heavy chain (HC) variable region (VH) comprising:
      a heavy chain complementarity determining region (HC-CDR) 1 having the amino acid sequence set forth in SEQ ID NO: 100,
      a HC-CDR2 having the amino acid sequence set forth in SEQ ID NO: 101, and
      a HC-CDR3 having the amino acid sequence set forth in SEQ ID NO: 102, 224 or 227; and
   (b) a light chain (LC) variable region (VL) comprising:
      a light chain complementarity determining region (LC-CDR) having the amino acid sequence set forth in SEQ ID NO: 104,
      a LC-CDR2 having the amino acid sequence of KAS or set forth in SEQ ID NO: 233, and
      a LC-CDR3 having the amino acid sequence set forth in SEQ ID NO: 105 or 234.

2. The isolated monoclonal antibody or an antigen binding fragment thereof of claim 1, wherein the isolated monoclonal antibody is a rabbit, a chimeric, or humanized antibody.

3. The isolated monoclonal antibody or an antigen-binding fragment thereof of claim 1, wherein the antigen-binding fragment is a recombinant ScFv (single chain fragment variable) antibody, Fab fragment, F(ab')2 fragment, or Fv fragment.

4. The isolated monoclonal antibody or an antigen binding fragment thereof of claim 1, wherein the isolated monoclonal antibody is a rabbit or a chimeric antibody.

5. The isolated monoclonal antibody or an antigen-binding fragment thereof of claim 4, wherein (a) the VH has the amino acid sequence at least 90% identical to SEQ ID NO: 99; and (b) the VL has the amino acid sequence at least 90% identical to SEQ ID NO: 103.

6. The isolated monoclonal antibody or an antigen-binding fragment thereof of claim 4, wherein (a) the VH has the amino acid sequence set forth in SEQ ID NO: 99; and (b) the VL has the amino acid sequence set forth in SEQ ID NO: 103.

7. The isolated monoclonal antibody or an antigen binding fragment thereof of claim 1, wherein the isolated monoclonal antibody is a humanized antibody.

8. The isolated monoclonal antibody or an antigen binding fragment thereof of claim 7, wherein (a) the VH has the amino acid sequence at least 90% identical to SEQ ID NO: 223, 225, 226, 228, 229, 230 or 231; and (b) the VL has the amino acid sequence at least 90% identical to SEQ ID NO: 232, 235, 236 or 237.

9. The isolated monoclonal antibody or an antigen binding fragment thereof of claim 7, wherein (a) the VH has the amino acid sequence set forth in SEQ ID NO: 223, 225, 226, 228, 229, 230 or 231; and (b) the VL has the amino acid sequence set forth in SEQ ID NO: 232, 235, 236 or 237.

10. A pharmaceutical composition comprising the isolated monoclonal antibody or an antigen-binding fragment thereof according to claim 1, and a pharmaceutically acceptable carrier.

11. An isolated nucleic acid that encodes the isolated monoclonal antibody according to claim 1.

12. A vector comprising the isolated nucleic acid of claim 11.

13. A host cell comprising the vector of claim 12.

14. The host cell of claim 13, wherein the host cell is a mammalian cell.

15. The host cell of claim 13, wherein the host cell is a CHO cell.

16. A process of producing an antibody, comprising culturing the host cell of claim 13 under conditions suitable for expressing the antibody, and recovering the antibody.

17. A hybridoma encoding or producing the isolated monoclonal antibody according to claim 1.

18. A chimeric antigen receptor (CAR) protein comprising an antigen-binding fragment according to claim 1.

19. An isolated nucleic acid that encodes a CAR protein of claim 18.

20. A vector comprising the isolated nucleic acid of claim 19.

21. An engineered cell comprising the isolated nucleic acid of claim 19.

22. The engineered cell of claim 21, wherein the cell is a T cell, NK cell, or macrophage.

23. A method of treating or ameliorating the effect of a cancer in a subject, the method comprising administering to the subject a therapeutically effective amount of the antibody or an antigen-binding fragment thereof according to claim 1 or an engineered cell expressing said antibody or the antigen binding fragment thereof.

24. The method of claim 23, wherein the method reduces or eradicates the tumor burden in the subject.

25. The method of claim 23, wherein the method reduces the number of tumor cells.

26. The method of claim 23, wherein the method eradicates the tumor in the subject.

27. The method of claim 23, wherein the cancer is a hematologic malignancy.

28. The method of claim 27, wherein the hematologic malignancy is selected from the group consisting of myelodysplastic syndromes, myeloproliferative neoplasms, chronic myelomonocytic leukemia (CMML), chronic myelocytic leukemia, acute myeloid leukemia (AML) acute myeloblastic leukemia, and polycythemia vera.

29. The method of claim 23, wherein the antibody or an antigen-binding fragment thereof is administered intravenously, intra-arterially, intra-tumorally, or subcutaneously.

30. The method of claim 25, further comprising administering to the subject one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, 1:5 Daunorubicin: cytarabine, an azacytidine, Azacitidine, a decitabine, an all-trans-retinoic acid (ATRA), an arsenic, an arsenic trioxide, a histamine dihydrochloride, Histamine Dihydrochloride, an interleukin-2, an aldesleukin, Interleukin-2 (IL-2), a gemtuzumab ozogamicin, Gemtuzumab ozogamicin, an FLT-3 inhibitor, a midostaurin, Midostaurin, a clofarabine, a farnesyl transferase inhibitor, a decitabine, an IDH1 inhibitor, an ivosidenib, Ivosidenib, an IDH2 inhibitor, an enasidenib, Enasidenib, a smoothened (SMO) inhibitor, a glasdegib, an arginase inhibitor, an IDO inhibitor, an epacadostat, a BCL-2 inihbitor, a venetoclax, Venetoclax, a platinum complex derivative, oxaliplatin, a kinase inhibitor, a tyrosine kinase inhibitor, a PI3 kinase inhibitor, a BTK inhibitor, an ibrutinib, Ibrutinib, an acalabrutinib, Acalabrutinib, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

31. The method according to claim 23, wherein said isolated monoclonal antibody or an antigen binding fragment thereof further comprises an antitumor drug linked thereto.

32. The method of claim 31, wherein said antitumor drug is linked to said antibody through a photolabile linker.

33. The method of claim 31, wherein said antitumor drug is linked to said antibody through an enzymatically-cleaved linker.

34. The method of claim 31, wherein said antitumor drug is a toxin, a radioisotope, a cytokine, or an enzyme.

35. The method according to claim 23, wherein said isolated monoclonal antibody or an antigen binding fragment thereof is conjugated to a liposome or nanoparticle.

36. A method of detecting a cancer cell or cancer stem cell in a sample or subject comprising:
   (a) contacting a subject or a sample from the subject with the antibody or an antigen-binding fragment thereof according to claim 1; and
   (b) detecting binding of said antibody to a cancer cell or cancer stem cell in said subject or sample.

37. The method of claim 36, wherein the sample is a body fluid or biopsy.

38. The method of claim 36, wherein the sample is blood, bone marrow, sputum, tears, saliva, mucous, serum, urine or feces.

39. The method of claim 36, wherein detection comprises immunohistochemistry, flow cytometry, FACS, ELISA, RIA or Western blot.

40. The method of claim 36, further comprising performing steps (a) and (b) a second time and determining a change in detection levels as compared to the first time.

41. The method of claim 36, wherein said isolated monoclonal antibody or an antigen binding fragment thereof further comprises a label.

42. The method of claim 41, wherein said label is a peptide tag, an enzyme, a magnetic particle, a chromophore, a fluorescent molecule, a chemo-luminescent molecule, or a dye.

* * * * *

UNITED STATES PATENT AND TRADEMARK OFFICE
CERTIFICATE OF CORRECTION

PATENT NO. : 12,202,895 B2
APPLICATION NO. : 17/275838
DATED : January 21, 2025
INVENTOR(S) : Zhiqiang An et al.

Page 1 of 1

It is certified that error appears in the above-identified patent and that said Letters Patent is hereby corrected as shown below:

In the Claims

In Claim 1, Column 195, Line 15, after "CDR)" insert --1--.

Signed and Sealed this
Eighteenth Day of November, 2025

John A. Squires
*Director of the United States Patent and Trademark Office*